(12) United States Patent
Labrie et al.

(10) Patent No.: US 9,090,651 B2
(45) Date of Patent: Jul. 28, 2015

(54) HELIX 12 DIRECTED PHARMACEUTICAL PRODUCTS

(75) Inventors: Fernand Labrie, Sainte-foy (CA); Shankar Singh, Sainte-foy (CA); Sylvain Gauthier, St. Augustin-de-Desmaures (CA); Yvon Frechette, Val-Belair (CA); Sylvain Chenard, Sainte-foy (CA); Rock Breton, Ancienne-Lorette (CA)

(73) Assignee: ENDORECHERCHE, INC. (CA)

( * ) Notice: Subject to any disclaimer, the term of this patent is extended or adjusted under 35 U.S.C. 154(b) by 1355 days.

(21) Appl. No.: 11/030,850

(22) Filed: Jan. 7, 2005

(65) Prior Publication Data

US 2005/0250749 A1 Nov. 10, 2005

Related U.S. Application Data

(60) Provisional application No. 60/535,121, filed on Jan. 7, 2004.

(51) Int. Cl.
*A61K 31/565* (2006.01)
*C07J 41/00* (2006.01)
*C07J 1/00* (2006.01)

(52) U.S. Cl.
CPC .......................................... *C07J 1/00* (2013.01)

(58) Field of Classification Search
CPC ......... C07J 31/006; C07J 41/00; C07J 43/003
USPC .................................. 552/641, 638; 514/178
See application file for complete search history.

(56) References Cited

U.S. PATENT DOCUMENTS

| | | | |
|---|---|---|---|
| 3,742,951 A | 7/1973 | Zaffaroni | 128/268 |
| 3,797,494 A | 3/1974 | Zaffaroni | 128/268 |
| 4,568,343 A | 2/1986 | Leeper et al. | 604/896 |
| 5,064,654 A | 11/1991 | Berner et al. | 424/448 |
| 5,071,644 A | 12/1991 | Viegas et al. | 514/772.7 |
| 5,071,657 A | 12/1991 | Oloff et al. | 424/486 |
| 5,723,455 A | 3/1998 | Tanabe et al. | 514/169 |
| 5,854,230 A | 12/1998 | Tanabe et al. | 514/173 |
| 6,060,503 A | 5/2000 | Labrie et al. | 514/428 |
| 6,083,940 A | 7/2000 | Tanabe et al. | 514/173 |
| 7,018,993 B2 | 3/2006 | Ohta et al. | 514/178 |

FOREIGN PATENT DOCUMENTS

| | | |
|---|---|---|
| EP | 0 254 341 | 1/1988 |
| EP | 0 279 982 | 8/1988 |
| EP | 1304334 A1 | 4/2003 |
| JP | 41 018 820 | 10/1963 |
| WO | WO 95/18821 | 7/1995 |
| WO | WO 97/11162 | 3/1997 |
| WO | WO 99/46279 | 3/1999 |
| WO | WO 02/00617 | 1/2002 |
| WO | WO 02/02589 A1 | 1/2002 |
| WO | WO 03/022835 | 9/2002 |
| WO | WO 03/068217 | 8/2003 |
| WO | WO 03/077919 A1 | 9/2003 |
| WO | WO 03/092588 A2 | 11/2003 |
| WO | WO 2005/066194 | 1/2005 |
| WO | WO 2006/133567 | 6/2006 |
| WO | WO 2008/124922 | 4/2008 |

OTHER PUBLICATIONS

Pazzagli et al., "Preparation and evaluation of steroid chemiluminescent tracers." Journal of Steroid Biochemistry, 19(18), pp. 407-412, 1983.*
International Search Report dated May 10, 2005.
Stanley, E.R., et al., "Development of Methods for the Quantitative in Vitro Analysis of Androgen-Dependent and Autonomous Shionogi Carcinoma 115 Cells" *Cell*, 10:35-44 (1977).
Ishioka, T., et al., "Novel Non-Steroidal/Non-Anilide Type Androgen Antagonists with an Isoxazolone Moiety" *Bioorganic & Medicinal Chemistry*, 10:1555=1566 (2002).
Muddana, S.S., et al, "11β-Alkyl-Δ⁹-19-Nortestosterone Derivatives: High-Affinity Ligands and Potent Partial Agonists of the Androgen Receptor" *J. Med. Chem.*, 47:4985-4988 (2004).
Kedishvili, N.Y. et al., "Evidence That the Human Gene for Prostate Short-chain Dehydrogenase/Reductase (PSDR1) Encodes a Novel Retinal Reductase (RalR1)" *The Journal of Biological Chemistry*, 277(No. 32):28909-28915 (2002).
Lin, B., et al., "Prostate Short-Chain Dehydrogenase Reductase 1 (PSDR1): A New Member of the Short-Chain Steroid Dehydrogenase/Reductase Family Highly Expressed in Normal and Neoplastic Prostate Epithelium" *Cancer Research*, 61:1611-1618 (2001).

(Continued)

*Primary Examiner* — Barbara P Badio
(74) *Attorney, Agent, or Firm* — Ostrolenk Faber LLP

(57) ABSTRACT

Compounds having the structure or their salts:

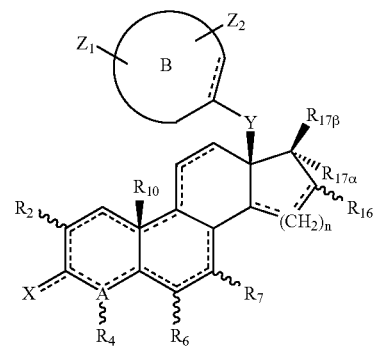

are used to treat or reduce le likelihood of acquiring androgen-dependent diseases, such as prostate cancer, benign prostatic hyperplasia, polycystic ovarian syndrome, acne, hirsutism, seborrhea, androgenic alopecia and male baldness. They can be formulated together with pharmaceutically acceptable diluent or carrier or otherwise made into any pharmaceutical dosage form. Some of these compounds having tissue-specific antiandrogenic activity and tissue-specific androgenic activity can be used to treat or reduce the risk of developing diseases related to loss of androgenic stimulation. Combinations with other active pharmaceutical agents are also disclosed.

33 Claims, 2 Drawing Sheets

(56) References Cited

OTHER PUBLICATIONS

Negro-Vilar, A., "Selective Androgen Receptor Modulators (SARMs):A Novel Approach to Androgen Therapy for the New Millennium" *The Journal of Clinical Endocrinology & Metabolism*, 84(No. 10):3459-3462 (1999).

Pérard, S., et al. "18-Functionalized steroids:synthesis of thioderivatives of progesterone" *Steroids*, 55:271-275 (1990).

Singh, S.M., et al., "Androgen Receptor Antagonists (Antiandrogens):Structure-Activity Relationships" *Current Medicinal Chemistry*, 7:211-247 (2000).

T. Mild, et al., Steroids, Chemical Abstracts, 66:18810 (1967) Caplus, abstract only.

U.S. Appl. No. 11/452,545, filed Jun. 14, 2006 by Fernand Labrie et al., entitled "*Helix 12 Directed Non-Steroidal Antiandrogens*".

U.S. Appl. No. 12/100,372, filed Apr. 9, 2008 by Fernand Labrie, et al., entitled "*17Alpha-Substituted Steroids as Systemic Antiandrogens and Selective Androgen Receptor Modulators*".

Taiwanese Search Report issued by the Taiwanese Patent Office on Jul. 12, 2010 in connection with corresponding Taiwanese Patent Application No. 094100344.

Office Action issued by the Japanese Patent Office on Dec. 21, 2010 in connection with corresponding Japanese Patent Application No. 548053/2006 and English language translation of Japanese Office Action.

Supplementary European Search Report dated Apr. 28, 2011 in corresponding European Application No. 05700249.5.

Declaration of Dr. Sylvain Gauthier under 37 C.F.R. 1.132 executed Feb. 16, 2015 and Addendum.

\* cited by examiner

A:

B:

HELIX 12 DIRECTED PHARMACEUTICAL PRODUCTS

CROSS-REFERENCE TO RELATED APPLICATION

The present application is a 35 U.S.C. §119 conversion of Provisional Application Ser. No. 60/535,121 filed Jan. 7, 2004.

BACKGROUND OF THE INVENTION

This invention relates to novel inhibitors of sex steroid activity, for example to compounds having antagonistic activity on sex steroid receptors. More particularly, the invention relates to certain steroid derivatives having specified side-chains at their 13-position and to metabolites thereof which block androgen action by acting, among other mechanisms, through the androgen receptors, while not activating such receptors in some or all androgen-sensitive tissues. When used to treat or reduce the risk of acquiring androgen-exacerbated diseases, when used to treat or reduce the risk of acquiring diseases related to loss of androgenic stimulation, compounds of the invention which activate androgen receptors in the target tissue may be effective even if they act as androgen antagonists in other tissues. These compounds may be effective even if they activate androgen receptors in tissues other than the target tissues.

BRIEF DESCRIPTION OF THE PRIOR ART

During the treatment of certain androgen-dependent diseases, it is important to greatly reduce or, if possible, to eliminate androgen-induced effects. For this purpose, it is desirable to both block access to the androgen receptors with "antiandrogens", thus preventing androgens from binding and activating those receptors, and also to reduce the concentration of androgens available to activate the receptors. It is possible that, even in the absence of androgens, unoccupied androgen receptors may be biologically active. Hence, antiandrogens which bind and block the receptors may produce better therapeutic results than therapy which only inhibits androgen production.

Antiandrogens may have a significant therapeutic effect in slowing or stopping the progress of androgen-dependent diseases, e.g. diseases whose onset or progress is aided by androgen receptor or androgen receptor modulator activation.

It is desired that an antiandrogen used in therapy to reduce androgen receptor activation have both good affinity for the androgen receptor and a substantial lack of inherent androgenic activity in the tissue of interest. The former refers to the ability of an antiandrogen to bind to the androgen receptor, and thus to block access to the receptor by androgens. The latter refers to the effect the antiandrogen has on the receptor once it binds thereto. Some antiandrogens may possess inherent androgenic activity ("agonistic activity") which undesirably activates the very androgen receptors whose activation they are intended to prevent. In other words, an antiandrogen with undesirable intrinsic androgenic activity may successfully bind to androgen receptors, desirably blocking access to those receptors by natural androgens, yet may undesirably itself activate the receptor in tissues where an exclusive anti-androgenic action is desired.

Known non-steroidal antiandrogens such as flutamide, casodex and anandron lack undesirable androgenic activity, but may not have receptor affinity as good as steroidal anti-androgens (i.e. androgen derivatives having a steroidal nucleus that is modified to provide antiandrogenic activity). Steroidal antiandrogens, however, are believed to more frequently possess undesirable agonistic characteristics, than non-steroidal antiandrogens.

The protein Prostate Short-Chain Dehydrogenase Reductase 1 (PSDR1) was first identified as a Short-Chain Steroid Dehydrogenase/Reductase that is highly expressed in Normal and Neoplastic Prostatic Epithelium (Lin B, Cancer Research 61:1611-8, 2001) without description of enzymatic activity or of its characterization. Recently, using the protein overexpressed in SF9 insect cells, the enzyme has been found to have retinal reductase activities catalyzing the transformation of retinal into retinol (Kedishvili-NY et al., JBC 277, 28909-15, 2002). The authors concluded that the enzyme is selective for retinoids and does not possess any significant oxidative or reductive activity toward the functional hydroxyl or ketone groups in positions 3, 17, or 20 of steroids.

There is thus a need in the Art for steroidal antiandrogens having very good affinity to the androgen receptor, while substantially lacking undesirable agonistic characteristics and having a good parenteral or oral bioavailability for systemic uses.

For the treatment of androgen-dependent skin diseases, most of known antiandrogens, such as flutamide, have unwanted systemic activity when applied on the skin and cannot generally be used without the risk of undesirable systemic effects.

For androgen-dependent skin-related diseases such as acne, hirsutism, seborrhea, androgenic alopecia, male baldness, it is believed that antiandrogens must not penetrate into the body in significant amounts and must not have antiandrogenic effect in tissues other than the one on the area of the skin where they are applied.

There is also thus a need in the Art for steroidal antiandrogens having good affinity for the androgen receptor and substantially lacking undesirable agonistic and systemic activity for topical use.

SUMMARY OF THE INVENTION

It is an object of the present invention to provide steroidal antiandrogens, having good affinity for the androgen receptor, while substantially lacking androgenic activity. These antiandrogens may be useful in the treatment of androgen-dependent diseases as described in more detail infra.

It is an object of the present invention to provide steroidal Selective Androgen Receptor Modulators (SARMs) i.e. compounds which are antiandrogens for some tissues, while having androgenic activity in other tissues. To qualify as a SARM, as defined herein, a compound must suppress androgenic activity in at least prostate or seminal vesicle tissues while enhancing androgenic activity in at least one other tissue or activity (e.g. muscle or brain or gonadotrophin feedback). (see A. Negro-Vilar, Selective Androgen Receptor Modulators (SARMs): A novel Approach to Androgen Therapy for the New Millenium, The Journal of Clinical Endocrinology and Metabolism, 84(10), 3459-3462, 1999).

In one embodiment, the invention provides a compound of the following molecular formula, or a salt of thereof:

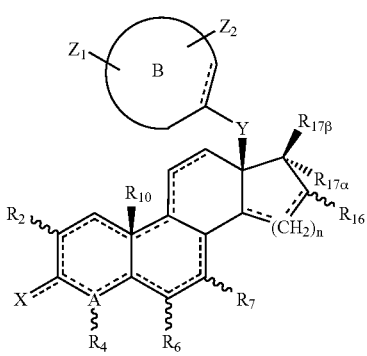

wherein n is an integer from 1 to 2;
Wherein dotted lines represent optional π-bonds;
Wherein A is selected from the group consisting of a carbon atom and a nitrogen atom;
Wherein B is selected from the group consisting of an aromatic moiety, a heterocyclic moiety, a cyclic moiety and a polycyclic moiety;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, or $C_2$-$C_{20}$ acyl)
Wherein X is selected from the group consisting of hydrogen, fluoride, chloride, bromide, iodide, cyanide, keto-oxygen, hydroxyl, NOH and a group transformed in vivo into hydroxyl or keto function;
Wherein Y is a spacing group having one to four atoms.
Wherein $Z_1$ is a hydrocarbon moiety additionally having at least a one sulfoxide group or nitrogen atom separated from B by one to four intervening atoms, and said nitrogen atom being an amine, an amide, an N-oxide, or a quaternary ammonium salt, $Z_1$, optionally, having other oxygen, sulphur, or nitrogen atoms.
Wherein $Z_2$ is selected from the group consisting of hydrogen, fluorine, chlorine, bromine, iodine, cyano, nitro, trifluoromethyl, alkoxy, methoxyl, $C_1$-$C_5$ straight or branched alkyl, $C_2$-$C_5$ straight or branched alkenyl, and $C_2$-$C_5$ straight or branched alkynyl.

In another embodiment, the invention provides topical or systemic pharmaceutical compositions containing the compounds of the invention together with pharmaceutically acceptable diluents or carriers.

In another aspect, compounds of the invention, or pharmaceutical compositions containing them, are used in the treatment or prevention of androgen-exacerbated skin related diseases such as acne, hirsutism, seborrhea, androgenic alopecia, male baldness and the like.

In another embodiment, compounds of the invention are used in the treatment or prevention of androgen-exacerbated systemic diseases such as prostate cancer or benign prostatic hyperplasia, precocious puberty, polycystic ovarian syndrome, hyperrandrogenic syndromes, and the like.

In another embodiment, treatment and prevention regimens for androgen-exacerbated diseases include use of the compounds disclosed herein, as part of a combination therapy which further utilizes other active compounds selected from the group consisting of 5alpha-reductase inhibitor, 17beta-hydroxysteroid dehydrogenase type 5 inhibitors, Prostate Short-Chain Dehydrogenase Reductase 1 ("PSDR-1") inhibitors, and other inhibitors of androgen biosynthesis.

In another aspect, compounds of the present invention having tissue-specific antiandrogenic activity and tissue-specific androgenic activity can be used to treat or reduce the risk of developing diseases related to loss of androgenic stimulation.

In another aspect, compounds of the invention are used in the manufacture of a medicament for treatment of diseases discussed herein.

It is another object to provide selective androgen receptor modulators for treatment (or reduction of the likelihood of acquiring) diseases related to loss of androgen stimulation.

It is another object to provide pharmaceutical compounds with good systemic bioavailability.

It is another object to provide pharmaceutical compositions which, when applied topically for purposes of providing local action, substantially lack systemic or non-local effects.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENTS

Figure 1:
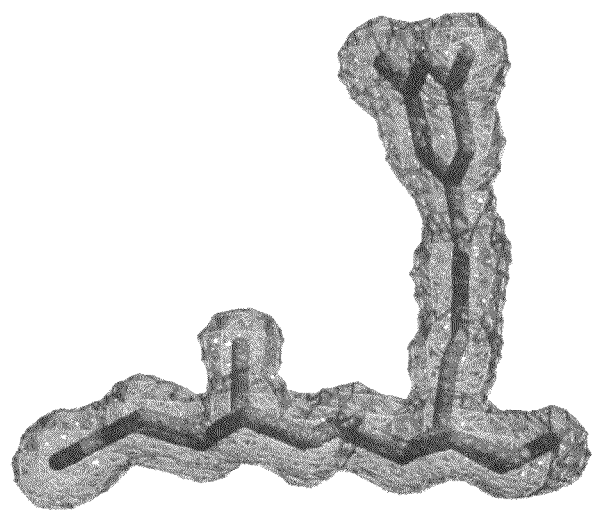
FIG. 1 (A: side-view, B: top-view) the showns the electron density around the EM-5744 molecule. The 2Fo-Fc map, computed with 1.75 Å resolution data, is illustrated at a 1σ level.
Figure 1:
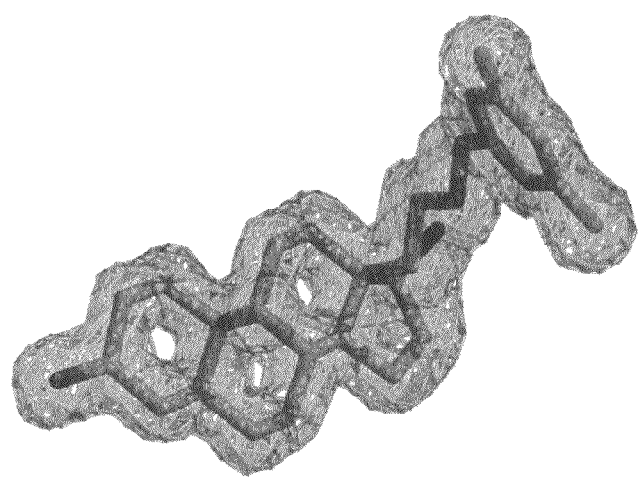

Previous structural studies on the hERα(LBD)-raloxifene crystal complex have revealed the structural basis of the mechanism of antagonism by raloxifene. It was then shown that the antagonist binds at the same site where the agonist binds within the core of the LBD but the two ligands demonstrate different binding modes. Indeed, each class of ligand induces a distinct conformation in the transactivation domain which is characterized by the different positioning of helix 12. Our molecular modeling based upon the crystallographic structure of the hAR(LBD)-R1881 complex has identified a narrow channel between the steroid binding site and the site occupied by helix 12 (see Ishioka et al., Novel Non-Steroidal/Non-Anilide Type Androgen Antagonists with Isoxazolone Moiety, Bioorganic & Medicinal Chemistry 10 (2002) 1555-1566; Muddana et al. 11β-alkyl-$\Delta^9$-19-Nortestosterone Derivatives: High-Affinity Ligands and Potent Partial Agonists of the Androgen Receptor, J. Med. Chem. 2004, 47, 4985-4988). We found that this narrow channel, mainly formed by the side chains of 5 residues ($Asn_{705}$, $Trp_{741}$, $Met_{742}$, $Thr_{877}$, and $Phe_{891}$) of the androgen receptor could accommodate a side chain only if it is positioned on carbon 18 of an androgen steroid nucleus. From this position on the steroid nucleus, a thin side chain passing through this opening could reach the surface of the receptor and disturb helix 12 positioning. $hER_\alpha(LBD)$ and hAR(LBD) meant human type α Estrogen Receptor Ligand Binding Domain and human Androgen Receptor Ligand Binding Domain, respectively.

Many compounds with long C-18 substituents have been synthesized in our laboratory and tested for their capacities to bind the androgen receptor and to inhibit the DHT-stimulated growth of mouse Shionogi mammary carcinoma cells. In the majority of cases, these molecules bind the receptor with high affinity but remain potent agonists. However, we have also obtained many very potent antagonists having a high affinity for the receptor, thus indicating that the structure of the side chain at position C-18 is of paramout importance. To understand the molecular basis of the agonistic and antagonistic properties of these different molecules, and to verify that a side chain positioned on C-18 is really able to pass through the channel and reach helix 12, we have attempted to crystallize some of these molecules (androgens and antiandrogens) in complex with the human androgen receptor ligand binding domain (hAR(LBD)) in order to determine and compare the tridimensional structures of these complexes. We have now obtained the complete structure for one of them (hAR(LBD)-EM-5744) determined at a 1.75 Å resolution.

EM-5744 is a DHT-based ligand possessing a strong affinity for the human androgen receptor in spite of its long side chain substituent added to the carbon atom at position 18 (see structure below). Indeed, the

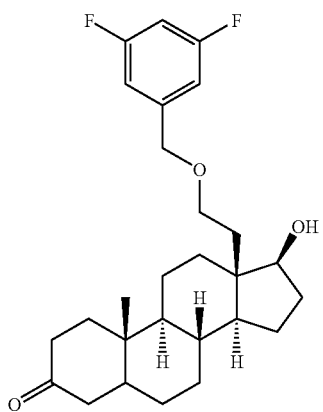

ligand EM-5744 binds with a relative binding affinity of 540 to the wild-type hAR as compared with a value of 180 for DHT and 100 for R1881. This ligand could be considered as an agonist since it fails to inhibit the DHT-stimulated growth of Shionogi cells when added to the culture medium at a concentration of $10^{-6}$ M while it possesses a significant agonistic activity at $10^{-7}$ M.

Figure 2:
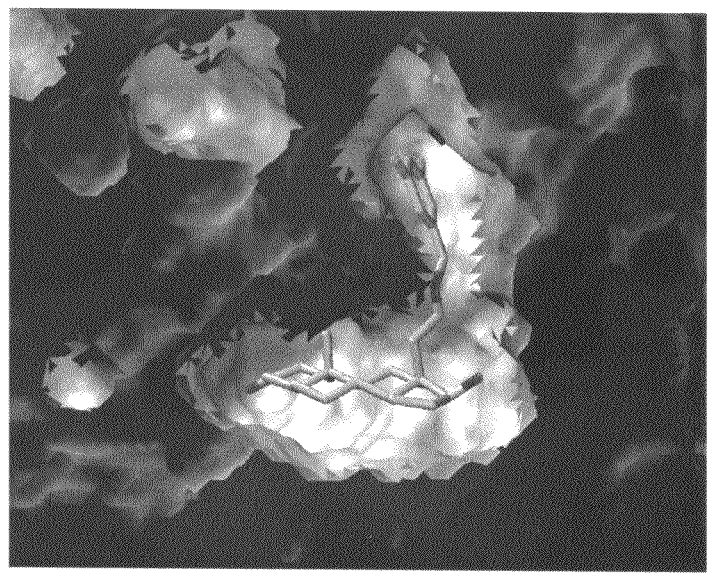
FIG. 2 shows the electrostatic surface representing the ligand binding cavity in the hAR(LBD)-EM-5744 complexed structure. The surface is colored according to the electrostatic potential: blue for positive, white for neutral, and red for negative.

As illustrated in FIGS. 1 and 2, in the crystallographic structure which has been determined, the steroid nucleus of EM-5744 is positioned within the ligand binding cavity and there are a total of 18 amino acid residues in hAR LBD that interact with the bound ligand (d≤3.9 Å). Most of these residues are hydrophobic and interact mainly with the steroid scaffold, whereas a few are polar and may form hydrogen bonds to the polar atoms on the ligand. The oxygen atom (O-3) of the A ring carbonyl group forms a hydrogen bond to $Arg_{752}$ (2.9 Å to $Arg_{752}$ $N^{\eta 2}$). There is also a water molecule near O-3 (3.2 Å) that is hydrogen-bonded to two other residues ($Arg752$ $N^{\eta 2}$ and $Met_{745}$ O). The $17_\beta$ hydroxyl group of EM-5744 forms hydrogen bonds to $ASN_{705}$ $O^{\delta 1}$ (2.8 Å) and $Thr_{877}$ $O^\gamma$ (2.8 Å), this being the same pattern observed in the hAR(LBD)-R1881 complex structure. Finally, the C-18 side chain is also well stabilized, mainly by numerous contacts with hydrophobic residues, and, as predicted, exits the steroid binding pocket through the channel. However, the side chain of EM-5744 is not well positioned to reach the cavity occupied by helix 12 and, consequently, can not disturb its positioning. This observation explains very well why this compound acts as an agonist in spite of the presence of its C-18 bulky side chain. Interestingly, an unexpected interaction has been observed between one of the fluor atoms at the extremity of the side chain of EM-5744 and the $N^{\eta 2}$ atom of residue $His_{874}$. A water molecule found at close proximity of these two atoms could also be involved. This interaction probably explains the higher affinity of EM-5744 for the hAR compared to DHT or R1881 which do not possess this third bond with the receptor. In order to accommodate the C-18 substituent of EM-5744 in a similar manner, the side chain of residue $Trp_{741}$, a residue forming the channel, is flipped 180° around its $C^\gamma$ and adopts a conformation which is very different from that observed with the same residue in the hAR(LBD)-R1881 complex structure. Other residues forming the ligand cavity also adopt different conformations, a possible consequence of the $Trp_{741}$ side chain movement. The present observations illustrate the remarkable plasticity of both, the ligand binding cavity and the narrow channel through which the C-18 side chain of EM-5744 exits from the pocket.

Binding of androgen receptors by the present compounds may modify the binding of co-activators and co-repressors to the androgen receptor, thus leading to accelerated apoptosis in androgen-sensitive tissues. Antiandrogens may even lead to cell death.

The present antiandrogens and pharmaceutical compositions containing them, may be utilized in accordance with the invention in the treatment of androgen-sensitive diseases whose progress or onset is aided by activation of androgen receptors or androgen receptor modulators.

These include but are not limited to prostate cancer, benign prostatic hyperplasia, acne, seborrhea, hirsutism, androgenic alopecia, male baldness, precocious puberty, polycystic ovarian syndrome and the like.

In certain circumstances (e.g. at certain concentrations) the compounds of the invention, and pharmaceutical compositions containing them, can be androgenic and may be utilized in accordance with the invention in the prevention and treatment of diseases regarding which androgens are beneficial such as muscle atrophy, abdominal fat accumulation, skin atrophy, anemia, bone loss, artherosclerosis, cardiovascular disease, type 2 diabetes, loss of energy or well being.

It is preferred that Y of General Formula I is selected from the group consisting of -$ACH_2CH_2$—, —$CH_2ACH_2$—, and —$CH_2CH_2A$-, wherein A is selected from the group consisting of O, S, $CH_2$, NRc, (Rc being H or $C_1$-$C_6$ alkyl) or Se. It is more preferred that Y is —$OCH_2CH_2$—.

In preferred embodiments B, of General Formula I, includes at least one pi bond. When B is aromatic it is preferably phenylene or pyridyl. When B is polycyclic it may include bridge atoms (such as occur in

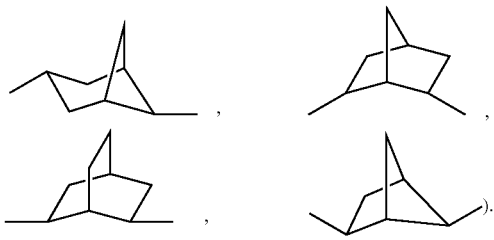

It is preferred that B is phenylene and $Z_1$ is in meta position with respect to the group Y. It is also preferred that $Z_1$ have a nitrogen atom separated from the phenylene ring by one intervening atoms.

In some embodiments, the invention utilizes a compound having the following molecular formula (II), or a salt of thereof:

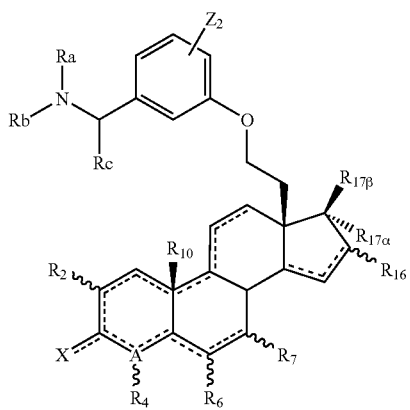

Wherein dotted lines represent optional π-bonds;
Wherein A is selected from the group consisting of carbon and nitrogen;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, $C_2$-$C_{20}$ acyl)
Wherein X is selected from the group consisting of a hydrogen, a cyanide, an oxygen atom forming a keto function, an hydroxyl, NOH, and a group transformed in vivo into hydroxyl or keto;
Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;
Wherein Ra, Rb, and Rc are independently selected from the group consisting of hydrogen, $C_1$-$C_{10}$ straight, or branched alkyl, $C_2$-$C_{10}$ straight or branched alkenyl, $C_2$-$C_{10}$ straight or branched alkynyl, a $C_3$-$C_7$ saturated or unsaturated cyclic hydrocarbon moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionnally substituted with fluoro, chloro, bromo, iodo, or cyano); or Rb an Rc together form a ring (optionnally substituted with fluoro, chloro, bromo, iodo, or cyano); and wherein Ra, Rb, and Rc may, optionally, have oxygen, sulphur, or nitrogen atoms.

In some embodiments, it is preferred that Ra or Rb is a cyclopentyl, cyclohexyl or cycloheptyl radical In some embodiments, it is preferred that Rc is selected from the group consisting of hydrogen, methyl and ethyl.

In other embodiments, the invention utilizes a compound having the following molecular formula (III) or a salt of thereof:

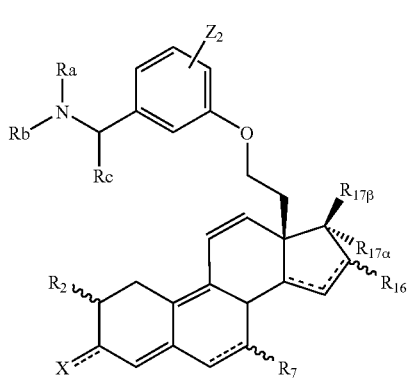

Wherein dotted lines represent optional π-bonds;
Wherein $R_2$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, $C_2$-$C_{20}$ acyl)
Wherein X is selected from the group consisting of hydrogen, fluoride, chloride, bromide, iodide, cyanide, keto-oxygen, hydroxyl, NOH and a group transformed in vivo into hydroxyl or keto function;
Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;
Wherein Ra, Rb, and Rc are independently selected from the group consisting of hydrogen, $C_1$-$C_{10}$ straight, or branched alkyl, $C_2$-$C_{10}$ straight or branched alkenyl, $C_2$-$C_{10}$ straight or branched alkynyl, a $C_3$-$C_7$ saturated or unsaturated cyclic hydrocarbon_moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionnally substituted with fluoro, chloro, bromo, iodo, or cyano); or Rb an Rc together form a ring (optionnally substituted with fluoro, chloro, bromo, iodo, or cyano); wherein Ra, Rb, and Rc may, optionally, have oxygen, sulphur, or nitrogen atoms.

It is preferred that X is oxygen or hydroxyl.

It is preferred that Z1 of General Formula I is selected from among the following moieties:

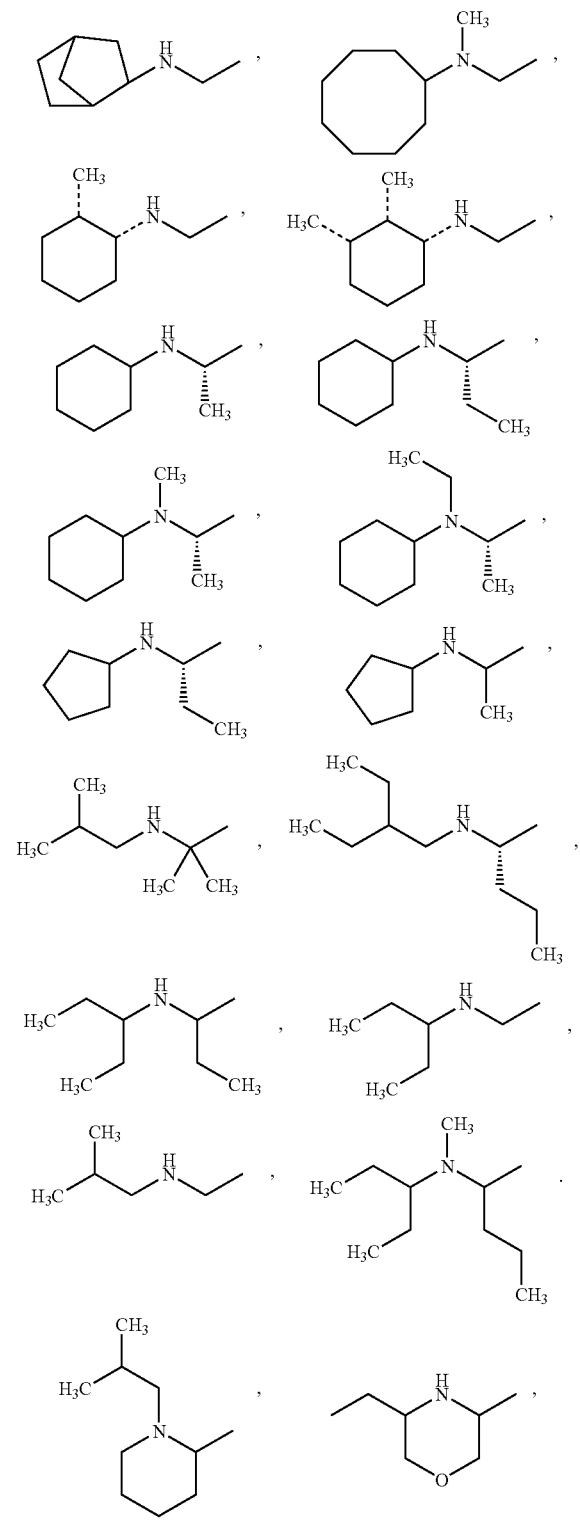

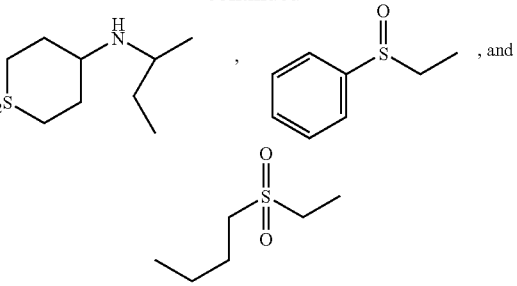

It is preferred that $Z_2$ is selected from the group consisting of hydrogen, fluorine, chlorine and cyano.

It is preferred that $R_2$ is selected from the group consisting of hydrogen and methyl.

It is preferred that $R_4$ is hydrogen.

It is preferred that $R_6$ is selected from the group consisting of hydrogen and dimethyl.

It is preferred that $R_7$ is selected from the group consisting of methyl, ethyl, vinyl and 2-propenyl.

It is preferred that $R_{10}$ is methyl.

It is preferred that $R_{17\alpha}$ is selected from the group consisting of hydrogen, methyl, ethyl, and ethinyl.

It is preferred that $R_{17\beta}$ is hydroxyl.

It is preferred that A is carbon.

It is preferred that, in General Structure I, n is 1.

In preferred embodiments two or preferably more of the preferences herein are used in combination.

It is preferred that_B is selected from the group consisting of phenylene and mono-substituted pyridyl and $Z_1$ is located in meta position with respect to the group Y and the nitrogen atom of $Z_1$ is separated from the phenylene or mono-substituted pyridyl ring by one intervening atoms.

It is preferred that, in General Structure II, X is oxygen, A is carbon, $Z_2$, $R_2$, $R_4$, $R_6$, $R_{16}$, and $R_{17\alpha}$ are hydrogen, $R_{10}$ is methyl, $R_{17\beta}$ is hydroxyl, $R_7$ is methyl, Ra, Rb and Rc are C2-C4 alkyl and more preferably Rc is ethyl.

It is preferred that, in General Structure III, X is oxygen, $Z_2$, $R_2$, and $R_{16}$ are hydrogen, $R_{17\alpha}$ is ethinyl, $R_{17\beta}$ is hydroxyl, $R_7$ is methyl, Ra, Rb and Rc are C2-C4 alkyl and more preferably Rc is ethyl.

The following compounds, EM-6445, EM-6680, EM-6842 and EM-6861 are especially preferred for topical application:

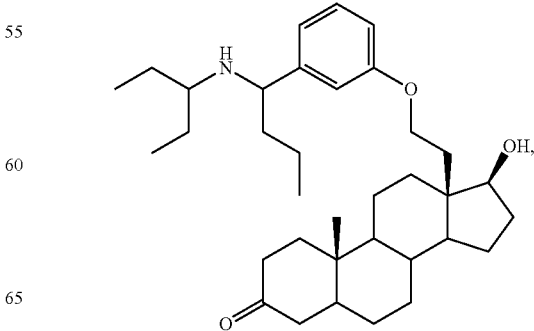

-continued

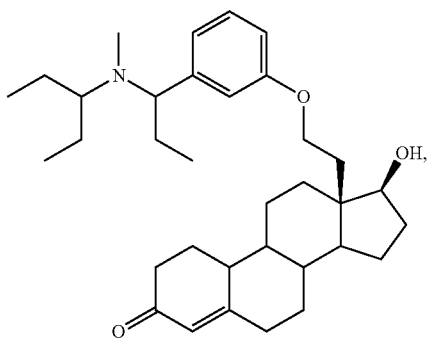

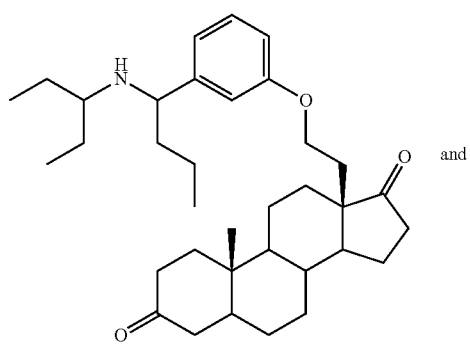

and

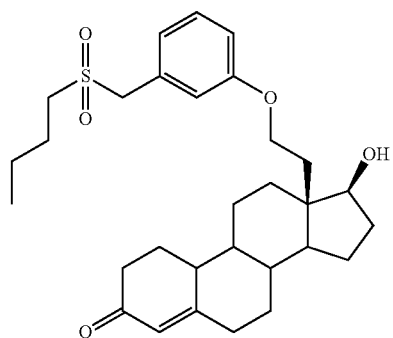

The following compounds EM-6798, and EM-7133 are especially preferred for systemic use:

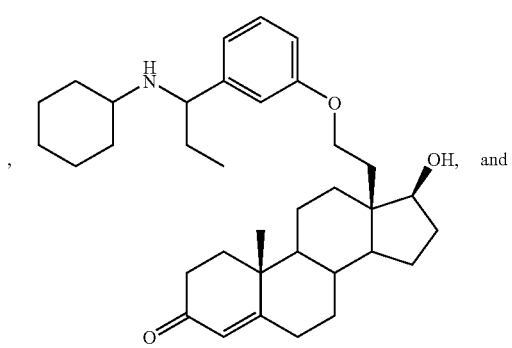

,

-continued

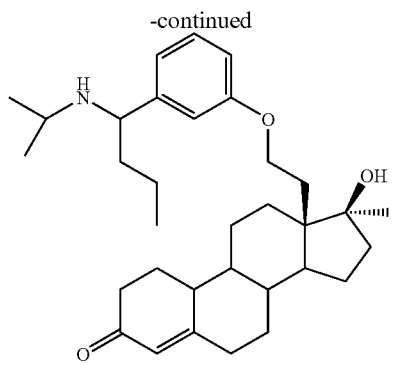

We believe that if A is nitrogen, the stability of the steroid nucleus will be increased and the oral bioavailability will be greater. We also believe that if n=2, the angle of the steroid nucleus and the side-chain will be slighty modified leading probably to a better interaction with the receptor.

A pharmaceutical composition comprising a pharmaceutically acceptable diluent or carrier and a therapeutically effective amount of at least one compound of the molecular formula or a salt of thereof:

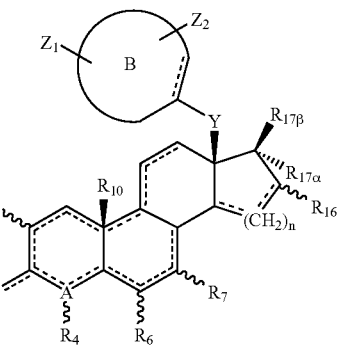

wherein n is an integer from 1 to 2;
Wherein dotted lines represent optional α-bonds;
Wherein A is selected from the group consisting of a carbon atom and a nitrogen atom;
Wherein B is selected from the group consisting of an aromatic moiety, a heterocyclic moiety, a cyclic moiety and a polycyclic moiety;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, or $C_2$-$C_{20}$ acyl)
Wherein X is selected from the group consisting of hydrogen, fluoride, chloride, bromide, iodide, cyanide, keto-oxygen, hydroxyl, NOH and a group transformed in vivo into hydroxyl or keto function;

Wherein Y is a spacing group having one to four atoms.

Wherein $Z_1$ is a hydrocarbon moiety additionally having at least a one sulfoxide group or nitrogen atom separated from B by one to four intervening atoms, and said nitrogen atom being an amine, an amide, an N-oxide, or a quaternary ammonium salt, $Z_1$, optionally, having other oxygen, sulphur, or nitrogen atoms.

Wherein $Z_2$ is selected from the group consisting of hydrogen, fluorine, chlorine, bromine, iodine, cyano, nitro, trifluoromethyl, alkoxy, $C_2$-$C_5$ straight or branched alkyl, $C_2$-$C_5$ straight or branched alkenyl, and $C_2$-$C_5$ straight or branched alkynyl.

A pharmaceutical composition comprising a pharmaceutically acceptable diluent or carrier and a therapeutically effective amount of at least one compound having a molecular formula selected from the group consisting of, or a salt of thereof:

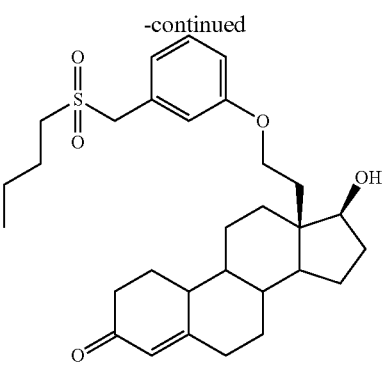
-continued

A pharmaceutical composition comprising a pharmaceutically acceptable diluent or carrier and a therapeutically effective amount of at least one compound having a molecular formula selected from the group consisting of, or a salt of thereof:

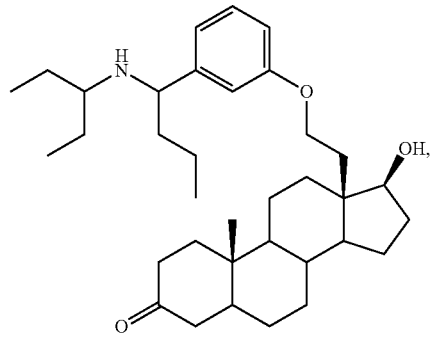

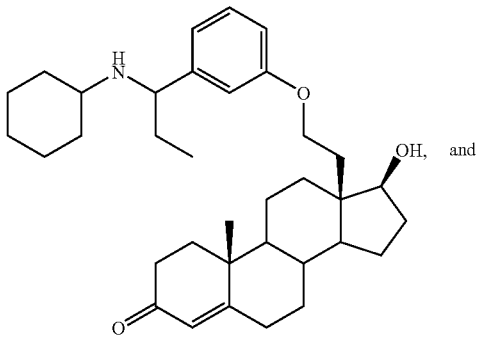
and

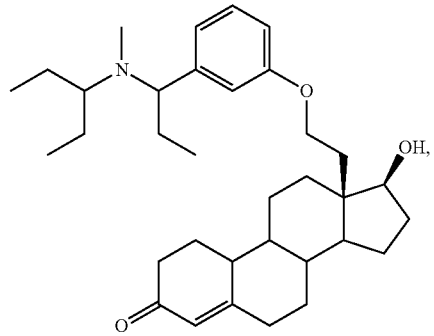

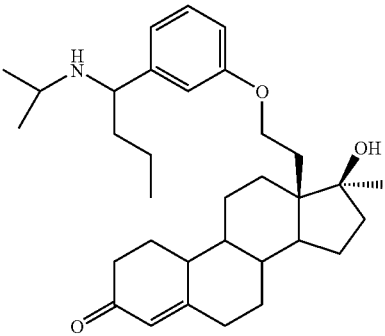

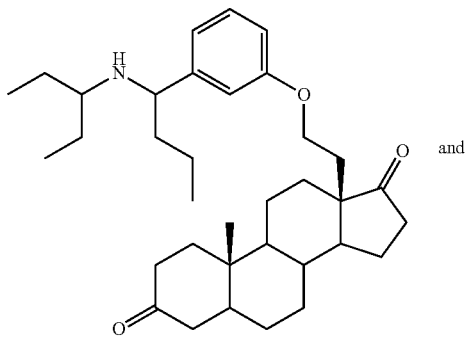
and

The antiandrogens of the invention are preferably formulated together with pharmaceutically acceptable diluent, excipient or carrier (including capsules) into pharmaceutical compositions at conventional antiandrogen concentrations for antiandrogens used in the prior art. Taking into account the higher potency of the compounds of this invention, the attending clinician may elect to modify the concentration and/or dosage in order to adjust the dose to the particular response of each patient. Preferably, the attending clinician will, especially at the beginning of treatment, monitor an individual patient's overall response and serum levels of antiandrogen (in comparison to the preferred serum concentrations discussed below), and monitor the patient's overall response to treatment, adjusting dosages as necessary where a given patients' metabolism or reaction to treatment is atypical. As discussed in more detail below, carriers, excipients or diluents include solids and liquids. When a composition is prepared other than for immediate use, an art-recognized preservative is typically included (e.g. benzyl alcohol). The novel pharmaceutical compositions of the invention may be used in the treatment of androgen-related diseases, or to reduce the likelihood of acquiring such diseases. When administered systemically (e.g., for treatment of prostate cancer, benign prostatic hyperplasia, precocious puberty, polycystic ovarian syndrome and other diseases not primarily affecting the skin) conventional diluents or carriers which are known in the art to be pharmaceutically acceptable for systemic use are used, e.g., saline, water, aqueous ethanol, oil, etc. The carrier is often a mixture of ingredients.

When formulated for systemic use, the antiandrogens may be prepared for administration in conventional ways such as orally or by injection. The antiandrogen can be administered, for example, by the oral route. The compounds of the present invention may be formulated with conventional pharmaceutical excipients, (e.g. spray dried lactose and magnesium stearate) into tablets or capsules for oral administration. Of course, taste-improving substances can be added in the case of oral administration forms. When capsules for oral ingestion are desired, any pharmaceutical capsules known in the art may be filled with the active ingredients of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed soft-gelatin capsules comprising a softener or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In soft-gelatin capsules, the active substance is preferably dissolved or suspended in suitable liquids, such as vegetable oils or liquid polyethylene glycols.

A dry delivery system, as described in U.S. Pat. Nos. 3,742,951, 3,797,494 or 4,568,343 may be used.

Alternatively, the active ingredient may be placed into a transdermal patch having structures known in the art, for example, structures such as those set forth in E.P. Patent No. 0279982.

Solvents or devices as described in U.S. Pat. Nos. 5,064,654, 5,071,644 or 5,071,657 can also be used to facilitate transdermal penetration when systemic effects are desired. When used to treat systemic diseases, the site of application on the skin should be changed in order to avoid excess local concentration of antiandrogens.

In some embodiments, the antiandrogens of the invention are utilized for the treatment of androgen related diseases of the skin such as acne, seborrhea, hirsutism, androgenic alopecia and male baldness. When used for any of these purposes, the antiandrogens are preferably administered topically together with a conventional topical carrier or diluent. When used topically, it is preferred that the diluent or carrier does not promote transdermal penetration of the active ingredients into the blood stream or other tissues where they might cause unwanted systemic effects.

When the compound is administered in a cutaneous or topical carrier or diluent, the carrier or diluent may be chosen from any known in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. The carrier or diluent is usually a mixture of several ingredients, including, but not limited to liquid alcohols, liquid glycols, liquid polyalkylene glycols, water, liquid amides, liquid esters, liquid lanolin, lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility, e.g. a mixture of ethanol or isopropanol with water.

A topical carrier may also include various other ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

The concentration of active ingredient in the ointment, cream, gel or lotion is typically from about 0.1 to 20 percent preferably between 1 and 5 percent and most preferably 2 percent (by weight relative to the total weight of the lotion, cream, gel or ointment). Within the preferred ranges, higher concentrations allow a suitable dosage to be achieved while applying the lotion, ointment, gel or cream in a lesser amount or with less frequency.

Several non-limiting examples infra describe the preparation of a typical lotion and gel, respectively. In addition to vehicles, one skilled in the art may choose other vehicles in order to adapt to specific dermatologic needs.

When antiandrogens are administered systemically, they are preferably administered orally or parenterally. Naturally, topical administration is preferred when the desired site of action is the skin.

Concentration of the active antiandrogen varies in a known manner depending upon the method of administering the pharmaceutical composition. A composition suitable for oral administration may preferably include at least one antiandrogen wherein the total concentration of all such antiandrogens in said pharmaceutical composition is from about 1% to 95% of the composition (by weight), and preferably from about 5% to about 20%. Where a combination of antiandrogens is used, the total dosage of the sum of all antiandrogens should be equal to the dosage range recited above. Blood level of the antiandrogen is a preferred criteria of adequate dosage which takes into account individual variation in absorption and metabolism.

When prepared for parental injection, the antiandrogen is preferably added at a concentration between about 0.1 mg/ml and about 100 mg/ml (preferably about 2.5 mg/ml to about 25 mg/ml).

When systemic activity is desired, it is necessary only that the antiandrogen be administered in a manner and at a dosage sufficient to allow blood serum concentration to obtain desired levels. Serum antiandrogen concentration should typically be maintained between 5 and 2000 micrograms per liter, preferably between 50 and 1000 micrograms per liter and most preferably between 50 and 500 micrograms per liter. Adequate serum levels may also be assessed by a patient's response to therapy.

For typical patients, the appropriate dosage of the antiandrogen to achieve desired serum concentration is between 10 and 2000 milligrams of active ingredient per day per 50 kg of body weight when administered orally. When administered by injection, about 2 to 1500 mg per day per 50 kg of body weight is recommended, preferably from 5 to 100.

For topical use lotion, ointment, gel or cream should be thoroughly rubbed into the skin so that no excess is plainly visible, and the skin is preferably not washed in that region for at least 30 minutes. The amount applied should provide at least 0.02 milligrams of antiandrogen per square centimeter (preferably from 0.1 to 1 mg/cm$^2$) per application. It is desirable to apply the topical composition to the effected region from 1 to 6 times daily, e.g. 3 times daily at approximately regular intervals.

Using human embryonic kidney cells stably transfected with human PSDR1 cDNA in culture, we have found that the enzyme possesses a predominant 17β-hydroxysteroid dehydrogenase activity, selective for 5α-reduced steroids, catalyzing the transformation of 5α-androstane-3,17-dione (5α-dione) into 5α-androstane-17β-ol-3-one (dihydrotestosterone, DHT) and of 5α-androstane-3α-ol-17-one (ADT) into 5α-androstane-3α,17β-diol (3α-diol).

Using RealTime PCR to quantify the mRNA expression levels of the enzyme in various human and mouse tissues, we have found that this enzyme is expressed in a wide range of tissues. It is strongly expressed in the human prostate, and at a lower level in the human liver, adrenal and placenta. In the mouse, it is highly expressed in the testis and in the preputial and clitoridal glands. It is also expressed in mouse seminal vesicles, epididymis, hypophysis, adrenals, liver, kidney, thymus, adipose tissue, skin, lung, esophagus, colon, mammary gland, uterus, vagina, and ovary. We believe that this enzyme plays an important role in the formation of the most potent natural androgen DHT.

In some embodiments of the invention, the antiandrogen of the invention is used in combination with another active ingredient as part of a combination therapy. For example, the novel antiandrogen may be utilized together with a separate 5α-reductase inhibitor, a type 5 or type 3 17β-hydroxysteroid dehydrogenase inhibitor, or a Prostate Short-Chain Dehydrogenase Reductase 1 inhibitor which may be incorporated into the same pharmaceutical composition as is the antiandrogen, or which may be separately administered. Combination therapy could thus include treatment with one or more compounds which inhibit the production of dihydrotestosterone or its precursors. In some preferred embodiments of the invention, the topical pharmaceutical composition further includes an inhibitor of steroid 5α-reductase activity. One such inhibitor ("Propecia or Proscar") is commercially available form Merck Sharp and Dohme. Another inhibitor <<Dutasteride>> which inhibits both 5α-reductase co-enzymes was registered by GlaxoSmithKline. Inhibitors of type 5 17β-hydroxysteroid dehydrogenase (more particularly compound EM-1404) are disclosed in the international publication WO 99/46279. Inhibitors of type 3 17β-hydroxysteroid dehydrogenase are disclosed in the International Publication WO 03/022835 A1. EM-1791, one of inhibitors of Prostate Short-Chain Dehydrogenase Reductase 1 (PSDR1) is easily synthesized from benzopyran compounds disclosed in the U.S. Pat. No. 6,060,503 as described in the following scheme;

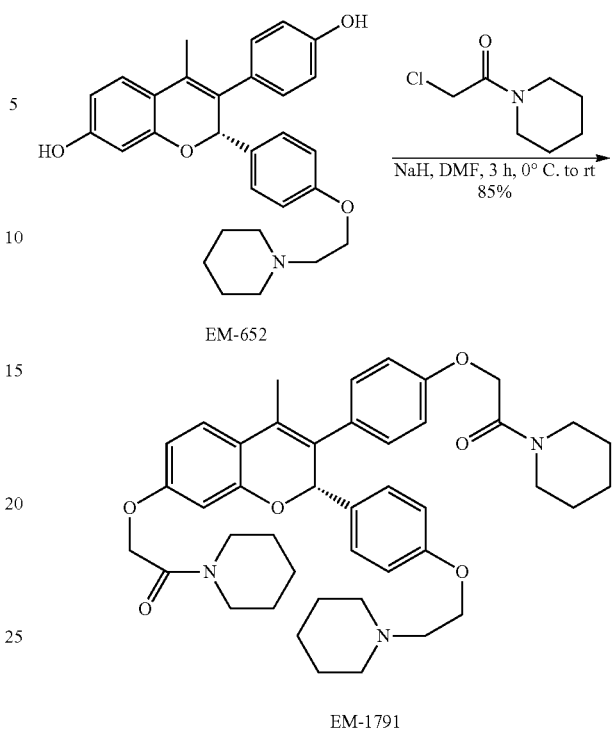

When 5alpha-reductase inhibitors are used in combination therapies, in accordance with the invention described herein, oral dosage is preferably between 0.1 mg and 100 mg per day per 50 kg body weight, more preferably between 0.5 mg/day and 10 mg/day, for example 5.0 mg per day of finasteride.

When type 5 17beta-hydroxysteroid dehydrogenase inhibitors are used in combination therapies, in accordance with the invention described herein, oral dosage is preferably between 5 mg and 500 mg per day per 50 kg body weight, more preferably between 10 mg/day and 400 mg/day, for example 300 mg per day of EM-1404.

When PSDR-1 inhibitors are used in combination therapies, in accordance with the invention described herein, oral dosage is preferably between 10 mg and 1000 mg per day per 50 kg body weight, more preferably between 25 mg/day and 1000 mg/day, for example 200 mg per day of EM-1791.

A patient in need of treatment or reducing the risk of onset of a given disease is one who has either been diagnosed with such disease or one who is susceptible to acquiring such disease. The invention is especially useful for individuals who, due to heredity, environmental factors or other recognized risk factor, are at higher risk than the general population of acquiring the conditions to which the present invention relates.

Except where otherwise stated, the preferred dosage of the active compounds of the invention is identical for both therapeutic and prophylactic purposes. The dosage for each active component discussed herein is the same regardless of the disease being treated (or prevented).

Where two are more different active agents are discussed as part of a combination therapy herein (e.g. an enzyme inhibitor and an antiandrogen), a plurality of different compounds are administered rather than a single compound having multiple activities.

Except where otherwise indicated, the term "compound" and any associated molecular structure may include any possible stereoisomers thereof, in the form of a racemic mixture or in optically active form.

Except where otherwise noted or where apparent from context, dosages herein refer to weight of active compounds unaffected by pharmaceutical excipients, diluents, carriers or other ingredients, although such additional ingredients are desirably included, as shown in the examples herein. Any dosage form (capsule, tablet, injection or the like) commonly used in the pharmaceutical industry is appropriate for use herein, and the terms "excipient", "diluent" or "carrier" include such non-active ingredients as are typically included, together with active ingredients in such dosage forms in the industry.

All of the active ingredients used in any of the combination therapies discussed herein may be formulated in pharmaceutical compositions which also include one or more of the other active ingredients. Alternatively, they may each be administered separately but sufficiently simultaneous in time so that a patient eventually has elevated blood levels or otherwise enjoys the benefits of each of the active ingredients (or strategies) simultaneously. In some preferred embodiments of the invention, for example, one or more active ingredients are to be formulated in a single pharmaceutical composition. In other embodiments of the invention, a kit is provided which includes at least two separate containers wherein the contents of at least one other container with respect to active ingredients contained therein. Two or more different containers are used in the combination therapies of the invention. Combination therapies discussed herein also include use of one active ingredient of the combination in the manufacture of a medicament for the treatment (or prevention) of the disease in question where the treatment or prevention further includes another active ingredient or strategy of the combination. For example, in prostate cancer therapy an LHRH agonist or antagonist or an inhibitor of type 3 17β-hydroxysteroid dehydrogenase can be used.

Preferred Compounds

Set forth in the tables below are lists of preferred compounds and their properties and efficacy. The tables I and II only include in vitro determination of androgenic/antiandrogenic activity on mouse mammary carcinoma Shionogi cells and determination of the binding to Human Androgen Receptors in transfected cells while tables 3 and 4 additionally include in vivo data. Detailed explanations of how the data were collected and reported follow the tables.

TABLE 1

| NAME | STRUCTURE | Shionogi Antiandrogenic activity | | Androgen Receptor |
|---|---|---|---|---|
| | | KiOH Flu/Ki compound | $IC_{50}$ (nM) | Binding (%) Human RBA R1881 = 100 |
| OH-FLU | 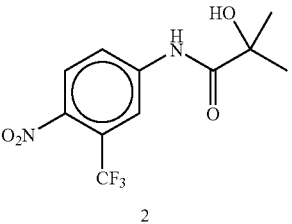 | 1 | 54.3 ± 4.8 (n = 39) | 0.29 0.1 |
| 1 | 2 | 3 | 4 | 5 |
| EM-6413 |  | 862 | 0.1 | 176 114 |

TABLE 1-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6445 | 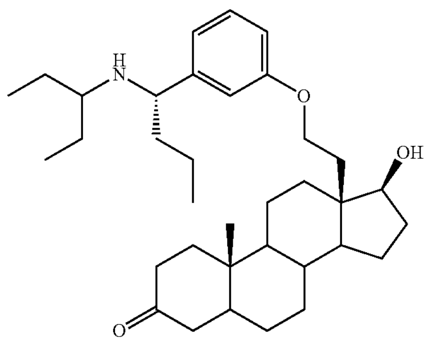 | 231 | 0.2 | 168 |
| EM-6526 | 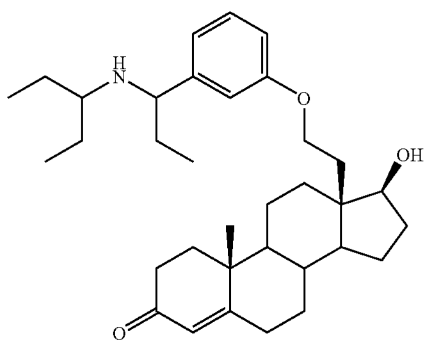 | 179<br>52 | 0.3<br>1.1 | 59 |
| EM-6537 | 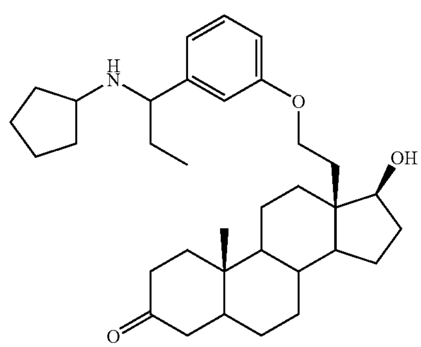 [SMILES: CCC(NC1CCCC1)c1cccc(OCC[C@]23CCC4C(CCC5CC(=O)CC[C@@]54C)C2CC[C@@H]3O)c1] | 155<br>112 | 0.4<br>0.3 | 88 |
| EM-6534 | 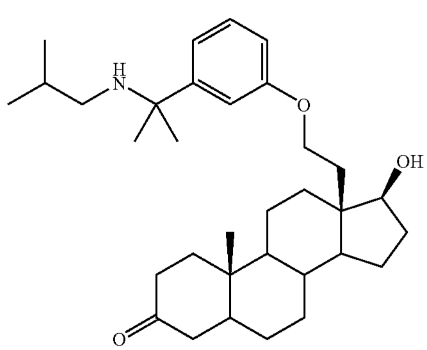 [SMILES: CC(C)CNC(C)(C)c1cccc(OCC[C@]23CCC4C(CCC5CC(=O)CC[C@@]54C)C2CC[C@@H]3O)c1] | 134<br>267 | 0.4<br>0.23 | 112 |

TABLE 1-continued
| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6536 | 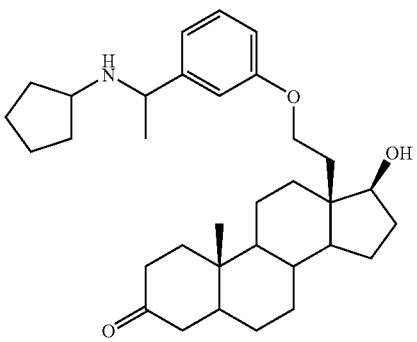 | 116<br>401 | 0.5<br>0.13 | 87 |
| EM-6415 | 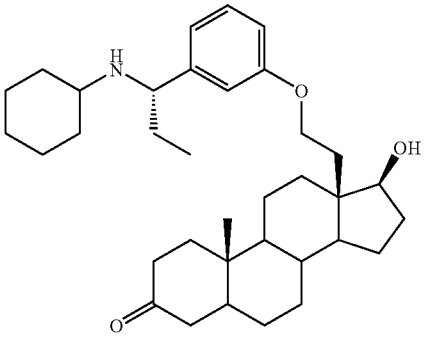 [SMILES: CC[C@H](NC1CCCCC1)c1cccc(OCC[C@]23CCC4C(CCC5CC(=O)CC[C@@]54C)C2CC[C@@H]3O)c1] | 105 | 0.47 | 230 |
| EM-6449 | 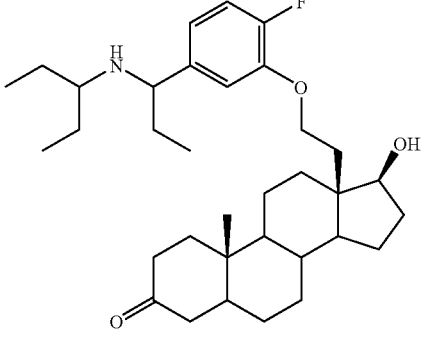 | 65 | 0.9 | 103 |
| EM-6409 | 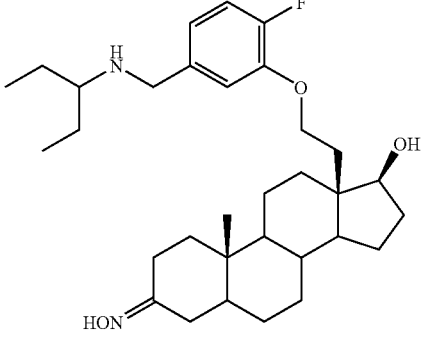 | 54 | 1.0 | 16 |

TABLE 1-continued
| NAME | STRUCTURE | Shionogi Antiandrogenic activity KiOH Flu/Ki compound | $IC_{50}$ (nM) | Androgen Receptor Binding (%) Human RBA R1881 = 100 |
|---|---|---|---|---|
| EM-6544 | 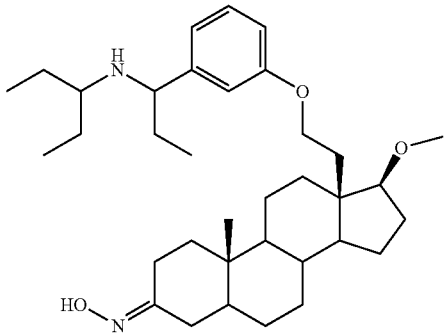 [SMILES: CCC(CC)NC(CC)c1cccc(OCC[C@]23CCC4C(CCC5C/C(=N/O)CC[C@@]54C)C2CC[C@@H]3OC)c1] | 37<br>15 | 1.5<br>2.7 | 29 |
| EM-6452 | 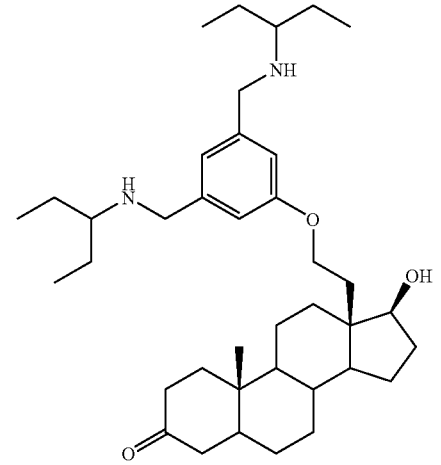 [SMILES: CCC(CC)NCc1cc(CNC(CC)CC)cc(OCC[C@]23CCC4C(CCC5CC(=O)CC[C@@]54C)C2CC[C@@H]3O)c1] | 31 | 1.8 | 104<br>104 |
| EM-6307 | 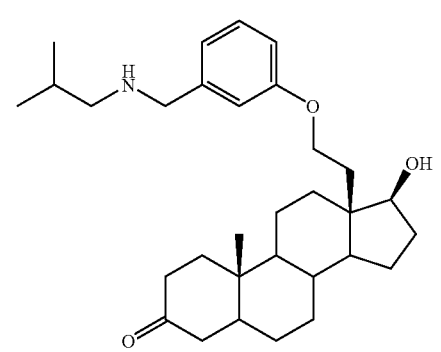 [SMILES: CC(C)CNCc1cccc(OCC[C@]23CCC4C(CCC5CC(=O)CC[C@@]54C)C2CC[C@@H]3O)c1] | 31<br>29 | 2.5<br>2.9 | 99 |
| EM-6522 | 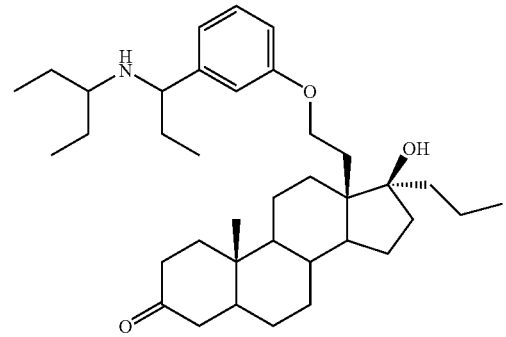 [SMILES: CCC[C@]1(O)CCC2C3CCC4CC(=O)CC[C@]4(C)C3CC[C@@]21CCOc1cccc(C(CC)NC(CC)CC)c1] | 30<br>14 | 1.9<br>3.9 | 41 |

TABLE 1-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6339 | 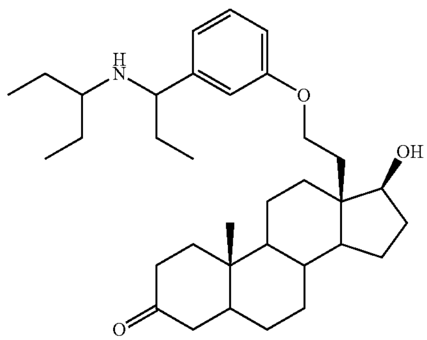 | 36 21 | 2.3 3.0 | 240 236 |
| EM-6509 | 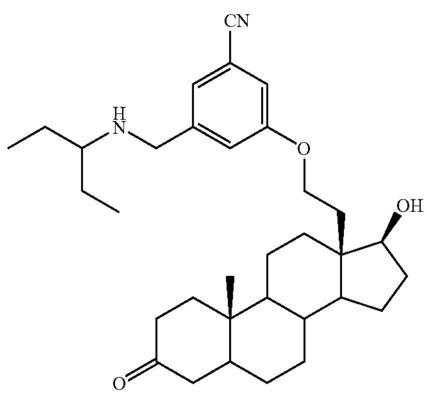 [SMILES: CCC(CC)NCc1cc(C#N)cc(OCC[C@]23CCC4C(CCC5CC(=O)CC[C@@]54C)C2CC[C@@H]3O)c1] | 28 | 1.9 | 119 |
| EM-6271 | 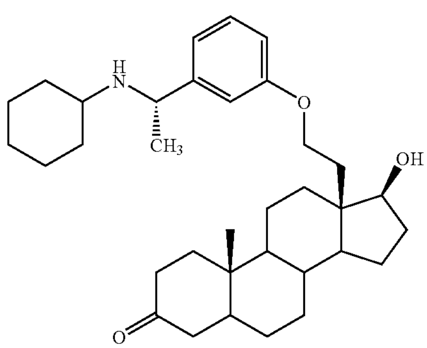 [SMILES: C[C@H](NC1CCCCC1)c1cccc(OCC[C@]23CCC4C(CCC5CC(=O)CC[C@@]54C)C2CC[C@@H]3O)c1] | 18 320 5315 | 1.4 0.2 <0.1 | 196 178 |

TABLE 2

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| OH-FLU | 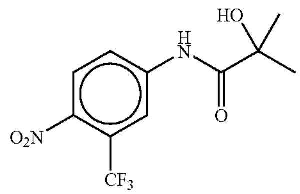 | 1 | 54.3 ± 4.8 (n = 39) | 0.29 0.1 |
| 1 | 2 | 3 | 4 | 5 |
| EM-6470 | 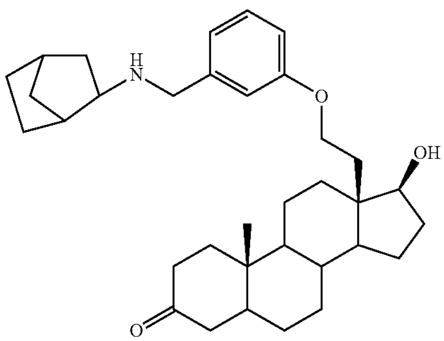 [SMILES: C[C@]12CCC(=O)CC1CCC1C2CC[C@@]2(CCOc3cccc(CNC4CC5CCC4C5)c3)C1CC[C@@H]2O] | 29 24 | 3.5 2.4 | 34 62 |
| EM-6493 | 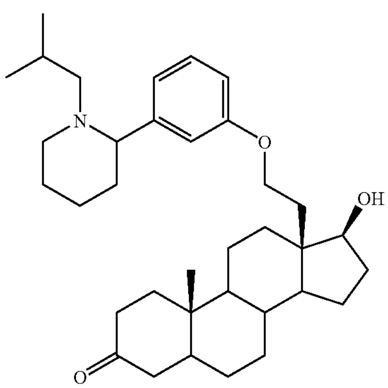 [SMILES: CC(C)CN1CCCCC1c1cccc(OCC[C@]23CCC4C(CCC5CC(=O)CC[C@@]54C)C2CC[C@@H]3O)c1] | 23 16 | 4.3 3.6 | 92 173 |
| EM-6438 | 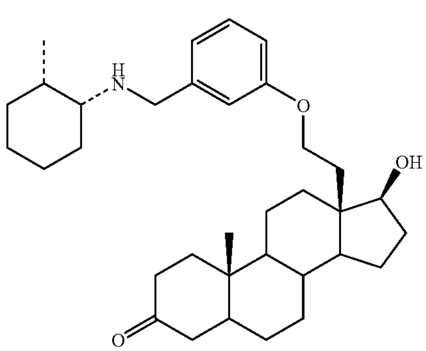 | 23 | 2.2 | 119 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6495 | 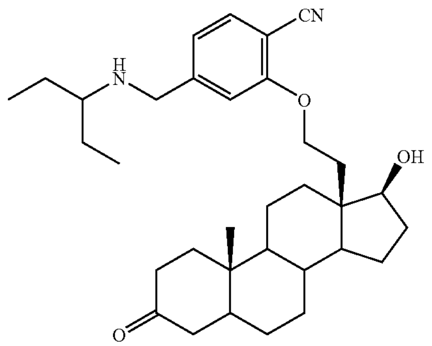 [SMILES: CCC(CC)NCc1ccc(C#N)c(OCC[C@]23CCC4C(CCC5CC(=O)CC[C@@]54C)C2CC[C@@H]3O)c1] | 21.5 22.8 | 4.7 2.5 | 83 102 |
| EM-6335 | 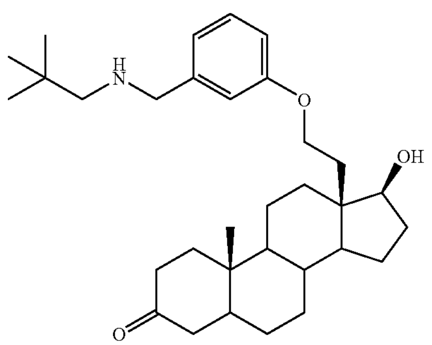 [SMILES: CC(C)(C)CNCc1cccc(OCC[C@]23CCC4C(CCC5CC(=O)CC[C@@]54C)C2CC[C@@H]3O)c1] | 4.7 21 | 17 2.9 | 106 86 |
| EM-6424 | 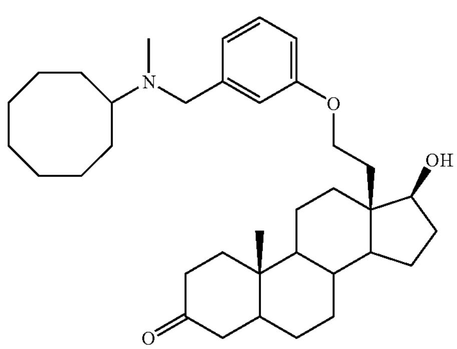 [SMILES: CN(Cc1cccc(OCC[C@]23CCC4C(CCC5CC(=O)CC[C@@]54C)C2CC[C@@H]3O)c1)C1CCCCCCC1] | 17 | 2.9 | 136 |
| EM-6557 | 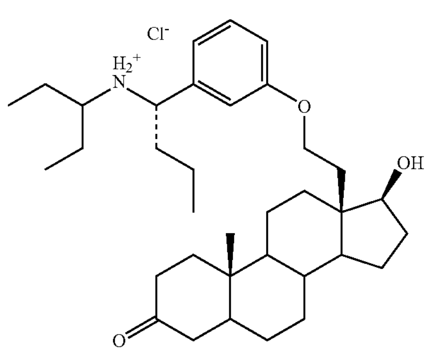 [SMILES: CCC[C@H]([NH2+]C(CC)CC)c1cccc(OCC[C@]23CCC4C(CCC5CC(=O)CC[C@@]54C)C2CC[C@@H]3O)c1 ; [Cl-]] | 18 | 0.3 | 31 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6572 | 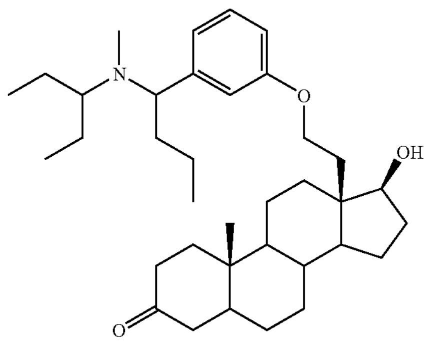 [SMILES: CCCC(c1cccc(OCC[C@]23CCC4C(CCC5CC(=O)CC[C@@]54C)C2CC[C@@H]3O)c1)N(C)C(CC)CC] | 18<br>39 | 0.3<br>1.9 | 744 |
| EM-6549 | 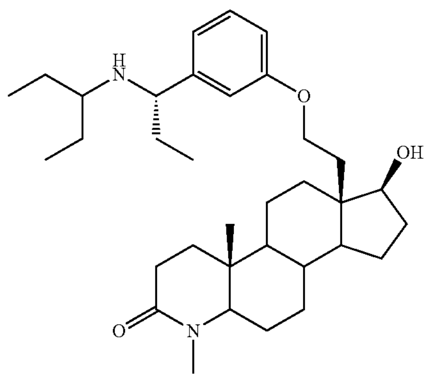 [SMILES: CCC(CC)N[C@@H](CC)c1cccc(OCC[C@]23CCC4C(CCC5N(C)C(=O)CC[C@]45C)C2CC[C@@H]3O)c1] | 16<br>9.1 | 3.5<br>6.0 | 5.8 |
| EM-6471 | 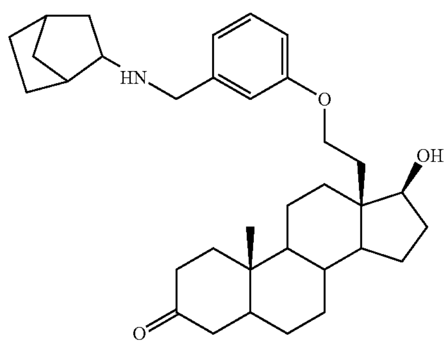 [SMILES: C[C@]12CCC(=O)CC1CCC1C2CC[C@@]2(CCOc3cccc(CNC4CC5CCC4C5)c3)C1CC[C@@H]2O] | 16<br>5.9 | 6.4<br>9.6 | 13 |
| EM-6437 | 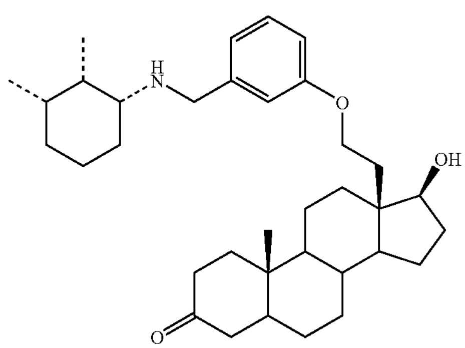 | 12.5 | 4.0 | 80 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6414 | 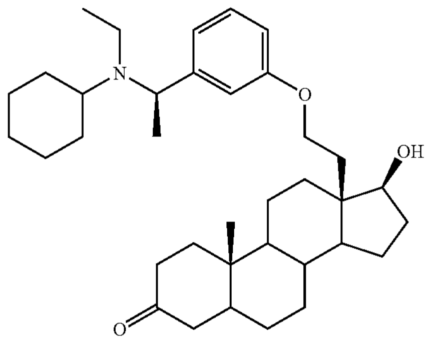 [SMILES: CCN(C1CCCCC1)[C@H](C)c1cccc(OCC[C@]23CCC4C(CCC5CC(=O)CC[C@@]54C)C2CC[C@@H]3O)c1] | 12 | 4.0 | 121 |
| EM-6453 | 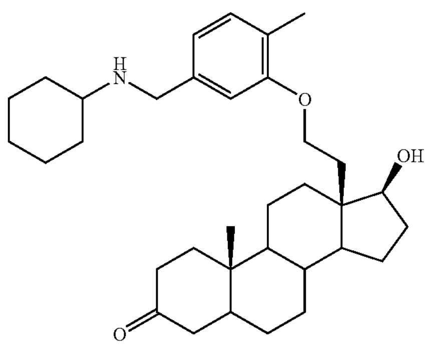 [SMILES: Cc1ccc(CNC2CCCCC2)cc1OCC[C@]12CCC3C(CCC4CC(=O)CC[C@@]43C)C1CC[C@@H]2O] | 12 | 4.7 | 33 |
| EM-6261 | 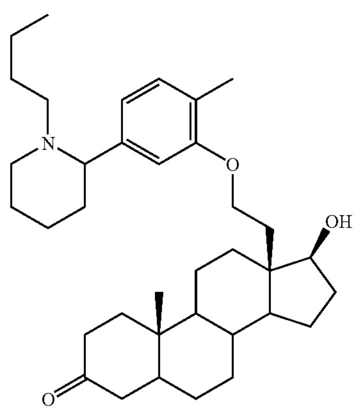 [SMILES: CCCCN1CCCCC1c1ccc(C)c(OCC[C@]23CCC4C(CCC5CC(=O)CC[C@@]54C)C2CC[C@@H]3O)c1] | 11.9 | 6.4 | 66<br>73 |
| EM-6427 | 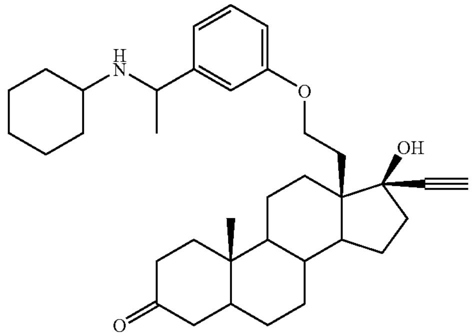 [SMILES: C#C[C@]1(O)CCC2C3CCC4CC(=O)CC[C@]4(C)C3CC[C@@]21CCOc1cccc(C(C)NC2CCCCC2)c1] | 11 | 4.5 | 40 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6492 | 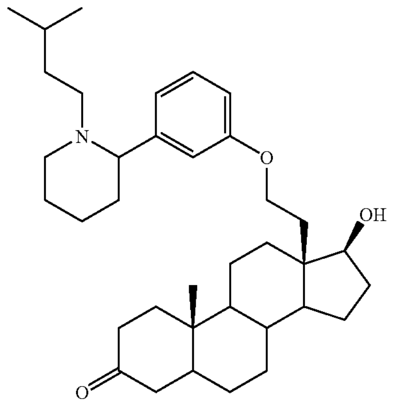 [SMILES: CC(C)CCN1CCCCC1c1cccc(OCC[C@]23CCC4C(CCC5CC(=O)CC[C@@]54C)C2CC[C@@H]3O)c1] | 10.4 8.0 | 9.6 7.1 | 68 115 |
| EM-6423 | 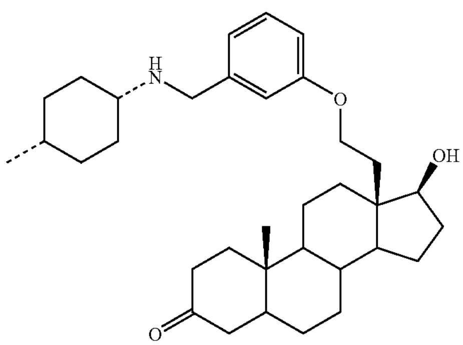 | 9.9 | 5.0 | 43 |
| EM-6555 | 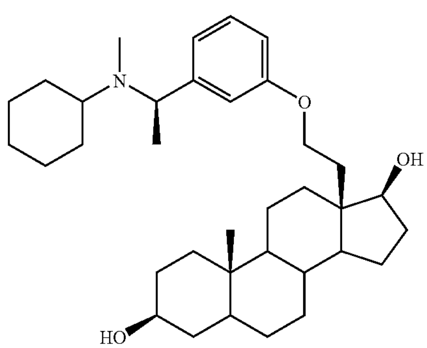 [SMILES: C[C@H](c1cccc(OCC[C@]23CCC4C(CCC5C[C@@H](O)CC[C@@]54C)C2CC[C@@H]3O)c1)N(C)C1CCCCC1] | 9.7 | 5.6 | 4.6 |
| EM-6556 | 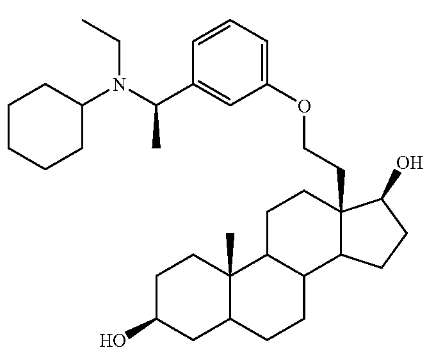 [SMILES: CCN(C1CCCCC1)[C@H](C)c1cccc(OCC[C@]23CCC4C(CCC5C[C@@H](O)CC[C@@]54C)C2CC[C@@H]3O)c1] | 9.2 | 1.7 | 6.9 |

TABLE 2-continued

| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-6494 | 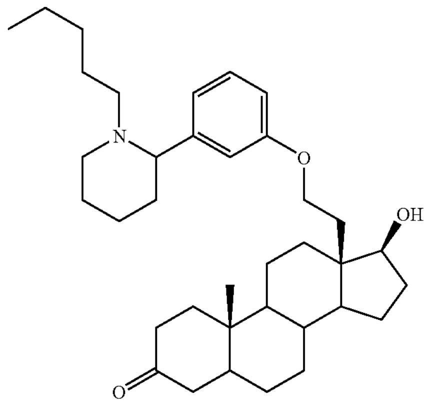 [SMILES: CCCCCN1CCCCC1c1cccc(OCC[C@]23CCC4C(CCC5CC(=O)CC[C@@]54C)C2CC[C@@H]3O)c1] | 9.5<br>5.4 | 10.5<br>10.5 | 63<br>97 |
| EM-6403 | 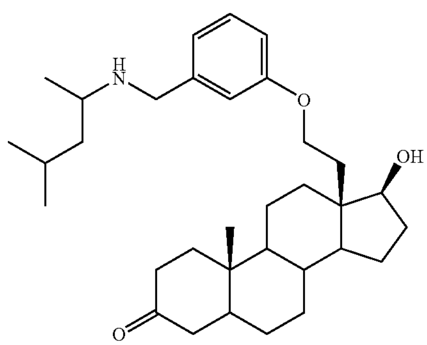 [SMILES: CC(C)CC(C)NCc1cccc(OCC[C@]23CCC4C(CCC5CC(=O)CC[C@@]54C)C2CC[C@@H]3O)c1] | 11 | 5.6 | 54 |
| EM-6567 | 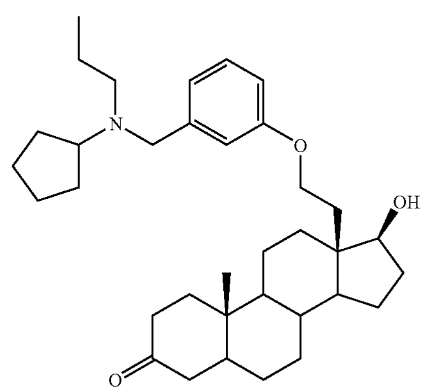 [SMILES: CCCN(Cc1cccc(OCC[C@]23CCC4C(CCC5CC(=O)CC[C@@]54C)C2CC[C@@H]3O)c1)C1CCCC1] | 11 | 5.5 | 126 |
| EM-6406 | 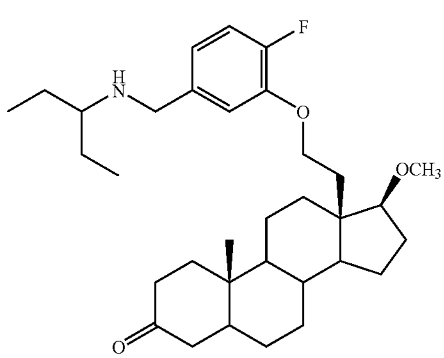 [SMILES: CCC(CC)NCc1ccc(F)c(OCC[C@]23CCC4C(CCC5CC(=O)CC[C@@]54C)C2CC[C@@H]3OC)c1] | 79 | 7.8 | 226 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6533 | 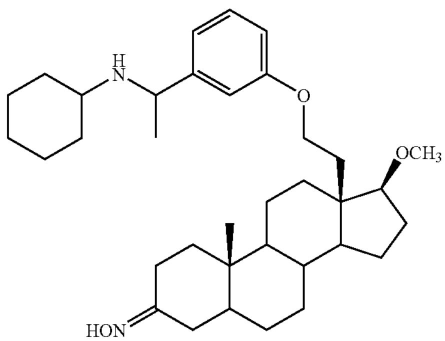 | 7.3 | 8.6 | 10 |
| EM-6531 | 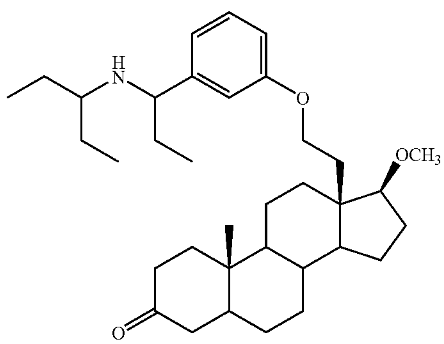 [SMILES: CCC(CC)NC(CC)c1cccc(OCC[C@]23CCC4C(CCC5CC(=O)CC[C@@]54C)C2CC[C@@H]3OC)c1] | 5.6<br>10 | 13<br>6 | 242<br>2683 |
| EM-6564 | 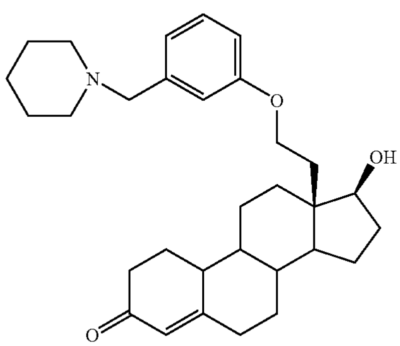 [SMILES: O=C1C=C2CCC3C(CC[C@@]4(CCOc5cccc(CN6CCCCC6)c5)C3CC[C@@H]4O)C2CC1] | 0.94 | 66 | 3.6 |
| EM-6577 | 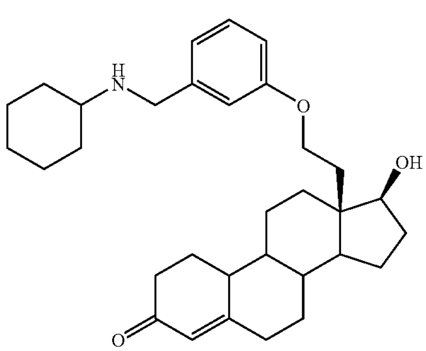 [SMILES: O=C1C=C2CCC3C(CC[C@@]4(CCOc5cccc(CNC6CCCCC6)c5)C3CC[C@@H]4O)C2CC1] | 0.9 | 57 | 3.4 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6666 | 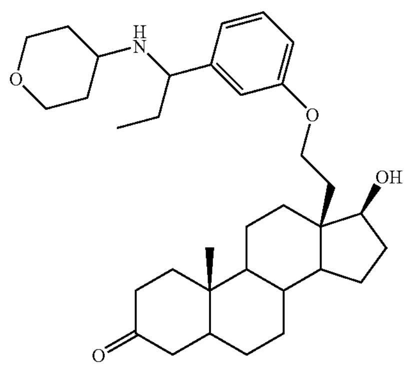 [SMILES: CCC(NC1CCOCC1)c1cccc(OCC[C@]23CCC4C(CCC5CC(=O)CC[C@@]54C)C2CC[C@@H]3O)c1] | 652 | 0.16 | 211.3 |
| EM-6700 | 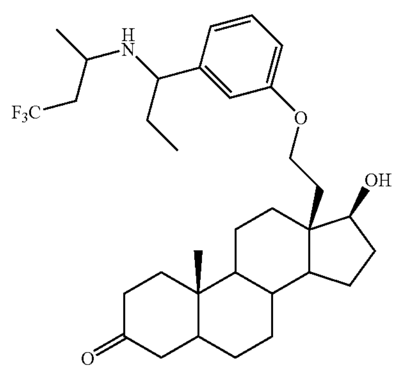 [SMILES: CCC(NC(C)CC(F)(F)F)c1cccc(OCC[C@]23CCC4C(CCC5CC(=O)CC[C@@]54C)C2CC[C@@H]3O)c1] | 1.1 | 49.9 | 670 |
| EM-6708 | 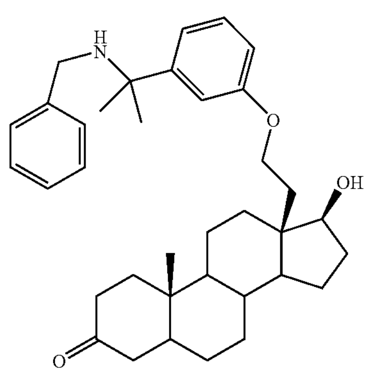 [SMILES: CC(C)(NCc1ccccc1)c1cccc(OCC[C@]23CCC4C(CCC5CC(=O)CC[C@@]54C)C2CC[C@@H]3O)c1] | 2.2 | 27.5 | 62 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6735 | 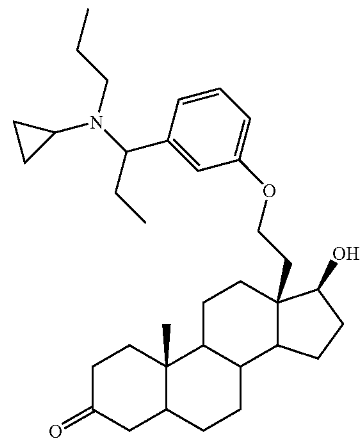 [SMILES: CCCN(C1CC1)C(CC)c1cccc(OCC[C@]23CCC4C(CCC5CC(=O)CC[C@@]54C)C2CC[C@@H]3O)c1] | 17.5 | 3.2 | 2385 |
| EM-6737 | 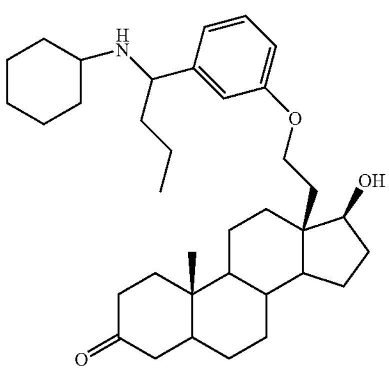 [SMILES: CCCC(NC1CCCCC1)c1cccc(OCC[C@]23CCC4C(CCC5CC(=O)CC[C@@]54C)C2CC[C@@H]3O)c1] | 48 | 1.6 | 292.5 |
| EM-6738 | 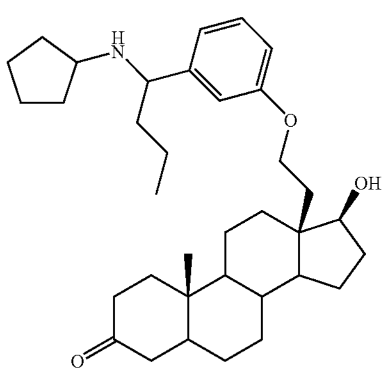 [SMILES: CCCC(NC1CCCC1)c1cccc(OCC[C@]23CCC4C(CCC5CC(=O)CC[C@@]54C)C2CC[C@@H]3O)c1] | 44 | 1.7 | 174.2 |

TABLE 2-continued

| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-6739 | 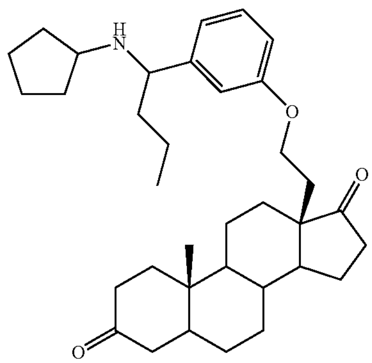 [SMILES: CCCC(NC1CCCC1)c1cccc(OCC[C@]23CCC4C(CCC5CC(=O)CC[C@@]54C)C2CCC3=O)c1] | 33 | 2.4 | 132.5 |
| EM-6740 | 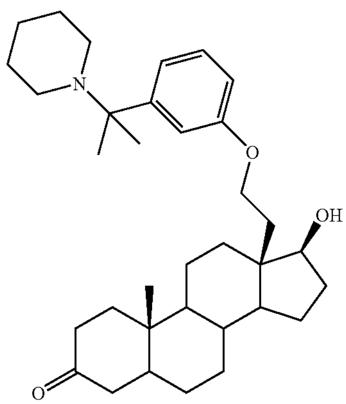 [SMILES: CC(C)(c1cccc(OCC[C@]23CCC4C(CCC5CC(=O)CC[C@@]54C)C2CC[C@@H]3O)c1)N1CCCCC1] | 5.2 | 15 | 42.5 |
| EM-6765 | 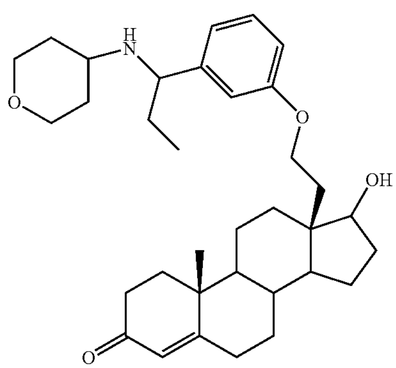 [SMILES: CCC(NC1CCOCC1)c1cccc(OCC[C@]23CCC4C(CCC5=CC(=O)CC[C@@]54C)C2CCC3O)c1] | 336 | 0.2 | 34.6 |
| EM-6766 | 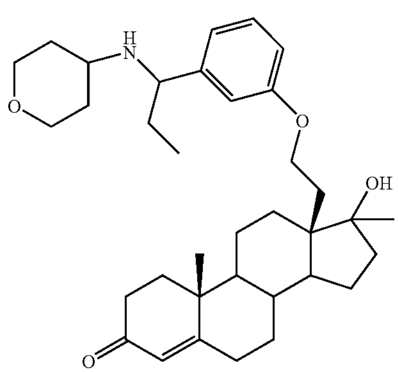 [SMILES: CCC(NC1CCOCC1)c1cccc(OCC[C@]23CCC4C(CCC5=CC(=O)CC[C@@]54C)C2CCC3(C)O)c1] | 129 | 0.5 | 55.9 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6791 | 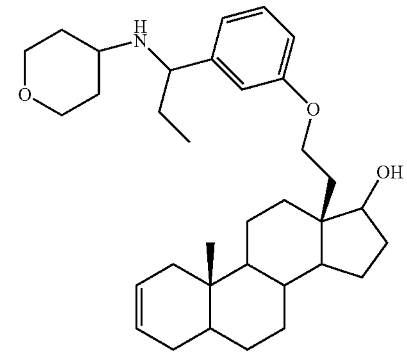 [SMILES: CCC(NC1CCOCC1)c1cccc(OCC[C@]23CCC4C(CCC5CC=CC[C@@]54C)C2CCC3O)c1] | 2.1 | 45.5 | 50.2 |
| EM-6836 | 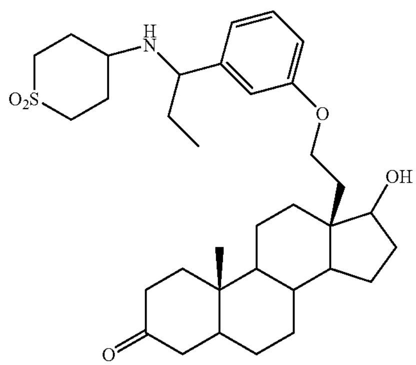 [SMILES: CCC(NC1CCS(=O)(=O)CC1)c1cccc(OCC[C@]23CCC4C(CCC5CC(=O)CC[C@@]54C)C2CCC3O)c1] | 42 | 2.4 | 62 |
| EM-6844 | 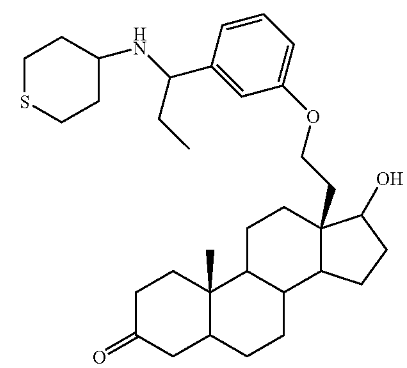 [SMILES: CCC(NC1CCSCC1)c1cccc(OCC[C@]23CCC4C(CCC5CC(=O)CC[C@@]54C)C2CCC3O)c1] | 34 | 2.1 | 506 |
| EM-6856 | 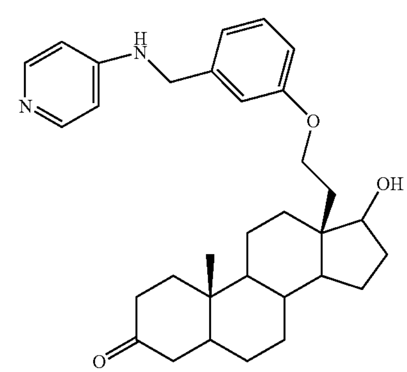 [SMILES: C[C@]12CCC(=O)CC1CCC1C2CC[C@]2(CCOc3cccc(CNc4ccncc4)c3)C(O)CCC12] | 1.9 | 32 | 6 |

TABLE 2-continued

| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-6857 | 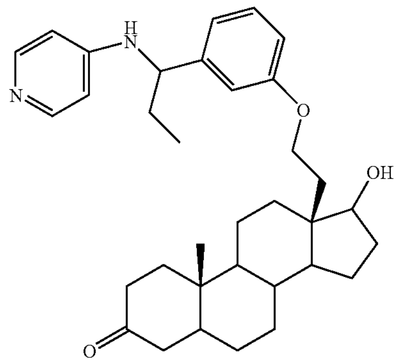 [SMILES: CCC(Nc1ccncc1)c1cccc(OCC[C@]23CCC4C(CCC5CC(=O)CC[C@@]54C)C2CCC3O)c1] | 0.87 | 63 | 5 |
| EM-6867 | 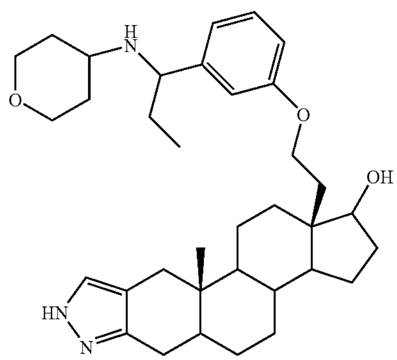 | 99 | 4.4 | 11.3 |
| EM-6876 | 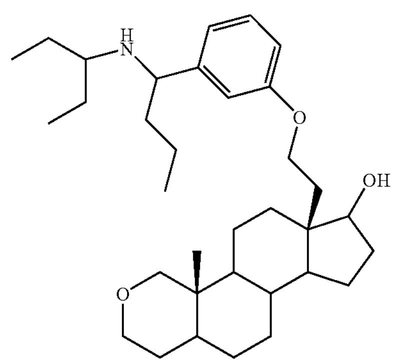 [SMILES: CCCC(NC(CC)CC)c1cccc(OCC[C@]23CCC4C(CCC5CCOC[C@@]54C)C2CCC3O)c1] | 3.1 | 16 | 44.4 |
| EM-6894 | 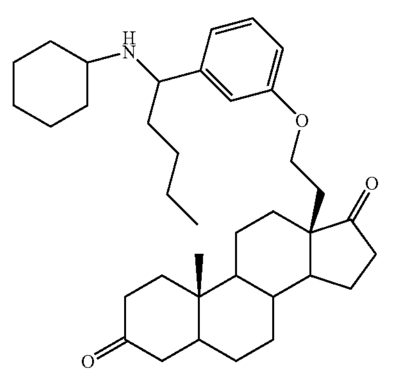 [SMILES: CCCCC(NC1CCCCC1)c1cccc(OCC[C@]23CCC4C(CCC5CC(=O)CC[C@@]54C)C2CCC3=O)c1] | 12 | 4.1 | 129.7 |

TABLE 2-continued

| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-6895 | 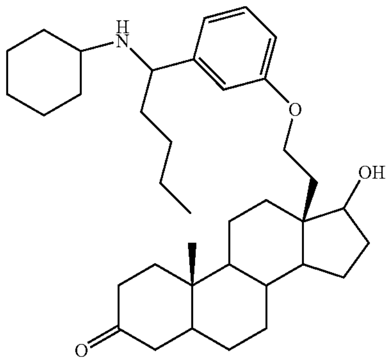 [SMILES: CCCCC(NC1CCCCC1)c1cccc(OCC[C@]23CCC4C(CCC5CC(=O)CC[C@@]54C)C2CCC3O)c1] | 11.5 | 4.2 | 115.5 |
| EM-6896 | 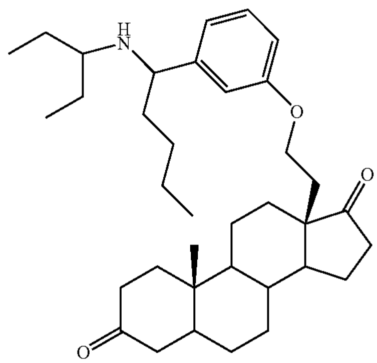 [SMILES: CCCCC(NC(CC)CC)c1cccc(OCC[C@]23CCC4C(CCC5CC(=O)CC[C@@]54C)C2CCC3=O)c1] | 15 | 3.2 | 314.6 |
| EM-6905 | 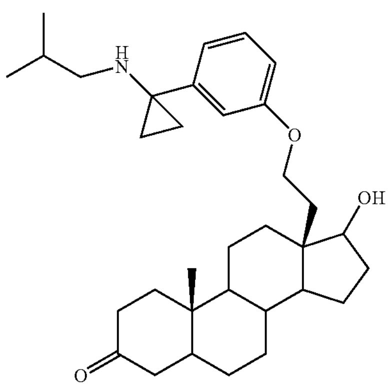 [SMILES: CC(C)CNC1(c2cccc(OCC[C@]34CCC5C(CCC6CC(=O)CC[C@@]65C)C3CCC4O)c2)CC1] | 18 | 4.4 | 274.8 |
| EM-6906 | 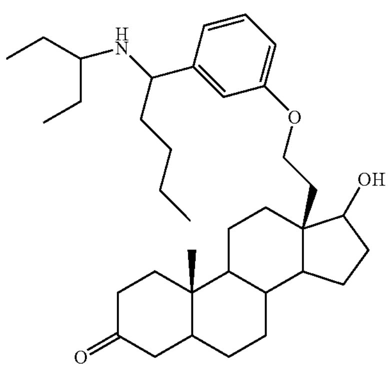 [SMILES: CCCCC(NC(CC)CC)c1cccc(OCC[C@]23CCC4C(CCC5CC(=O)CC[C@@]54C)C2CCC3O)c1] | 154 | 0.5 | 372 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-6908 | 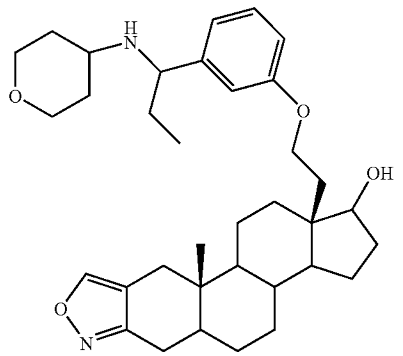 [SMILES: CCC(NC1CCOCC1)c1cccc(OCC[C@]23CCC4C(CCC5Cc6nocc6C[C@@]54C)C2CCC3O)c1] | 6.5 | 7.4 | 13 |
| EM-6972 | 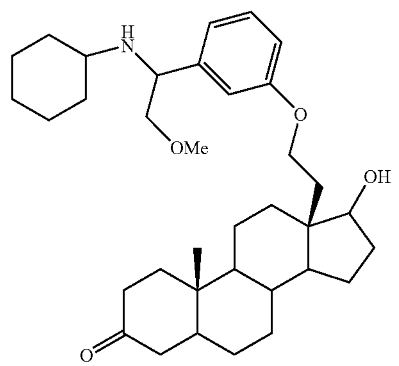 [SMILES: COCC(NC1CCCCC1)c1cccc(OCC[C@]23CCC4C(CCC5CC(=O)CC[C@@]54C)C2CCC3O)c1] | 37 | 1.2 | 151 |
| EM-6996 | 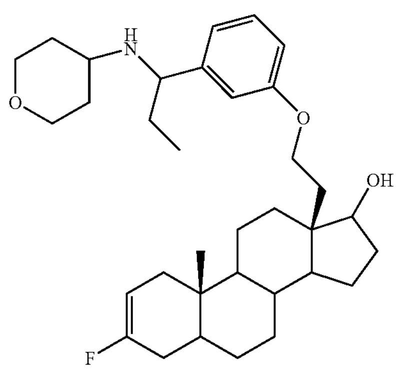 [SMILES: CCC(NC1CCOCC1)c1cccc(OCC[C@]23CCC4C(CCC5CC(F)=CC[C@@]54C)C2CCC3O)c1] | 2 | 37.3 | 32 |
| EM-7001 | 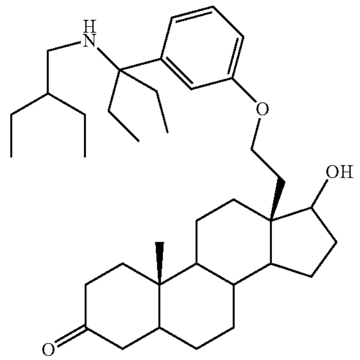 [SMILES: CCC(CC)CNC(CC)(CC)c1cccc(OCC[C@]23CCC4C(CCC5CC(=O)CC[C@@]54C)C2CCC3O)c1] | 4.7 | 17 | 1981 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-7002 | 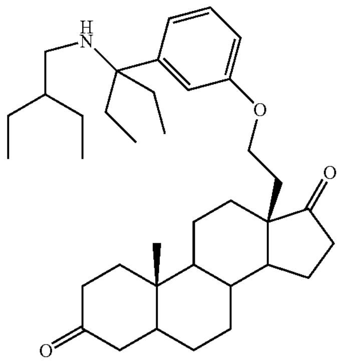 [SMILES: CCC(CC)CNC(CC)(CC)c1cccc(OCC[C@]23CCC4C(CCC5CC(=O)CC[C@@]54C)C2CCC3=O)c1] | 3.4 | 23 | 2088 |
| EM-7055 | 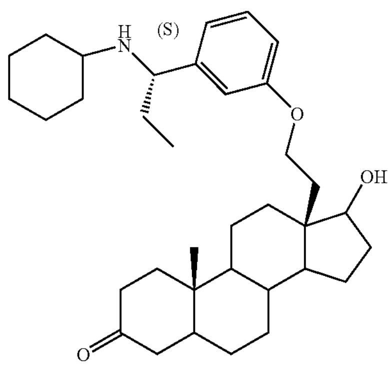 | 191 | 0.64 | 242 |
| EM-7062 | 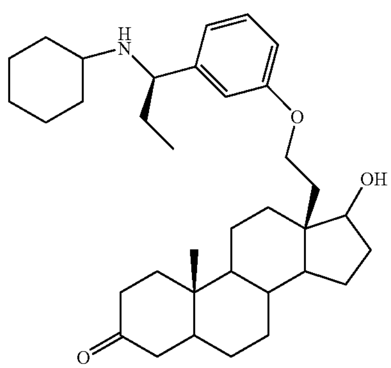 [SMILES: CC[C@@H](NC1CCCCC1)c1cccc(OCC[C@]23CCC4C(CCC5CC(=O)CC[C@@]54C)C2CCC3O)c1] | 85 | 0.7 | 535 |
| EM-7063 | 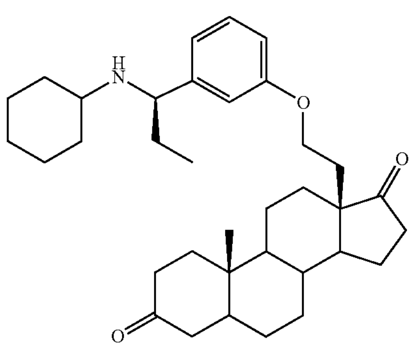 [SMILES: CC[C@@H](NC1CCCCC1)c1cccc(OCC[C@]23CCC4C(CCC5CC(=O)CC[C@@]54C)C2CCC3=O)c1] | 120 | 0.51 | 115 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-7093 | 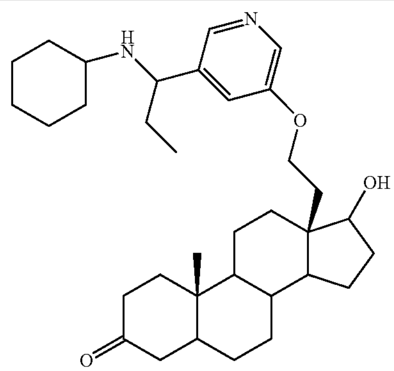 [SMILES: CCC(NC1CCCCC1)c1cncc(OCC[C@]23CCC4C(CCC5CC(=O)CC[C@@]54C)C2CCC3O)c1] | 392 | 0.16 | 361.8 |
| EM-7094 | 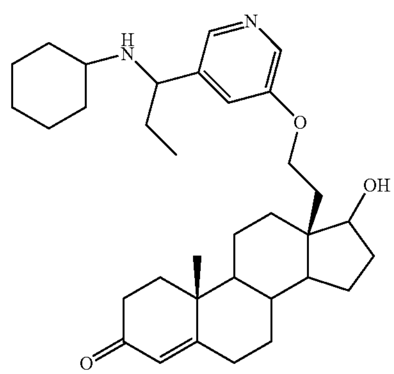 [SMILES: CCC(NC1CCCCC1)c1cncc(OCC[C@]23CCC4C(CCC5=CC(=O)CC[C@@]54C)C2CCC3O)c1] | 43.2 | 1.4 | 70.8 |
| EM-7104 | 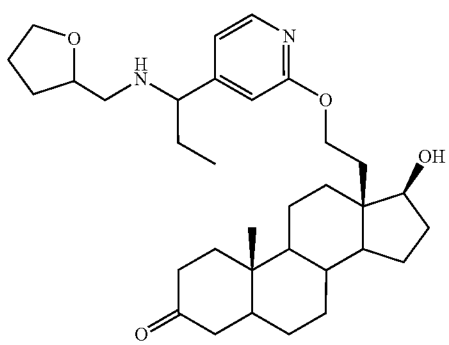 [SMILES: CCC(NCC1CCCO1)c1ccnc(OCC[C@]23CCC4C(CCC5CC(=O)CC[C@@]54C)C2CC[C@@H]3O)c1] | 22 | 2.8 | 54.3 |
| EM-7106 | 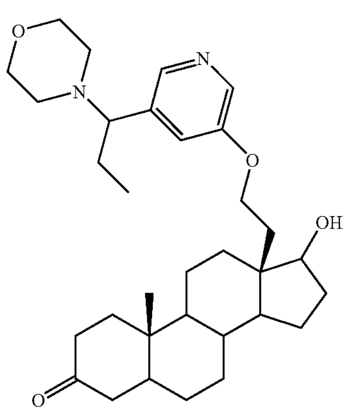 [SMILES: CCC(c1cncc(OCC[C@]23CCC4C(CCC5CC(=O)CC[C@@]54C)C2CCC3O)c1)N1CCOCC1] | 0.77 | 81 | 2.5 |

TABLE 2-continued

| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-7107 | 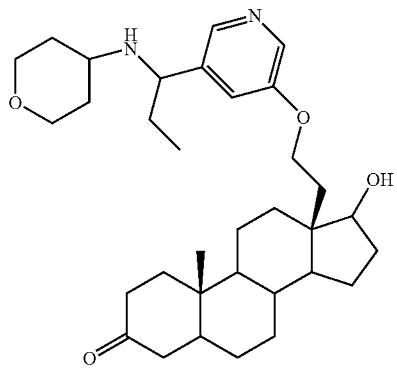 | 61 | 1 | 66.2 |
| EM-7111 | 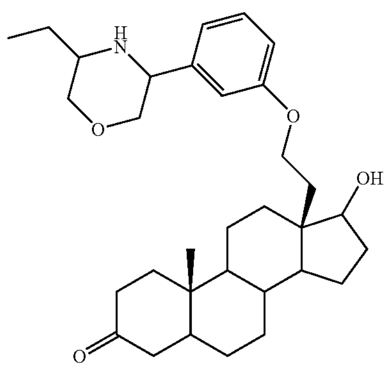 [SMILES: CCC1COCC(c2cccc(OCC[C@]34CCC5C(CCC6CC(=O)CC[C@@]65C)C3CCC4O)c2)N1] | 5 | 13 | 39 |
| EM-7131 | 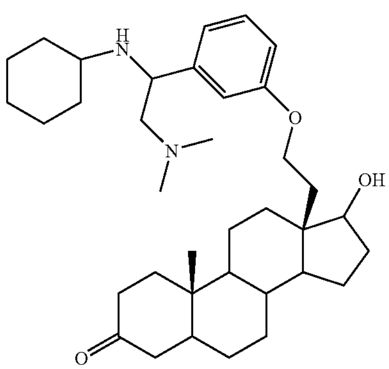 [SMILES: CN(C)CC(NC1CCCCC1)c1cccc(OCC[C@]23CCC4C(CCC5CC(=O)CC[C@@]54C)C2CCC3O)c1] | 5.1 | 35 | 125.7 |
| EM-7136 | 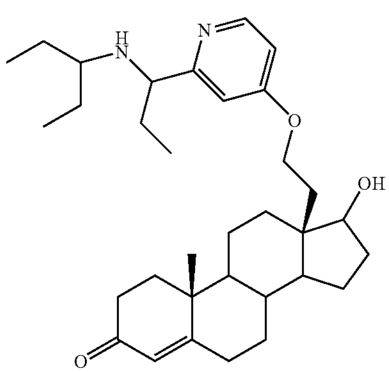 [SMILES: CCC(CC)NC(CC)c1cc(OCC[C@]23CCC4C(CCC5=CC(=O)CC[C@@]54C)C2CCC3O)ccn1] | 242 | 0.2 | 92.7 |

TABLE 2-continued
| NAME | STRUCTURE | Shionogi Antiandrogenic activity KiOH Flu/Ki compound | IC$_{50}$ (nM) | Androgen Receptor Binding (%) Human RBA R1881 = 100 |
|---|---|---|---|---|
| EM-7165 | 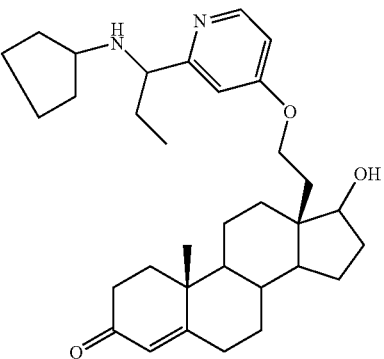 [SMILES: CCC(NC1CCCC1)c1cc(OCC[C@]23CCC4C(CCC5=CC(=O)CC[C@@]54C)C2CCC3O)ccn1] | 51 | 1.4 | 26.6 |
| EM-7166 | 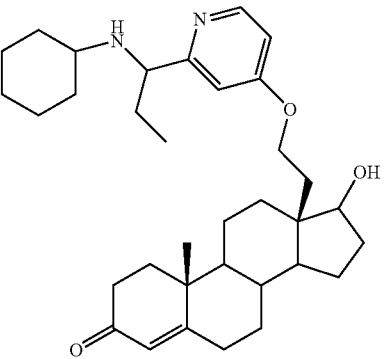 [SMILES: CCC(NC1CCCCC1)c1cc(OCC[C@]23CCC4C(CCC5=CC(=O)CC[C@@]54C)C2CCC3O)ccn1] | 16 | 3.5 | 22.3 |
| EM-7167 | 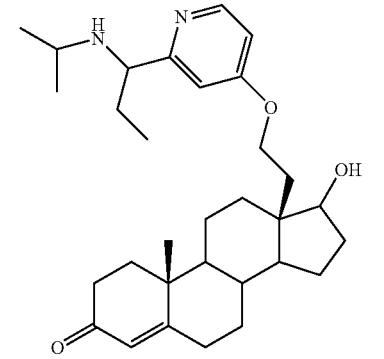 [SMILES: CCC(NC(C)C)c1cc(OCC[C@]23CCC4C(CCC5=CC(=O)CC[C@@]54C)C2CCC3O)ccn1] | NA | NA | 42 |
| EM-7170 | 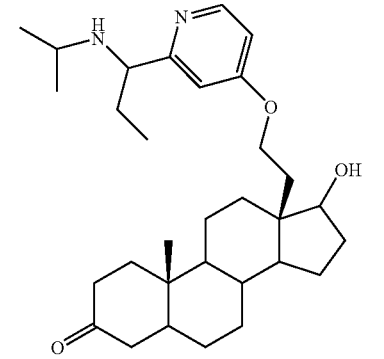 | NA | NA | 120.6 |

TABLE 2-continued

| NAME | STRUCTURE | Shionogi Antiandrogenic activity | | Androgen Receptor |
|---|---|---|---|---|
| | | KiOH Flu/Ki compound | IC$_{50}$ (nM) | Binding (%) Human RBA R1881 = 100 |
| EM-7176 | 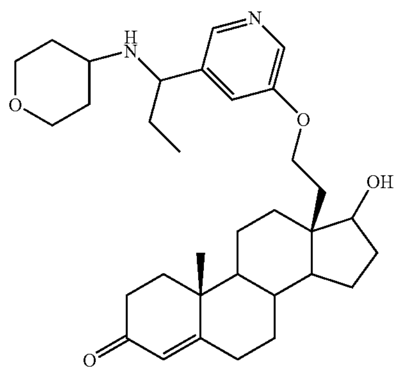 [SMILES: CCC(NC1CCOCC1)c1cncc(OCC[C@]23CCC4C(CCC5=CC(=O)CC[C@@]54C)C2CCC3O)c1] | 7.7 | 7.2 | 16 |
| EM-7184 | 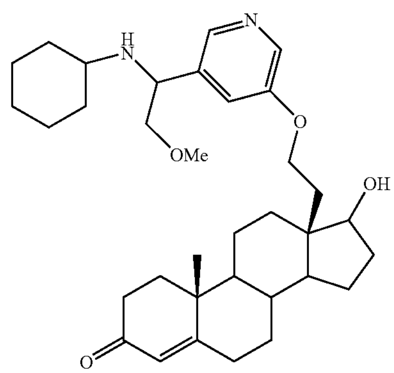 [SMILES: COCC(NC1CCCCC1)c1cncc(OCC[C@]23CCC4C(CCC5=CC(=O)CC[C@@]54C)C2CCC3O)c1] | 8.3 | 7.4 | 57 |
| EM-7221 | 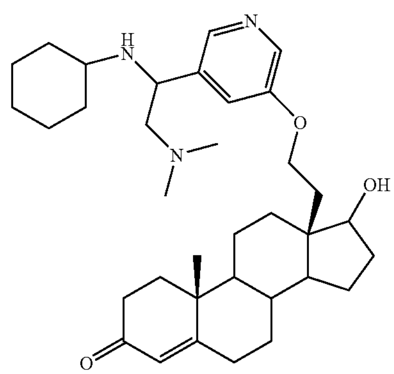 [SMILES: CN(C)CC(NC1CCCCC1)c1cncc(OCC[C@]23CCC4C(CCC5=CC(=O)CC[C@@]54C)C2CCC3O)c1] | 3.6 | 11 | 20 |
| EM-6960 | 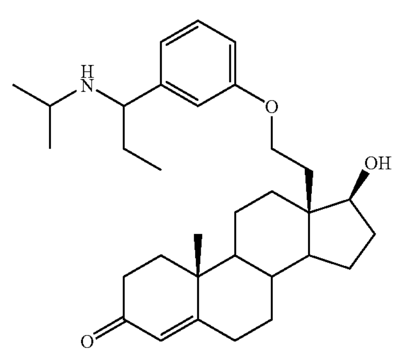 [SMILES: CCC(NC(C)C)c1cccc(OCC[C@]23CCC4C(CCC5=CC(=O)CC[C@@]54C)C2CC[C@@H]3O)c1] | 3158 | <0.1 | 147 |

Legend of the Tables 1 and 2:

In Column 1, the laboratory name of the antiandrogens is reported.

In Column 2, the molecular structure of the antiandrogens is reported.

Column 3 represents the ratio of Inhibition Constant (Ki value) of the inhibition of DHT-stimulated Shionogi mouse mammary carcinoma cell number for hydroxyflutamide versus the tested compound. Higher values are preferable.

Column 4 represents the dose (expressed in nM) that inhibits by 50% ($IC_{50}$) the DHT-stimulated Shionogi mouse mammary carcinoma cell number. Lower values are preferable.

Column 5 represents the Relative Binding Affinity (RBA) of the antiandrogen expressed as percentage (%) on Human Androgen Receptor in transfected cells relative to R1881 as calculated by the formula:

% $RBA = 100 \times IC_{50} R1881 / IC_{50}$ (compound)

Higher values are preferable.

TABLE 3

| NAME 1 | STRUCTURE 2 | IN VITRO | | IN VIVO Rat s.c. (+DHT) | |
|---|---|---|---|---|---|
| | | Shionogi Antiandrogenic activity | Androgen Receptor Binding (%) | | |
| | | KiOH Flu/Ki compound 3 | $IC_{50}$ (nM) 4 | Human RBA R1881 = 100 5 | Prostate % inhibition 6 | SV % inhibition 7 |
| EM-6928 | | 2270 | 0.04 | 146 181 | 49 0 | 0 0 |
| EM-6798 | | 769 212 | 0.1 0.3 | 118 | 20 34 17 (1 mg, po) | 29 29 19 (1 mg, po) |
| EM-7133 | | 51 | 1.1 | 55 | 32 | 40 |

TABLE 3-continued

| NAME 1 | STRUCTURE 2 | IN VITRO | | IN VIVO Rat s.c. (+DHT) | |
|---|---|---|---|---|---|
| | | Shionogi Antiandrogenic activity | Androgen Receptor Binding (%) | | |
| | | KiOH Flu/Ki compound 3 | IC$_{50}$ (nM) 4 | Human RBA R1881 = 100 5 | Prostate % inhibition 6 | SV % inhibition 7 |
| EM-7136 | | 242 | 0.2 | 93 | 27 | 35 |
| EM-6418 | | 99 | 5.0 | 31 | 16 (per os) 21 | 32 (per os) 13 |
| EM-7218 | | Na | NA | 112 | 35 | 0 |
| EM-7118 | | 8.4 | 7.2 | 176 | 31 | 0 |

TABLE 3-continued

| | | IN VITRO | | IN VIVO Rat s.c. (+DHT) | |
|---|---|---|---|---|---|
| | | Shionogi Antiandrogenic activity | Androgen Receptor Binding (%) | | |
| NAME 1 | STRUCTURE 2 | KiOH Flu/Ki compound 3 | IC$_{50}$ (nM) 4 | Human RBA R1881 = 100 5 | Prostate % inhibition 6 | SV % inhibition 7 |
| EM-7164 | | 9.3 | 6.0 | 27 | 30<br>0 | 0<br>0 |
| EM-6918 | | NA | NA | 120 | 29 | 0 |
| EM-7216 | | NA | NA | 77 | 28 | 0 |
| EM-6993 | | 4.8 | 16.4 | 35 | 25<br>0 | 0<br>0 |

TABLE 3-continued

| | | IN VITRO | | IN VIVO Rat s.c. (+DHT) | |
|---|---|---|---|---|---|
| | | Shionogi Antiandrogenic activity | Androgen Receptor Binding (%) | | |
| NAME 1 | STRUCTURE 2 | KiOH Flu/Ki compound 3 | $IC_{50}$ (nM) 4 | Human RBA R1881 = 100 5 | Prostate % inhibition 6 | SV % inhibition 7 |
| EM-6841 | | 723 | 0.1 | 139 | 21 | 5 |
| EM-6761 | | 57 | 1.2 | 141 | 33 | 0 |
| EM-6654 | | 12 | 9.5 | 25 | 0 | 72 25 |
| EM-6680 | | 49 | 1.2 | 140 | 0 0 (p.o.) | 40 21 |

TABLE 3-continued

|  |  | IN VITRO | | IN VIVO Rat s.c. (+DHT) | |
|---|---|---|---|---|---|
|  |  | Shionogi Antiandrogenic activity | Androgen Receptor Binding (%) | | |
| NAME 1 | STRUCTURE 2 | KiOH Flu/Ki compound 3 | $IC_{50}$ (nM) 4 | Human RBA R1881 = 100 5 | Prostate % inhibition 6 | SV % inhibition 7 |
| EM-6681 | | 53 | 1.1 | 56 | 15 | 19 |
| EM-6733 | | 44 | 1.3 | 62 | 34<br>23<br>34<br>(p.o.) | 15<br>0<br>6<br>(p.o.) |
| EM-6753 | | 3.0 | 19 | 8.2 | 0<br>0 | 0<br>6 |
| EM-6847 | | 1.6 | 46 | 3.2 | NA | NA |

TABLE 3-continued

| | | IN VITRO | | IN VIVO Rat s.c. (+DHT) | |
|---|---|---|---|---|---|
| | | Shionogi Antiandrogenic activity | Androgen Receptor Binding (%) | | |
| NAME 1 | STRUCTURE 2 | KiOH Flu/Ki compound 3 | IC$_{50}$ (nM) 4 | Human RBA R1881 = 100 5 | Prostate % inhibition 6 | SV % inhibition 7 |
| EM-6860 | | 11 | 5.2 | 33 | 12 | 0 |
| EM-6861 | | 1.9 | 32 | 3.0 | NA | NA |
| EM-6902 | | 1300 | 0.060 | 107 | 2 | 0 |
| EM-7075 | | 6.5 | 9.7 | 57 | 0 | 0 |

TABLE 3-continued

|  |  | IN VITRO | | IN VIVO Rat s.c. (+DHT) | |
|---|---|---|---|---|---|
|  |  | Shionogi Antiandrogenic activity | Androgen Receptor Binding (%) | | |
| NAME 1 | STRUCTURE 2 | KiOH Flu/Ki compound 3 | $IC_{50}$ (nM) 4 | Human RBA R1881 = 100 5 | Prostate % inhibition 6 | SV % inhibition 7 |
| EM-7127 | | 67 | 0.91 | 128 | 20 | 0 |
| EM-7128 | | 75 | 0.75 | 120 | 41 | 2 |
| EM-7129 | | 58 | 0.96 | 197 | 37 | 10 |
| EM-7230 | | (>10) | | 39 | 0 | 0 |

Legend of the Table 3:

In Column 1, the laboratory name of the antiandrogens is reported.

In Column 2, the molecular structure of the antiandrogens is reported.

Column 3 represents the ratio of Inhibition Constant (Ki value) of the inhibition of DHT-stimulated Shionogi mouse mammary carcinoma cell number for hydroxyflutamide versus the tested compound. Higher values are preferable.

Column 4 represents the dose (expressed in nM) that inhibits by 50% ($IC_{50}$) the DHT-stimulated Shionogi mouse mammary carcinoma cell number. Lower values are preferable.

Column 5 represents the Relative Binding Affinity (RBA) of the antiandrogen expressed as percentage (%) on Human Androgen Receptor in transfected cells relative to R1881 as calculated by the formula:

$\% RBA = 100 \times IC_{50} R1881 / IC_{50}$ (compound)

Higher values are preferable.

Column 6 represents the % of antiandrogenic efficacy in rat prostate, expressed in percentage of inhibition:
Where the percentage of inhibition (% inhib) is calculated by the following formula:

$\% Inhib = 100 - [W(\text{compound}) - W(\text{control}) / W(\text{DHT}) - W(\text{control})] \times 100.$ W is the weight of the prostate.
Higher values are preferable.

Column 7 represents the % of antiandrogenic efficacy in rat seminal vesicle, expressed in percentage of inhibition:
Where the percentage of inhibition (% inhib) is calculated by the following formula:

$\% Inhib = 100 - [W(\text{compound}) - W(\text{control}) / W(\text{DHT}) - W(\text{control})] \times 100.$ W is the weight of the seminal vesicle.
Higher values are preferable.

TABLE 4

| Name 1 | STRUCTURE 2 | Antiandrogenic activity in Hamster Ear Area | | Prostate Rat Inh % inh (0.5 mg, per os) 5 | SV RAT Inh % inh (0.5 mg, per os) 6 | Shionogi | | RBA human 9 |
|---|---|---|---|---|---|---|---|---|
| | | Dose 3 | Inh Vs Cx (%) 4 | | | $IC_{50}$ (nM) 7 | VS OH-FLU 8 | |
| EM-6680 | 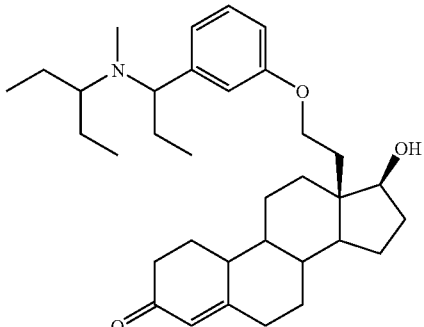 | 10 μg | 64.7 | 0 s.c. 0 | 40 s.c. 21 | 3.9 1.2 | 28 49 | 140% |
| EM-6842 | 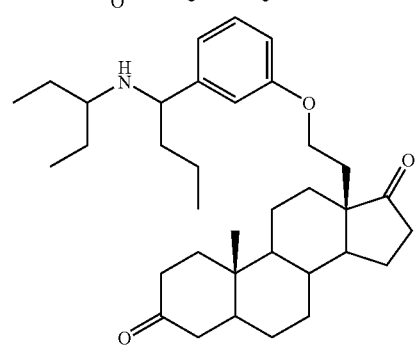 | 10 μg | 63.8 | 18 | 27 | 0.4 | 183 | 451% |
| EM-6628 | 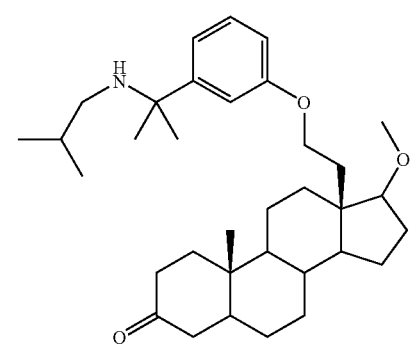 [SMILES: COC1CCC2C3CCC4CC(=O)CC[C@]4(C)C3CC[C@]12CCOc1cccc(C(C)(C)NCC(C)C)c1] | 10 μg | 58.1 | 15 | 0 | 5.9 | 14 | 796% |

TABLE 4-continued

| Name | STRUCTURE | Antiandrogenic activity in Hamster Ear Area | | Prostate Rat Inh % inh (0.5 mg, per os) | SV RAT Inh % inh (0.5 mg, per os) | Shionogi | | RBA human |
|---|---|---|---|---|---|---|---|---|
| | | Dose | Inh Vs Cx (%) | | | IC$_{50}$ (nM) | VS OH-FLU | |
| 1 | 2 | 3 | 4 | 5 | 6 | 7 | 8 | 9 |
| EM-6446 | | 10 μg<br>10 μg<br>100 μg | 56<br>53<br>79 | 11 | 3 | 1 | 51 | 715% |
| EM-6339 | | 10 μg<br>10 μg<br>100 μg | 55<br>56<br>67 | 3<br>16<br>25 | 0<br>0<br>31 | 2.3<br>3.0 | 36<br>21 | 236% |
| EM-6414 | | 10 μg<br>10 μg<br>100 μg | 55<br>37<br>64 | 6 | 28 | 4 | 1 | 71% |
| EM-6415 | | 10 μg<br>10 μg<br>100 μg | 52<br>68<br>84 | 14 | 0 | 1.4 | 29 | 185% |

TABLE 4-continued

| Name 1 | STRUCTURE 2 | Antiandrogenic activity in Hamster Ear Area | | Prostate Rat Inh % inh (0.5 mg, per os) 5 | SV RAT Inh % inh (0.5 mg, per os) 6 | Shionogi | | RBA human 9 |
|---|---|---|---|---|---|---|---|---|
| | | Dose 3 | Inh Vs Cx (%) 4 | | | IC$_{50}$ (nM) 7 | VS OH-FLU 8 | |
| EM-6445 | | 10 μg<br>10 μg<br>100 μg | 52<br>89<br>96 | 3 | 0 | 0.2 | 231 | 336% |
| EM-6741 | | 10 μg | 51.7 | NA | NA | 0.6 | 153 | 230% |
| EM-6736 | | 10 μg | 49.5 | NA | NA | 1.8 | 43 | 154% |
| EM-6640 | | 10 μg | 46.3 | 10 | 0 | 18 | 5.3 | 438% |

TABLE 4-continued

| Name 1 | STRUCTURE 2 | Antiandrogenic activity in Hamster Ear Area | | Prostate Rat Inh % inh (0.5 mg, per os) 5 | SV RAT Inh % inh (0.5 mg, per os) 6 | Shionogi | | RBA human 9 |
| --- | --- | --- | --- | --- | --- | --- | --- | --- |
| | | Dose 3 | Inh Vs Cx (%) 4 | | | $IC_{50}$ (nM) 7 | VS OH-FLU 8 | |
| EM-6493 | *(structure)* | 10 μg<br>10 μg<br>100 μg | 44<br>26<br>63 | 15 | 19 | 3.6 | 16 | 173% |
| EM-6494 | *(structure)* | 10 μg<br>10 μg<br>100 μg | 52<br>21<br>68 | 0 | 1 | 10.5 | 5.4 | 97% |
| EM-6534 | *(structure)* | 10 μg<br>10 μg<br>100 μg | 48<br>42<br>84 | 9 | 16 | 0.23 | 267 | 112% |

Legend of Table 4:

In Column 1, the laboratory name of the antiandrogens is reported.

In Column 2, the molecular structure of the antiandrogens is reported.

Column 3 represents the daily dose for 14 days of tested compound dissolved in ten μL solution of ethanol:propylene Glycol (1:1; v:v) applied onto a region between the two cartilage ridges of the ventral surface of left pinna.

Column 4 represents the percentage of inhibition of the area of the sebaceous glands of the left ear of the treated animals versus the area of the sebaceous glands of the left ear of the control animals.

Column 5 represents the % of antiandrogenic efficacy in rat prostate, expressed in percentage of inhibition:
Where the percentage of inhibition (% inhib) is calculated by the following formula:

$$\% \text{Inhib} = 100 - [W(\text{compound}) - W(\text{control})/W(\text{DHT}) - W(\text{control})] \times 100.$$

W is the weight of the prostate.

Higher values are preferable.

Column 6 represents the % of antiandrogenic efficacy in rat seminal vesicle, expressed in percentage of inhibition:
Where the percentage of inhibition (% inhib) is calculated by the following formula:

% Inhib=100−[W(compound)−W(control)/W(DHT)−W(control)]×100.

W is the weight of the seminal vesicle.
Higher values are preferable.

Column 7 represents the dose (expressed in nM) that inhibits by 50% ($IC_{50}$) the DHT-stimulated Shionogi mouse mammary carcinoma cell number. Lower values are preferable.

Column 8 represents the ratio of Inhibition Constant (Ki value) of the inhibition of DHT-stimulated Shionogi mouse mammary carcinoma cell number for hydroxyflutamide versus the tested compound. Higher values are preferable.

Column 9 represents the Relative Binding Affinity (RBA) of the antiandrogen expressed as percentage (%) on Human Androgen Receptor in transfected cells relative to R1881 as calculated by the formula:

% $RBA = 100 \times IC_{50} R1881/IC_{50}$ (compound)

Higher values are preferable.

Efficacy of the Preferred Inhibitors

A In Vitro Assays of Androgenic/Antiandrogenic Activity of Antiandrogens

Androgenic/antiandrogenic activity of preferred compounds has been measured using the Shionogi mouse mammary carcinoma cells.

1. Materials

Minimal essential culture medium (MEM), non-essential amino acids, and fetal calf serum were purchased from Flow Laboratories. In order to remove endogenous steroids, serum was incubated overnight at 4° C. with 1% activated charcoal (Norit A, Fisher) and 0.1% Dextran T-70 (Pharmacia). A 2-h supplementary adsorption was performed at 25° C. in order to further remove protein-bound steroids. Serum was also inactivated by a 20-min incubation at 56° C.

5α-dihydrotestosterone (DHT) was obtained from Steraloids. The antiandrogen hydroxyflutamide (OH-FLU) was kindly supplied by Drs. T. L. Nagabuschan and R. Neri (Schering Corporation, Kenilworth, U.S.A.).

2. Cell Dispersion, Culture and Cloning

Shionogi male mice bearing androgen-sensitive mammary tumors were obtained from Drs. Keishi Matsumoto, Osaka, Japan, and Yvonne Lefebvre, Ottawa, Canada. For primary culture, tumors were excised and washed in ice-cold sterile 25 mM Hepes buffer (137 mM NaCl; 5 mM KCl; 0.7 mM $Na_2HPO_4$; 10 mM glucose, pH 7.2). After mincing with scissors, the tumor minces were digested for 2 h at 37° C. in Hepes buffer containing 3.8 mg/ml collagenase (Clostridium, Boehringer), 1.5 mg/ml hyaluronidase II (Sigma), and 3% bovine serum albumin fraction V (Schwartz-Mann). Dispersed cells were collected by centrifugation (500×g for 10 min), washed twice by suspension in minimal essential medium (MEM) containing 5% dextran-coated charcoal-treated fetal calf serum (DCC-FCS), 1% non-essential amino acids, 10 IU/ml penicillin, 50 μg/ml streptomycin, and 100 nM dihydrotestosterone (DHT) (Steraloids).

Cells were plated in the same medium at a density of 75 000 cells/ml in 75 $cm^2$ flasks under an atmosphere of 5% carbon dioxide in air at 37° C. The medium was changed weekly. Antiandrogens were dissolved in ethanol and kept in stock solutions chosen to yield final ethanol concentrations less than 0.01% in the culture medium. Such a concentration of ethanol does not affect cell growth.

Cells were subcultured at near-confidence by gentle digestion in a solution of 0.1% pancreatin (Flow Laboratories) in Hepes buffer containing 3 mM ethylenediaminetetraacetic acid (EDTA) (pH 7.2). Cells were pelleted by centrifugation, resuspended in culture medium, counted in a Coulter counter, and replated as described above. Soft agar cloning was performed as described (Stanley et al., Cell 10: 3544, 1977) in the presence of 100 nM DHT.

3. Measurement of Cell Growth

Cells were plated in 24-well plates at a density of 20 000 cells/well. The indicated increasing concentrations of agents were added to triplicate dishes, and cells were grown for 10-12 days with changes of medium every 3-4 days. Cell number was measured by direct counting in a Coulter counter.

4. Calculations and Statistical Analysis $IC_{50}$ values of antiandrogens were calculated according to a least-square regression as described by Rodbard, Endocrinology. Statistical significance was calculated according to Kramer multiple-range test.

B Androgen Receptor (AR) Assays

1. Tissue Preparation

Preparation of Human Embryonic Kidney (HEK-293) Cells Transfected with Human Androgen Receptor (hAR): Cells were cultured in 6-well Falcon flasks to approximately $3 \times 10^5$ cells/well in Dulbecco's modified Eagle's medium (DMEM) supplemented with 10% fetal calf serum at 37° C. under a 95% air, 5% $CO_2$ humidified atmosphere. Five μg of pCMVneo-hAR plasmid were transfected using the lipofectin transfection kit (Life Technologies, Ontario, Canada). After 6 h of incubation at 37° C., the transfection medium was removed and 2 ml of DMEM were added. Cells were further cultured for 48 h and then transferred into 10 cm petri dishes and cultured in DMEM containing 700 μg/ml of G-418 in order to inhibit the growth of non-transfected cells. Medium containing G-418 was changed every two days until resistant colonies were observed. Positive clones were selected by PCR. HEK 293 cells transfected with hAR were amplified and frozen until being used for the binding assay.

HEK-293 hAR-expressing Cells Cytosol Preparation: On the morning of the binding assay, a pellet of HEK-293 hAR cells was thawed and suspended in buffer A (25 mM Tris-HCl, 1.5 mM EDTA disodium salt, 10 mM α-monothioglycerol, 10% glycerol, and 10 mM sodium molybdate, pH 7.4; 625 000 cells/0.1 ml). The cell suspension was sonicated for three periods of 30 sec (with intervals for cooling) and then centrifuged at 105 000×g for 90 min.

2. Androgen Receptor Assay

Androgen binding was measured using the hydroxylapatite (HAP) assay. In brief, the radioactive steroid [$^3$H]R1881 solubilized in ethanol was diluted into buffer B (10 mM Tris-HCl, 1.5 mM EDTA disodium salt, 10 mM ∝-monothioglycerol, pH 7.4). Aliquots of the cell cytosol preparation (0.1 ml) were then incubated with 5 nM [$^3$H]R1881 (0.1 ml, ~100 000 cpm) in the presence or absence of the indicated concentrations of unlabeled compounds (0.1 ml, prepared in buffer B containing 30% ethanol) for 16-18 h at 0-4° C. Triamcinolone acetonide (TAC; 100 nM) was added to mask progesterone receptors. Unbound steroids were separated by incubation for 40 min at 0-4° C. with 0.3 ml HAP prepared in buffer P (50 mM Tris-HCl, 10 mM $KH_2PO_4$, pH 7.4). After incubation with HAP and 10 min of centrifugation at 1000×g, the pellet was washed 3 times with 1 ml of buffer P. Thereafter, the radioactivity was extracted from the pellet by incubation at room temperature for 60 min with 1 ml of ethanol. After centrifugation, the supernatant was decanted into a scintillation vial and the pellet was extracted again with ethanol. After the addition of scintillation liquid, the radioactivity was measured in a liquid scintillation counter.

3. Calculations and Statistical Analysis $IC_{50}$ values of antiandrogens were calculated according to a least-square regression as described by Rodbard, Endocrinology. Statistical significance was calculated according to Kramer multiple-range test. Relative Binding Affinity (RBA) of the antiandrogen in percentage relatively to R1881 is calculated by the formula:

$\% RBA = 100 \times IC_{50} R1881/IC_{50}$ (compound)

C Systemic Antiandrogenic/Androgenic Activity (Immature Male Rats)

1. Animals

Immature male rats (Crl:CD(SD)Br) 22 to 24-day old were obtained from Charles-River, Inc. (St-Constant, Quebec, Canada) and housed up to 5 per cage in plastic bins in a temperature (23±1° C.)- and light (12 h light/day, lights on at 7 h15)-controlled environment. The rats were fed rodent chow and tap water ad libitum. The day following their arrival, the animals were orchidectomized (CX) under Isoflurane anesthesia via scrotal route and randomly assigned to groups of 5 animals. For antiandrogenic activity, one silastic implant of dihydrotestosterone (DHT; length of implant: 1 cm) was inserted subcutaneously in the dorsal area of animals at the time of orchidectomy. One group of 5 animals was CX only as control (no DHT implant inserted).

2. Treatments

To evaluate the antiandrogenic activity, tested compounds were administered subcutaneously once daily at a dose of 0.5 mg/animal for antiandrogenitic activity or 0.2 mg/animal for androgenic activity for 7 days (SD 1 to 7). Compounds were solubilized (when possible) in dimethylsulfoxide (DMSO, 10% final concentration) and administered as suspension in 0.4% methylcellulose. Rats in CX control and CX+DHT control groups received the vehicle alone during the 7-day period. One group of animals received the antiandrogen Flutamide as reference. The animals were killed by cervical dislocation under isoflurane anesthesia on the 8th morning following castration. The ventral prostate and seminal vesicles were rapidly dissected and weighed.

3. Calculations and Statistical Analysis

For antiandrogenic activity, the percentage of inhibition (% inhib) is calculated by the following formula:

$\% Inhib = 100 - [W(\text{compound}) - W(\text{control})/W(\text{DHT}) - W(\text{control})] \times 100.$ W is the weight of the prostate or the seminal vesicle.

D—In Vivo Assessment of Topical Antiandrogenic Activity

The antiandrogenic activity of compounds for topical use was determined using the ear sebaceous glands model in the male hamster.

1. Animals

Male Golden Syrian Hamsters (SYR) of 110-120 g were obtained from Harlan Sprague-Dawley (Madison, USA) and housed up to 2 per plastic cage in a temperature (22±3° C.) and light (12 h light/day, lights on at 7 h15)-controlled environment. The hamsters were fed with Certified Rodent Diet 5002 (pellet) and had access to tap water ad libitum. The animals were acclimatized for at least five days prior to beginning the study. Animals were randomly assigned to groups of eight hamsters. One group of hamsters were castrated under isoflurane-induced anesthesia on the day of dosing initiation (SD 1) and used as control group.

2. Treatments

To evaluate the antiandrogenic activity, the tested compounds were applied topically on the inner part of the left ear, once daily, for 14 days. A ten-μL solution of acetone:ethanol:propylene Glycol (1:1:2; v:v:v) containing 0.1, 0.3 or 1.0 mg/mL of the tested compound was carefully applied onto a region between the two cartilage ridges of the ventral surface of the left pinna. For animals of the castrated and intact control groups, one ten-μL vehicle was applied onto the left ear. No solution was applied on the right ear.

3. Post-Mortem Observations and Measurements

On Study Day 15, the hamsters were euthanized by cervical dislocation under isoflurane anesthesia. The left and right ears were collected attached together by the head skin, flat fixed on a paper and then immersed in 10% neutral buffered formalin. Punctures making a circular hole of 6 mm were made on the flat fixed ear in the region where the solution has been applied. These punch-made specimens were collected from each ear. Using a scalpel blade, the collected 6 mm round ear specimens were cut in the middle between the two cartilage ridges. The two equal parts of the ear round specimens were embedded in paraffin. After processing the tissue, the two parts were vertically embedded parallel to each other in such a way that the flat 6 mm area was facing out. From each paraffin block, one section (5 μm thick) was cut and collected on a glass slide. Thus, each slide contained two elongated sections of 6 mm length. Slides were stained with hematoxylin and eosin.

4. Analysis of Sebaceous Gland Area

Using the video camera and the lens number X5 of the light microscope, the resulting field appearing on the screen has a length of 0.953 mm. When the first 6 mm long section was examined from the left to the right, the first and second fields were ignored and the third and fourth fields were captured for analysis by the image analyzer. Each field has the length of 0.953 mm. With the help of the screen mouse, the sebaceous glands within the whole field length (0.953 mm) were marked. Also, an area having the length of the whole field and the height between stratum granulosum and the upper edge of the cartilage was drawn.

The total area of the sebaceous glands ($\mu m^2$) in each examined field was calculated by the Image Analyser. We also measured the total area, which has the length of 0.953 mm and the height between stratum granulosum and the cartilage. In addition, the percentage of the area occupied by the glands was obtained. Thus, for each ear, two sections were cut and two fields from each section were analyzed. The total of the four readings was averaged and the mean standard error of the mean was calculated by the image analyzer. The results were expressed in $\mu m^2$ as the total surface of glands per field and also as percentage of the area occupied by the glands in the tissue.

Some non-limiting examples of preferred active compounds are discussed below together with preferred synthesis techniques.

E—In Vivo Assessment of SARM Effect.

In absence of exogenous androgens (DHT 1-cm length implant), on immature rats, compound EM-7216 of the following structure:

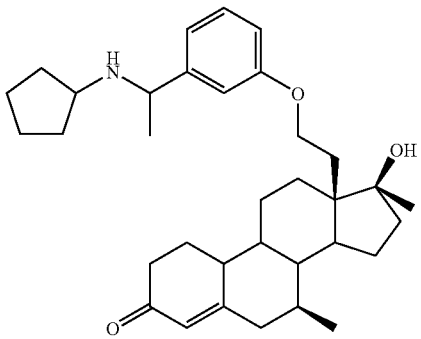 [SMILES: CC(NC1CCCC1)c1cccc(OCC[C@]23CCC4C5CCC(=O)C=C5C[C@H](C)C4C2CC[C@]3(C)O)c1]

stimulates at the dose of 0.2 mg/day s.c. the weight of ventral prostate (370%), seminal vesicle (200%) and levator ani (238) while in presence of exogenous androgens (DHT 1-cm length implant), the same compounds at the dose of 0.5 mg/day s.c. inhibits 28% of the stimulated weight of ventral prostate and has no inhibiting effect on the stimulated weight of seminal vesicle and levator ani.

EXAMPLES OF SYNTHESIS OF PREFERRED INHIBITORS

Proton NMR spectra were recorded on a Brucker AC-F 300 instrument or a Brucker Avance 400 MHz. The following abbreviations have been used: s, singlet; d, doublet; dd, doublet of doublet; t, triplet; q, quadruplet; and m, multiplet. The chemical shifts (δ) were referenced to chloroform (7.26 ppm for $^1$H and 77.00 ppm for $^{13}$C) and were expressed in ppm. Thin-layer chromatography (TLC) was performed on 0.25 mm Kieselgel 60F254 plates (E. Merck, Darmstadt, FRG). For flash chromatography, Merck-Kieselgel 60 (230-400 mesh A.S.T.M.) was used. Unless otherwise noted, starting material and reactant were obtained commercially and were used as such or purified by standard means. All solvents and reactants purified and dried were stored under argon. Anhydrous reactions were performed under an inert atmosphere, the set-up assembled and cooled under argon. Organic solutions were dried over magnesium sulfate, evaporated on a rotatory evaporator and under reduced pressure. Starting materials and reagents were available from Aldrich Chemical Company, Inc. (Milwaukee, Wis.).

List of Abbreviations

DMAP 4-dimethylaminopyridine
DMF dimethylformamide
THF Tetrahydrofuran
Tf$_2$O Triflic anhydride Example I Synthesis of 19-nortestosterone derivatives Scheme 1, 2, and 3 report the flow chart of these syntheses.

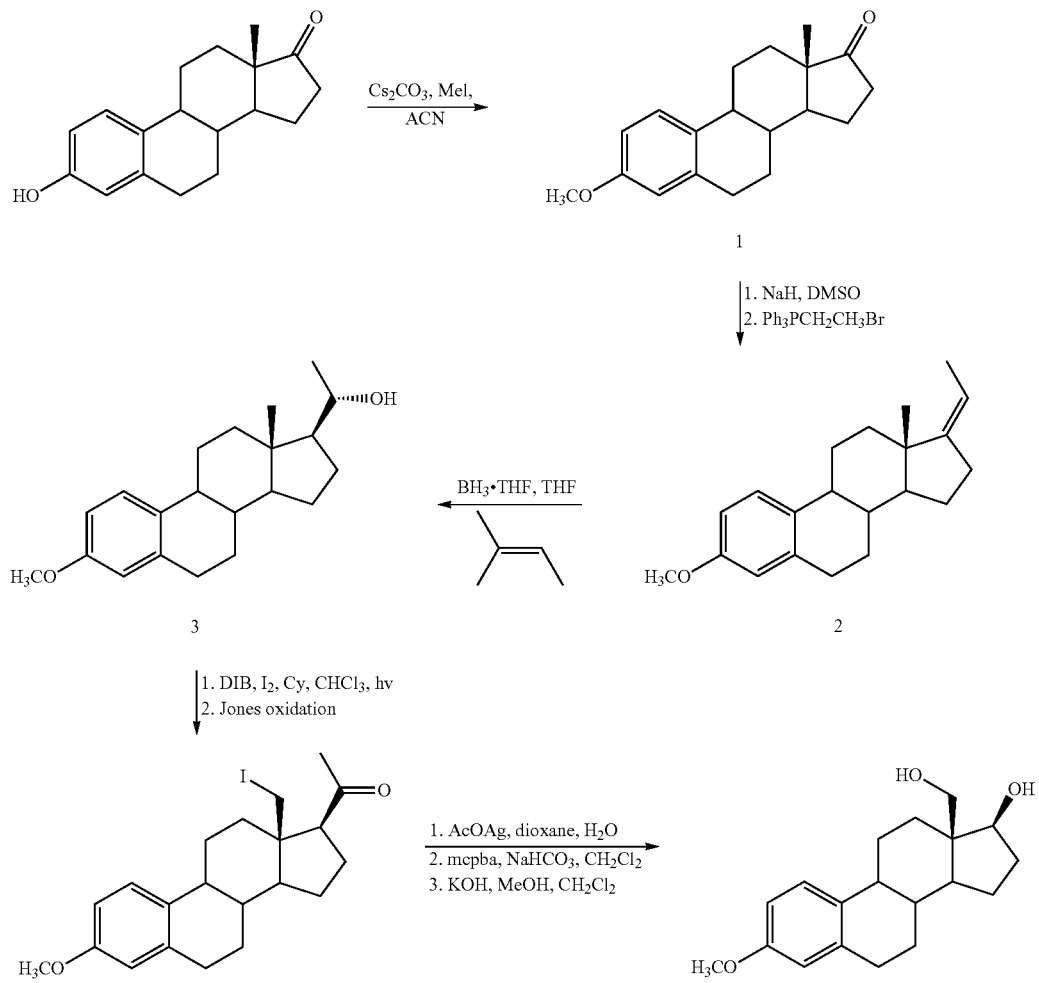

SCHEME 1

3-Methoxy-1,3,5(10)-estratrien-17-one (1)

A suspension of estrone (500 g, 1.85 mol), cesium carbonate (662.8 g, 2.034 mol), and methyl iodide (575 mL, 9.245 mol) in 4.5 L of acetonitrile was refluxed for 4 hours in a dry 12 L three-neck round-bottom flask equipped with a mechanical stirrer. The residual methyl iodide was then distilled out of the flask. The reaction mixture was cooled to room temperature, poured on 6 L of cold water, and stirred for 30 minutes. The suspension was filtered on fritted glass and washed several times with water. The wet powder was dried overnight in a vacuum oven to provide 3-methoxy-1,3,5(10)-estratriene-17-one (1) in quantitative yield (525 g). $^1$H NMR (400 MHz, CDCl$_3$) δ: 0.93 (s, 3H, C$_{18}$:—CH$_3$), 3.81 (s, 3H, CH$_3$—O—), 6.67 (d, 1H, J=2.5 Hz, C$_4$—H), 6.75 (dd, 1H, J=2.5 and 8.6 Hz, C$_2$—H), 7.23 (d, 1H, J=8.6 Hz, C$_1$—H) ppm. M.p.: 168-171° C.

3-Methoxy-cis-19-nor-1,3,5(10),17(20)-pregnatetraen (2)

In a dry 12 L three-neck round-bottom flask equipped with a mechanical stirrer, under an argon atmosphere, was placed 74.9 g (1.85 mol) of sodium hydride (60% dispersion in mineral oil) and 900 mL of dry DMSO was then added. The mixture was stirred at 75° C. for 45 minutes. The mixture was then cooled to 10° C. with a cold water bath, and a solution of 686.5 g of ethyltriphenylphosphonium bromide (1.849 mol) in 1.5 L of dry DMSO was rapidly added, followed by a solution of 3-methoxy-1,3,5(10)-estratrien-17-one (1) (262.9 g, 0.9244 mol) in 1.8 L of dry benzene. The mixture was heated to 60° C. during 16 hours and then cooled to room temperature, and poured into 2 L of cold water. The aqueous media was extracted with diethyl ether (3×1 L). The organic phases were combined, washed with water (5×1 L) and brine (1 L), and dried over magnesium sulfate. The organic phase was then concentrated in vacuo, and the obtained residue was triturated 15 minutes at room temperature in hexanes (1.5 L). The mixture was filtrated over silica gel, washed several times with hexanes, and concentrated under reduced pressure to provide 304 g of a mixture of alkenes (95:5 cis:trans ratio) in mineral oil which was used without further purification. $^1$H NMR (400 MHz, CDCl$_3$) δ: 0.94 (s, 3H, C$_{18}$:—CH$_3$), 1.73 (dt, 3H, J=1.9 and 7.2 Hz, C$_{21}$:—CH$_3$), 3.81 (s, 3H, CH$_3$—O—), 5.19 (m, 1H, C$_{20}$:—CH=), 6.67 (d, 1H, J=2.6 Hz, C$_4$—H), 6.75 (dd, 1H, J=2.6 and 8.6 Hz, C$_2$—H), 7.24 (d, 1H, J=8.6 Hz, C$_1$—H) ppm.

3-Methoxy-19-nor-1,3,5(10)-pregnatrien-20α-ol (3)

In a dry 12 L three-neck round-bottom flask equipped with a mechanical stirrer, under an argon atmosphere, was placed 1.265 L (1.265 mol) of borane tetrahydrofuran complex (1M), and the system was cooled to 0° C. A solution of 268 mL (2.53 mol) of 2-methyl-2-butene in 250 mL of dry tetrahydrofuran was added dropwise over a one hour period. Then, the mixture was stirred one hour at room temperature. A solution of 187.5 g of crude 3-methoxy-cis-19-nor-1,3,5(10),17(20)-pregnatetraen (2) in 650 mL of dry tetrahydrofuran was rapidly added to the disiamyl borane solution, and the mixture was stirred for 4 hours. The flask was then cooled to 0° C., and a mixture of 1.5 L of a 10% aqueous sodium hydroxide solution and 750 mL of hydrogen peroxide (33%) were carefully added. The mixture was stirred for 2 hours at room temperature and extracted with methylene chloride (3×700 mL). The organic phases were combined, washed with water (700 mL), brine (500 mL), then dried over magnesium sulfate, and concentrated in vacuo to provide a viscous oil. The residual 3-methyl-2-butanol was distilled off with a high vacuum pump. The crude material was triturated 3 hours in hexanes (1 L) to provide 142 g (79% yield for 2 steps) of a white powder contaminated with few impurities. $^1$H NMR (400 MHz, CDCl$_3$) δ: 0.72 (s, 3H, C$_{18}$:—CH$_3$), 1.29 (d, 3H, J=6.2 Hz, C$_{21}$:—CH$_3$), 3.77 (m, 1H, C$_{20}$:—βCH—), 3.80 (s, 3H, CH$_3$—O—), 6.65 (d, 1H, J=2.7 Hz, C$_4$—H), 6.73 (dd, 1H, J=2.7 and 8.6 Hz, C$_2$—H), 7.22 (d, 1H, J=8.6 Hz, C$_1$—H) ppm.

18-Iodo-3-methoxy-19-nor-1,3,5(10)-pregnatrien-20α-ol (4)

In a 5 L three-neck round-bottom flask equipped with a mechanical stirrer, 3-methoxy-19-nor-1,3,5(10)-pregnatrien-20α-ol (3), (114 g, 363 mmol) was dissolved in 200 mL of dry chloroform. Dry cyclohexane (2.7 L) was added, and argon was bubbled 10 minutes while stirring. Iodosobenzene diacetate (128.6 g, 399.4 mmol) was added in one portion followed by iodine (92.2 g, 363 mmol). The flask was placed in a 15-20° C. water bath, and two lamps equipped with 100 W incandescent bulb were turned on. The purple solution was stirred until almost all of the starting material was consumed (monitored by TLC, about one hour). The temperature of the solution flask should not exceed 35° C. The solution was then diluted with diethyl ether (1 L) and washed with 10% aqueous sodium thiosulfate solution (2×500 mL, or until the purple color disappeared), water (500 mL), and brine (300 mL). The organic phase was dried over magnesium sulfate and concentrated in vacuo to provide 151 g of a viscous brown oil which was used in the next step without further purification. $^1$H NMR (400 MHz, CDCl$_3$) δ:1.34 (d, 3H, J=6.2 Hz, C$_{21}$:—CH$_3$), 3.35 (s, 2H, C$_{18}$:—CH$_2$—), 3.80 (s, 3H, CH$_3$—O—), 4.27 (t, 1H, J=6 Hz, C$_{20}$:-βCH—), 6.66 (d, 1H, J=2.7 Hz, C$_4$—H), 6.74 (dd, 1H, J=2.7 and 8.6 Hz, C$_2$—H), 7.23 (d, 1H, J=8.6 Hz, C$_1$—H) ppm.

18-Iodo-3-methoxy-19-nor-1,3,5(10)-pregnatrien-20-one (5)

In a 3 L three-neck round-bottom flask equipped with a magnetic stirrer, was placed 151 g of the previous crude oil containing 18-iodo-3-methoxy-19-nor-1,3,5(10)-pregnatrien-20α-ol (4). The substrate was dissolved in methylene chloride (1 L), and the obtained solution was cooled to 0° C. in an ice bath. A Jones reagent solution (220 mL, 8N) was added portionwise while stirring. The reaction was stirred one hour at 0° C., quenched with water (2 L), and extracted with methylene chloride (3×700 mL). The organic phases were combined, washed with water (3×1 L) and brine (500 mL), dried over magnesium sulfate, and concentrated in vacuo. The crude oil was triturated in diethyl ether (250 mL) to provide 28.6 g (18% yield for 2 steps) of a yellow solid. $^1$H NMR (400 MHz, CDCl$_3$) δ: 2.35 (s, 3H, C$_{21}$:—CH$_3$), 3.22 (dd, 1H, J=0,9 and 10,8 Hz, C$_{18}$:—CH$_2$—), 3.33 (dd, 1H, J=0.9 and 10.8 Hz, C$_{18}$:—CH$_2$—), 3.80 (s, 3H, CH$_3$—O—), 6.66 (d, 1H, 2.7 Hz, C$_4$—H), 6.75 (dd, 1H, J=2.7 and 8.6 Hz, C$_2$—H), 7.23 (d, 1H, J=8.6 Hz, C$_1$—H) ppm.

18-Hydroxy-3-methoxy-19-nor-1,3,5(10)-pregnatrien-20-one (6)

In a 1 L flask equipped with a magnetic stirrer, was placed a solution of 28.6 g (65.2 mmol) of 18-iodo-3-methoxy-19-nor-1,3,5(10)-pregnatrien-20-one (5) in 350 mL of 1,4-dioxane and 35 mL of water. Silver acetate (14.2 g, 85.0 mmol)

was added and the mixture was stirred at reflux for 2 hours. The reaction mixture was then cooled to room temperature and filtered on a pad of celite. After several washes with methylene chloride, the filtrate was concentrated in vacuo to provide 24.5 g of a brownish solid which was used for the next step without purification. $^1$H NMR (400 MHz, CDCl$_3$) δ: 1.53 (s, 3H, C$_{21}$:—CH$_3$), 3.74 (s, 2H, C$_{18}$:—CH$_2$—), 3.80 (s, 3H, CH$_3$—O—), 6.65 (d, 1H, J=2.7 Hz, C$_4$—H), 6.73 (dd, 1H, J=2.7 and 8.6 Hz, C$_2$—H), 7.22 (d, 1H, J=8.6 Hz, C$_1$—H) ppm.

18-Acetoxy-3-methoxy-1,3,5(10)-estratrien-17β-ol (7)

To a solution of 24.5 g of crude 18-hydroxy-3-methoxy-19-nor-1,3,5(10)-pregnatrien-20-one (6) in 500 mL of methylene chloride, was added 18.8 g of sodium bicarbonate (224 mmol) followed by 42.9 g of 60% metachloroperbenzoic acid (149 mmol). The mixture was stirred for two hours and carefully treated with a 10% aqueous sodium bisulfite solution (150 mL). After removing the methylene chloride in vacuo, the residue was taken in water (500 mL) and extracted with ethyl acetate (3×500 mL). The organic phases were combined, washed successively with a saturated aqueous sodium carbonate solution (500 mL), water (500 mL), and brine (300 mL), dried over magnesium sulfate, and concentrated in vacuo to provide 21.5 g of crude material which contained around 10% of isomeric 17β-acetate. The crude product was chromatographied on silica gel (85/15 toluene/acetone) to provide 14.6 g of the mixture of monoacetates in the same ratio. $^1$H NMR (400 MHz, CDCl$_3$) δ: 2.11 (s, 3H, CH$_3$COO—), 3.80 (s, 3H, CH$_3$—O—), 3.90 (t, 1H, J=8.6 Hz, C$_{17}$: -αCH—), 4.25 (d, 1H, J=11.8 Hz, C$_{18}$:—CH$_2$—), 4.39 (d, 1H, J=11.8 Hz, C$_{18}$:—CH$_2$—), 6.67 (d, 1H, J=2.7 Hz, C$_4$—H), 6.74 (dd, 1H, J=2.7 and 8.6 Hz, C$_2$—H), 7.21 (d, 1H, J=8.6 Hz, C$_1$—H) ppm.

18-Hydroxy-=methoxy-1,3,5(10)-estratrien-17β-ol (8)

A solution of compound 7 (14.6 g) in methanol (125 mL) and methylene chloride (20 mL) was treated at room temperature with a 20% methanolic potassium hydroxide solution (10 mL). The solution was stirred 30 minutes and neutralized at pH 7 with 10% aqueous hydrochloric acid solution. The solvents were evaporated in vacuo, and the resulting aqueous phase was extracted with ethyl acetate (3×75 mL). The organic phases were combined, washed with water (75 mL) and brine (50 mL), dried over magnesium sulfate, and concentrated to provide 13.0 g of crude diol. The solid was triturated in diethyl ether (75 mL) to give 7.7 g of the desired diol 8 (39% yield for last three steps). $^1$H NMR (400 MHz, CDCl$_3$) δ: 3.76 (d, 1H, 11.7 Hz, C$_{18}$:—CH$_2$—), 3.80 (s, 3H, CH$_3$—O—), 3.92 (d, 1H, J=11.5 Hz, C$_{18}$:—CH$_2$—), 4.02 (t, 1H, J=8.5 Hz, C$_{17}$:-αCH—), 6.65 (d, 1H, J=2.6 Hz, C$_4$—H), 6.74 (dd, 1H, J=2.6 and 8.6 Hz, C$_2$—H), 7.23 (d, 1H, J=8.6 Hz, C$_1$—H) ppm.

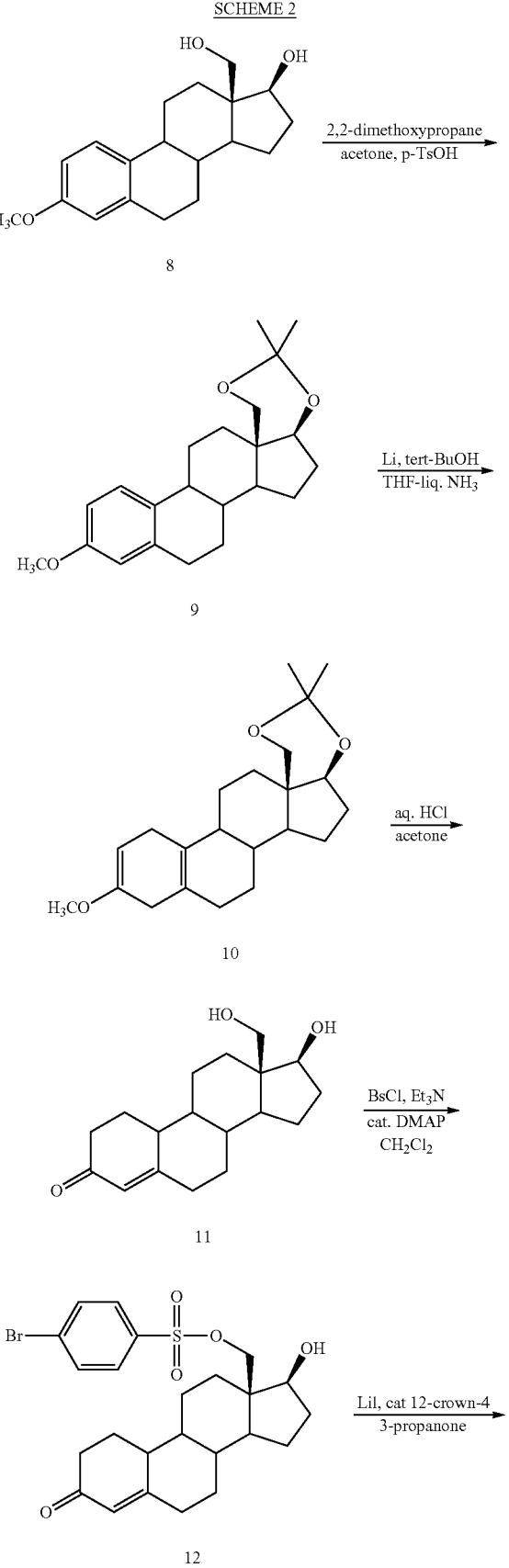

SCHEME 2

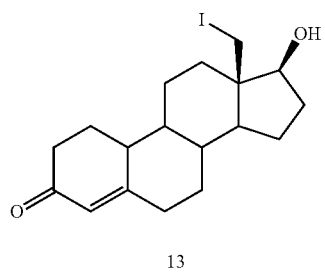

13

Preparation of Compound 9

To a stirred suspension of 8 (5.13 g, 17.0 mmol) in a 1:1 mixture of acetone and 2,2-dimethoxypropane (80 mL) was added 81 mg (0.43 mmol) of p-toluenesulfonic acid monohydrate at room temperature. Within 5 min, a clear solution resulted, and after 15-20 min, most of the solvent was evaporated on a rotary evaporator. The residue was taken up in 200 mL of ethyl acetate, washed with two portions of saturated aqueous $NaHCO_3$, and with brine. After drying over $Na_2SO_4$, the solvent was evaporated. The resulting pale oil, which weighed 5.63 g (97%), was used without further purification. $^1H$ NMR (400 MHz, $CDCl_3$) δ: 1.42 (s, 3H, acetonide $CH_3$), 1.43 (s, 3H, acetonide $CH_3$), 2.85-2.90 (m, 2H, C6-$H_2$), 3.63-3.77 (m, 2H, C18-$H_2$), 3.80 (s, 3H, $OCH_3$), 3.99-4.04 (m, 1H, C17-H), 6.66 (ca. d, 1H, J=2.6 Hz, C4-H), 6.75 (dd, 1H, J=2.8 Hz, 8.6 Hz, C2-H), 7.23 (d, 1H, J=8.6 Hz, C1-H).

Preparation of Compound 10

Approximately 120 mL of ammonia was collected in a 1 L, three-neck flask cooled to −78° C. and fitted with a dry-ice condenser. A solution of 9 (5.63 g, 16.4 mmol) in dry THF (total of 150 mL) was added to the liquid ammonia, followed by 150 mL of tert-butanol. Lithium wire (ca. 320 mmol), rinsed with hexanes, was finally added in small pieces (1-2 cm) to the reaction mixture. The cold bath was then removed, and the reduction was allowed to take place, over 2.5 h, at reflux (ca. −33° C.). After completion (as verified by TLC), the reaction was quenched by the addition of solid $NH_4Cl$ (43 g, 0.80 mol) in small portions, followed by 75 mL of water (dropwise at first). The mixture was stirred at room temperature for several hours to evaporate the ammonia, and was then diluted with 250 mL of EtOAc. After separation of the phases, the organic layer was washed with water and brine; the combined aqueous layers were extracted once with EtOAc, and this fraction was combined to the original organic phase. Drying ($Na_2SO_4$) and evaporation in vacuo gave the crude compound 10 that was used without purification.

Preparation of Compound 11

The crude enol ether 10 was dissolved in 250 mL of acetone, and 25 mL of 1N HCl was added. After stirring at room temperature for 2.5 h, the solution was basified with 75 mL of saturated aqueous $NaHCO_3$. Most of the acetone was removed on a rotary evaporator, and the residue was partitioned between EtOAc (250 mL) and water, and the organic layer was treated as described for compound 10. The crude diol 11 was obtained as an oil that eventually crystallized into a white solid. $^1H$ NMR (400 MHz, $CDCl_3$) δ: 3.72-4.02 (m, 3H, C17-H, C18-$H_2$), 5.85 (s, 1H, C4-H); $^{13}C$ NMR (100 MHz, $CDCl_3$) δ: 23.25, 25.44, 26.47, 30.59, 30.73, 30.89, 35.23, 36.41, 40.15, 42.38, 45.46, 49.15, 49.41, 60.36 (C18), 83.16 (C17), 124.53 (C4), 166.68 (C5), 200.21 (C3).

Preparation of Compound 12

To a cold (0° C.) solution of 1.74 g (6 mmol) of 11 in 100 mL of $CH_2Cl_2$ were added successively: triethylamine (1.35 mL, 9.69 mmol), 4-bromobenzenesulfonyl chloride (2.13 g, 8.34 mmol), and 4-(dimethylamino)pyridine (73 mg, 0.60 mmol). After 5 min, the cold bath was removed, and the solution was stirred at room temperature until complete reaction (ca. 2 h), as observed by TLC. The solution was then transferred quantitatively to a separatory funnel, and washed twice with water, 1N HCl, saturated aqueous $NaHCO_3$, and brine. Drying ($Na_2SO_4$) was followed by evaporation of the solvent. The product mixture was used in the next step without purification. $^1H$ NMR (400 MHz, $CDCl_3$) δ: 3.78-3.88 (m, 1H, C17-H), 4.17 (AB doublet, 1H, J=10.0 Hz, C18-$H_2$), 4.31 (AB doublet, 1H, J=10.0 Hz, C18-$H_2$), 5.85 (s, 1H, C4-H), 7.75 (AB doublet, 2H, J=8.7 Hz, Ar—H), 7.84 (AB doublet, 2H, J=8.7 Hz, Ar—H).

Preparation of Compound 13

The mixture of the crude product 12, LiI (beads, 4.00 g, 30.0 mmol), and 12-crown-4 (97 μL, 0.60 mmol) in 3-pentanone (80 mL, bp 102° C.) was heated under reflux for 3 h; complete reaction was confirmed by TLC analysis. Most of the solvent was evaporated in vacuo, and the residue was taken up in 175 mL of EtOAc; this solution was washed with an aqueous 5% solution of sodium thiosulfate (2×15 mL), saturated aqueous $NaHCO_3$, and brine and drying ($Na_2SO_4$). After flash chromatography (silica gel, 1:1 EtOAc/hexanes) of the product mixture, the resulting oil was precipitated from hexanes, and the solid triturated with 20% EtOAc in hexanes. Compound 13 was obtained as a slightly coloured solid weighing 809 mg (34% overall from 8). $^1H$ NMR (400 MHz, $CDCl_3$) δ: 3.30-3.40 (m, 2H, C18-$H_2$), 3.90-4.00 (m, 1H, C17-H), 5.86 (s, 1H, C4-H).

SCHEME 3

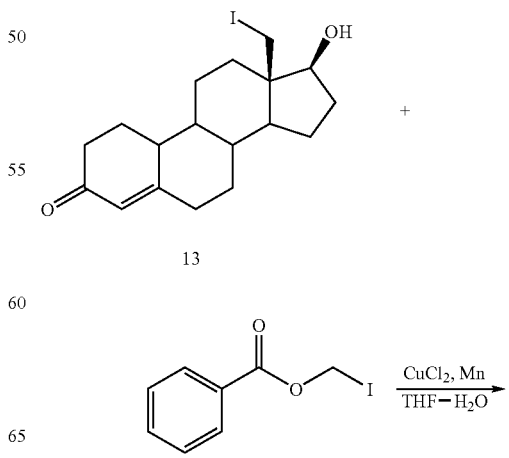

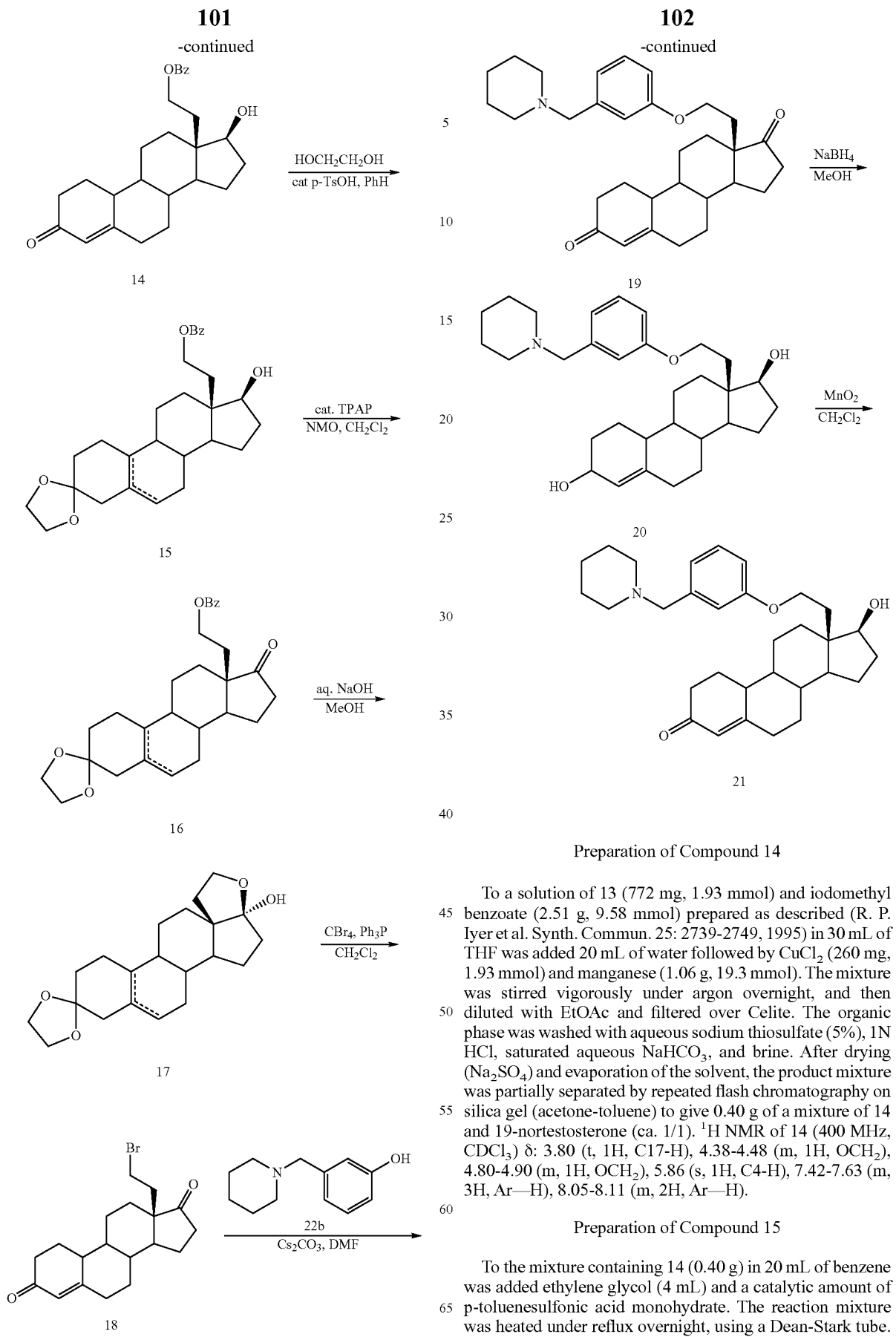

Preparation of Compound 14

To a solution of 13 (772 mg, 1.93 mmol) and iodomethyl benzoate (2.51 g, 9.58 mmol) prepared as described (R. P. Iyer et al. Synth. Commun. 25: 2739-2749, 1995) in 30 mL of THF was added 20 mL of water followed by $CuCl_2$ (260 mg, 1.93 mmol) and manganese (1.06 g, 19.3 mmol). The mixture was stirred vigorously under argon overnight, and then diluted with EtOAc and filtered over Celite. The organic phase was washed with aqueous sodium thiosulfate (5%), 1N HCl, saturated aqueous $NaHCO_3$, and brine. After drying ($Na_2SO_4$) and evaporation of the solvent, the product mixture was partially separated by repeated flash chromatography on silica gel (acetone-toluene) to give 0.40 g of a mixture of 14 and 19-nortestosterone (ca. 1/1). $^1$H NMR of 14 (400 MHz, $CDCl_3$) δ: 3.80 (t, 1H, C17-H), 4.38-4.48 (m, 1H, $OCH_2$), 4.80-4.90 (m, 1H, $OCH_2$), 5.86 (s, 1H, C4-H), 7.42-7.63 (m, 3H, Ar—H), 8.05-8.11 (m, 2H, Ar—H).

Preparation of Compound 15

To the mixture containing 14 (0.40 g) in 20 mL of benzene was added ethylene glycol (4 mL) and a catalytic amount of p-toluenesulfonic acid monohydrate. The reaction mixture was heated under reflux overnight, using a Dean-Stark tube. After evaporation of the benzene, the mixture was taken up in EtOAc and washed with saturated aqueous NaHCO$_3$, and brine. After drying (Na$_2$SO$_4$), evaporation of the solvent, and flash chromatography (silica gel, 30% EtOAc in hexanes), a mixture of 15 (two isomers: $\Delta^{5,6}$ and $\Delta^{5,10}$) and the corresponding 19-nortestosterone derivative was obtained.

Preparation of Compound 16

To 50 mg of the mixture containing 15 was reacted at room temperature with 4-methylmorpholine N-oxide (40 mg, 0.34 mmol) and tetrapropylammonium perruthenate (5 mg, 0.014 mmol) in 5 mL of CH$_2$Cl$_2$ in the presence of 4 Å molecular sieves (activated, powdered, 55 mg). After 1 h, the reaction mixture was filtered over Celite. After stripping of the solvent, flash chromatography of the residue (silica gel, 30% EtOAc in hexanes) gave 46 mg of a mixture of products 16 (two isomers) and the protected derivative of 19-nortestosterone carried out from the previous step. $^1$H NMR of 16 (400 MHz, CDCl$_3$) δ: 3.92-4.03 (m, 4H, OCH$_2$CH$_2$O), 4.16-4.26 (m, 1H, OCH$_2$), 4.38-4.48 (m, 1H, OCH$_2$), 4.51 (s, <1H, C6-H), 7.40-7.60 (m, 3H, Ar—H), 7.98-8.03 (m, 2H, Ar—H).

Preparation of Compound 17

To 15 mg of the mixture containing 16, dissolved in 2.5 mL of methanol, was treated with 2 drops of 3N NaOH. After stirring for 1 h at room temperature, 15 mL EtOAc was added, and the resulting solution was washed with brine and dried over Na$_2$SO$_4$. After purification by flash chromatography (silica gel, 30%-50% EtOAc in hexanes), 6 mg of 17 (two isomers: $\Delta^{5,6}$ and $\Delta^{5,10}$) was obtained. $^1$H NMR (400 MHz, CDCl$_3$) δ: 3.60-4.07 (m, 6H, OCH$_2$CH$_2$O, OCH$_2$), 5.50 (d, <1H, J=5.4 Hz, C6-H).

Preparation of Compound 18

To substrate 17 (6 mg, 0.017 mmol) in 2 mL of CH$_2$Cl$_2$ were added carbon tetrabromide (a total of 31 mg, 0.093 mmol in three portions over 6 h) and triphenylphosphine (a total of 28 mg, 0.11 mmol in three portions over 6 h). After about 6 h of reaction at room temperature, 10 mL of EtOAc was added, and the resulting solution was washed with water, saturated aqueous NaHCO$_3$, and brine, dried over Na$_2$SO$_4$, and evaporated. Purification by flash chromatography (silica gel, 40% EtOAc in hexanes) yielded 3 mg (ca. 50%) of 18. $^1$H NMR (400 MHz, CDCl$_3$) δ: 3.17-3.29 (m, 1H, BrCH$_2$), 3.30-3.42 (m, 1H, BrCH$_2$), 5.89 (s, 1H, C4-H).

Preparation of Compound 19

A solution of 10 mg (0.027 mmol) of 18, 10 mg (0.052 mmol) of 22b (prepared following the general method described in Example II), and 35 mg (0.11 mmol) of cesium carbonate in 1 mL of DMF was heated at 80° C. for 2 h. After addition of a mixture of 5 mL saturated aqueous NaHCO$_3$ and 5 mL brine, the product was extracted with three portions of CH$_2$Cl$_2$. Drying (Na$_2$SO$_4$) and evaporation of the solvent was followed by flash chromatography (silica gel, 1:1 acetone-toluene). 9 mg of a mixture containing product 19 was obtained and used directly in the next step. $^1$H NMR of 19 (400 MHz, acetone-d$_6$) δ: 3.40 (s, 2H, ArCH$_2$N), 3.81-3.93 (m, 1H, OCH$_2$), 3.95-4.07 (m, 1H, OCH$_2$), 5.75 (s, 1H, C4-H).

Preparation of Compound 20

To 9 mg of the mixture containing 19, in 3 mL of cold (0° C.) MeOH, was added 5 mg (0.13 mmol) of sodium borohydride. The reaction mixture was allowed to warm to room temperature over 30 min, and was then worked-up as described for the preparation of compound 19, to give 8 mg of crude 20. After combining this sample with 9 mg of another batch of impure 20, purification by reverse-phase column chromatography (LiChroprep RP-18 gel from EM Science, eluent system: acetonitrile-methanol-water) yielded 6 mg of compound 20. $^1$H NMR (400 MHz, acetone-d$_6$) δ: 3.35-3.45 (m, 2H, ArCH$_2$N), 3.72-3.80 (m, 1H, C17-H), 4.00-4.14 (m, 2H, C3-H, OCH$_2$), 4.48-4.58 (m, 1H, OCH$_2$), 5.38 (s, 1H, C4-H), 6.80-6.90 (m, 2H, Ar—H), 6.96 (s, 1H, Ar—H), 7.20 (t, 1H, J=7.8 Hz, Ar—H).

Preparation of Compound 21

Substrate 20 (6 mg, 0.013 mmol) in 2.5 mL of CH$_2$Cl$_2$ was reacted with MnO$_2$ (activated, 11 mg, 0.13 mmol) at room temperature over 16 h. At this point, $^1$H NMR analysis revealed an incomplete reaction, therefore the mixture was re-submitted to the above reaction conditions for another 25 h. After filtration over Celite, purification by flash chromatography (silica gel, 25%-50% acetone in hexanes) yielded 3.2 mg of target compound 21. $^1$H NMR (300 MHz, acetone-d$_6$) δ: 3.40 (s, 2H, ArCH$_2$N), 3.77 (t, 1H, C17-H), 3.90-4.20 (m, 2H, OCH$_2$, OH), 4.47-4.60 (m, 1H, OCH$_2$), 5.72 (s, 1H, C4-H), 6.76-6.90 (m, 2H, Ar—H), 6.95 (s, 1H, Ar—H), 7.19 (t, 1H, J=7.8 Hz, Ar—H).

Example II

General procedure for the synthesis of N-(3-hydroxybenzyl)-amine (22)

This procedure is described in Scheme 4

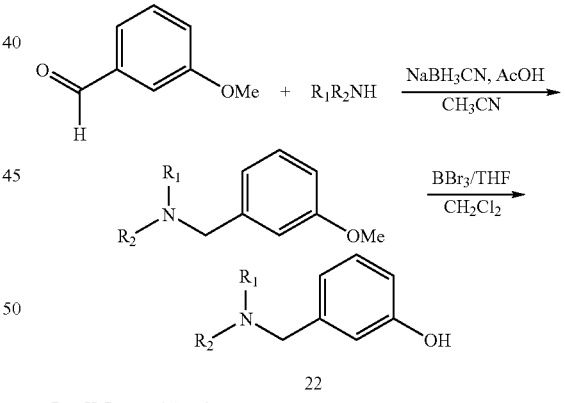

SCHEME 4 a: R$_1$ = H, R$_2$ = cyclohexyl
b: R$_1$, R$_2$ = (CH2)$_5$

N-(3-methoxybenzyl)-cyclohexylamine

A solution of m-anisaldeyde (500 mg, 3.67 mmol) and cyclohexylamine (420 µL, 3.67 mmol) in acetonitrile (30 mL) was stirred for 4 h and slowly treated with sodium cyanoborohydride (227 mg, 4.4 mmol). Glacial acetic acid was added until pH~6 (pH paper), and the solution was stirred for 16 h. Conc. HCl (0.5 mL) was added and acetonitrile was evaporated under reduced pressure. The crude residue was quenched with water (100 mL) and extracted with ethyl acetate. The aqueous phase was basified with 10% aqueous NaOH until pH>7 and extracted with dichloromethane (3×50 mL). The organic phase was dried over magnesium sulfate, filtered, and evaporated under reduced pressure without heating to provide 670 mg of N-(3-methoxybenzyl)-cyclohexylamine (83% yield) as a light oil. $^1$H NMR (300 MHz, acetone-$d_6$) δ 1.05-1.30 (m, 5H), 1.58 (m, 1H), 1.72 (m, 2H), 1.89 (m, 2H), 2.45 (m, 1H), 3.77 (s, 2H), 3.79 (s, 3H), 6.77 (dd, J=2.1 and 8.2 Hz, 1H), 6.92 (d, J=7.5 Hz, 1H), 6.96 (s, 1H), 7.21 (t, J=7.8 Hz, 1H) ppm.

N-(3-hydroxybenzyl)-cyclohexylamine (22)

Under argon atmosphere, BBr3 (9.1 mL of 1M solution in $CH_2Cl_2$ 9.1 mmol) was slowly added at 0° C. to a solution of N-(3-methoxybenzyl)-cyclohexylamine in $CH_2Cl_2$ (40 mL). After stirring 3 h at room temperature, the reaction mixture was quenched with saturated sodium bicarbonate and extracted with ethyl acetate. The organic phase was washed with brine, dried over magnesium sulfate, filtered, and evaporated to provide 314 mg of cyclohexylamine 22 (50% yield) which was used without further purification. $^1$H NMR (300 MHz, acetone-$d_6$) δ 1.12-1.31 (m, 5H), 1.59 (m, 1H), 1.73 (m, 2H), 1.92 (m, 2H), 2.53 (m, 1H), 3.77 (s, 2H), 6.70 (dd, J=1.9 and 8.9 Hz, 1H), 6.84 (d, J=7.4 Hz, 1H), 6.91 (s, 1H), 7.12 (t, J=7.8 Hz, 1H) ppm. N-(3-hydroxybenzyl)-piperidine 22b was obtained using the same procedure (25% overall yield). $^1$H NMR (300 MHz, acetone-$d_6$) δ 1.50-2.30 (m, 6H), 2.80-3.50 (m, 4H), 4.18 (s, 2H), 6.94 (m, 1H), 7.24 (m, 2H), 7.34 (s, 1H), 8.91 (br s, 1H), 11.24 (br s, 1H) ppm.

Example III

Synthesis of 19-nortestosterone derivatives

This procedure is described in Schemes 5-14

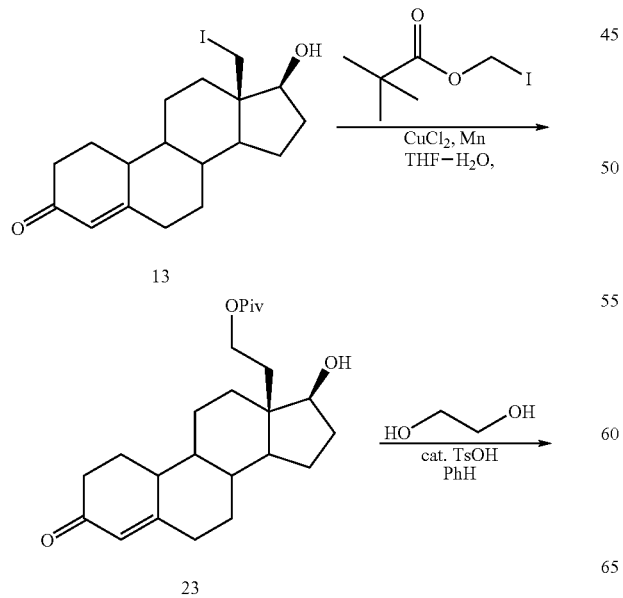

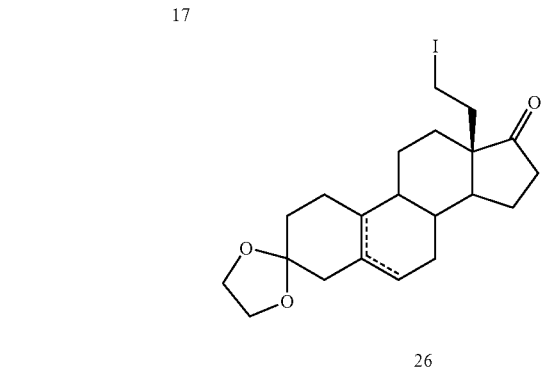

Preparation of Compound 23

Substrate 13 (1.00 g, 2.50 mmol) was dissolved in 50 mL of THF. Water (40 mL) was added, and argon was bubbled through the solution for 10-15 min (and continued throughout the reaction). With the reaction flask immersed in a water bath at room temperature, approximately 5 equivalents of iodomethyl pivalate (prepared according to: Synth. Commun. 25 (18): 2739, 1995) were added, followed by $CuCl_2$ (336 mg, 2.50 mmol) and manganese (1.37 g, 24.9 mmol). During the course of one hour, a further 2.5 equivalents (total of 4.5 g, 18.6 mmol) of iodomethyl pivaloate was added in several portions. After another 2 h, the mixture was diluted with EtOAc and filtered over Celite. The organic phase was washed with aqueous sodium thiosulfate (5%), 1N HCl, saturated aqueous NaHCO$_3$, and brine. After drying (Na$_2$SO$_4$) and evaporation of the solvent, the product mixture was separated by flash chromatography (silica gel, 20-30% EtOAc in hexanes) to give 0.44 g (ca. 45%) of 23 of acceptable purity. $^1$H NMR (400 MHz, CDCl$_3$) δ: 1.23 (s, 9H, C(CH$_3$)$_3$), 3.74 (t, 1H, J=8.5 Hz, C17-H), 4.10-4.20 (m, 1H, OCH$_2$), 4.50-4.60 (m, 1H, OCH$_2$), 5.85 (s, 1H, C4-H).

Preparation of Compound 24

In a reaction flask fitted with a Dean-Stark trap, enone 23 (0.44 g, 1.1 mmol) was reacted with ethylene glycol (4 mL), with a catalytic amount of p-toluenesulfonic acid, under reflux in benzene (20 mL). After completion of the reaction (ca. 4 h, as judged by TLC), the solvent was evaporated and the crude mixture was dissolved in EtOAc, washed twice with saturated aqueous NaHCO$_3$, and with brine, and dried (Na$_2$SO$_4$). Purification by flash chromatography (silica gel, 30-40% EtOAc in hexanes) yielded 0.46 g (94%) of 24 as well as a small amount of unreacted 23.

Preparation of Compound 25

To a solution of alcohol 24 (0.46 g, 1.1 mmol) in 20 mL of dichloromethane were added powdered molecular sieves (4 Å, 530 mg) and 4-methylmorpholine N-oxide (379 mg, 3.24 mmol). After cooling this solution to 0° C., tetrapropylammonium perruthenate (19 mg, 0.054 mmol) was added and, after 5 min, the cold bath was removed and the reaction mixture was stirred at room temperature for 1 h. The solid was removed by filtration over Celite. Purification by flash chromatography (silica gel, 20-30% EtOAc in hexanes) furnished 0.41 g (89%) of 25 as a white solid. $^1$H NMR (400 MHz, CDCl$_3$) δ: 1.18 (s, 9H, C(CH$_3$)$_3$), 5.51 (d, J=5.9 Hz, C6-H of the major $\Delta^{5,6}$ isomer).

Preparation of Compound 17

Hydrolysis of pivaloate ester 25 (0.54 g, 1.25 mmol) was carried out with 3N NaOH (3 mL) in 25 mL of methanol at room temperature over 22 h. The solvent was then partially evaporated, the crude product was diluted with EtOAc (50 mL) and washed twice with brine, and dried over Na$_2$SO$_4$. Compound 17 (white solid, 383 mg, 89%) was separated from a small amount of unreacted starting material (ca. 8% recovery) by flash chromatography (silica gel, 50% EtOAc in hexanes). $^1$H NMR (400 MHz, acetone-d$_6$) δ: 3.60-4.00 (m, 6H, OCH$_2$, OCH$_2$CH$_2$O), 5.35-5.42 (m, C6-H of the major $\Delta^{5,6}$ isomer).

Preparation of Compound 26

Lactol 17 (107 mg, 0.309 mmol) was dissolved in toluene (10 mL), and the following reagents were added in turn: imidazole (106 mg, 1.56 mmol), triphenylphosphine (244 mg, 0.930 mmol), and iodine (227 mg, 0.894 mmol). The mixture was heated at 70° C. for 25 min and, after cooling to room temperature, it was diluted with EtOAc and washed with water, aqueous sodium thiosulfate (5%), saturated aqueous NaHCO$_3$, and brine. Drying (Na$_2$SO$_4$), followed by evaporation of the solvent and purification by flash chromatography (silica gel, 10-30% EtOAc in hexanes) gave 129 mg (91%) of iodide 26. $^1$H NMR (400 MHz, acetone-d$_6$) δ: 2.90-3.02 (m, 1H, ICH$_2$), 3.17-3.29 (m, 1H, ICH$_2$), 3.80-3.98 (m, 4H, OCH$_2$CH$_2$O), 5.37-5.44 (m, C6-H of the major $\Delta^{5,6}$ isomer).

SCHEME 6

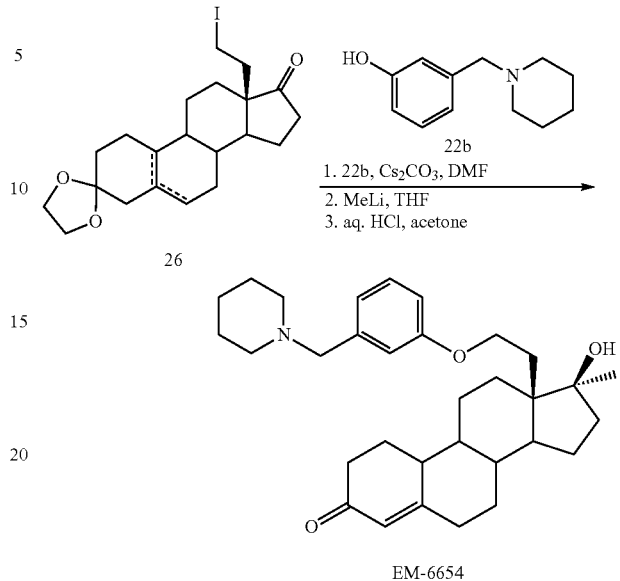

Preparation of EM-6654

A mixture of phenol 22b (62 mg, 0.324 mmol) and cesium carbonate (200 mg, 0.614 mmol) in 2.5 mL of dimethylformamide was heated at 70° C. for 15 min before the dropwise addition of iodide 26 (70 mg, 0.153 mmol) in 2.5 mL of DMF over 10 min. The mixture was stirred for an additional period of 1 h, and was then diluted with ethyl acetate, washed with water, saturated aqueous NaHCO$_3$, and brine, and dried (Na$_2$SO$_4$). Partial purification by chromatography on silica gel, using acetone-hexanes (20-35%) as eluent, furnished 72 mg of impure coupling product which was dissolved in 3 mL of THF, and subsequently treated with a total of 0.80 mL of a 1.6 M solution of methyllithium in ether at 0° C. The cold bath was removed, and after about 1 h, the reaction was quenched with saturated aqueous NaHCO$_3$. Dilution with ethyl acetate and work-up as above gave the crude 17α-methylated product which was deprotected with 1N HCl (aq., 1.5 mL) in acetone (3 mL) over 4 h at room temperature. After a standard work-up, purification by reverse-phase column chromatography (LiChroprep RP-18 gel from EM Science, eluent system: acetonitrile-methanol-water) yielded 30 mg (40% over 3 steps) of the target compound. $^1$H NMR (400 MHz, acetone-d$_6$) δ: 1.26 (s, 3H, C17-CH$_3$), 3.40 (s, 2H, NCH$_2$Ar), 4.01-4.13 (m, 1H, OCH$_2$), 4.49-4.61 (m, 1H, OCH$_2$), 5.73 (m, 1H, C4-H), 6.78-6.90 (m, 2H, Ar—H), 6.95 (s, 1H, Ar—H), 7.19 (t, 1H, J=7.8 Hz, Ar—H).

SCHEME 7

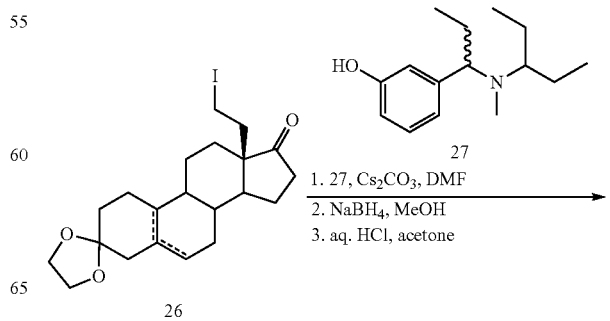

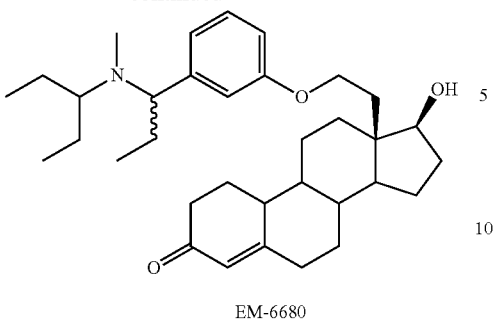

EM-6680

Preparation of EM-6680

Coupling of iodide 26 (34 mg, 0.075 mmol) and phenol 27 (29 mg, 0.15 mmol) with $Cs_2CO_3$ (100 mg, 0.31 mmol) was effected as described for EM-6654. Repeated flash chromatography on silica gel gave 27 mg of impure product. Reduction of the C17 ketone with $NaBH_4$ (15 mg, 0.40 mmol) in 3 mL of methanol, from 0° C. to room temperature over 20 min, was followed by a standard work-up (dilution with EtOAc, and aqueous washes). Deprotection of the C3 position of under acidic conditions, followed by reverse-phase column chromatography (as described for EM-6654), yielded 14.7 mg (38% over 3 steps) of the target compound. $^1$H NMR (400 MHz, acetone-$d_6$) δ: 0.65-0.73 (m, 3H, $CH_3$), 0.75-0.90 (m, 6H, 2×$CH_3$), 2.12 (two s, 3H, $NCH_3$), 3.38-3.47 (m, 1H, NCHAr), 3.73-3.85 (m, 1H, C17-H), 4.00-4.18 (m, 2H, $OCH_2$, OH), 4.50-4.62 (m, 1H, $OCH_2$), 5.73 (m, 1H, C4-H), 6.78-6.90 (m, 2H, Ar—H), 6.93-6.98 (m, 1H, Ar—H), 7.20 (t, 1H, J=7.8 Hz, Ar—H).

SCHEME 8

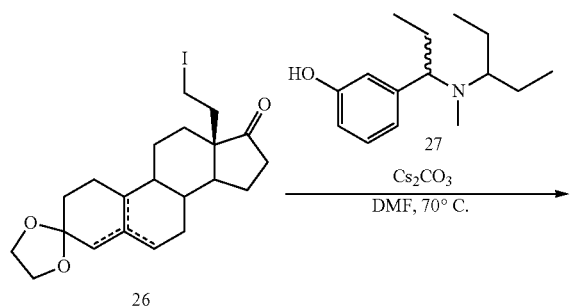

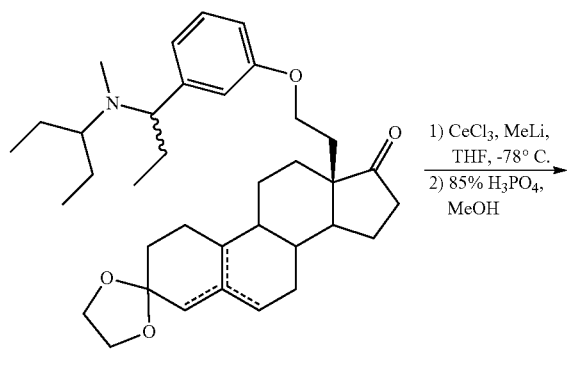

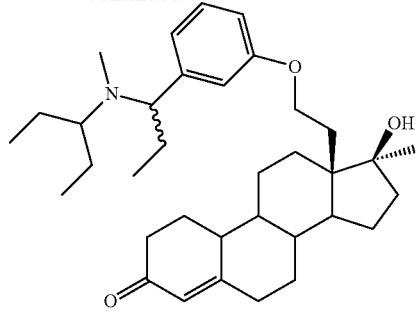

EM-6902

Preparation of 28

A mixture of phenol 27 (41 mg, 0.18 mmol) and cesium carbonate (114 mg, 0.35 mmol) in 2.5 mL of dimethylformamide was heated at 70° C. for 15 min before the dropwise addition of iodide 26 (40 mg, 0.088 mmol) in 2.5 mL of DMF over 10 min. The mixture was stirred for an additional period of 1 h 40 min, and was then diluted with ethyl acetate, washed with water (3×), saturated aqueous $NaHCO_3$, and brine, and dried ($Na_2SO_4$). Partial purification by chromatography on silica gel, using ethyl acetate-hexanes (20-50%) as eluent, furnished 22 mg of impure coupling product 28.

Preparation of EM-6902

Cerium chloride (104 mg, 0.422 mmol) was activated by stirring in THF for 20 h at room temperature. This suspension was cooled to −78° C. and methyllithium was added (1.6M/THF, 0.281 mL, 0.422 mmol). After 35 min, a solution of the steroid 28 (22 mg, 0.042 mmol) in THF (2 mL) was added dropwise. The mixture was stirred for an additional 45 min and was then quenched with a saturated aqueous $NH_4Cl$, and extracted with ethyl acetate (3×). The combined organic layer was washed with water, saturated aqueous $NaHCO_3$ and brine, and dried ($Na_2SO_4$). Partial purification by flash chromatography (silica gel, 1-10% MeOH—$CH_2Cl_2$ with 0.5% $Et_3N$) furnished 13 mg (60%) of 17α-methylated product which was deprotected with 85% $H_3PO_4$ (0.5 mL) in methanol (1 mL) over 1 h at room temperature. The reaction was neutralized with saturated aqueous $NaHCO_3$ (pH 9) and extracted with EtOAc (3×). The combined organic layer was washed with saturated aqueous $NaHCO_3$, water and brine, and dried ($Na_2SO_4$). Purification by flash chromatography (silica gel, 3-10% MeOH—$CH_2Cl_2$) furnished 8 mg (67%) of the target compound. $^1$H NMR (400 MHz, acetone-$d_6$) δ: 0.66-0.73 (m, 3H, $CH_3$), 0.79-0.90 (m, 6H, 2$CH_3$), 1.26 (s, 3H, $CH_3$), 2.12 (s, 3H, $NCH_3$), 3.38-3.47 (m, 1H, NCHAr), 3.70-3.75 (s, 1H, OH), 4.00-4.18 (m, 1H, $OCH_2$), 4.50-4.60 (m, 1H, $OCH_2$), 5.73 (m, 1H, 4-CH), 6.78-6.90 (m, 2H, Ar), 6.93-6.98 (m, 1H, Ar), 7.20 (t, 1H, J=7.8 Hz, Ar).

SCHEME 9

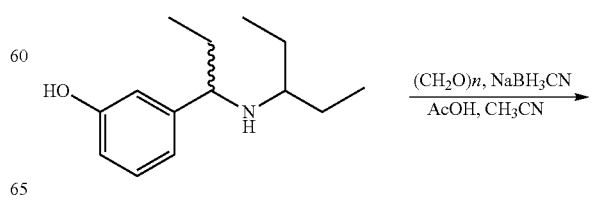

-continued

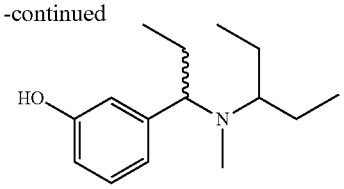

27

Preparation of Amine 27

To a solution of amine 29 (described in [0273]) (615 mg, 2.75 mmol) in dry acetonitrile (30 mL) was added paraformaldehyde (330 mg, 11.0 mmol). The mixture was stirred for 90 min at room temperature. After, sodium cyanoborohydride (345 mg, 5.5 mmol) was added, followed by acetic acid (0.236 mL, 4.13 mmol). The milky reaction mixture was stirred at room temperature overnight and quenched with concentrated hydrochloric acid. Acetonitrile was evaporated and the residue was diluted with water and washed with diethyl ether (2×). The aqueous phase was basified with a solution of sodium hydroxide (10%) and extracted with diethyl ether (3×). The combined organic layer was dried ($Na_2SO_4$), filtered, and concentrated to give amine 27 (626 mg, 95%). $^1$H NMR (400 MHz, acetone-$d_6$) δ: 0.68 (t, 3H, J=7.4 Hz), 0.80-0.84 (m, 6H), 1.16-1.91 (m, 6H), 2.09 (s, 3H, NCH₃), 2.38-2.45 (m, 1H), 3.36-3.39 (m, 1H, NCHAr), 6.69-6.77 (m, 2H, Ar), 6.82 (s, 1H, Ar), 7.12 (t, 1H, J=7.8 Hz, Ar).

3-one-3-ethylene-ketal-18-[N-(3'-pentyl)-1'-phenyl-butylamino-3'-oxy-methylen)]-19-nor-androstenedione (31)

To a stirred solution of 30 (36 mg, 0.15 mmol) dissolved in DMF (0.5 mL) $Cs_2CO_3$ (100 mg, 0.30 mmol) was added and heated at 70° C. for 15 min. Then, the 3-one-3-ethylene-ketal-18-(iodo-methylen)-19-nor-androstenedione 26 (35 mg, 0.076 mmol) dissolved in 1 mL DMF was added drop by drop, and the mixture heated for 1 h at 70° C. Then, the cooled mixture was diluted with AcOEt and the organic phase was washed with aqueous $NaHCO_3$ solution, $H_2O$, brine, dried over $Na_2SO_4$, and filtered. The solvent was removed and the obtained white solid was purified by flash chromatography over silica gel and eluted with 5% vol. methanol/dichloromethane with 0.5% $Et_3N$ to give 28 mg of product 31 (65% yield) as a white solid. $^1$H NMR (400 MHz, acetone-$d_6$) δ: 0.78-0.92 (m, 9H, 3CH₃), 2.53-2.62 (m, 1H,16-CH), 3.70 (t, 1H, J=6.8 Hz, —CH—Ar), 3.84-3.96 (m, 5H, one H of —CH₂—O—Ar and 4H of —O—CH₂—CH₂—O—), 3.98-4.06 (m, 1H of —CH₂—O—Ar), 5.42 (s br, 1H, 4-CH), 6.70-6.75 (m, 1H, Ar—H), 6.88-6.95 (m, 2H, Ar—H), 7.16-7.22 (m, 1H, Ar—H) ppm.

3-one-3-ethylene-ketal-18-[N-(3'-pentyl)-1'-phenyl-butylamino-3'-oxy-methylen)]-19-nor-testosterone (32)

To a ice cooled solution of 31 (28 mg, 0.049 mmol) dissolved in MeOH (4 mL), $NaBH_4$ (4 mg, 0.10 mmol) was

SCHEME 10

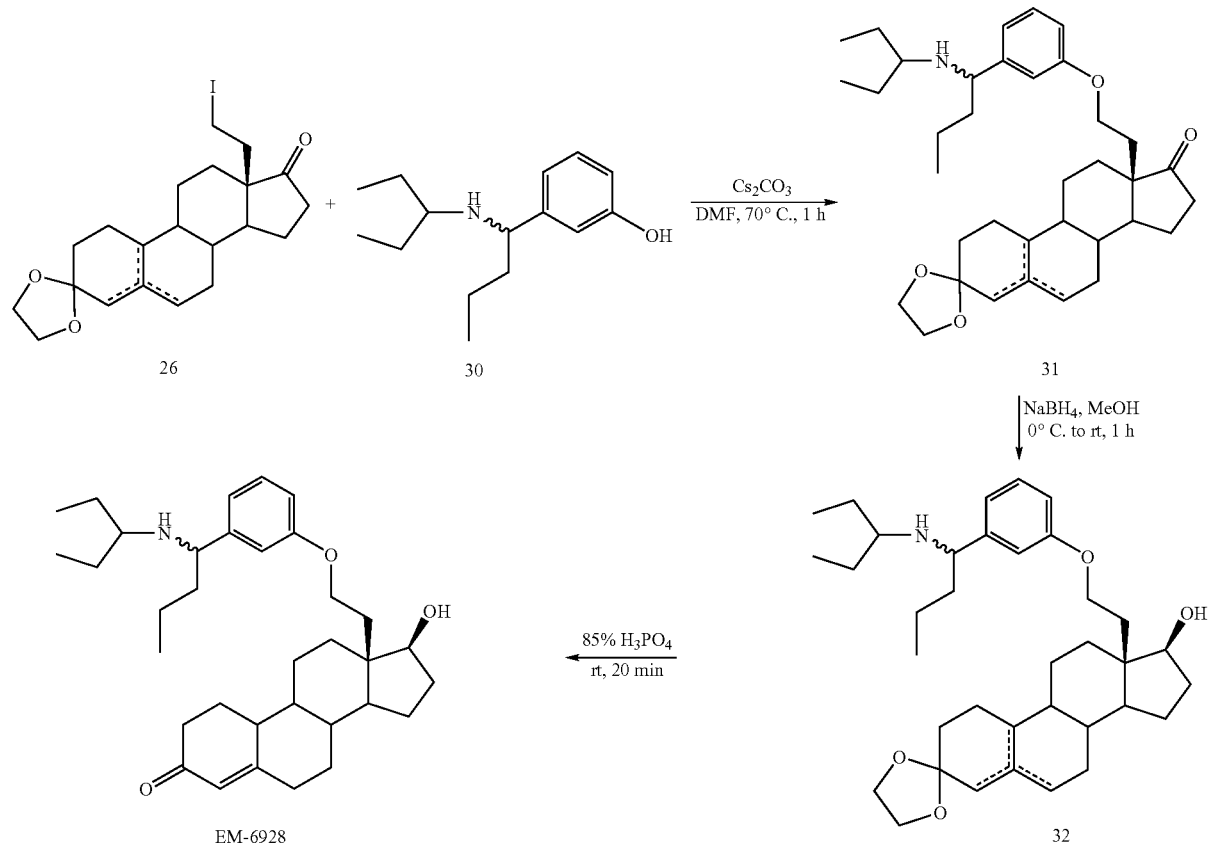

added. The mixture was allowed to warm to room temperature and stirred for 1 h. Then, the clear solution was diluted with dichloromethane and the organic phase was washed with aqueous NaHCO$_3$ solution, H$_2$O, brine, dried over Na$_2$SO$_4$, and filtered. The solvent was removed and the obtained brut compound 32 (28 mg) was used in the next step, without further purification.

18-[N-(3'-pentyl)-1'-phenyl-butylamino-3'-oxy-methylen]-19-nor-testosterone (EM-6928)

To solid 32 (28 mg, 0.049 mmol), 85% H$_3$PO$_4$ (1 mL) was added at room temperature and stirred for 20 min. Then, the 1-(3'-hydroxyphenyl)-N-(3'-pentyl)-butylamine (30)

The 1-(3'-hydroxyphenyl)-N-(3'-pentyl)-butylamine (30) was synthesized in three steps from 3-methoxybenzonitrile, as presented in Scheme 42 (R$_1$=propyl, R$_2$=3-pentyl, R$_3$=H). $^1$H NMR (400 MHz, acetone-d$_6$) δ: 0.78-0.88 (m, 9H, 3CH$_3$), 1.18-1.68 (m, 8H), 2.20-2.23 (m, 1H), 3.64 (t, 1H, J=6.8 Hz, —CH—Ar), 6.67-6.70 (m, 1H, Ar—H), 6.80-6.84 (m, 1H, Ar—H), 6.83-6.84 (m, 1H, Ar—H), 7.12 (t, 1H, J=7.7 Hz, Ar—H) ppm.

SCHEME 11

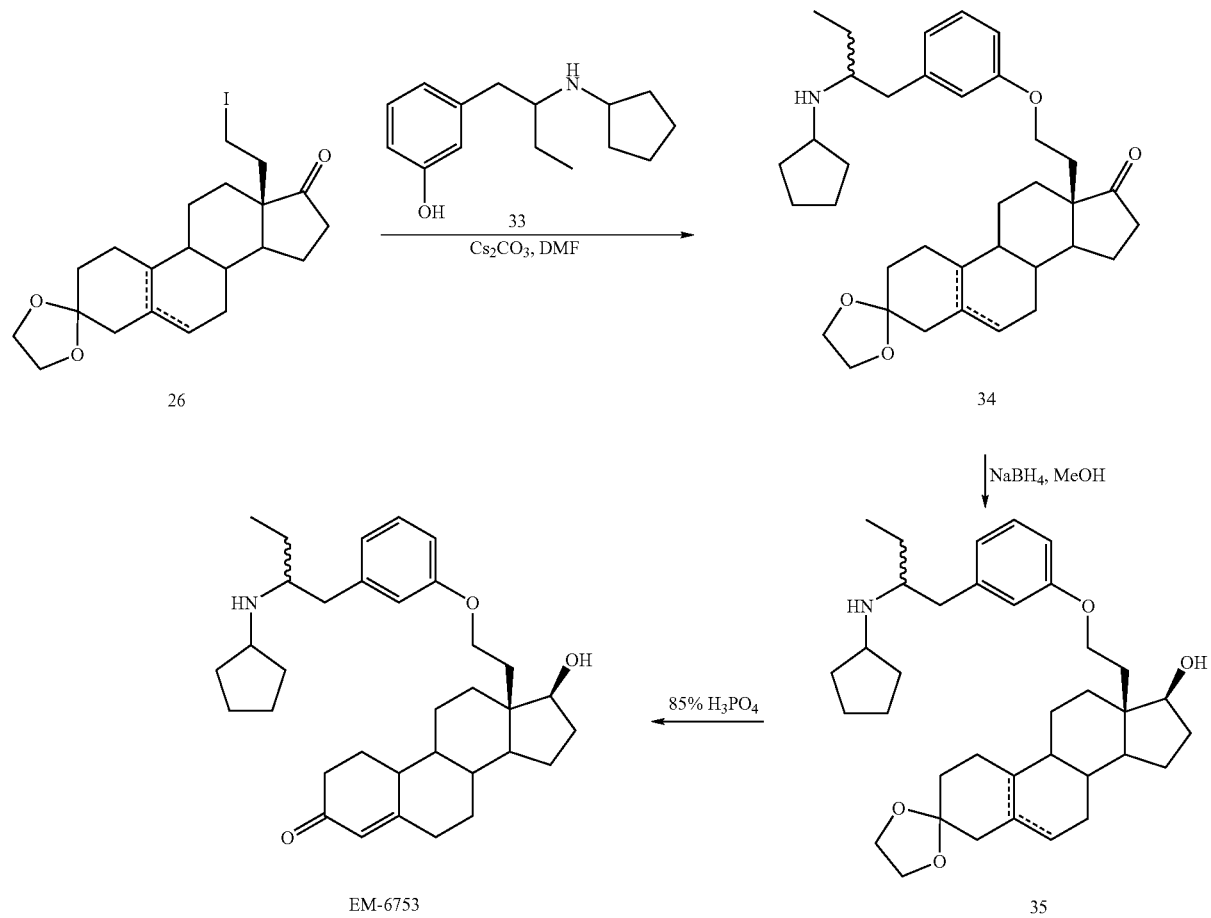

Preparation of EM-6753

Coupling of iodide 26 (70 mg, 0.15 mmol) and phenol 33 (72 mg, 0.30 mmol) with Cs$_2$CO$_3$ (200 mg, 0.60 mmol) was effected as described for EM-6680. Flash chromatography (silica gel, 0-10% MeOH in CH$_2$Cl$_2$) gave 88 mg of impure product. Reduction of the C17 ketone with NaBH$_4$ (50 mg, 1.3 mmol) in 10 mL of methanol, from 0° C. to room temperature over 20 min, was followed by a standard work-up (dilution with EtOAc, and aqueous washes). Deprotection of the C3 position under acidic conditions (85% H$_3$PO$_4$), followed by reverse-phase column chromatography, yielded 32 mg (40% over 3 steps) of the target compound EM-6753. $^1$H mixture was diluted with AcOEt and neutralized with aqueous NaHCO$_3$ solution; the organic phase was washed with H$_2$O, brine, dried over Na$_2$SO$_4$, and filtered. The solvent was removed and the obtained brut compound was purified by flash chromatography over silica gel by graduate elution with 5-40% acetone/hexanes to give 13 mg of product (33% yield for three steps). $^1$H NMR (400 MHz, acetone-d$_6$) δ: 0.80-0.93 (m, 9H, 3CH$_3$), 3.69 (t, 1H, J=6.8 Hz, —CH—Ar), 3.83 (t, 1H, J=8.7 Hz, 17-CHα), 4.06-4.18 (m, 1H, —CH$_2$—O—Ar), 4.50-4.62 (m, 1H, —CH$_2$—O—Ar), 5.73 (s, 1H, 4-CH), 6.78-6.82 (m, 1H, Ar—H), 6.84-6.90 (m, 1H, Ar—H), 7.01-7.07 (m, 1H, Ar—H), 7.20 (t, 1H, J=7.7 Hz, Ar—H) ppm.

NMR (400 MHz, CDCl$_3$) δ: 1.03 (t, J=7.5 Hz, 3H), 2.82 (m, 2H), 3.04 (m, 1H), 3.22 (m, 2H), 3.81 (m, 1H), 4.17 (m, 1H), 4.42 (m, 1H), 5.86 (s, 1H), 6.68-6.81 (m, 3H), 7.22 (t, J=7.8 Hz, 1H).

SCHEME 12

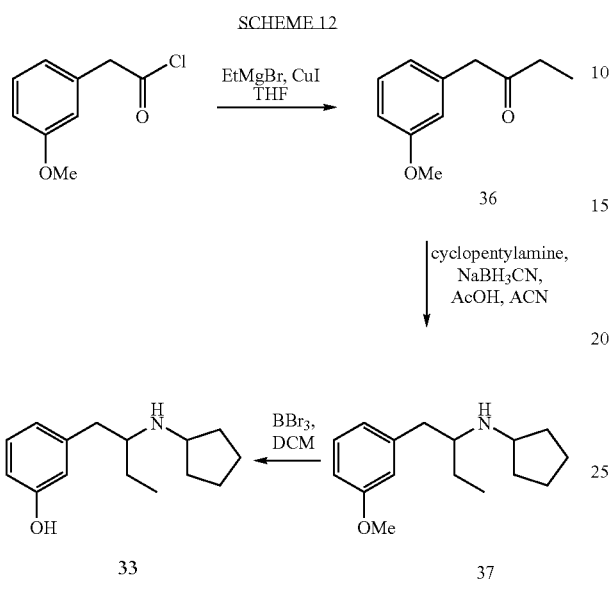

Preparation of Compound 36

To an ice-cooled solution of 3-methoxyphenylacetyl chloride (2.0 mL, 12.8 mmol) and CuI (185 mg, 1.0 mmol) in anhydrous THF (40 mL) was added dropwise a solution of EtMgBr (1M/THF, 12.8 mL, 12.8 mmol). The mixture was stirred for 1 h at 0° C. After completion of the reaction (TLC), the reaction was quenched by addition of saturated aqueous NH$_4$Cl. The mixture was extracted with diethyl ether (3×). The combined organic layer was washed with H$_2$O and brine, dried over MgSO$_4$, filtered, and concentrated under reduced pressure. The crude compound was purified by flash chromatography (silica gel, 10% EtOAc in hexanes) to give 1.87 g (82%) of pure 36. $^1$H NMR (400 MHz, CDCl$_3$) δ: 1.05 (t, J=7.3 Hz, 3H), 2.52 (q, J=7.3 Hz, 2H), 3.68 (s, 2H), 3.82 (s, 3H), 6.77 (s, 1H), 6.82 (m, 2H), 7.26 (t, J=7.8 Hz, 1H).

Preparation of Compound 33

Compound 33 was prepared from ketone 36 (1.84 g, 10.3 mmol) and cyclopentylamine using the described procedure in scheme 42. The crude compound was purified by flash chromatography (silica gel, 0-10% MeOH in CH$_2$Cl$_2$) to give 890 mg (40%, 2 steps) of aminophenol 33. $^1$H NMR (400 MHz, CDCl$_3$) δ: 1.05 (t, J=7.5 Hz, 3H), 1.23-1.95 (m, 10H), 2.53 (m, 10H), 2.94 (m, 1H), 3.06 (m, 1H), 3.28 (m, 1H), 6.73 (s, 1H), 6.76 (m, 2H), 7.23 (t, J=7.9 Hz, 1H).

SCHEME 13

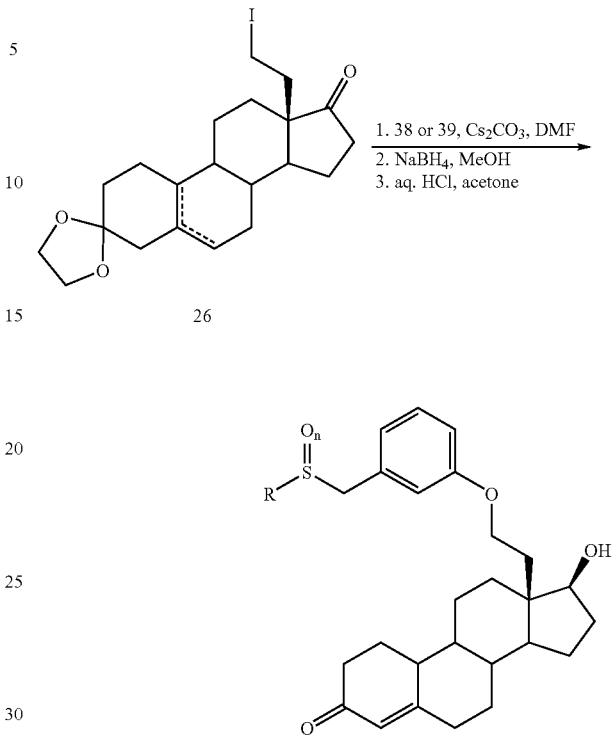

EM-6847 (n = 1, R = Ph)
EM-6881 (n = 2, R = n-Bu)

Preparation of EM-6847 and EM-6881

EM-6847 and EM-6881 were prepared by alkylation of chiral iodo derivative 26 with the corresponding phenols 38 and 39 followed by reduction and deprotection according to the general procedure described for EM-6680.

EM-6847 (4 mg, 21%), white solid. $^1$H NMR (400 MHz, acetone-d$_6$) δ: 3.75 (m, 1H, H-17α), 4.05 (m, 2H, —CH$_2$O— and OH), 4.14 (m, 2H, —CH$_2$SO—), 4.5 (m, 1H, —CH$_2$O—), 5.73 (s, 1H, H-4), 6.68 (d, J=7.5 Hz, 1H, Ar), 6.78 (bs, 1H, Ar), 6.9 (d, J=7.5 Hz, 1H, Ar), 7.18 (t, J=7.9 Hz, 1H, Ar), 7.55 (s, 5H, Ar).

EM-6881 (3 mg, 20%), oil. $^1$H NMR (400 MHz, acetone-d$_6$) δ: 0.92 (t, J=7.4 Hz, 3H, Me), 1.44 (m, 2H, —CH$_2$—), 1.76 (m, 2H, —CH$_2$—), 3.0 (m, 2H, —CH$_2$SO$_2$—), 3.80 (m, 1H, H-17α), 4.15 (m, 2H, —CH$_2$O— and OH), 4.35 (s, 2H, —CH$_2$SO$_2$—), 4.6 (m, 1H, —CH$_2$O—), 5.73 (s, 1H, H-4), 7.01 (m, 2H, Ar), 7.11 (s, 1H, Ar), 7.31 (t, J=7.9 Hz, 1H, Ar).

SCHEME 14

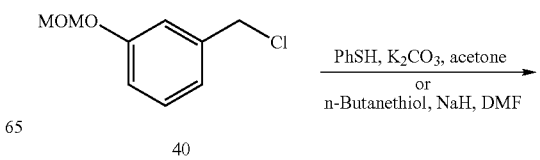

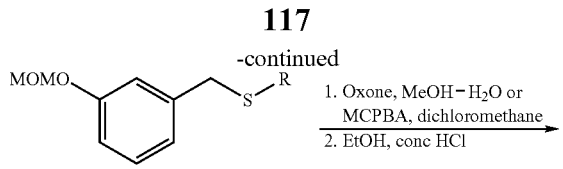

R = Ph, 41
R = n-Bu, 42

1. Oxone, MeOH-H₂O or MCPBA, dichloromethane
2. EtOH, conc HCl

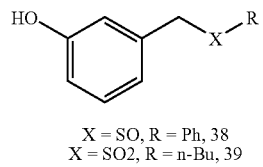

X = SO, R = Ph, 38
X = SO2, R = n-Bu, 39

Preparation of Sulfide 41

To a stirred mixture of thiophenol (0.41 mL, 4.0 mmol), K₂CO₃ (1.13 g, 8.0 mmol) and NaI (2 mg) in acetone (7 mL) was added 3-methoxymethoxybenzyl chloride (40) (757 mg, 4.0 mmol) in acetone (3 mL). The mixture was refluxed for 12 h, then cooled to room temperature. Water was added and the product extracted with ether. The combined phase was washed with brine, dried over Na₂SO₄, and concentrated. The crude residue was purified by flash chromatography eluting with 1% AcOEt-hexanes to yield sulfide 41 (904 mg, 85%). ¹H NMR (400 MHz, CDCl₃) δ: 3.48 (s, 3H, OMe), 4.11(s, 2H, —CH₂—S), 5.16 (s, 2H, —CH₂—O), 6.92-6.98 (m, 2H, Ar), 6.98 (s, 1H, Ar), 7.2-7.35 (m, 6H, Ar).

Preparation of Sulfoxide 38

To an ice cooled solution of sulfide 41 (600 mg, 2.3 mmol) in MeOH (75 mL) was added dropwise a solution of oxone® (708 mg, 1.15 mmol) in water (25 mL). The mixture was stirred for 1 h, then MeOH was evaporated and the residue extracted with ether (3×). The combined organic phase was washed with 20% NaHSO₃, water, and brine. The solvent was removed to give sulfoxide (640 mg, 96%) which was directly used in the next step. A solution of the above sulfoxide in EtOH (3 mL) was heated with conc HCl (0.5 mL) at 60° C. for 2 h. After cooling at room temperature, the solvents were removed and the resulting solid was recrystallized in dichloromethane-ether to give phenol 38 (200 mg, 37%). ¹H NMR (400 MHz, CDCl₃) δ: 4.02 (s, 2H, —CH₂—SO), 6.46 (d, J=7.5 Hz, 1H, Ar), 6.47 (bs, 1H, OH), 6.76 (s, 1H, Ar), 6.81 (d, J=8.1 Hz, 1H, Ar), 7.10 (bt, J=7.8 Hz, 1H, Ar), 7.48 (m, 5H, Ar).

Preparation of Sulfide 42 n-Butanethiol (0.69 mL, 6.4 mmol) was added dropwise to a cold suspension of NaH (60% oil dispersion, 307 mg, 7.7 mmol) in DMF (10 mL). After 30 min, the resulting solution was treated with 3-methoxymethoxybenzyl chloride (40) (595 mg, 3.2 mmol) and stirred for an additional hour at room temperature. The reaction mixture was quenched with saturated NH₄Cl and extracted with ether. The combined organic phase was washed with brine, dried over Na₂SO₄, and concentrated. The crude residue was purified by flash chromatography eluting with 1% AcOEt-Hexanes to yield n-butyl-sulfide 42 (248 mg, 32%). ¹H NMR (400 MHz, CDCl₃) δ: 0.90 (t, J=7.3 Hz, 3H, —CH₃), 1.40 (m, 2H, —CH₂—CH₂), 1.56 (m, 2H, —CH₂—CH₂), 2.44 (t, J=7.5 Hz, 2H, —CH₂—S), 3.50 (s, 3H, OMe) 3.69 (s, 2H, —CH₂—S), 5.20 (s, 2H, —CH₂—O), 6.96 (d, J=7.2 Hz, 1H, Ar), 6.98 (d, J=7.3 Hz, 1H, Ar), 7.01 (s, 1H, Ar), 7.24 (t, J=7.8 Hz, 1H, Ar).

Preparation of Sulfone 39

To a solution of sulfide 42 (160 mg, 0.66 mmol) in dichloromethane (10 mL) was added m-CPBA (575 mg, 3.33 mmol). The mixture was stirred for 12 h at room temperature, washed with saturated NaHCO₃ (3×) and brine. After drying over Na₂SO₄, the solvent was evaporated to give crude sulfone which was directly used in the next step. Deprotection was carried out as described for preparation of sulfoxide 38. The crude residue was purified by flash chromatography eluting with 20% AcOEt-hexanes to yield sulfone 39 (103 mg, 78%). ¹H NMR (400 MHz, CDCl₃) δ: 0.94 (t, J=7.4 Hz, 3H, —CH₃), 1.43 (m, 2H, —CH₂—CH₂), 1.81 (m, 2H, —CH₂—CH₂), 2.88 (m, 2H, —CH₂—SO₂), 4.19 (s, 2H, —CH₂—SO₂), 5.10 (bs, 1H, OH), 6.90 (m, 1H, Ar), 6.94 (m, 2H, Ar), 7.01 (s, 1H, Ar), 7.29 (m, 1H, Ar).

Example IV

Synthesis of (+/−)-19-nortestosterone derivatives

This procedure is described in Schemes 15-18

SCHEME 15

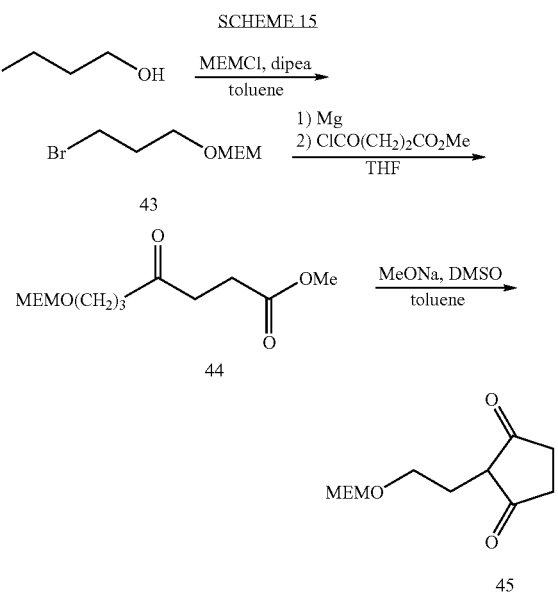

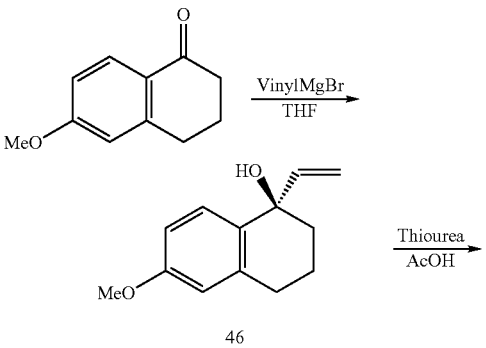

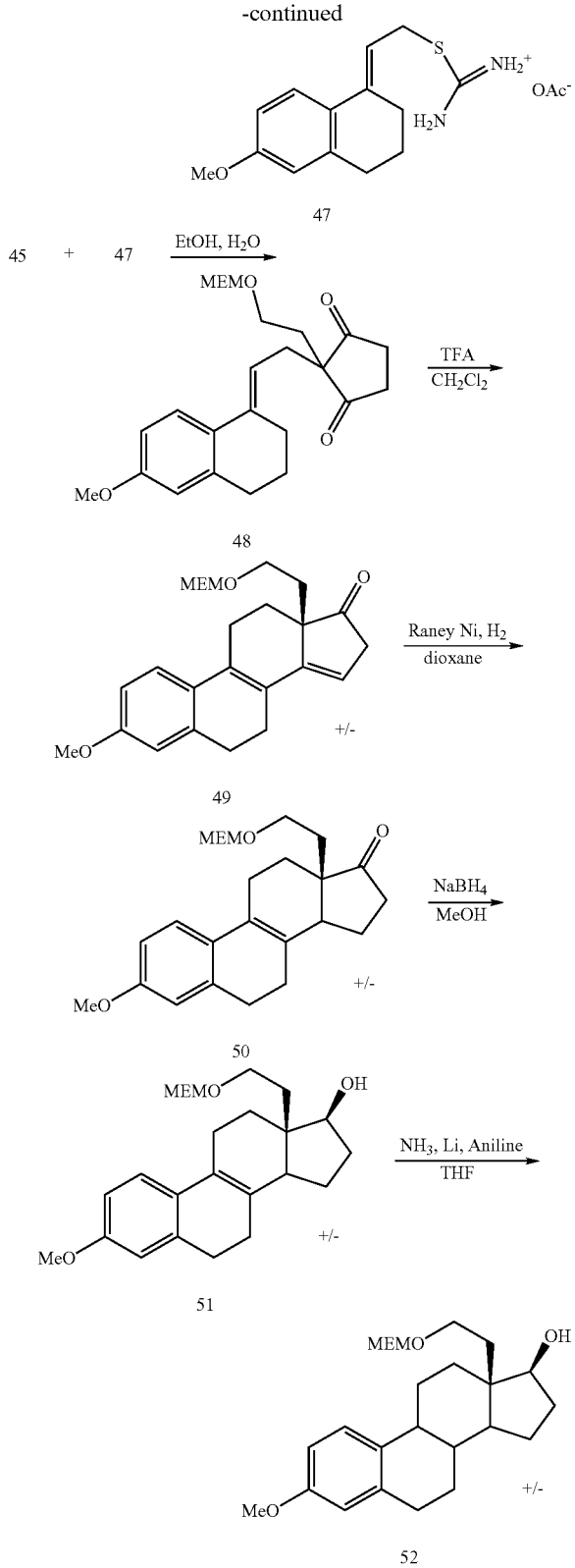

3-Bromo-1-(2-methoxyethoxymethyl)-propane (43)

Under argon atmosphere, a solution of 3-bromo-1-propanol (200 g, 1.44 mol) and MEM chloride (214 mL, 1.87 mol) in toluene (1.6 L) was cooled at 0° C., treated with N,N-diisopropylethylamine (326 mL, 1.87 mol) (the amine was added dropwise, over a 2 h period, to maintain the internal temperature below 5° C.), and stirred for 16 h to rt. The reaction mixture was quenched with water (1 L) and extracted with ethyl acetate (3×1 L). The combined organic phase was washed with 5% aqueous HCl solution (2×400 mL) and brine, dried over $MgSO_4$, filtered, and evaporated to give 314 g of crude product 43. Distillation of the crude oil (bp 74-77° C./0.9 mm) gave the compound 43 (234 g, 75%) as a colorless oil. $^1H$ NMR (400 MHz, $CDCl_3$) δ 2.12 (quintuplet, J=6.2 Hz, 2H), 3.40 (s, 3H), 3.52 (t, J=6.5 Hz, 2H), 3.57 (m, 2H), 3.69 (q, J=5.4 Hz, 2H), 4.73 (s, 2H) ppm.

Methyl-4-((2-methoxyethoxymethyl)-propyl)$_4$-oxobutyrate (44)

A 5 L 3-neck round bottom flask was fitted with a thermocouple probe, a 2 L dropping funnel, an inlet argon, and a mechanical stirrer. After the addition of magnesium (65.6 g, 2.7 mol), entire system was flame dried. Then, 100 mL of dry THF and 5 mL of neat 43 was added dropwise with vigorous stirring over a period of 5 minutes. When the temperature was arised to 30° C., the flask was placed in an ice bath and a solution of 43 (234 g, 1.08 mol) in THF (1 L) was added dropwise to maintain the temperature below 15° C. The mixture was stirred for 1 h at rt. The Grignard solution was titrated to 0.71 M (0.71 mol, 66%). The freshly Grignard solution was transferred in a 1 L dropping funnel. A 5 L 3-neck round bottom flask was fitted with this charged dropping funnel, an argon inlet, and a magnetic stirrer. Dry THF (0.8 L), copper chloride (3.5 g, 0.036 mol), and methyl 4-chloro-4-oxobutyrate (88 mL, 0.71 mol) were introduced into the 5 L flask and the mixture was cooled at 0° C. The Grignard solution was added dropwise over a period of 1.5 h at 0° C. After the addition, the mixture was strirred for 0.5 h at 0° C. A solution of saturated aqueous $NH_4Cl$ (1 L) was added and the mixture was extracted with ethyl acetate (3×1 L). The combined organic phase was washed with a 5% aqueous $NH_4OH$ solution (2×1 L) and brine (3×1 L), dried over magnesium sulfate, and rotary evaporated to give 121 g (65%) of crude product 44. $^1H$ NMR (400 MHz, $CDCl_3$) δ 1.91 (quintuplet, J=7.1 Hz, 2H), 2.56-2.66 (m, 4H), 2.76 (t, J=6.5 Hz, 2H), 3.42 (s, 3H), 3.57 (m, 4H), 3.70 (m, 5H), 4.71 (s, 2H) ppm.

2-((2-Methoxyethoxymethyl)-ethyl)-cyclopentane-1,3-dione (45)

In a 5 L 3-neck round bottom flask fitted with mechanical stirrer, a distillation system, a 2 L dropping funnel, and an argon inlet, was poured sodium methoxide solution (25 wt. % solution in methanol, 200 mL). Toluene (1.0 L) was added and methanol was removed off by distillation with an heating mantle. To the sodium methoxide suspension, methyl sulfoxide (13.4 mL, 0.4 eq) was added and a solution of 44 (121.0 g, 0.46 mol) in toluene (2.0 L) was slowly added over a period of 2 h. The distillation was continued during the addition and additional 30 minutes (until 0.5 L residual toluene). The reaction mixture was cooled and water (1 L) was added. Toluene was extracted and thrown away. The aqueous phase was acidified with 10% HCl until pH 1 and extracted with dichloromethane (4×800 mL). The combined organic phase was washed with brine, dried over magnesium sulfate, and rotary evaporated to give the cyclopentanedione 45 (81.3 g, 75%) as a brown heavy oil. $^1H$ NMR (400 MHz, $CD_3OD$) δ

2.42 (t, J=7.1 Hz, 2H), 2.51 (s, 4H), 3.38 (s, 3H), 3.55-3.61 (m, 4H), 3.67 (m, 2H), 4.68 (s, 2H) ppm.

6-Methoxy-1,2,3,4-tetrahydro-1α-vinyl-1β-naphtol (46)

A solution of vinylmagnesium bromide (1.0 M in THF, 1700 mL) was transferred in a 12 L 3-neck round bottom flask fitted with a thermocouple probe, a 2 L dropping funnel, an inlet argon, and a mechanical stirrer. At rt, a solution of 6-methoxy-1-tetralone (250 g, 1.42 mol) in 830 mL of THF was added dropwise over a period of 2.5 h, maintaining the internal temperature below 30° C. The mixture was stirred at rt for 0.5 h. At rt, a solution of saturated aqueous NH$_4$Cl (1 L) was slowly added by maintaining the internal temperature below 30° C. The THF was decanted and rotary concentrated. The residual aqueous phase was extracted with ethyl acetate (3×1 L). The combined organic phase was washed with brine, dried over magnesium sulfate and rotary evaporated to give 269 g (93%) of crude tetralol 46. $^1$H NMR (400 MHz, CDCl$_3$) δ 1.80-2.05 (m, 4H), 2.70-2.90 (m, 2H), 3.81 (s, 3H), 5.21 (d, J=10.6 Hz, 1H), 5.33 (d, J=17.1 Hz, 1H), 6.04 (dd, J$_1$=17.1 Hz, J$_2$=10.6 Hz, 1H), 6.64 (m, 1H), 6.77 (m, 1H), 7.32 (d, J=8.6 Hz, 1H) ppm (described in Tetrahedron, 18, 1355 (1962)).

2-(3,4-Dihydro-6-methoxy-1(2H)-naphthylidene) ethylisothiuronium acetate (47)

At 0° C., to a stirred mixture of crude tetralol 46 (269 g, 1.32 mol) and thiourea (100 g, 1.32 mol) was added 370 mL of glacial acetic acid. The reaction mixture was stirred at rt for approximatively 1 h. When thiourea was completely dissolved, the reaction mixture was poured in diethyl ether (8 L), stirred for 2 h and the precipitated salt was filtered to afford 285 g (62% from 6-methoxy-1-tetralone) of compound 47. $^1$H NMR (400 MHz, acetone-d$_6$) δ 1.82 (m, 2H), 1.89 (s, 3H), 2.61 (m, 2H), 2.77 (m, 2H), 3.77 (s, 3H), 3.86 (d, J=7.8 Hz, 2H), 6.04 (m, 1H), 6.69 (m, 1H), 6.75 (m, 1H), 7.56 (d, J=8.8 Hz, 1H) ppm (described in JOC, 33, 3126 (1968)).

2-[2-(3,4-Dihydro-6-methoxy-1(2H)-naphthylidene) ethyl]-2-(2-methoxyethoxymethyl)-ethyl-cylclopentane-1,3-dione (48)

To a stirred mixture of isothiuronium acetate (47) (113.8 g, 0.35 mol) and the cyclo-pentane-1,3-dione (45) (81.3 g, 0.35 mol) was added ethanol (1.7 L) and water (640 mL). The reaction mixture was refluxed under argon for 3 h. The mixture was cooled and the solvents were evaporated to dryness.

(±)-13-(2-(2-Methoxyethoxymethyl)-ethyl)-3-methoxygona-1,3,5(10),8,14-pentaen-17-one (49)

Under argon atmosphere and at rt, a solution of the dione (48) (crude, 0.35 mol max.) in dichloromethane (1.4 L), was treated with trifluoroacetic acid (81 mL, 1.05 mol) diluted in dichloromethane (200 mL) over a period of 0.5 h and stirred for 2 h (monitored by TLC). The reaction mixture was quenched with saturated aqueous NaHCO$_3$ solution (1 L) and extracted with dichloromethane (2×500 mL). The combined organic phase was washed with brine, dried over magnesium sulfate, and rotary evaporated to give 145 g of crude product (49). The crude product was purified by filtration on fritted funnel (SiO$_2$) and by flash chromatography on SiO$_2$ (hexanes to hexanes-ethyl acetate/8-2) to provide 52 g (37%, from 2 steps) of diene (49). $^1$H NMR (400 MHz, acetone-d$_6$) δ 1.55 (m, 1H), 1.90 (m, 2H), 2.10 (m, 1H), 2.35 (m, 1H), 2.60-2.90 (m, 6H), 3.28 (m, 4H), 3.40-3.55 (m, 4H), 3.59 (t, J=3.2 Hz, 2H), 3.81 (s, 3H), 4.56 (m, 2H), 6.06 (m, 1H), 6.79 (m, 2H), 7.29 (d, J=9.3 Hz, 1H) ppm.

(±)-13-(2-(2-Methoxyethoxymethyl)-ethyl)-3-methoxygona-1,3,5(10),8-tetraen-17-one (50)

A mixture of 49 (9.7 g, 24.4 mmol) and Raney® nickel (26 mL) in dioxane (220 mL) was stirred under H$_2$ (g) (1 atm) at room temperature for 25 min. The mixture was filtered through Celite pad and washed several times with ethyl acetate. The solvents were removed by evaporation to give quantitatively (9.7 g) the desired compound.

(±)-13-(2-(2-Methoxyethoxymethyl)-ethyl)-3-methoxygona-1,3,5(10),8-tetraen-17-ol (51)

To the ketone 50 (58.0 g, 0.145 mol) in methyl alcohol (1 L) was added by portion NaBH$_4$ (5.5 g, 0.145 mol) at 0° C. The solution was stirred for 20 min then quenched with saturated aqueous NH$_4$Cl solution (500 mL); and methanol was evaporated. The residue was diluted with ethyl acetate (1 L) and washed with brine, dried over magnesium sulfate and rotary evaporated to give 55.6 g (95%) of crude product 51.

(±)-13-(2-(2-Methoxyethoxymethyl)-ethyl)-3-methoxygona-1,3,5(10)-trien-17-ol (52)

A solution of 51 (46.9 g, 0.12 mol) in aniline (250 mL) and dry THF (2 L) was added to ammonia (800 mL). Lithium metal (4.9 g, 0.72 mol) was added in pieces, and the blue mixture was stirred at −20° C. At −78° C., a solution of saturated aqueous NH$_4$Cl was added upon depletion of lithium and the ammonia was allowed to evaporate. The solution was extracted with ethyl acetate (3×500 mL), water (500 mL), and brine. The organic phase was dried over anhydrous magnesium sulfate, the solvent was removed in vacuo, and the product 52 was purified by column chromatography on SiO$_2$ (hexanes to hexanes-acetone/8-3) to provide 48.3 g (82%, over three steps from 49). $^1$H NMR (400 MHz, acetone-d$_6$) δ 1.11-2.36 (m, 14H), 2.85 (m, 2H), 3.25-4.00 (m, 15H), 4.63 (m, 2H), 6.63 (m, 1H), 6.69 (m, 1H), 7.20 (d, J=8.6 Hz, 1H) ppm.

SCHEME 16

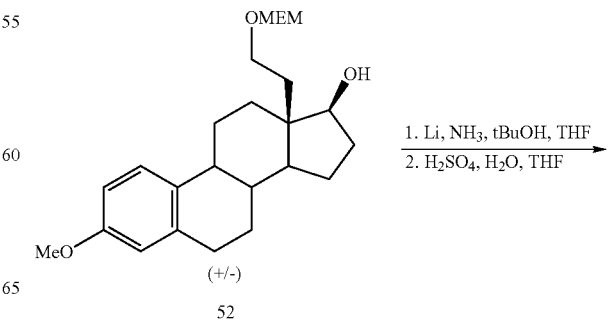

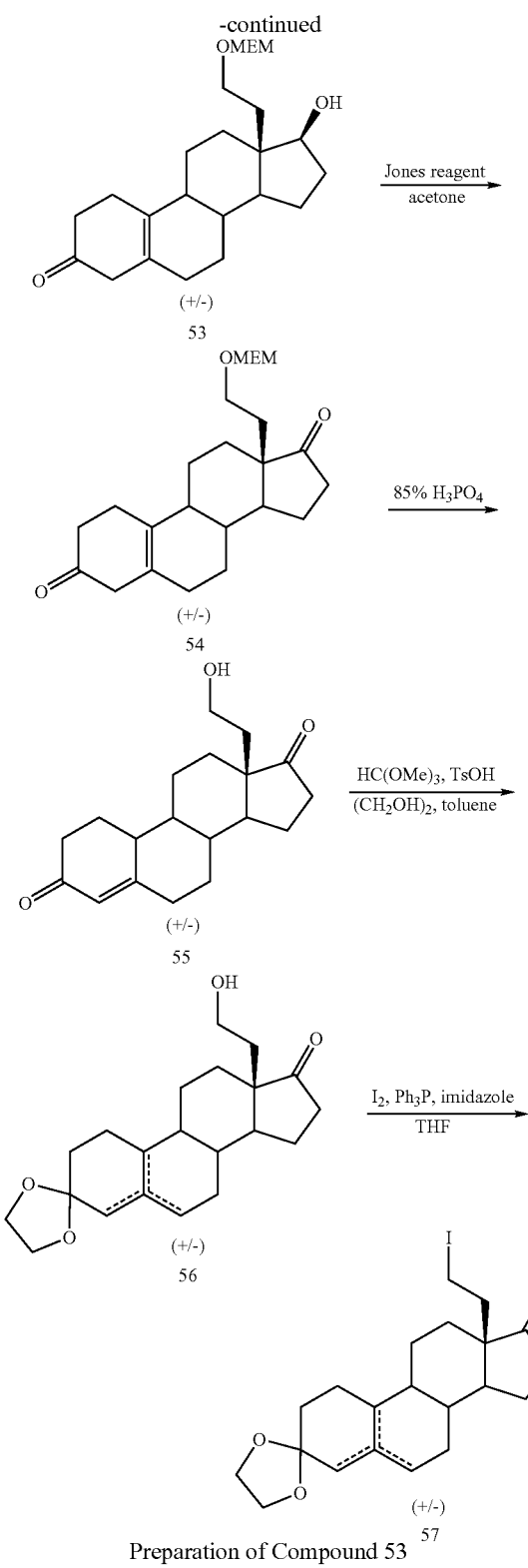

Preparation of Compound 53

In a dry 2 L three-neck round-bottom flask equipped with a mechanical stirrer and a dry-ice condenser, under an argon atmosphere, a solution of 52 (18.75 g, 0.046 mol) in 200 mL of 2-methyl-2-propanol and 200 mL of THF was added at −78° C. to 125 mL of liquid ammonia. Lithium metal (2.95 g, 0.425 mol) was added in pieces, and the blue mixture was stirred at −33° C. for one hour. Ammonium chloride (45 g, 0.840 mol) was added in portions to the mixture, followed cautiously by 100 mL of water. The ammonia was allowed to evaporate at 22° C. The residue was extracted with ethyl acetate (3×250 mL). The organic phases were combined, washed with water (3×250 mL) and brine (200 mL), dried over magnesium sulfate, and concentrated in vacuo. The crude product was dissolved in 275 mL of THF, and 100 mL of water, at 0° C. Concentrated sulfuric acid (18M, 18 mL, 0.324 mol) was added in portions to the mixture, and it was allowed to stir for 15 minutes. The mixture was neutralized with triethylamine (100 mL), and extracted with ethyl acetate (3×300 mL). The combined organic phases were washed with water (250 mL) and brine (200 mL), dried over magnesium sulfate, and concentrated in vacuo. A portion of the crude product 53 was used in the next step.

Preparation of Compound 54

To a cooled solution (0° C.) of compound 53 (10.6 g, 27 mmol) in acetone (400 mL) was added dropwise a 2.7M solution of Jones reagent (15 mL; 41 mmol). TLC analysis showed the completion of the reaction in 30 minutes; the excess of oxidant was then destroyed by the addition of 2-propanol. The solvents were removed to give a green residue which was dissolved in EtOAc, washed with water (2×), brine, dried over $MgSO_4$, and concentrated under reduced pressure to give quantitatively the desired compound 54 (10.5 g).

Preparation of Compound 55

Compound 55 was prepared from 54 (10.5 g, 27 mmol) using the procedure described for compound 67. The crude compound was purified by flash chromatography (silica gel, 10-30% acetone in hexanes) to give 3.7 g (45%) of 55. $^1$H NMR (400 MHz, $CDCl_3$) δ: 3.81-3.98 (m, 2H, —$CH_2OH$), 5.86 (s, 1H, 4-CH).

Preparation of Compound 56 (Racemate of Compound 17)

To a stirred toluene (235 mL) solution containing enone 55 (2.82 g, 9.33 mmol), ethylene glycol (21 mL, 373 mmol), trimethyl orthoformate (3.1 mL, 28 mmol), and PTSA (88 mg, 0.93 mmol) were added at room temperature. Stirring was continued for 40 min, then the mixture was quenched with $Et_3N$ (pH 7-8) and diluted with EtOAc. The organic phase was washed with $H_2O$ (3×), brine, dried over $Na_2SO_4$, and filtered. The solvent was removed and the residue was partially purified by flash chromatography (silica gel, 10-30% acetone in hexanes with 0.5% $Et_3N$) to give 2.3 g of the dioxolane 56 as a yellow foam (71%).

Preparation of Compound 57 (Racemate of Compound 26)

Compound 56 (2.3 g, 6.6 mmol) was dissolved in THF (200 mL), and the following reagents were added in turn: imidazole (1.8 g, 26.4 mmol), triphenylphosphine (3.5 g, 13.2 mmol), and iodine (2.5 g, 9.9 mmol). The mixture was stirred at room temperature for 40 min, diluted with EtOAc and washed with water, aqueous sodium thiosulfate (5%), saturated aqueous $NaHCO_3$, and brine. Drying ($Na_2SO_4$), followed by evaporation of the solvent and purification by flash chromatography (silica gel, 1-15% acetone in hexanes with 0.5% $Et_3N$) gave 2.2 g (73%) of iodide 57. $^1$H NMR (400 MHz, acetone-$d_6$) δ: 2.45-258 (m, 1H, $CH_2I$), 3.17-3.28 (m, 1H, $CH_2I$), 3.85-3.97 (m, 4H, $OCH_2CH_2O$), 5.31 (s, 4-CH of the major $\Delta^{4,5}$ isomer).

SCHEME 17
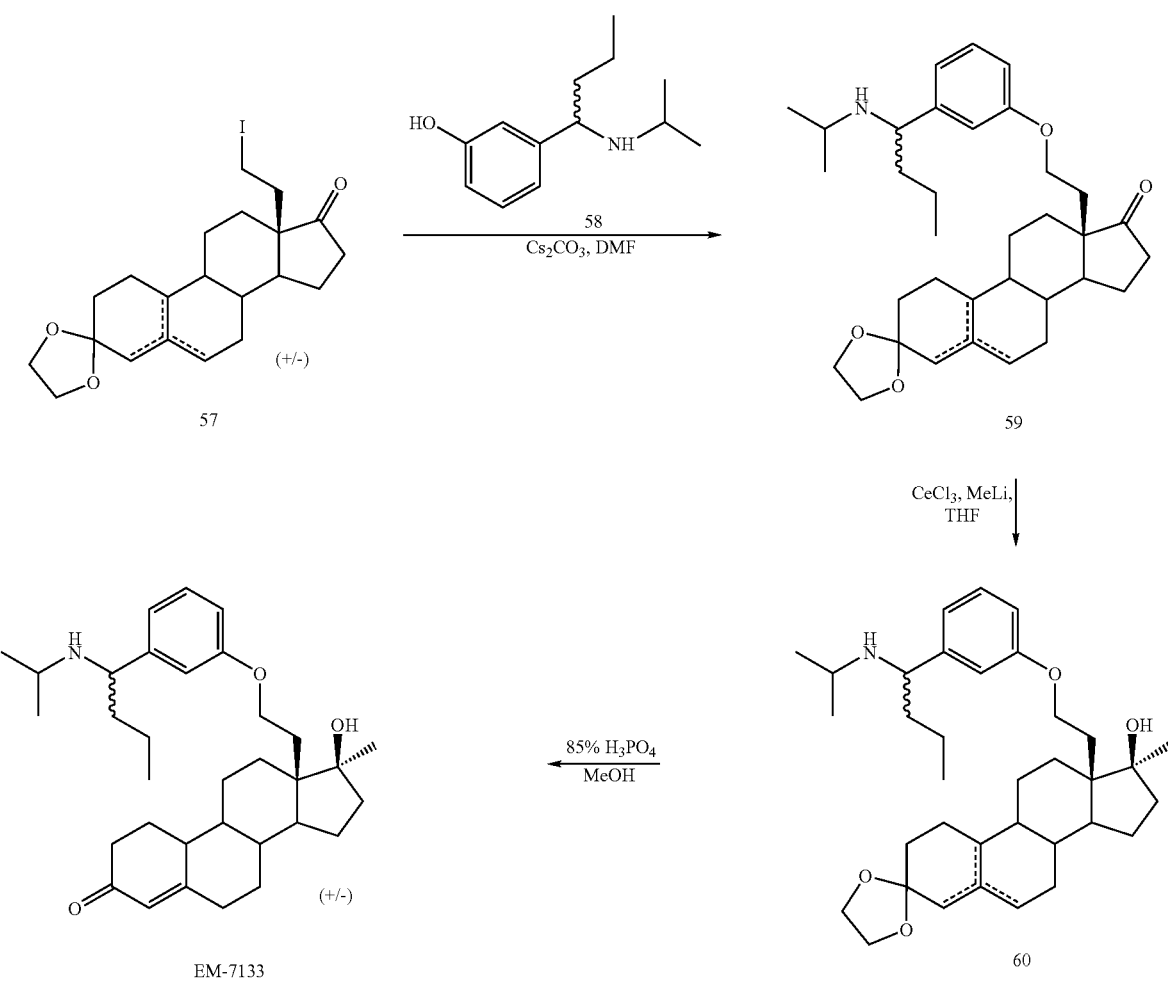
Preparation of Compound EM-7133
EM-7133 was prepared from iodide 57 (65 mg, 0.15 mmol) and phenol 58 (50 mg, 0.25 mmol) using the described procedure for compound EM-6902. The crude compound was purified by reverse-phase chromatography (30-0% H$_2$O in MeOH) to afford 13.1 mg (16%, 3 steps) of EM-7133. $^1$H NMR (400 MHz, acetone-d$_6$) δ: 0.87 (t, J=7.4 Hz, 3H), 0.92-0.98 (m, 6H), 1.26 (s, 3H), 3.67 (t, J=6.8 Hz, 1H), 3.75 (s, 1H), 4.07 (m, 1H), 4.59 (m, 1H), 5.73 (s, 1H), 6.79-6.87 (m, 2H), 6.99 (s, 1H), 7.19 (t, J=7.8 Hz, 1H).
SCHEME 18
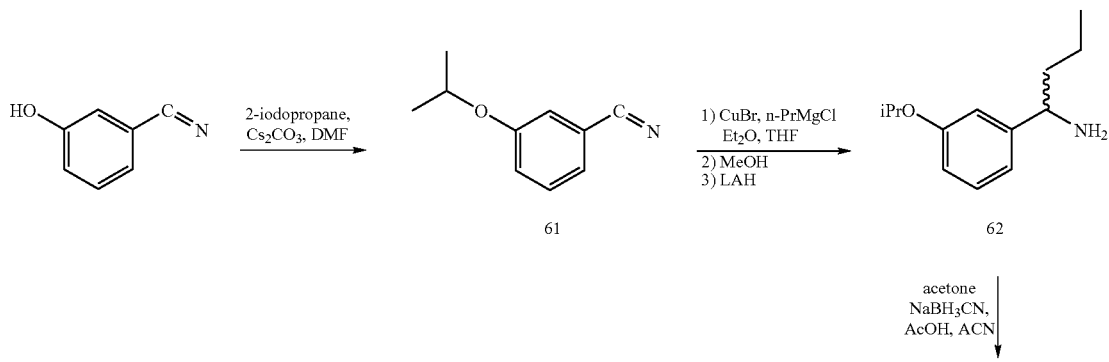

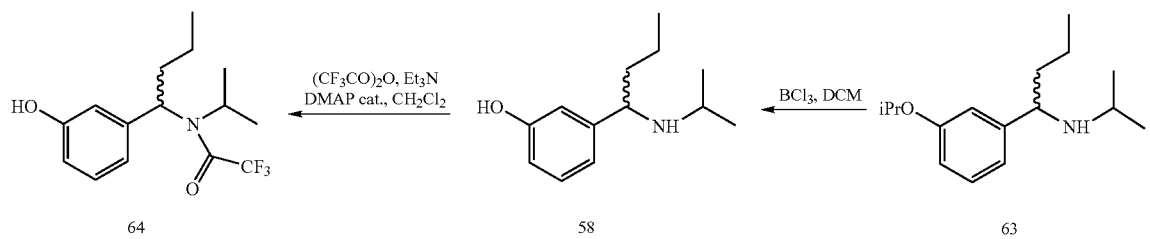

Preparation of Compound 58

Compound 58 was prepared from commercially available 3-cyanophenol in 4 steps using the described procedure in scheme 42 (isopropoxy group was used instead of methoxy group). The crude compound was used for the next step without further purification. $^1$H NMR (400 MHz, CD$_3$OD) δ: 0.89 (t, J=7.4 Hz, 3H), 0.92-1.20 (m, 2H), 1.07 (t, J=7.4 Hz, 6H), 1.66-1.79 (m, 2H), 2.68 (m, 1H), 3.73 (m, 1H), 6.70-6.79 (m, 3H), 7.18 (t, J=7.8 Hz, 1H).

Example V

Synthesis of (+/−)-4,9-estradiene Derivatives

This procedure is described in Scheme 19

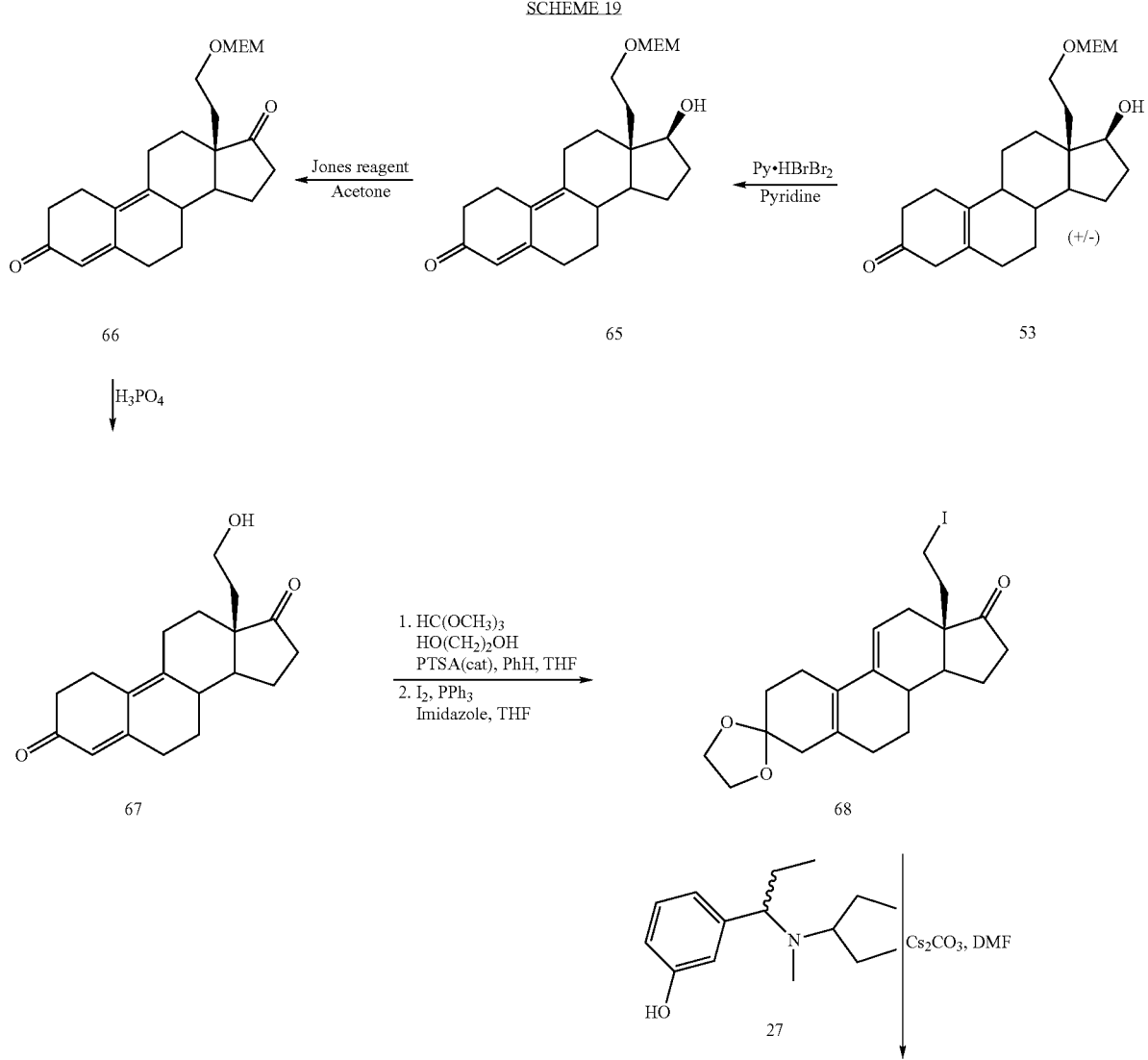

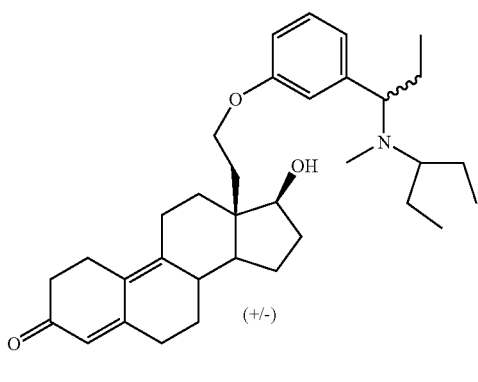

EM-6860

1. NaBH₄, MeOH
2. H₃PO₄, MeOH

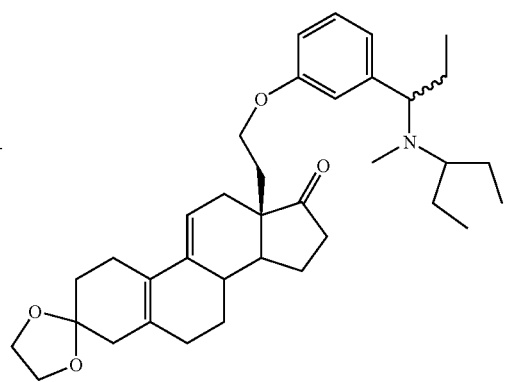

69

Preparation of Compound 65

The crude product 53 (from scheme 16) was dissolved in dry pyridine (80 mL), and cooled to 0° C. Pyridinium tribromide (19.3 g, 0.060 mol) was added portionwise and the mixture was stirred at 22° C. for 16 h. The solution was diluted with water (150 mL), and acidified with concentrated HCl (aq) to pH 2 and 3. The product was extracted with ethyl acetate (3×250 mL), and the combined organic phase wAS successively washed with a saturated aqueous sodium bicarbonate solution (250 mL), water (250 mL), and brine (200 mL). The solution was dried over magnesium sulfate and evaporated in vacuo, to provide 18.7 g of a brown solid (compound 65) which was used without further purification. $^1$H NMR (400 MHz, CDCl₃) δ: 3.42 (s, 3H, CH₂O—), 3.58-3.89 (m, 6H, —OCH₂CH₂O— and —CH₂O—), 3.65 (t, 1H, J=8,7 Hz, 17α-H), 4.79 (s, 2H, —OCH₂O—), 5.70 (s, 1H, 4-H) ppm.

Preparation of Compound 66

In a 500 mL round-bottom flask equipped with a magnetic stirrer, 18.7 g of crude compound 65 was dissolved in acetone (150 mL), and cooled at 0° C. A 8N solution of Jones reagent (15 mL) was added dropwise over this mixture. Then, isopropanol (50 mL) was added to the reaction to neutralize the oxidant. The mixture was evaporated in vacuo, and the residue was dissolved in ethyl acetate (250 mL), washed successively with a saturated aqueous sodium bicarbonate solution (250 mL), water (2×200 mL), and brine (200 mL). The solution was dried over magnesium sulfate and the solvent was removed in vacuo, providing 12.7 g of a brown oil. The crude material was purified by column chromatography (5:95 to 25:75 acetone:hexane) to yield 6.1 g of a yellow oil (34% over four steps from 52). $^1$H NMR (400 MHz, CDCl₃) δ: 3.41(s, 3H, CH₃O—), 3.54-3.71 (m, 6H, —OCH₂CH₂O— and —CH₂O—), 4.67 (s, 2H, —OCH₂O—), 5.73 (s, 1H, 4-H) ppm.

Preparation of Compound 67

Crude 66 was placed in a 250 mL round-bottom flask equipped with a magnetic stirrer and treated with 30 mL of phosphoric acid (85% wt in water solution); then, the mixture was stirred vigorously for one hour at 22° C. The solution was then diluted with ethyl acetate (150 mL) and water (150 mL). The aqueous phase was extracted with ethyl acetate (5×100 mL). The organic phases were combined, washed with a saturated aqueous sodium bicarbonate solution (150 mL), water (150 mL), and brine (150 mL). The solution was dried over magnesium sulfate and evaporated in vacuo to provide 4.5 g of a yellow solid, which was used without further purification. $^1$H NMR (400 MHz, CDCl₃) δ: 3.87 (bs, 2H, —CH₂O—), 5.72 (s, 1H, 4-H) ppm.

Preparation of Compound 68

The crude 67 (1.6 g, 5.33 mmol) was placed in a 250 mL round-bottom flask equipped with a magnetic stirrer, dissolved in a mixture of toluene (80 mL) and THF (20 mL), and treated with ethylene glycol (18.2 mL, 293 mmol) and trimethylorthoformate (3.2 mL, 29.3 mmol), followed by paratoluenesulfonic acid (0.139 g, 0.73 mmol). The solution was stirred for 30 minutes at room temperature. A saturated aqueous sodium bicarbonate solution (100 mL) was added, and the mixture was extracted with ethyl acetate (3×100 mL). The combined organic phase was washed with water (3×100 mL) and brine (50 mL), and then dried over magnesium sulfate to furnish 2.34 g of crude acetal. In a dry 500 mL round-bottom flask equipped with a magnetic stirrer and an argon inlet, the crude acetal was dissolved in THF (200 mL). The solution was cooled at 0° C. and treated with imidazole (2.31 g, 34.0 mmol) and triphenylphosphine (5.35 g, 20.4 mmol) until complete dissolution. Iodine (4.83 g, 19.0 mmol) was then added in portions. The ice bath was removed and the mixture was stirred for two hours. The reaction was diluted with ethyl acetate (100 mL), and a 10% aqueous sodium thiosulfate solution (40 mL) was added until the purple color disappeared. The phases were separated, and the organic phase was washed with water (2×100 mL), brine (100 mL), and dried over magnesium sulfate. The crude material (9.0 g) was purified by column chromatography (5:95 to 30:70 ethyl acetate: hexane) to yield 0.92 g of a yellow solid (19% over three steps from 66). $^1$H NMR (400 MHz, CDCl₃) δ: 2.93 (m, 1H, —CH₂I), 3.12 (m, 1H, —CH₂I), 4.00 (s, 4H, —OCH₂CH₂O—), 5.54 (s, 1H, 11-H) ppm.

Preparation of Compound 69

Coupling of iodide 68 (75 mg, 0.165 mmol) and phenol 27 (81 mg, 0.34 mmol), in the presence of Cs₂CO₃ (128 mg, 0.39 mmol) was effected as described for EM-6654. Repeated flash chromatography on silica gel afforded 32 mg of pure 69 (35% yield). $^1$H NMR (400 MHz, CDCl₃) δ: 0.67 (t, 3H, J=7.3 Hz, CH₃CH₂CHAr—), 0.81 (t, 3H, J=7.4 Hz, CH₃CH₂CHN—), 0.84 (t, 3H, J=7.4 Hz, CH₃CH₂CHN—), 3.17 (bs, 1H, ArCH—), 3.32 (s, 3H, CH₃N—), 3.42 (m, 1H, —NCH—), 3.93 (s, 4H, —OCH₂CH₂O—), 3.87-4.08 (m, 2H, —CH₂O—), 5.57 (m, 1H, 11-H), 6.69 (dd, 1H, J=1.7 Hz and 8.1 Hz, Ar—H), 6.83 (s, 1H, Ar—H), 6.85 (d, 1H, J=7.6 Hz, Ar—H), 7.19 (t, 1H, J=7.9 Hz, Ar—H) ppm.

Preparation of EM-6860

Reduction of compound 69 with NaBH$_4$ (4 mg, 0.11 mmol), in 3 mL of methanol at 0° C. for 15 minutes, was followed by a standard work-up (dilution with ethyl acetate and aqueous washes). The crude material was reacted with 85% H$_3$PO$_4$ (1 mL) at 22° C. for 15 minutes. The mixture was basified by addition of a saturated aqueous sodium carbonate solution (25 mL). The aqueous phase was extracted with ethyl acetate (3×50 mL). The combined extract was washed with water, brine, and dried over magnesium sulfate. The crude product was purified by reverse phase column-chromatography (as described for EM-6654), providing 18 mg of a white solid (60% yield from 69). $^1$H NMR (400 MHz, CDCl$_3$) δ: 0.68 (t, 3H, J=7.3 Hz, CH$_3$CH$_2$CHAr—), 0.82 (t, 3H, J=7.4 Hz, CH$_3$CH$_2$CHN—), 0.84 (t, 3H, J=7.4 Hz, CH$_3$CH$_2$CHN—), 2.88-3.01 (m, 4H, CH$_3$N— and ArCH), 3.43 (m, 1H, —NCH—), 3.80 (m, 1H, C$_{17}$:—CH(OH)), 4.22 (m, 2H, —CH$_2$O— and —OH), 4.58 (m, 1H, —CH$_2$O—), 5.58 (s, 1H, 4-H), 6.84 (m, 2H, Ar—H), 6.95 (s, 1H, Ar—H), 7.20 (t, 1H, J=7.8 Hz, Ar—H) ppm.

Example VI

Synthesis of (+/−)-4,9,11-estratriene Derivatives

This procedure is described in Scheme 20

SCHEME 20

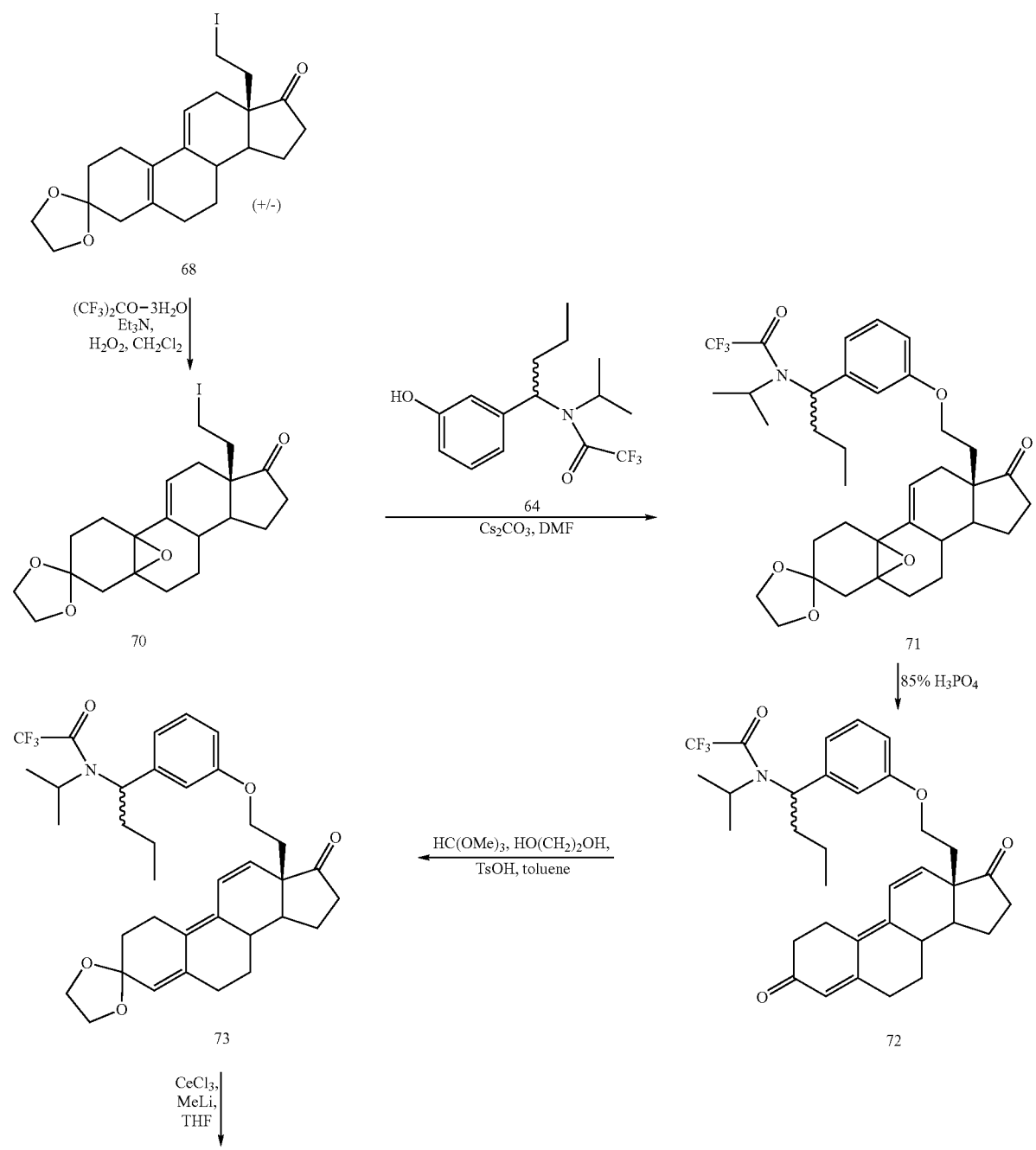

-continued

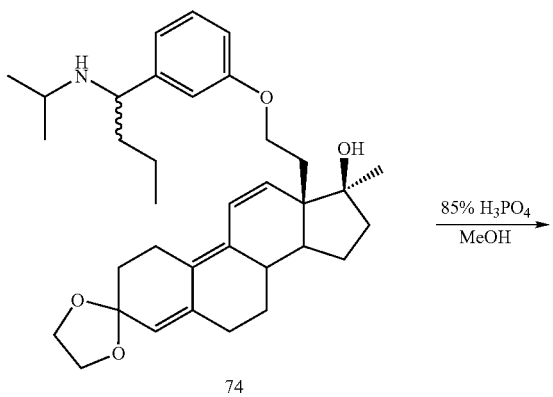

74

85% H₃PO₄
MeOH
→

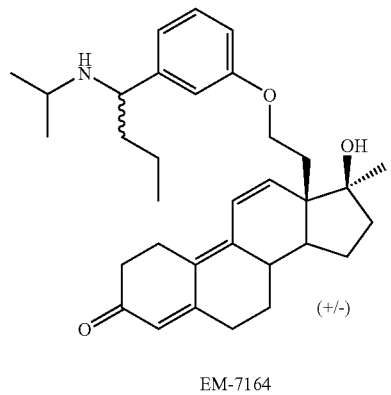

EM-7164
(+/-)

Preparation of Compound 70

Substrate 68 (0.90 g, 2.0 mmol) was dissolved in 20 mL of dichloromethane and the following reagents were added: pyridine (100 µL), hexafluoroacetone trihydrate (100 µL), and hydrogen peroxide (50% solution, 0.50 mL). The mixture was stirred vigorously in the dark for about 18 h, and was then cooled to 0° C. before addition of 1 mL of a 5% aqueous solution sodium thiosulfate. After 10 min, the mixture was diluted with water, and extracted three times with dichloromethane. Drying (Na₂SO₄) and evaporation to dryness was followed by flash chromatography (silica gel, 20-30% EtOAc in hexanes containing a few drops of triethylamine). 0.74 g (79%) of compound 70 was obtained as a 5/1 mixture of α and β isomers of the $\Delta^{5,10}$ epoxide. ¹H NMR (400 MHz, acetone-d₆) δ: 2.90-3.05 (m, 1H, ICH₂), 3.18-3.33 (m, 1H, ICH₂), 3.80-3.98 (m, 4H, OCH₂CH₂O), 5.86-5.93 (m, α-H5), 6.03-6.10 (m, β-H5).

Preparation of Compound 72

Compound 71 was prepared from epoxy-iodide 70 (90 mg, 0.19 mmol) and phenol 64 (100 mg, 0.33 mmol) using the described procedure for compound 28. The crude compound was used for next step without further purification. Compound 72 was prepared from 71 using the described procedure for compound 55. The crude compound was purified by reverse-phase chromatography (30-0% H₂O in MeOH) to give 70 mg (60%, 2 steps) of trienone 72. ¹H NMR (400 MHz, acetone-d₆) δ: 0.83-1.02 (m, 3H), 1.38 (m, 6H), 3.55 (m, 1H), 4.09 (m, 2H), 4.94 (m,1H), 5.74 (s, 1H), 6.55 (d, J=10 Hz, 1H), 6.72 (d, J=10 Hz, 1H), 6.97 (s, 1H), 7.07 (m, 2H), 7.37 (t, J=7.9 Hz, 1H).

Preparation of Compound EM-7164

Compound 73 was prepared from trienone 72 (70 mg, 0.12 mmol) using the described procedure for compound 56. The crude compound was used for next step without further purification. Compound EM-7164 was prepared from ketal 73 (70 mg, 0.12 mmol) using the described procedure for compound EM-6902. The crude compound was purified by reverse-phase chromatography (30-0% H₂O in MeOH) to give 20 mg (35%, 3 steps) of EM-7164. ¹H NMR (400 MHz, acetone-d₆) δ: 0.85 (t, J=7.4 Hz, 3H), 0.90-0.97 (m, 6H), 1.29 (s, 3H), 3.65 (m, 1H), 4.04 (m, 1H), 4.08 (m, 1H), 4.57 (m,1H), 5.70 (s, 1H), 6.49 (d, J=10 Hz, 1H), 6.74 (m, 2H), 6.84 (m, 1H), 6.91 (m, 1H), 7.17 (t, J=7.9 Hz, 1H).

Preparation of Compound 64

To an ice-cooled solution of amine 58 (Scheme 18)(102 mg, 0.49 mmol) in dry dichloromethane (8.0 mL) was added trifluoroacetic anhydride (0.22 mL, 1.5 mmol), Et₃N (0.37 mL, 2.5 mmol), and DMAP (6.0 mg, 0.05 mmol). The mixture was stirred for 2 h at room temperature. The reaction mixture was diluted with EtOAc and washed with saturated aqueous NaHCO₃ and brine. The organic phase was dried over MgSO₄, filtered, and evaporated under reduce pressure. The crude compound was purified by flash chromatography (silica gel, 5-30% EtOAc in hexanes) to give 130 mg (87%) of trifluoroacetamide 64. ¹H NMR major conformation (400 MHz, acetone-d₆) δ: 1.00 (m, 3H), 1.39 (m, 6H), 1.89 (m, 2H), 2.30 (m, 2H), 3.55 (m, 1H), 4.91 (m, 1H), 6.85 (m, 1H), 6.96 (m, 2H), 7.27 (m, 1H), 8.53 (s, 1H).

Example VII

Synthesis of (+/−)-7α-methyl-19-nortestosterone Derivatives

This procedure is described in Schemes 21-23

SCHEME 21

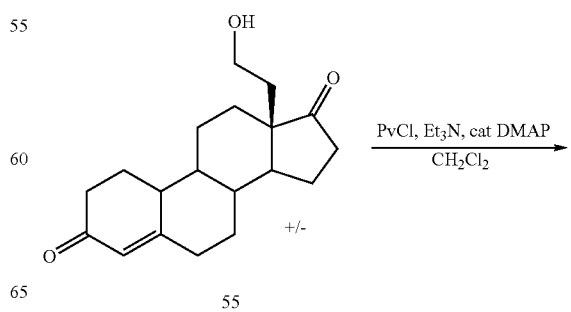

55
+/−

PvCl, Et₃N, cat DMAP
CH₂Cl₂
→

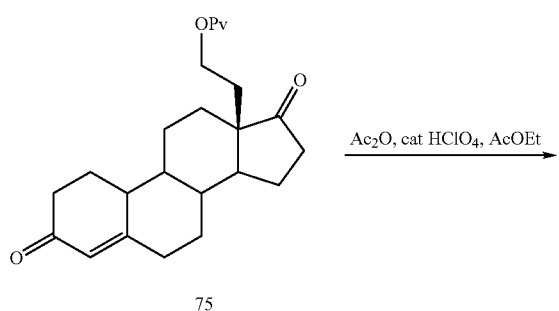

75

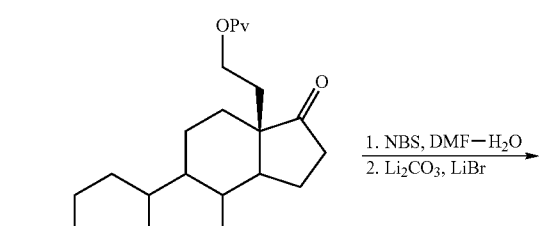

76

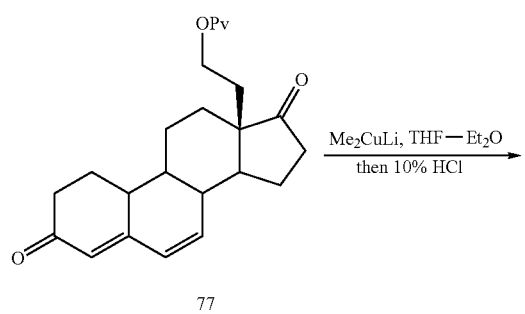

77

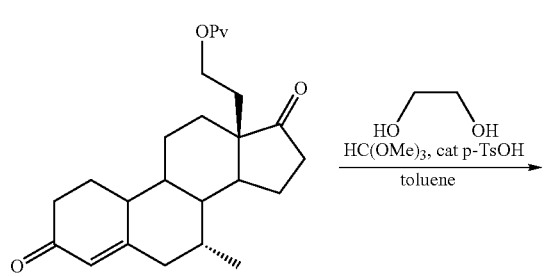

78

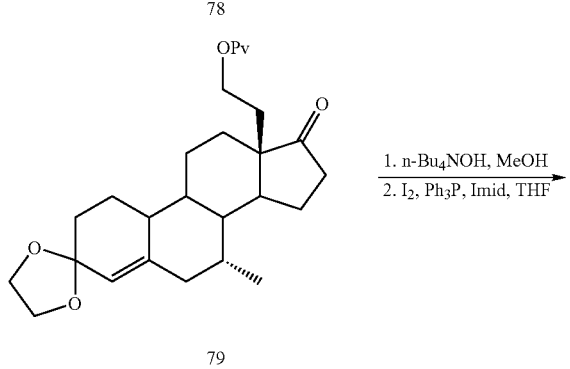

79

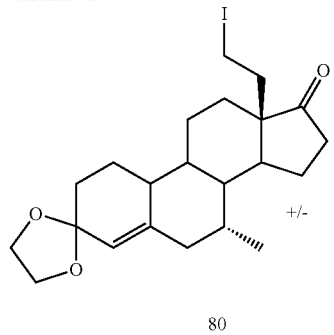

80

Preparation of Compound 75

To a stirred solution of enone 55 (5.15 g, 17.0 mmol) in anhydrous dichloromethane (100 mL), triethylamine (8.65 mL, 62.3 mmol) and 4-(dimethylaminopyridine) (190 mg, 1.55 mmol) were successively added, followed by trimethylacetylchloride (5.75 mL, 46.7 mmol). The mixture was stirred at room temperature for 5 h and quenched at 0° C. with a 10% HCl solution. Extraction with dichloromethane, followed by washing with saturated $NaHCO_3$ and brine, drying over $Na_2SO_4$, and concentration afforded an oily residue. Purification by flash chromatography on silica gel eluting with 5% acetone-hexanes gave pivaloate 75 (4.75 g, 72%). $^1H$ NMR (400 MHz, acetone-$d_6$) δ: 1.16 (s, 9H, tert-butyl), 3.98 (m, 1H, —$CH_2$—O), 4.04 (m, 1H, —$CH_2$—O), 5.75 (s, 1H, H-4).

Preparation of Compound 76

To a stirred solution of 75 (4.75 g, 12.0 mmol) in AcOEt (450 mL) were added acetic anhydride (11.5 mL, 120 mmol) and 70% aqueous $HClO_4$ (105 μL). After 10 min at room temperature, MeOH (12 mL) was added and the mixture was stirred for another 10 min. The solution was then quenched with saturated $NaHCO_3$ and extracted with AcOEt. The combined organic layer was washed with brine, dried over $Na_2SO_4$, and the solvent evaporated to give enol acetate 76 (5.2 g, 100%) which was sufficiently pure for the next step. $^1H$ NMR (400 MHz, acetone-$d_6$) δ: 1.15 (s, 9H, tert-butyl), 2.10 (s, 3H, OAc), 3.97 (m, 1H, —$CH_2$—O), 4.04 (m, 1H, —$CH_2$—O), 5.52 (bt, J=2.5 Hz, 1H, H-6), 5.77 (d, J=1.9 Hz, 1H, H-4).

Preparation of Compound 77

To an ice-cooled solution of enol acetate 76 (5.2 g, 12.0 mmol) in DMF (70 mL) was successively added water (1.4 mL) and N-bromosuccinimide (2.34 g, 13.2 mmol). After stirring at 0° C. for 1 h in the dark, $Li_2CO_3$ (2.13 g, 28.8 mmol) was added, followed by LiBr (1.14 g, 13.2 mmol). The flask was then placed into a preheated oil bath (120° C.) and stirring was maintained for 2 h. The mixture was cooled to room temperature and poured into an iced-cooled solution of 10% HCl. The brown precipitate was filtered, washed with water, and redissolved in AcOEt. After washing once with saturated $NaHCO_3$ and brine, the organic phase was dried over $Na_2SO_4$ and concentrated. The residue was purified by flash chromatography eluting with 10% acetone-hexanes afforded dienone 77 (2.54 g, 55%). $^1H$ NMR (400 MHz, acetone-$d_6$) δ: 1.16 (s, 9H, tert-butyl), 3.99 (m, 1H, —$CH_2$—O), 4.05 (m, 1H, —$CH_2$—O), 5.73 (s, 1H, H-4), 6.35 (bt, J=1.8 Hz, 2H, H-6 and H-7).

Preparation of Compound 78

A solution of lithium dimethylcuprate in dry ether (20 mL) was firstly prepared under argon at −10° C. from copper (I) iodide (99.999% purity, 2.47 g, 13.0 mmol) and MeLi (1.6 M solution in ether, 14.6 mL, 23.4 mmol). After cooling at −30° C., a solution of dienone 77 (1.0 g, 2.6 mmol) in dry tetrahydrofuran (40 mL) was added via a cannula. Stirring was continued for 40 min and the mixture was cooled to −78° C. before addition of 10% HCl (10 mL). The cooling bath was removed and the mixture allowed to warm to room temperature. After stirring for 1 h (complete isomerization was evaluated by TLC), the reaction mixture was poured into a mixture of saturated NaHCO$_3$ and saturated NH$_4$Cl. The two phases were vigorously stirred until all the solids have disappeared. After extraction with AcOEt, the combined phase was washed with brine, dried over Na$_2$SO$_4$, and concentrated. The amorphous residue was purified by flash chromatography eluting with 10% acetone-hexanes to yield enone 78 (820 mg, 79%). $^1$H NMR (400 MHz, acetone-d$_6$) δ: 0.85 (d, J=7.2 Hz, 3H, Me), 1.16 (s, 9H, tert-butyl), 3.98 (m, 1H, —CH$_2$—O), 4.07 (m, 1H, —CH$_2$—O), 5.75 (s, 1H, H-4).

Preparation of Compound 79

Protection of enone 78 (2.2 g, 5.5 mmol) was carried out as described for the preparation of 56, but 5 h of stirring at room temperature was required to be complete. The crude residue was purified by flash chromatography eluting with 5% acetone-hexanes (+1% Et$_3$N) to yield ketal 79 (1.93 g, 79%). $^1$H NMR (400 MHz, acetone-d$_6$) δ: 0.81 (d, J=7.2 Hz, 3H, Me), 1.16 (s, 9H, tert-butyl), 3.81-4.02 (m, 6H), 5.30 (s, 1H, H-4).

Preparation of Iodo Ketal 80

To a stirred solution of 79 (2.0 g, 4.4 mmol) in MeOH (15 mL), n-tetrabutylammonium hydroxide (1M in MeOH, 8.8 mL, 8.8 mmol) was added. Stirring was continued for 16 h before addition of water. MeOH was evaporated and the residue extracted with dichloromethane (3×). The combined organic phase was washed with water and brine. The solvent was removed to give crude lactol (1.6 g) which was used directly in the next step. Iodination was carried out as described for the preparation of 57. The crude residue was purified by flash chromatography eluting with 2% AcOEt-toluene (+1% Et$_3$N) to yield iodoketal 80 (1.85 g, 79%) as a white solid. $^1$H NMR (400 MHz, acetone-d$_6$) δ: 0.81 (d, J=7.2 Hz, 3H, Me), 2.85 (m, 1H, —CH$_2$—I), 3.2 (m, 1H, —CH$_2$—I), 3.81-3.93 (m, 4H), 5.31 (s, 1H, H-4).

SCHEME 22

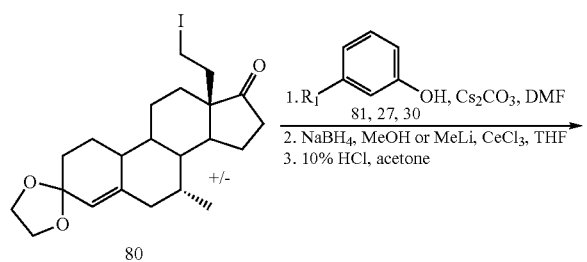

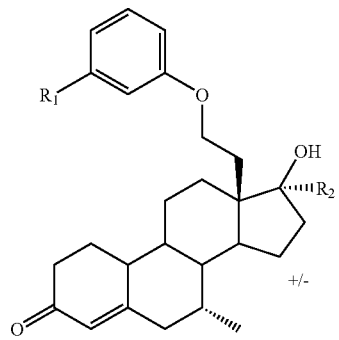

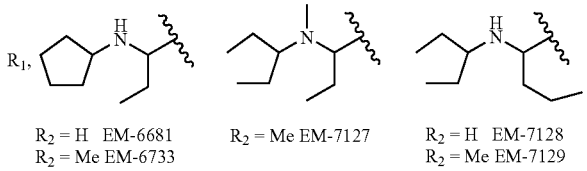

R$_2$ = H  EM-6681
R$_2$ = Me EM-6733

R$_2$ = Me EM-7127

R$_2$ = H  EM-7128
R$_2$ = Me EM-7129

Preparation of EM-6681, EM-6733, EM-7127, EM-7128 and EM-7129

All theses amines were prepared from racemic iodo 80 and the corresponding phenols according to the procedure for the synthesis of EM-6680 and EM-6902.

EM-6681 (from phenol 81 synthesized from described procedure of scheme 42, 19 mg, 43%). $^1$H NMR (400 MHz, acetone-d$_6$) δ: 0.81 (d, J=7.2 Hz, 3H, Me-7α), 0.83 (t, J=7.7 Hz, 3H, Me), 2.88 (m, 1H, —CHN—), 3.52 (t, J=6.4 Hz, 1H, —CHN—), 3.81 (t, J=8.5 Hz, 1H, H-17α), 4.11 (m, 1H, —CH$_2$O—), 4.54 (m, 1H, —CH$_2$O—), 5.74 (s, 1H, H-4), 6.81 (d, J=8.2 Hz, 1H, Ar), 6.88 (d, J=7.5 Hz, 1H, Ar), 7.01 (s, 1H, Ar), 7.22 (dd, J=7.3 Hz and 8.2 Hz, 1H, Ar).

EM-6733 (from phenol 81, 12.5 mg, 44%). $^1$H NMR (400 MHz, MeOH-d$_4$) δ: 0.75 (t, J=7.3 Hz, 3H, Me), 0.83 (d, J=7.1 Hz, 3H, Me-7α), 1.27 (s, 3H, Me-17α), 2.85 (m, 1H, —CHN), 3.55 (m, 1H, —CHN), 4.10 (m, 1H, —CH$_2$O—), 4.45 (m, 1H, —CH$_2$O—), 5.83 (s, 1H, H-4), 6.85 (m, 2H, Ar), 6.93 (s, 1H, Ar), 7.24 (t, J=7.8 Hz, 1H, Ar).

EM-7127 (from phenol 27, 18 mg, 39%). $^1$H NMR (400 MHz, MeOH-d$_4$) δ: 0.68 (m, 3H, Me), 0.82 (m, 9H, 3Me), 1.27 (s, 3H, Me-17α), 2.17 (bs, 3H, N-Me), 3.42 (m, 1H, —CHN—), 4.07 (m, 1H, —CH$_2$O—), 4.56 (m, 1H, —CH$_2$O—), 5.83 (s, 1H, H-4), 6.85 (m, 2H, Ar), 6.91 (s, 1H, Ar), 7.19 (t, J=7.8 Hz, 1H, Ar).

EM-7128 (from phenol 30, 13.3 mg, 43%). $^1$H NMR (400 MHz, MeOH-d$_4$) δ: 0.83 (m, 9H, 3Me), 0.89 (t, J=7.4 Hz, 3H, Me), 3.42 (m, 1H, —CHN—), 3.76 (t, J=8.5 Hz, 1H, H-17α), 4.12 (m, 1H, —CH$_2$O—), 4.45 (m, 1H, —CH$_2$O—), 5.83 (s, 1H, H-4), 6.84 (d, J=7.6 Hz, 2H, Ar), 6.92 (s, 1H, Ar), 7.23 (t, J=7.7 Hz, 1H, Ar).

EM-7129 (from phenol 30, 14 mg, 29%). $^1$H NMR (400 MHz, MeOH-d$_4$) δ: 0.82 (m, 9H, 3Me), 0.89 (t, J=7.4 Hz, 3H, Me), 1.27 (s, 3H, Me-17α), 3.65 (m, 1H, —CHN—), 4.08 (m, 1H, —CH$_2$O—), 4.46 (m, 1H, —CH$_2$O—), 5.83 (s, 1H, H-4), 6.83 (d, J=7.8 Hz, 2H, Ar), 6.91 (s, 1H, Ar), 7.22 (t, J=7.8 Hz, 1H, Ar).

SCHEME 23

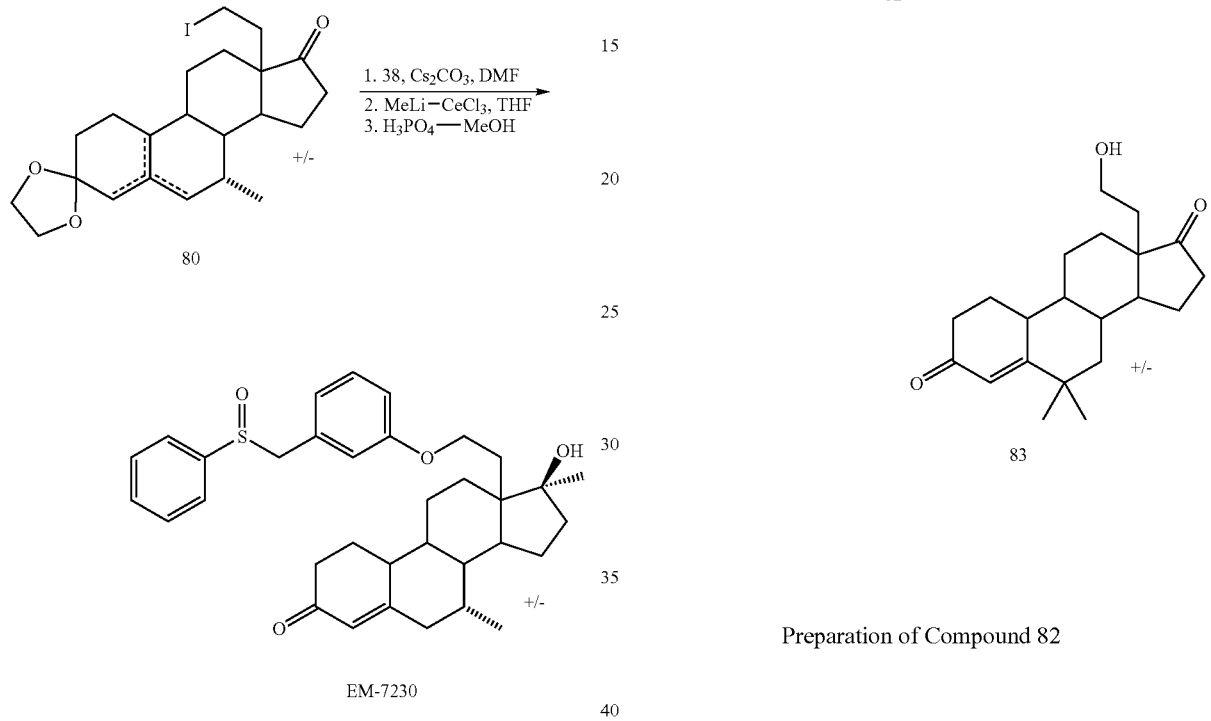

EM-7230

Preparation of EM-7230

This compound was prepared in three steps from 80 as described for EM-6902. $^1$H NMR (400 MHz, acetone-d$_6$) δ: 0.82 (d, 3H, J=7.1 Hz, C7-CH$_3$), 1.28 (s, 3H, C17-CH$_3$), 3.90-4.20 (m, 3H, ArCH$_2$, OCH$_2$), 4.45-4.55 (m, 1H, OCH$_2$), 5.75 (br.s, 1H, C4-H), 6.62-6.92 (m, 3H, Ar—H), 7.12-7.20 (m, 1H, Ar—H), 7.48-7.60 (m, 5H, S(O)Ph).

Example VIII

Synthesis of (+/−)-6,6-dimethyl-19-nortestosterone Derivatives

This procedure is described in Schemes 24 and 25

SCHEME 24

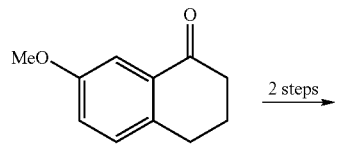

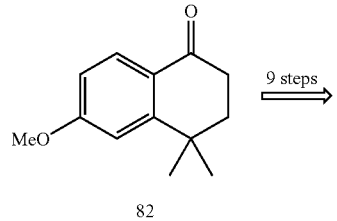

Preparation of Compound 82

Compound 82 (27.6 g, 0.14 mol) was prepared from commercially available 7-methoxy-1-tetralone (26.5 g, 0.15 mol) in 2 steps (87% crude) according to U.S. Pat. No. 6,313,107 patent procedure. The crude compound was used in the next step without further purification. $^1$H NMR (400 MHz, CDCl$_3$) δ: 1.39 (s, 6H), 2.02 (t, J=6.9 Hz, 2H), 2.70 (t, J=6.9 Hz, 3H), 3.89 (s, 3H), 6.84 (m, 1H), 6.89 (m, 1H), 8.04 (m, 1H).

Preparation of Compound 83

Compound 83 was prepared from tetralone 82 (27.6 g, 0.14 mol) in 9 steps using the described procedure for compound 55. The crude compound was purified by flash chromatography (silica gel, 10-70% acetone in hexanes) to give 4.1 g (9%, 9 steps) of alcohol 83. $^1$H NMR (400 MHz, CDCl$_3$) δ: 1.17 (s, 3H), 1.18 (s, 3H), 3.80 (m, 2H), 5.99 (m, 1H).

SCHEME 25

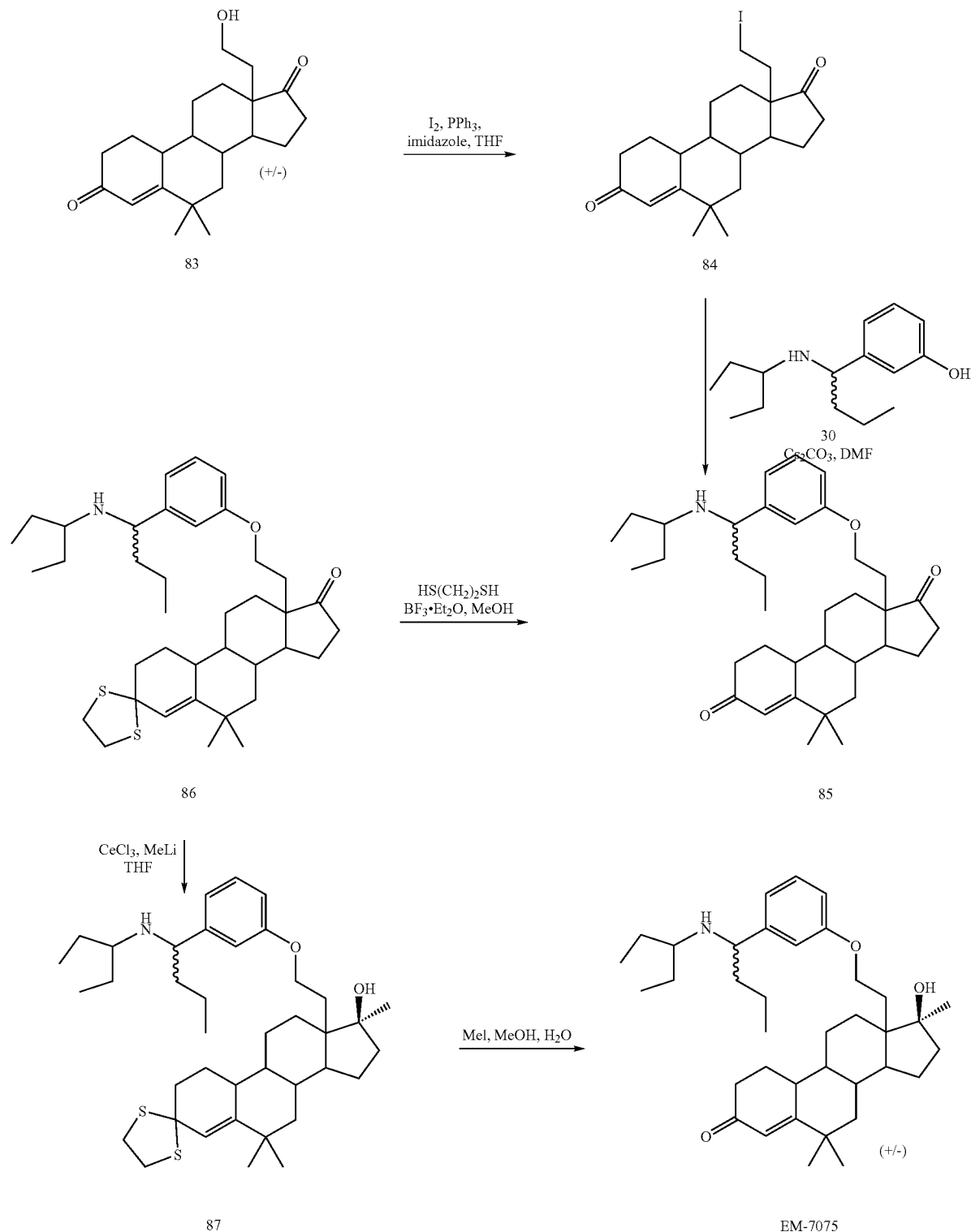

Preparation of Compound 84

Compound 84 was prepared from 83 (310 mg, 0.94 mmol) using the procedure described for compound 57. The crude compound was purified by flash chromatography (silica gel, 1-15% acetone in hexanes) to give 330 mg (80%) of pure iodide 84. $^1$H NMR (400 MHz, acetone-$d_6$) δ: 1.19 (s, 3H), 1.24 (s, 3H), 2.96 (m, 1H), 3.24 (m, 1H), 5.84 (m, 1H).

Preparation of Compound 85

Compound 85 was prepared from iodide 84 (170 mg, 0.39 mmol) and phenol 30 (170 mg, 0.80 mmol) (prepared by using the described procedure in scheme 42) using the described procedure for compound 28. The crude compound was purified by reverse-phase column chromatography (30-0% $H_2O$ in MeOH) to give 77 mg (36%) of pure 85. $^1$H NMR (400 MHz, acetone-$d_6$) δ: 0.80-0.89 (m, 9H), 1.19 (s, 3H), 1.25 (s, 3H), 3.70 (t, J=6.9 Hz, 1H), 3.88 (m, 1H), 4.03 (m, 1H), 5.86 (m, 1H), 6.74 (m, 1H), 6.91 (m, 2H), 7.21 (t, J=7.9 Hz, 1H).

Preparation of Compound 86

To a solution of compound 85 (77 mg, 0.14 mmol) in 10 mL of anhydrous methanol were added 1,2-ethanedithiol (11.7 μL, 0.14 mmol) and $BF_3.Et_2O$ (53.4 μL, 0.42 mmol). The mixture was stirred at room temperature for 2 h. After completion of the reaction, as judged by TLC, 2.0 mL of a NaOH (10%) solution were added and the solvent was evaporated. The crude mixture was dissolved in EtOAc, washed with $H_2O$, brine, and dried over $MgSO_4$. The crude compound was purified by flash chromatography (silica gel, 0-10% MeOH in $CH_2Cl_2$) to give 35 mg (36%) of thioketal 86. $^1$H NMR (400 MHz, acetone-$d_6$) δ: 0.80-0.89 (m, 9H), 1.12 (s, 3H), 1.13 (s, 3H), 3.17-3.41 (m, 4H), 3.70 (t, J=6.9 Hz, 1H), 3.88 (m, 1H), 4.03 (m, 1H), 5.68 (s, 1H), 6.74 (m, 1H), 6.91 (m, 2H), 7.21 (t, J=7.9 Hz, 1H).

Preparation of Compound EM-7075

Compound 87 was prepared from thioketal 86 (35 mg, 0.05 mmol) using the described procedure for compound EM-6902. The crude compound (35 mg) was used for the next step without further purification. The thioketal group, stable in acidic conditions, was then deprotected using MeI (1.0 mL, 16 mmol) in a MeOH/$H_2O$ (95:5) solution. The mixture was refluxed for 16 h. After completion of the reaction, as judged by TLC, the solvent was evaporated. The residue was diluted with saturated aqueous $NaHCO_3$ and extracted with EtOAc (3×). The combined organic layer was washed with $H_2O$, brine, and dried over $MgSO_4$. The crude compound was purified by reverse-phase chromatography (30-0% $H_2O$ in MeOH) to afford 15.4 mg (41%) of EM-7075. $^1$H NMR (400 MHz, acetone-$d_6$) δ: 0.80-0.89 (m, 9H), 1.16 (s, 3H), 1.22 (s, 3H), 1.26 (s, 3H), 3.70 (t, J=6.9 Hz, 1H), 3.76 (s, 1H), 4.09 (m, 1H), 4.57 (m, 1H), 5.83 (m, 1H), 6.79-7.17 (m, 3H), 7.20 (t, J=7.9 Hz, 1H).

Example IX

Synthesis of 19-nordihydrotestosterone Derivatives

This procedure is described in Schemes 26 to 30

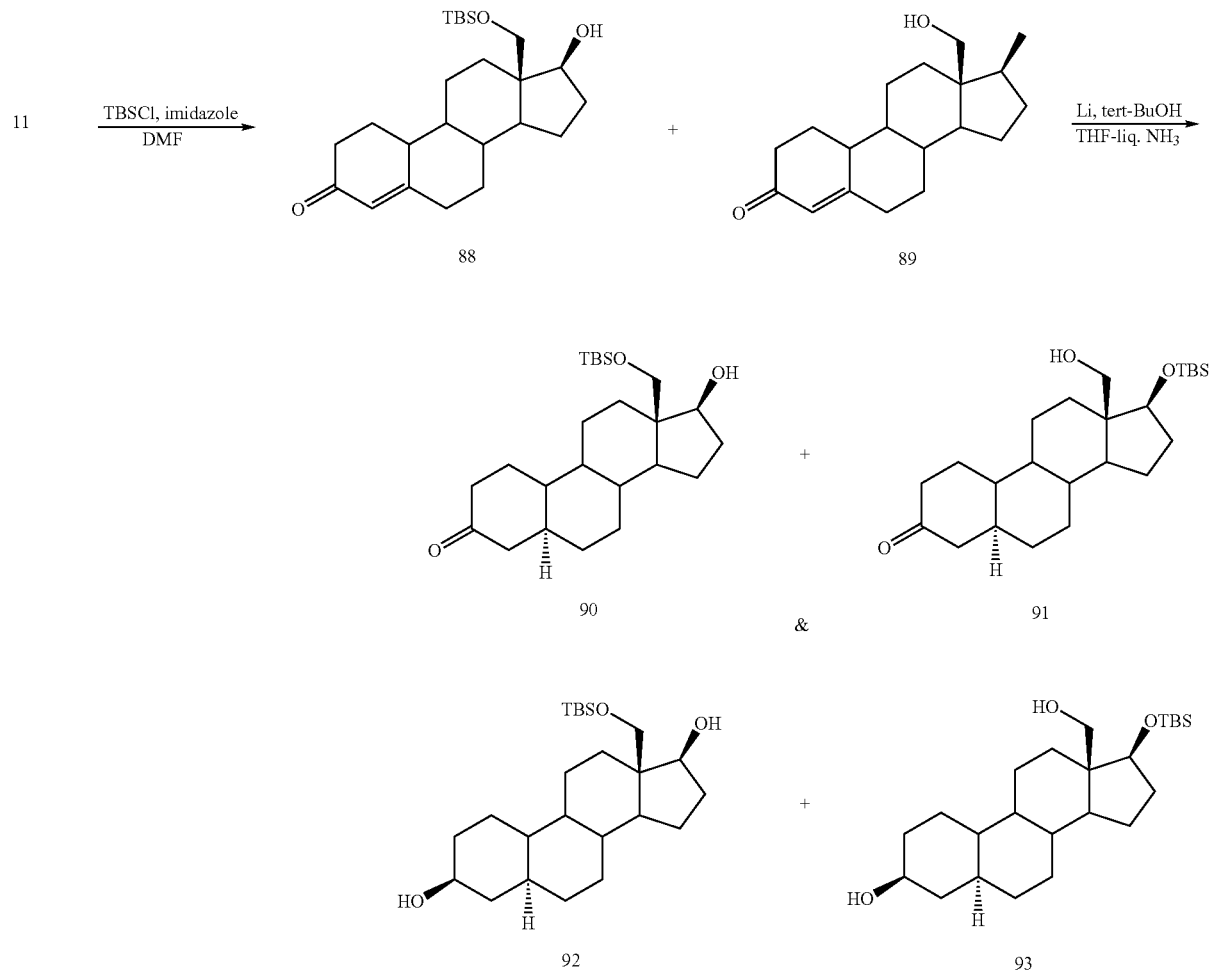

SCHEME 26

Preparation of the Mixture of 88+89

A solution of the crude diol 11 (4.82 g, <16.6 mmol) in 60 mL of DMF was cooled to 0° C. before the addition of imidazole (1.69 g, 24.8 mmol). Tert-butyldimethylsilyl chloride (3.25 g, 21.6 mmol) in DMF (15 mL) was added dropwise over 10 min. After an additional 40 min, the solution was diluted with 400 mL of EtOAc, and washed with 50 mL portions of 1N HCl (twice), saturated aqueous NaHCO$_3$, and brine. Drying over Na$_2$SO$_4$ and evaporation of the solvent gave an orange oil (7.35 g) composed mostly of isomer 88, together with some 89 and traces of diol 11.

Preparation of the Mixture of 90+91

Ammonia (ca. 200 mL) was condensed in a 500 mL, three-neck flask fitted with a dry-ice condenser and immersed in a dry-ice-acetone bath. Small (1-2 cm) portions of lithium wire (ca. 0.41 mol), rinsed in hexanes, were added to the liquid ammonia. After the addition was complete, the blue solution was allowed to stir for at least 5 min before the slow addition of the mixture containing 88 and 89 in THF (40 mL) and tert-butanol (16 mL, 0.17 mol). After completion of the reaction (1.5-2.5 h), as judged by TLC, the mixture was quenched and worked-up as described for compound 10. Flash chromatography of the crude product (20% EtOAc in hexanes) yielded 3.2 g of a mixture of 90 and 91 as a gum. Note: In some cases, over-reduction to alcohols 92 and 93 occurred, and these products were recycled as described below.

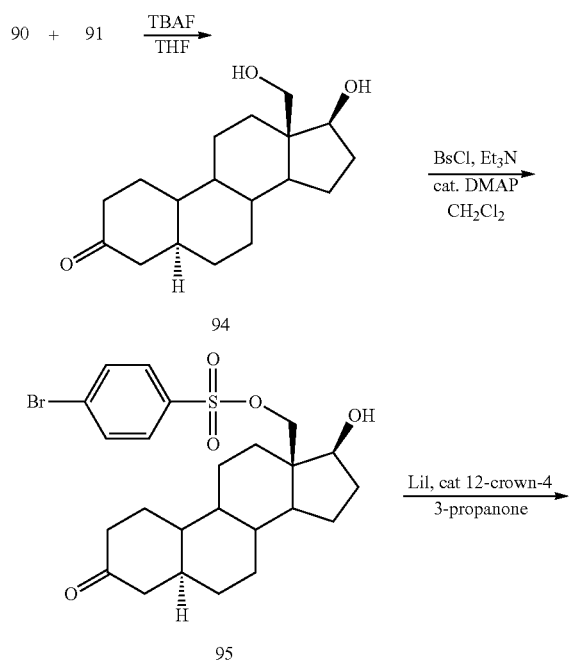

SCHEME 27

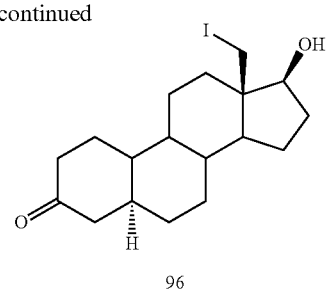

96

Preparation of Compound 29 from the Mixture of Compounds 90 and 91

The mixture of 90 and 91 (3.2 g, 7.9 mmol) was dissolved in 50 mL of THF. To this cold (0° C.) solution was added tetrabutylammonium fluoride (1M in THF, 9.5 mL, 9.5 mmol). After stirring for 20 min at 0° C., 100 mL of EtOAc was added, and the solution was washed twice with 1N HCl, then with saturated aqueous NaHCO$_3$, and with brine. Drying (Na$_2$SO$_4$) and evaporation of the solvent was followed by flash chromatography on silica gel (eluting with 30% acetone in toluene), resulting in 2.12 g of 94 as a white solid. $^1$H NMR (400 MHz, CDCl$_3$) δ: 3.74-3.99 (m, 3H, C17-H, C18-H$_2$); $^{13}$C NMR (100 MHz, CDCl$_3$) δ: 23.31, 25.14, 30.37, 30.50, 30.74, 31.09, 33.67, 40.84, 41.26, 43.65, 45.62, 45.67, 47.75, 48.54, 49.49, 60.54 (C18), 83.56 (C17), 211.97 (C3).

Preparation of Compound 95

To a cold (0° C.) solution of 2.12 g (7.25 mmol) of 94 in 150 mL of CH$_2$Cl$_2$ were added successively: triethylamine (1.6 mL, 11 mmol), 4-bromobenzenesulfonyl chloride (2.59 g, 10.1 mmol), and 4-(dimethylamino)pyridine (88 mg, 0.72 mmol). After 5 min, the cold bath was removed, and the solution was stirred at room temperature until complete reaction (ca. 3 h), as observed by TLC. The solution was then transferred quantitatively to a separatory funnel, and washed twice with water, 1N HCl, saturated aqueous NaHCO$_3$, and brine. Drying (Na$_2$SO$_4$) was followed by evaporation of the solvent. The crude product mixture containing mostly 95, with some of the 17β-OSO$_2$Ar isomer, was used directly in the next step. $^1$H NMR (400 MHz, CDCl$_3$) δ: 3.79 (t, 1H, J=8.6 Hz, C17-H), 4.11 (AB d, 1H, J=10.0 Hz, C18-H$_2$), 4.27 (AB d, 1H, J=10.0 Hz, C18-H$_2$), 7.64-7.92 (m, 4H, Ar—H).

Preparation of Compound 96

The mixture of the crude product 95, LiI (beads, 4.84 g, 36.2 mmol), and 12-crown-4 (0.12 mL, 0.74 mmol) in 3-pentanone (100 mL, bp 102° C.) was heated under reflux for 3 h; complete reaction was confirmed by TLC analysis. Most of the solvent was evaporated in vacuo, and the residue was taken up in 175 mL of EtOAc; this solution was washed with an aqueous 5% solution of sodium thiosulfate (2×15 mL), saturated aqueous NaHCO$_3$, and brine. Drying (Na$_2$SO$_4$) and stripping of the solvent gave a solid that was triturated with 30% EtOAc in hexanes. Compound 96 was obtained as a white solid weighing 1.458 g. More 96 was recovered from the mother liquor after flash chromatography on silica gel (40% EtOAc in hexanes) and trituration as above, for a total yield of 1.49 g (22.5% overall yield from 8). $^1$H NMR (400 MHz, CDCl$_3$) δ: 3.34 (s, 2H, C18-H$_2$), 3.94 (t, 1H, J=8.5 Hz, C17-H).

Preparation of Compound 94 from the Mixture of Compounds 92 and 93

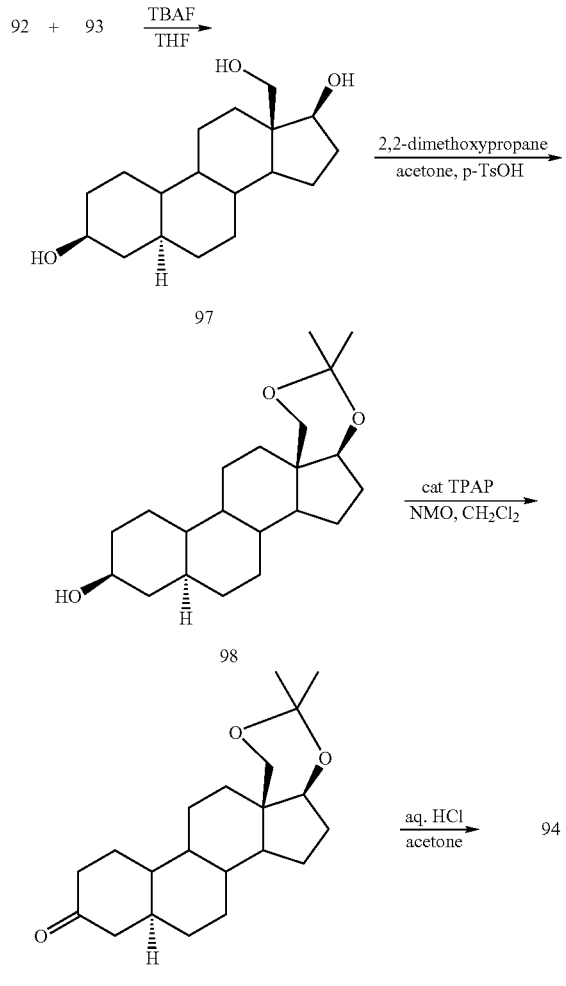

Preparation of Compound 97

The mixture of 92 and 93 in THF was treated with tetrabutylammonium fluoride as described above for the preparation of 94. Crude product 97 was used without purification. $^1$H NMR (400 MHz, CDCl$_3$+CD$_3$OD) δ: 3.48-3.62 (m, 1H, C3-H), 3.64-3.93 (m, 3H, C17-H, C18-H$_2$); $^{13}$C NMR (100 MHz, CDCl$_3$+CD$_3$OD) δ: 23.07, 24.84, 28.26, 30.18, 30.56, 30.97, 33.18, 35.29, 40.98, 41.04, 42.84, 45.18, 45.99, 47.92, 49.50, 60.45 (C18), 70.07 (C3), 83.17 (C17).

Preparation of Compound 98

Protection of diol 97 to acetonide 98 was carried out as described for the synthesis of 9. Compound 98 was purified by flash chromatography on silica gel, using 20%-40% EtOAc in hexanes as eluent. $^1$H NMR (400 MHz, CDCl$_3$) δ: 1.37 (s, 3H, CH$_3$), 1.40 (s, 3H, CH$_3$), 3.52-3.73 (m, 3H, C3-H, C18-H$_2$), 3.86-3.93 (m, 1H, C17-H).

Preparation of Compound 99

To a solution of 98 (1.94 g, 5.80 mmol) in 50 mL of CH$_2$Cl$_2$ were added 4 Å molecular sieves (activated, powdered, 2.9 g, 0.50 g/mmol of substrate) and 4-methylmorpholine N-oxide (2.04 g, 17.4 mmol). The solution was cooled to 0° C., and tetrapropylammonium perruthenate (102 mg, 0.29 mmol) was added. After a few minutes, the cold bath was removed and the mixture was stirred at room temperature for 1 h. Filtration over Celite and flash chromatography (silica gel, 30% EtOAc in hexanes) gave 1.76 g (91%) of 99. $^1$H NMR (400 MHz, CDCl$_3$) δ: 1.38 (s, 3H, CH$_3$), 1.40 (s, 3H, CH$_3$), 3.61-3.73 (m, 2H, C18-H$_2$), 3.89-3.96 (m, 1H, C17-H).

Preparation of Compound 94 from 99

Treatment of acetonide 99 (1.86 g, 5.59 mmol), dissolved in 50 mL of acetone, with 5 mL of 1N HCl over 2 h at room temperature gave, after the work-up described for 11 and purification by flash chromatography (20%-30% acetone in toluene), 1.26 g (77%) of diol 94.

SCHEME 29

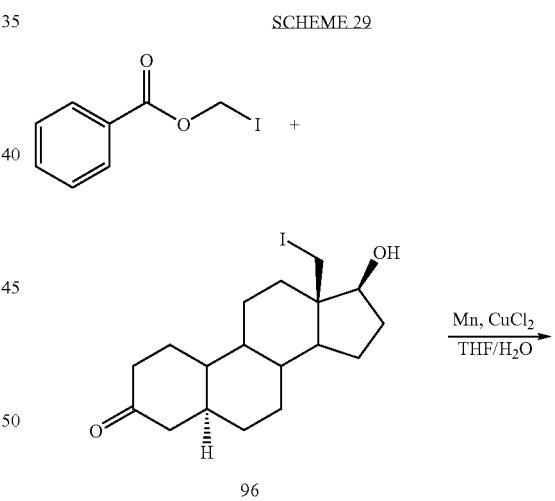

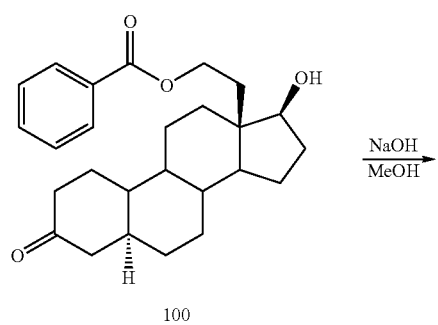

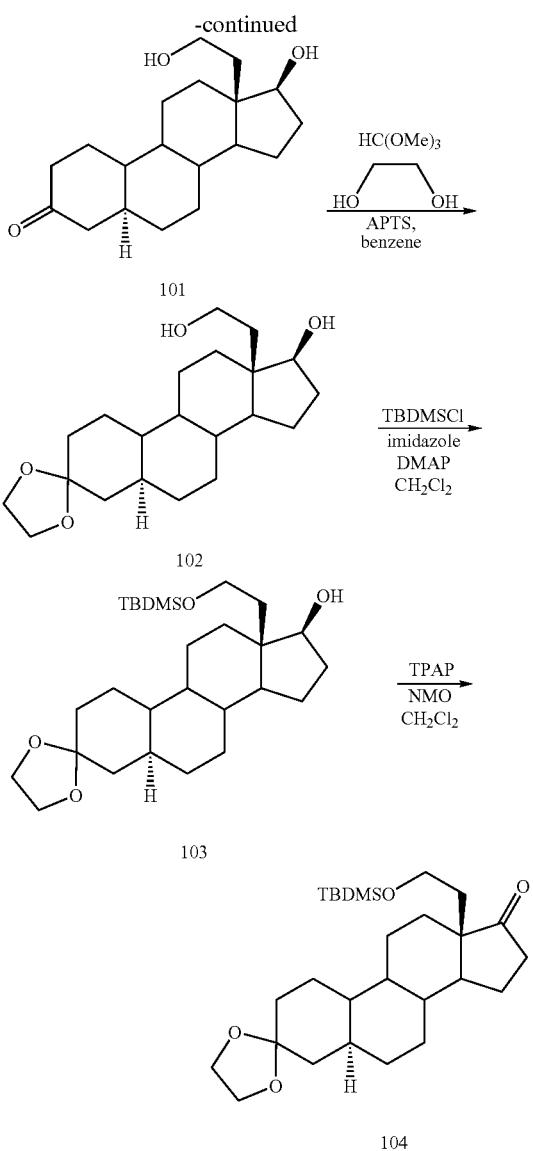

lated as by-products and characterized. $^1$H-NMR (400 MHz, CDCl$_3$) δ: 3.78 (t, 1H, J=8.4 Hz, 17-CHα), 4.39-4.43 (m, 1H, —CH$_2$—O—CO—Ar), 4.79-4.83 (m, 1H, —CH$_2$—O—CO—Ar), 7.42-7.50 (m, 2H, Ar—H), 7.57-7.61 (m, 1H, Ar—H), 8.08 (d, 2H, J=7.3 Hz, Ar—H) ppm.

4,5α-dihydro-18-(hydroxymethylene)-19-nortestosterone (101)

To a stirred solution of a mixture of 4,5α-dihydro-18-(benzoyloxymethylene)-19-nortestosterone (100) (234 mg, 0.57 mmol) and 19-norDHT in MeOH (10 mL), an aqueous solution of 3N NaOH (570 μL, 1.71 mmol) was added at room temperature. Stirring was continued for 16 h, then the MeOH was evaporated and the residue was dissolved in AcOEt. The organic phase was washed with H$_2$O (2×), brine, dried over Na$_2$SO$_4$, and filtered. The solvent was removed and the residue purified by flash chromatography over silica gel, by graduate elution with 10% Acetone/Hex. to 40% Acetone/Hex., to give 141 mg of diol 101 (81% yield) and 140 mg of 19-norDHT. $^1$H-NMR (400 MHz, CDCl$_3$) δ: 3.14 (br s, 2H, 2×—OH), 3.72 (t, 1H, J=8.7 Hz, 17-CHα), 3.77-3.80 (m, 2H, —CH$_2$—OH) ppm.

4,5α-dihydro-3,3-(ethylenedioxy)-18-(hydroxymethylene)-19-nortestosterone (102)

To a stirred solution of 4,5α-dihydro-18-(hydroxymethylene)-19-nortestosterone (101) (96 mg, 0.31 mmol) in anhydrous benzene (12 mL), ethylene glycol (700 μL, 12.5 mmol), trimethylorthoformate (105 μL, 0.94 mmol), and PTSA (6 mg, 0.03 mmol) were added at room temperature. Stirring was continued for 90 min, then the mixture was quenched with a saturated NaHCO$_3$ aqueous solution and diluted with CH$_2$Cl$_2$. The organic phase was washed with H$_2$O (3×), brine, dried over Na$_2$SO$_4$, and filtered. The solvent was removed and the residue purified by flash chromatography over silica gel, by graduate elution with 10% Acetone/CHCl$_3$ to 40% Acetone/CHCl$_3$ with 0.5% Et$_3$N, to give 90 mg of the acetal-diol 102 (82% yield) as a white solid. $^1$H-NMR (400 MHz, CDCl$_3$) δ: 2.30 (br s, 2H, 2×—OH), 3.73 (t, 1H, J=8.7 Hz, 17-CHα), 3.72-3.80 (m, 2H, —CH$_2$—OH), 3.958 (s, 2H, —CH$_2$—O-ketal), 3.963 (s, 2H, —CH$_2$—O-ketal) ppm; IR (KBr) 3200-3350 (—OH) cm$^{-1}$.

4,5α-dihydro-3,3-(ethylenedioxy)-18-(tert-butyldimethylsilyloxymethylene)-19-nortestosterone (103)

To a stirred solution of 4,5α-dihydro-3,3-(ethylenedioxy)-18-(hydroxymethylene)-19-nortestosterone (102) (85 mg, 0.24 mmol) in anhydrous dichloromethane (3 mL), imidazole (50 mg, 0.73 mmol), 4-(dimethylamino)pyridine (30 mg, 0.24 mmol), and tert-butyldimethylsilyl chloride (50 mg, 0.31 mmol) were added at room temperature. Stirring was continued for 30 min, then the mixture was diluted with AcOEt. The organic phase was washed with H$_2$O (5×), brine, dried over Na$_2$SO$_4$, and filtered. The solvent was removed and the obtained white solid was used in the next step without purification. $^1$H-NMR (400 MHz, CDCl$_3$) δ: 0.11 (s, 6H, 2×—CH$_3$), 0.93 (s, 9H, tert-butyl) 3.58 (t, 1H, J=8.2 Hz, 17-CHα), 3.76 (t, 2H, —CH$_2$—OTBDMS), 3.949 (s, 2H, —CH$_2$—O-ketal), 3.953 (s, 2H, —CH$_2$—O-ketal) ppm; IR (KBr) 3416 (17-βOH) cm$^{-1}$.

4,5α-dihydro-3,3-(ethylenedioxy)-18-(tert-butyldimethylsilyloxymethylene)-19-norandrostenedione (104)

To a stirred solution of 4,5α-dihydro-3,3-(ethylenedioxy)-18-(tert-butyldimethylsilyl-oxymethylene)-19-nortestoster- 4,5α-dihydro-18-(benzoyloxymethylene)-19-nortestosterone (100)

To 18-iodo-19-norDHT 96 (1085 mg, 2.69 mmol) dissolved in THF (35 mL), a solution of iodomethyl benzoate (3540 mg, 13.48 mmol) in THF (5 mL) was added at room temperature with stirring under argon. To this solution, H$_2$O (30 mL) and CuCl$_2$ (365 mg, 2.69 mmol) were added, and the system was purged 3 times with argon. Manganese (1500 mg, 26.9 mmol) was added in one portion. The reaction was left stirring for 24 h, then the mixture was filtered over Celite, the THF evaporated, and the aqueous phase diluted with AcOEt. The organic phase was washed with H$_2$O, brine, dried over Na$_2$SO$_4$, and filtered. The solvent was removed and the residue purified by flash chromatography over silica gel, by graduate elution with 5% AcOEt/Hex. to 30% AcOEt/Hex., to give 475 mg of a mixture of compound 100 and 19-norDHT. By $^1$H-NMR analysis, the composition of this mixture was 53% mol of product 100 (296 mg, 27% yield) and 47% mol of 19-norDHT (179 mg). The homo-coupling products of iodomethyl benzoate and 18-iodo-19-norDHT were also isoone (103) (125 mg, 0.27 mmol) in anhydrous dichloromethane (3 mL), powdered 4 Å molecular sieves (135 mg), 4-methylmorpholine N-oxide (95 mg, 0.80 mmol), and tetrapropylammonium perruthenate (10 mg, 0.02 mmol) were added at room temperature. Stirring was continued for 2 h, then the mixture was filtered over Celite and directly purified by flash chromatography over silica gel, by graduate elution with Hexanes to 20% AcOEt/Hexanes with 0.5% Et$_3$N, to give 87 mg of product 104 (70% yield). $^1$H-NMR (400 MHz, CDCl$_3$) δ: 0.043 (s, 3H, —CH$_3$), 0.050 (s, 3H, —CH$_3$), 0.89 (s, 9H, tert-butyl) 2.00-2.14 (m, 1H, 16-CH), 2.41-2.50 (m, 1H, 16-CH), 3.42-3.53 (m, 1H, —CH$_2$—OTBDMS), 3.58-3.65 (m, 1H, —CH$_2$—OTBDMS), 3.961 (s, 2H, —CH$_2$—O-ketal), 3.966 (s, 2H, —CH$_2$—O-ketal) ppm; IR (NaCl) 1736 (C=O) cm$^{-1}$.

SCHEME 30

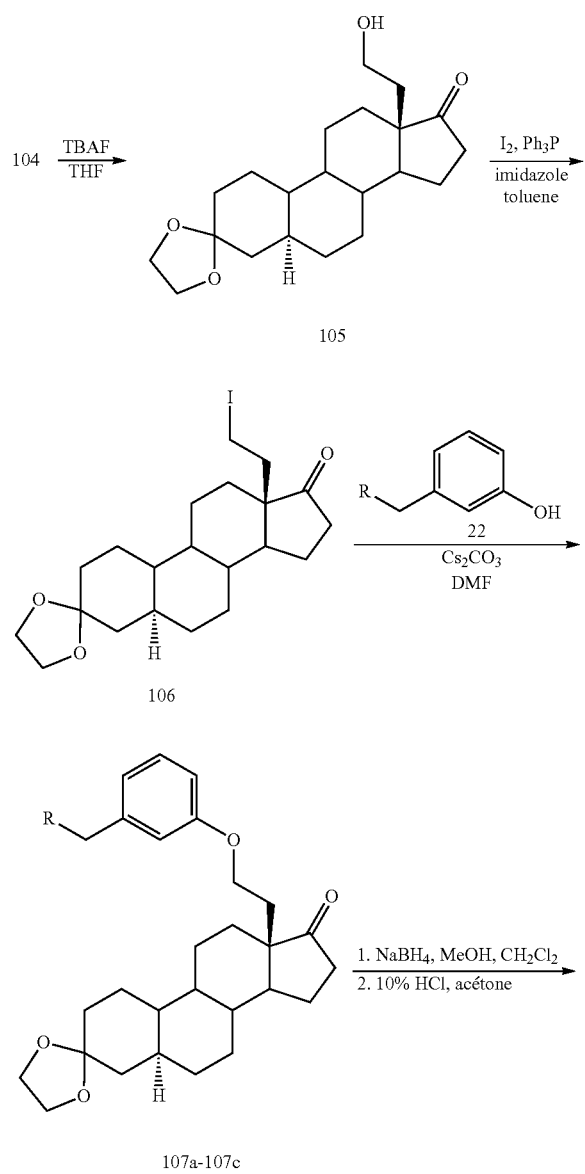

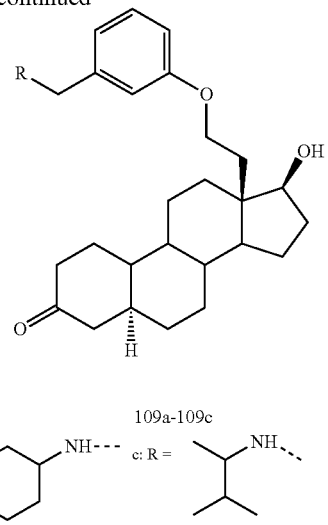

109a-109c

4,5α-dihydro-3,3-(ethylenedioxy)-18-(hydroxymethylene)-19-norandrostenedione (105)

To a stirred solution of 4,5α-dihydro-3,3-(ethylenedioxy)-18-(tert-butyldimethylsilyl-oxymethylene)-19-norandrostenedione (104) (99 mg, 0.21 mmol) in THF (3 mL), a 1M THF solution of tetrabutylammonium fluoride (640 µL, 0.64 mmol) was added at room temperature and refluxed for 50 min. Then, the mixture was cooled, diluted with dichloromethane, and the organic phase was washed with H$_2$O, brine, dried over Na$_2$SO$_4$, and filtered. The solvent was removed and the obtained white solid was purified by flash chromatography over silica gel, by graduate elution with 10% AcOEt/Hexanes to 40% AcOEt/Hexanes with 0.5% Et$_3$N, to give 64 mg of product 105 (86% yield) as a white solid. $^1$H-NMR (400 MHz, CDCl$_3$) δ: 2.02-2.15 (m, 1H, 16-CH), 2.42-2.54 (m, 1H, 16-CH), 3.68-3.86 (m, 2H, —CH$_2$—OH), 3.963 (s, 2H, —CH$_2$—O-ketal), 3.967 (s, 2H, —CH$_2$—O-ketal) ppm; IR (KBr) 3387 (—OH) cm$^{-1}$; LRMS calc. for C$_{21}$H$_{32}$O$_4$ 348.48, found [M+H]+349.2 m/z.

4,5α-dihydro-3,3-(ethylenedioxy)-18-(iodomethylene)-19-norandrostenedione (106)

To a stirred solution of 4,5α-dihydro-3,3-(ethylenedioxy)-18-(hydroxymethylene)-19-norandrostenedione (105) (43 mg, 0.12 mmol) in anhydrous toluene (3 mL), imidazole (42 mg, 0.62 mmol), Ph$_3$P (98 mg, 0.37 mmol), and iodine (88 mg, 0.34 mmol) were added at room temperature and heated for 25 min at 70° C. Then, the mixture was cooled, diluted with AcOEt, and the organic phase was washed with a 5% aqueous Na$_2$S$_2$O$_3$ solution, H$_2$O, brine, dried over Na$_2$SO$_4$, and filtered. The solvent was removed and the obtained white solid was purified by flash chromatography over silica gel, by graduate elution with 5% AcOEt/Hexanes to 20% AcOEt/Hexanes with 0.5% Et$_3$N, to give 51 mg of product 106 (90% yield) as a white solid. $^1$H-NMR (400 MHz, CDCl$_3$) δ: 2.02-2.15 (m, 1H, 16-CH), 2.42-2.54 (m, 1H, 16-CH), 2.90-3.00 (m, 1H, —CH$_2$—I), 3.08-3.18 (m, 1H, —CH$_2$—I), 3.961 (s, 2H, —CH$_2$—O-ketal), 3.967 (s, 2H, —CH$_2$—O-ketal) ppm.

4,5α-dihydro-3,3-(ethylenedioxy)-18-(piperidine-N-benzyl-3'-oxymethylene)-19-norandrostenedione (107a)

To a stirred solution of N-(3-hydroxybenzyl)piperidine (22b) (13 mg, 0.065 mmol) in DMF (0.5 mL), Cs$_2$CO$_3$ (43 mg, 0.13 mmol) was added and heated at 70° C. for 15 min. Then, a solution of 4,5α-dihydro-3,3-(ethylenedioxy)-18-(iodomethylene)-19-norandrostenedione (106) (15 mg, 0.032 mmol) in DMF (1 mL) was slowly added, and the mixture heated for 2 h at 70° C. Then, the cooled mixture was diluted with AcOEt, and the organic phase was washed with aqueous NaHCO$_3$ solution, H$_2$O, brine, dried over Na$_2$SO$_4$, and filtered. The solvent was removed and the obtained white solid was purified by flash chromatography over silica gel, by graduate elution with 10% acetone/Hexanes to 30% acetone/Hexanes with 0.5% Et$_3$N, to give 12 mg of product 107a (70% yield) as a white solid. 2 mg of alkene was also isolated. $^1$H-NMR (400 MHz, acetone-d$_6$) δ: 2.34 (br s, 4H, 2×α-CH$_2$— of piperidine), 2.48-2.60 (m, 1H, 16-CH), 3.39 (s, 2H, Ar—CH$_2$—), 3.78-3.92 (m, 1H, —CH$_2$—O—Ar), 3.89 (s, 4H, 2×—CH$_2$—O-ketal), 3.94-4.02 (m, 1H, —CH$_2$—O—Ar), 6.68-6.74 (m, 1H, Ar—H), 6.83-6.90 (m, 2H, Ar—H), 7.14-7.22 (m, 1H, Ar—H) ppm.

4,5α-dihydro-3,3-(ethylenedioxy)-18-(piperidine-N-benzyl-3'-oxymethylene)-19-nortestosterone (108a)

To a ice cooled solution of 4,5α-dihydro-3,3-(ethylenedioxy)-18-(piperidine-N-benzyl-3'-oxymethylene)-19-norandrostenedione (107a) (12 mg, 0.023 mmol) in a mixture of MeOH (2 mL) and dichloromethane (1 mL), NaBH$_4$ (2 mg, 0.05 mmol) was added. The mixture was allowed to warm to room temperature and stirred for 1 h. Then, the clear solution was diluted with dichloromethane, and the organic phase was washed with an aqueous NaHCO$_3$ solution, H$_2$O, brine, dried over Na$_2$SO$_4$, and filtered. The solvent was removed, and the obtained crude compound 108a (12 mg) was used in the next step without purification.

4,5α-dihydro-18-(piperidine-N-benzyl-3'-oxymethylene)-19-nortestosterone (109a)

To a stirred solution of 4,5α-dihydro-3,3-(ethylenedioxy)-18-(piperidine-N-benzyl-3'-oxymethylene)-19-nortestosterone (108a) (12 mg, 0.023 mmol) in acetone (2 mL), a 1M solution of hydrochloric acid (600 μL) was added at room temperature and stirred for 2 h. Then, the mixture was diluted with dichloromethane, and the organic phase was washed with aqueous NaHCO$_3$ solution (2×), H$_2$O (2×), brine, dried over Na$_2$SO$_4$, and filtered. The solvent was removed and the obtained crude compound 109a (10 mg, 91% yield) was submitted for biological test without purification. $^1$H-NMR (300 MHz, CD$_3$OD) δ: 3.54 (s, 2H, Ar—CH$_2$—), 3.72 (t, 1H, J=8.7 Hz, 17-CHα), 4.02-4.14 (m, 1H, —CH$_2$—O—Ar), 4.38-4.50 (m, 1H, —CH$_2$—O—Ar), 6.84-6.90 (m, 2H, Ar—H), 6.91-6.97 (m, 1H, Ar—H), 7.20-7.29 (m, 1H, Ar—H) ppm.

4,5α-dihydro-3,3-(ethylenedioxy)-18-(cyclohexylamine-N-benzyl-3'-oxymethylene)-19-norandrostenedione (107b)

Compound 107b was prepared according to compound 107a procedure using N-(3-hydroxybenzyl)-cyclohexylamine (22a). Compound 107b was obtained in 57% yield as a white solid. $^1$H-NMR (300 MHz, CD$_3$OD) δ: 3.73 (s, 2H, Ar—CH$_2$—), 3.80-3.91 (m, 1H, —CH$_2$—O—Ar), 3.90 (s, 4H, 2×—CH$_2$—O-ketal), 3.92-4.02 (m, 1H, —CH$_2$—O—Ar), 6.70-6.78 (m, 1H, Ar—H), 6.82-6.91 (m, 2H, Ar—H), 7.13-7.22 (m, 1H, Ar—H) ppm.

4,5α-dihydro-3,3-(ethylenedioxy)-18-(cyclohexylamine-N-benzyl-3'-oxymethylene)-19-nortestosterone (108b)

Compound 108b was prepared according to compound 108a procedure.

4,5α-dihydro-18-(cyclohexylamine-N-benzyl-3'-oxymethylene)-19-nortestosterone (109b)

Compound 109b was prepared according to compound 109a procedure and obtained in quantitative yield. $^1$H-NMR (300 MHz, CD$_3$OD) δ: 3.72 (t, 1H, J=8.6 Hz, 17-CHα), 3.79 (s, 2H, Ar—CH$_2$), 4.00-4.13 (m, 1H, —CH$_2$—O—Ar), 4.38-4.48 (m, 1H, —CH$_2$—O—Ar), 6.82-6.91 (m, 2H, Ar—H), 6.92-6.99 (m, 1H, Ar—H), 7.19-7.28 (m, 1H, Ar—H) ppm.

4,5α-dihydro-3-,3-(ethylenedioxy)-18-(1',2'-dimethylpropylamine-N-benzyl-3"-oxy-methylene)-19-norandrostenedione (107c)

Compound 107c was prepared according to compound 107a procedure using N-(3'-hydroxybenzyl)-1,2-dimethylpropylamine (obtained from 1,2-dimethylpropylamine and 3-hydroxybenzylalcohol). The obtained compound 107c was contaminated with some aminophenol. $^1$H-NMR (300 MHz, CD$_3$OD) δ: 0.87 (d, 3H, J=6.7 Hz, —CH$_3$), 0.89 (d, 3H, J=6.8 Hz, —CH$_3$), 1.00 (d, 3H, J=6.3 Hz, —CH$_3$), 2.43-2.54 (m, 1H, CH$_3$—CH—NH—), 3.58-3.80 (m, 4H, —CH$_2$—O—Ar and ArCH$_2$—), 3.90 (s, 4H, 2×—CH$_2$—O-ketal), 6.64-6.70 (m, 1H, Ar—H), 6.73-6.82 (m, 1H, Ar—H), 7.10-7.19 (m, 1H, Ar—H) ppm.

4,5α-dihydro-3,3-(ethylenedioxy)-18-(1',2'-dimethylpropylamine-N-benzyl-3"-oxy-methylene)-19-nortestosterone (108c)

Compound 108c was prepared according to compound 108a procedure.

4,5α-dihydro-18-(1',2'-dimethylpropylamine-N-benzyl-3"-oxymethylene)-19-nortestosterone (109c)

Compound 109c was prepared according to compound 109a procedure. The crude compound 109c was purified by reverse phase chromatography with 2-2-1 CH$_3$CN-MeOH—H$_2$O as eluant to give the desired product (50% yield) as a white solid. $^1$H-NMR (300 MHz, CD$_3$OD) δ: 0.88 (d, 3H, J=6.9 Hz, —CH$_3$), 0.90 (d, 3H, J=6.8 Hz, —CH$_3$), 1.01 (d, 3H, J=6.4 Hz, —CH$_3$), 2.46-2.58 (m, 1H, CH$_3$—CH—NH—), 3.60-3.78 (m, 1H, 17-CHα), 4.01-4.17 (m, 1H, —CH$_2$—O—Ar), 4.38-4.47 (m, 1H, —CH$_2$—O—Ar), 6.80-6.90 (m, 2H, Ar—H), 6.91-6.98 (m, 1H, Ar—H), 7.19-7.28 (m, 1H, Ar—H) ppm.

Example X
Synthesis of Dihydrotestosterone Derivatives
This procedure is described in Scheme 31
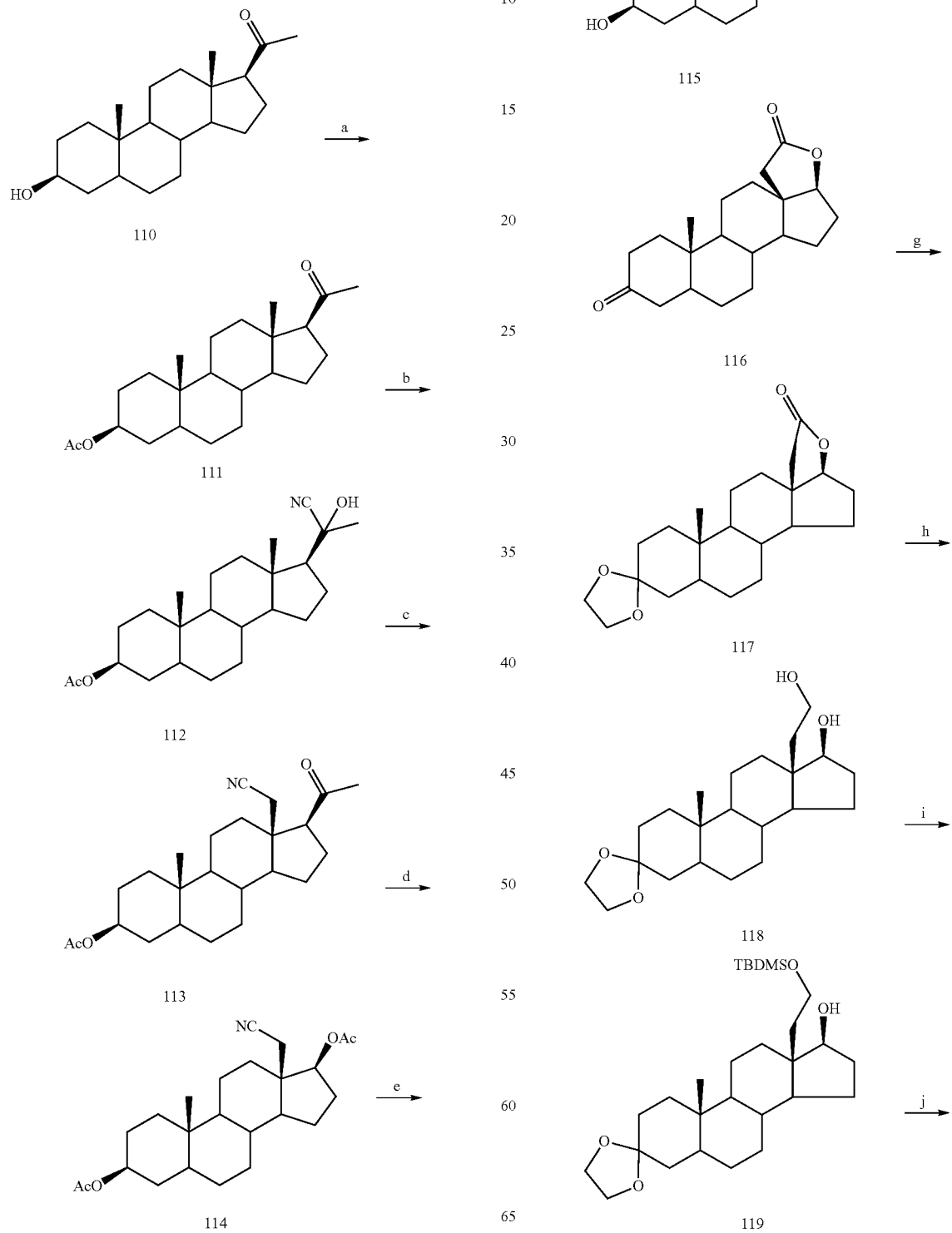
SCHEME 31

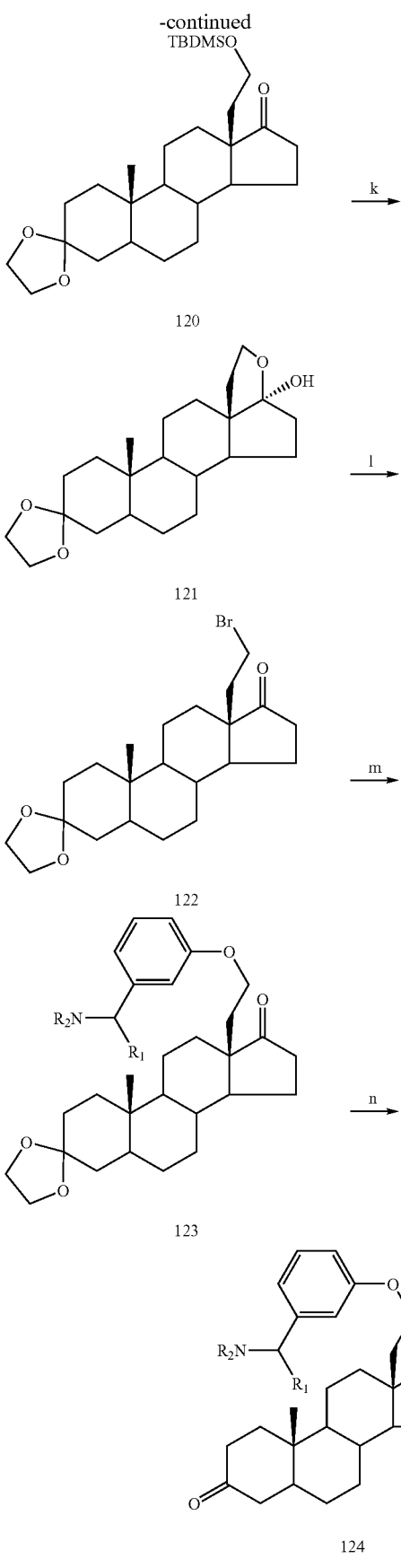

Conditions:

a) Ac₂O, pyridine; b) 1) TMSCN, ZnI₂, CH₂Cl₂, 2) 10% HCl, acetone; c) Pb(OAc)₄, CaCO₃, I₂, hn, cyclohexane/benzene; d) m-CPBA, 1,2-dichloroethane, 50° C.; e) 1) NaOMe, MeOH, 2) 10% HCl; f) Jone's reagent, acetone; g) HC(OMe)₃, TsOH, (CH₂OH)₂/benzene; h) LAH, THF; i) TBDMSCl, Et₃N, DMAP, DCM; j) TPAP, N-Me-morpholine-N-oxide, DCM; k) TBAF, THF; l) Ph₃P, CBr₄, DCM; m) sub-phenol, Cs₂CO₃, DMF or actone; n) 1) NaBH₄, MeOH, 0° C.-rt, 2) 10% aq HCl, acetone, rt 3β-Acetoxy-5α-pregnan-20-one (111)

To a stirred suspension of 5α-pregnan-3β-ol-20-one (110) (200 g; 0.628 mol) in pyridine (1750 mL) was added acetic anhydride (593 mL; 6.28 mol). Solid was dissolved after 2 hours and the reaction was left for overnight at room temperature. The reaction mixture was diluted with diethyl ether (5 L) and transferred into a 12 L separatory funnel. The mixture was stirred, while 10% HCl (150 mL) was added by careful monitoring of temperature (maximum temp 35° C.) by an ice bath. The organic layer was washed with ice cold 10% HCl (8×500 mL), with saturated NaHCO₃, dried (MgSO₄) and concentrated under reduced pressure. The pale yellow solid was dried at 40° C. overnight to give the 3-acetylated compound 111 (223 g; 99%). ¹H NMR (300 MHz, CDCl₃) δ: 0.58(s, 3H), 0.81(s, 3H), 2.01(s, 3H), 2.10(s, 3H), 2.51(t, 1H, J=9 Hz), 4.67(sept, 1H, J=5 Hz).

3β-Acetoxy-5α-pregnan-20-cyano-20-ol (112)

To a cooled solution (0° C.) of compound 111 (223 g; 0.619 mol) in CH₂Cl₂ (4 L) were added ZnI₂ (9.89 g; 0.031 mol), followed by TMSCN (165 mL; 1.238 mol). The reaction was allowed to warm to room temperature and TLC revealed the completion of the reaction in 1 h30. The volatile substances were removed under reduced pressure (to avoid a two phase system during hydrolysis) and the residue was dissolved in 3 L of acetone and 500 mL of 10% HCl. After 1 hour, 4 L of ice water were added with a strong agitation. The precipitate was recovered by filtration and dried under reduced pressure to give cyanohydrin 112 (232 g; 97%). ¹H NMR (300 MHz, CDCl₃) δ: 0.83(s, 3H), 0.99(s, 3H), 1.61(s, 3H), 2.01(s, 3H), 4.67(sept, 1H, J=5 Hz).

3β-Acetoxy-5α-pregnan-18-cyano-20-one (113)

Cyanohydrin 112 (15 g; 0.039 mol) was partially dissolved in cyclohexane (1 L) and benzene (500 mL) in a 5 L three necked R.B. flask equipped with condensers. The mixture was deoxygenated for 15 minutes with argon. Then, calcium carbonate (11.6 g; 0.116 mol), lead tetraacetate (34.3 g; 0.077 mol) and iodine (9.8 g; 0.039 mol) were added successively and the mixture was irradiated with two 250 W IR lamps. The purple reaction mixture was primarly heated directly with a heat gun until temperature reached to 50° C. Reaction was complete in 1 hr. The reaction mixture was cooled with 700 mL of ice water, diluted with EtOAc (1 L) and transferred in a 6 L funnel. The organic layer was washed with water (2×500 mL), with 5% sodium thiosulfate solution (1×500 mL), with brine (1×500 mL), dried and concentrated in reduced pressure. The residue was purified by flash chromatography over silica gel (hex:EtOAc; 8:2) to afford the 18-cyano compound 113 (9.08 g; 61%). ¹H NMR (400 MHz, CDCl₃): δ 0.84(s, 3H), 2.05(s, 3H), 2.20(d, 1H, J=17 Hz), 2.31(s, 3H), 2.53(d, 1H, J=17 Hz), 2.35(dt, 1H, J=13&2 Hz), 2.72(t, 1H, J=9 Hz), 4.70(sept, 1H, J=5 Hz).

3β-17β-Diacetoxy-18-cyano-5α-androstane (114)

A solution of compound 113 (1 g; 0.0026 mol) in 1,2-dichloroethane (8 mL) was treated with 3-chloroperoxybenzoic acid (2.9 g; 0.013 mol) and heated at 50° C. for 6 hours. Another portion of m-CPBA (2.9 g) was added and the reaction was left at 50° C. for overnight. The reaction mixture was then diluted with EtOAc and washed with 5% $Na_2S_2O_3$ solution, 5% $K_2CO_3$ solution, brine, dried over $MgSO_4$ and concentrated under reduced pressure. The residue was purified by flash chromatography on silica gel (EtOAc:hex 7:3) to afford compound 114 (742 mg; 71%). $^1$H NMR (400 MHz, $CDCl_3$) δ: 0.84(s, 3H), 2.03(s, 3H), 2.13(s, 3H), 2.25(d, 1H, J=17 Hz), 2.44(d, 1H, J=17 Hz), 4.69(sept, 1H, J=5 Hz), 4.85(dd, 1H, J=7 & 2 Hz).

3β-Hydroxy-5α-androstane-17β-18β-(17-oxa-tetrahydrofuran-20-one) (115)

Compound 114 (15.5 g; 0.038 mol) was dissolved in MeOH (500 mL) and NaOMe (20.7 g; 0.38 mol) was added in portions over 5 minutes. The mixture was stirred at room temperature for 2 hr. 10% HCl (200 mL) was added slowly and the solution was heated at 60° C. for another 2 hr, to ensure the hydrolysis of imidate. The major part of the methanol was removed under reduced pressure and the crude was extracted with $CH_2Cl_2$, washed with brine, dried over $MgSO_4$ and concentrated under reduced pressure to give the target compound 115 (11.7 g; 97%) which was used in next step without purification. $^1$H NMR (400 MHz, $CDCl_3$).δ: 0.79(s, 3H), 2.27(d, 1H, J=18 Hz), 2.41(d, 1H, J=18 Hz), 3.61(sept, 1H, J=5 Hz), 4.54(dd, 1H, J=8 &2 Hz).

3-Keto-5α-androstane-17β-18β-(17-oxa-tetrahydrofuran-20-one) (116)

To a cooled solution (0° C.) of compound 115 (11.7 g; 0,036 mol) in 700 mL acetone was added dropwise 2.7M solution of Jones reagent (20.3 mL; 0.055 mol). TLC showed the completion of the reaction in 15 min and the excess of oxidant was destroyed by addition of 2-propanol. The solvents were removed to give a green residue which was dissolved in $CH_2Cl_2$, washed with brine, dried over $MgSO_4$, concentrated under reduced pressure and purified by chromatography on silica gel to give the desired compound 116 (9.1 g; 78%). $^1$H NMR (300 MHz, $CDCl_3$).δ: 0.98(s, 3H), 4.53 (dd, 1H, J=8 & 2 Hz).

Dioxolane 117

To a solution containing lactone 116 (6.34 g, 20 mmol) in 120 mL benzene/ethylene glycol (3/1, v/v), were added trimethyl orthoformate (6.56 mL, 60 mmol) and p-toluenesulfonic acid monohydrate (190 mg, 1 mmol). The reaction mixture was stirred under argon at room temperature for 2 hr, quenched with 100 mL of saturated sodium bicarbonate. Extraction with ethyl acetate, followed by washing, drying over and concentration of the organic phase afforded 7.35 g of the crude dioxolane 117 as yellow oil; IR (KBr): 1769 (C=O, lactone) $cm^{-1}$; $^1$H NMR (acetone-$d_6$).δ: 0.84 (s, 3H, 19-$CH_3$), 2.22 and 2.49 (two d, 2H, J=8.4 Hz, $CH_2$COO), 3.88 (s, 4H, 3-dioxolane), 4.50 (dd 1H, J=8.4 & 1.7 Hz, 17α-CH).

Diol 118

To a solution of dioxolane 117 (7.2 g, 20 mmol) in THF (100 mL) was added carefully LiAlH4 (760 mg, 20 mmol) in portions, with stirring under argon at 0° C. The reaction mixture was allowed to warm to room temperature overnight. After completion of the reaction, the mixture was cooled to 0° C. and quenched by careful addition of 300 mL of Rochelle salt, then extracted with ethyl acetate. The organic phase was washed with water (3×200 mL), dried over $MgSO_4$, and concentrated under reduced pressure to afford 6.67 g of diol 118 as white solid, which was used in the next step without purification; IR (KBr): 3540 (OH) $cm^{-1}$; $^1$H NMR (acetone-$d_6$).δ: 0.84 (s, 3H, 19-$CH_3$) 3.62 (m, 2H, $CH_2$OH), 3.78 (m, 1H, 17α-H), 3.87 (s, 4H, 3-dioxolane), 4.42 (s, 1H, OH-diol), 4.83 (t, 1H, J=4.8 Hz, OH-diol).

Silyl Ether 119

To a stirred solution of diol 118 (6.67 g) in dry dichloromethane (100 mL), under argon, were added successively triethylamine (6.5 mL, 46 mmol), TBDMSCl (2.76 g, 18.3 mmol) and DMAP (108 mg, 0.91 mmol) at room temperature. The mixture was stirred for 4 h at room temperature. The reaction was quenched by the addition of water (300 mL) and the mixture was extracted with dichloromethane. The organic phase was concentrated under reduced pressure and the crude product extracted with ethyl acetate. The organic phase was washed several times with water, then filtered and dried over a pad of cotton and magnesium sulfate. Evaporation of the solvent afforded 8.97 g of silyl ether 119 as white solid, which was used in the next step; IR (KBr): 3540 (OH) $cm^{-1}$; $^1$H NMR (acetone-$d_6$).δ: 0.09(s, 6H, —Si($CH_3$)$_2$ TBDMS), 0.86 (s, 3H, 19-$CH_3$), 0.92 (s, 9H, $^t$Bu, TBDMS), 3.59-3.62 and 4.03-4.06 (m, 2H, $CH_2$OSi), 3.74-3.80 (m, 1H, 17α-H), 3.88 (s, 4H, 3-dioxolane), 4.07-4.10 (m, 1H, OH-diol).

Ketone 120

To a solution of the crude silyl ether 119 (8.94 g) was solubilized in dry dichloromethane (100 mL) under argon, were added succsessively molecular sieves (5.6 g), N-methylmorpholine-N-oxide (6.56 g, 56.02 mmol) and tetrapropyl ammonium perruthenate (352 mg, 1 mmol) as a catalyst. The resulting mixture was stirred at room temperature for 4 hours, concentrated under reduced pressure and filtered over silica with hexanes: acetone (80:20) to give 8 g of the ketone 120 as foam. The product was used in next step without any purification; IR (NaCl, film): 1738 (C=O) $cm^{-1}$; $^1$H NMR (acetone-$d_6$).δ: 0.06 (s, 6H, —Si($CH_3$)$_2$, TBDMS), 0.89 (s, 9H, $^t$Bu, TBDMS), 0.90 (s, 3H, 19-$CH_3$), 3.50-3.58 and 3.63-3.72 (m, 2H, $CH_2$OSi), 3.88 (s, 4H, 3-dioxolane).

Hemiketal 121

To a stirred solution of ketone 120 (8 g, 16.78 mmol) in THF (100 mL), was added dropwise 1.0 M THF solution of tetrabutylammonium fluoride (34 ml). The reaction mixture was stirred at room temp overnight, then quenched by the addition of water (100 mL) and extracted with ethyl acetate (200 mL). The organic phase was washed with water (3×150 mL), filtered over magnesium sulfate and concentrated under reduced pressure. Purification of the crude product by flash chromatography with hexane:acetone (80:20) afforded 4.71 g of hemiketal 121 as white foam; $^1$H NMR (acetone-$d_6$).δ: 0.90 (s, 3H, 19-$CH_3$), 3.60-3.66 and 3.68-3.76 (m, 2H, C$H_2$O), 3.88 (s, 4H, 3-dioxolane), 4.52 (s, 1H, 17α-OH).

18β-bromomethyl-17-ketone 122

To a solution of hemiketal 121 (4.71 g, 11.03 mmol) in dry dichloromethane (100 mL) were added successively triphenylphosphine (4.45 g, 16.55 mmol) and carbon tetrabromide (9,15 g, 27.58 mmol). The reaction mixture was stirred for 15 minutes at room temp, then quenched with saturated sodium bicarbonate (50 mL). After extraction with dichloromethane, the combined organic phase was concentrated under reduced pressure. Purification of the crude product by flash chromatography with hexanes:acetone (85:15) gave 5.16 g of the bromocompound 122. The overall yield for the 6 steps was 60.6%. $^1$H NMR (acetone-d$_6$) δ: 0.88 (s, 3H, 19-CH$_3$), 2.40-2.60 (m, 1H, 16-CH$_2$) 3.13-3.22 and 3.40-3.49 (m, 2H, CH$_2$Br), 3.87 (s, 4H, 3-dioxolane).

18-(amino-benzyl-3-oxymethylene)-17β-hydroxy-3-ketone 124

The synthesis of EM-6470 (compound 59, R$_1$=H; R$_2$=exo-norbornan-2-yl) is a representative procedure for these series of compounds: Bromosteroid 122 (32 mg, 0.075 mmol) was added to a mixture of cesium carbonate (73 mg, 0.225 mmol), sodium iodide (1 mg) as a catalyst, aminophenol (40 mg, 0.184 mmol) and acetone (7 mL). The mixture was refluxed overnight and was allowed to cool to room temperature. Saturated sodium bicarbonate was added and the product was extracted with dichloromethane (3×15 mL). The combined organic layers were washed with brine (2×10 mL), dried and concentrated to give the crude product 123. The crude was diluted with MeOH (5 mL) and sodium borohydride (10 mg, 0.264 mmol) was added at 0° C. The ice-bath was removed and the mixture was stirred 2 hours. Saturated sodium bicarbonate was added and the product was extracted with dichloromethane (3×15 mL). The combined organic layers were washed with brine (2×10 mL), dried and concentrated to give the crude product, which was diluted with acetone (10 mL) and 10% HCl was added (2 mL) while stirring. The mixture was kept at room temperature for 1 hr with stirring. Saturated sodium bicarbonate was added and the product was extracted with dichloromethane (3×15 mL). The combined organic layers were washed with brine (2×10 mL), dried and concentrated to give the crude product which was purified by column chromatography over silica gel to provide EM-6470 (124) (13.3 mg, 33% for the three steps). $^1$H NMR(400 MHz, acetone-d$_6$) δ: 7.20 (t, 1H, J=7.8 Hz), 7.05 (s, 1H), 6.90 (d, 1H, J=7.5 Hz), 6.80-6.84 (m, 1H), 4.55-4.60 (m, 1H), 4.08-4.18 (m, 1H), 3.72-3.80 (m, 3H), 2.64-2.70 (m, 1H), 2.45 (m, 1H), 2.35 (m, 1H), 1.09 (s, 3H).

Example XI

Synthesis of 18-(monoalkylamino-benzyl-3-oxymethylene)-5α-androstan-17β-hydroxy-3-ketone This synthesis is described in Schemes 32-38

SCHEME 32

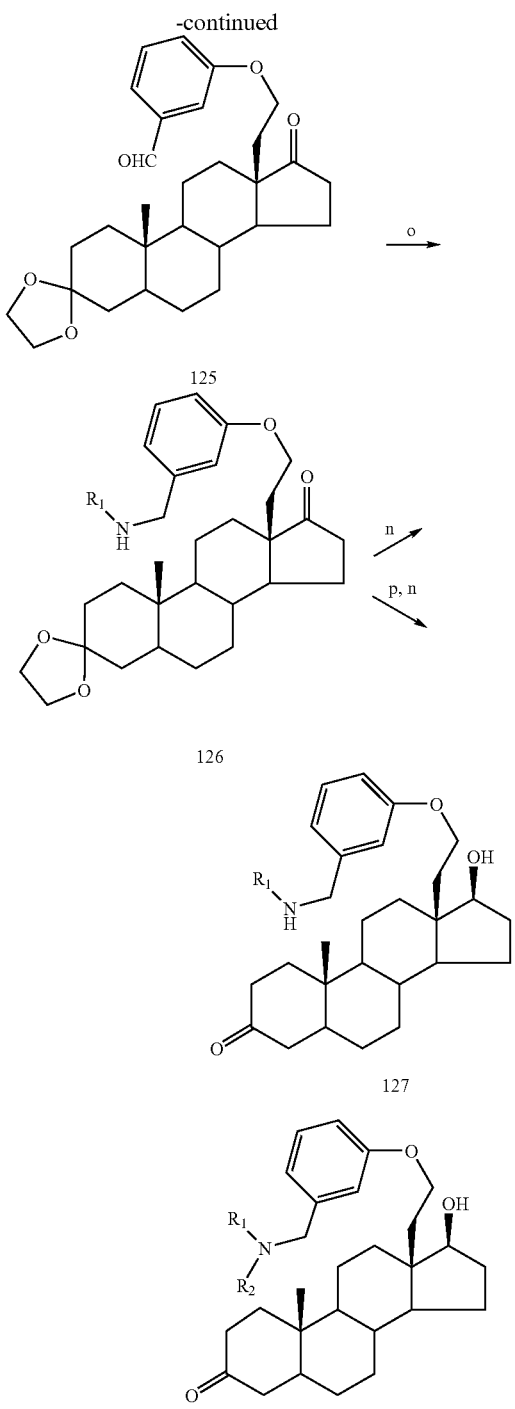

Conditions
m) subtituted-phenol, Cs$_2$CO$_3$, DMF or actone; n) 1) NaBH$_4$, MeOH, 0° C.-rt, 2) 10% aq HCl, acetone, rt; o) RNH$_2$, NaBH$_3$CN, AcOH, p) RCHO or R$_1$R$_2$CO, NaBH$_3$CN, AcOH 3-Alkoxybenzaldehyde 125

Bromosteroid 122 (180 mg, 0.423 mmol) and cesium carbonate (551 mg, 1.69 mmol) were added to a mixture of 3-hydroxybenzaldehyde (78 mg, 0.634 mmol) in DMF (21 mL). The mixture was stirred at 80° C. for 30 min. The mixture was allowed to cool to room temperature. Water (50 mL) was added and the product was extracted with ethyl acetate (3×50 mL). The combined organic layers were washed with water and brine (2×20 mL), dried and concentrated to give the crude product which was purified by column chromatography over silica gel to provide the pure product 125 (136 mg, 69%). $^1$H NMR(400 MHz, acetone-d$_6$) δ: 10.01 (s, 1H), 7.51=7.53 (m, 2H), 7.39-7.41 (m, 1H), 7.20-7.23 (m, 1H), 4.10-4.20 (m,1H), 3.92-4.00(m,1H), 3.88-3.90(m,4H), 2.50-2.60(m,1H), 0.89 (s, 3H).

EM-6511 (compound 62, R$_1$=1,2-dimethylpropyl)

The aldehyde 125 (20 mg, 0.0429 mmol) and 1,2-dimethylpropylamine (7.5 μL, 0.0643 mmol), was diluted with ethanol (2 mL). Catalytic quantity of acetic acid was added to the mixture followed by sodium cyanoborohydride (4 mg, 0.0643 mmol). The mixture was stirred overnight at room temperature. A solution of 10% sodium hydroxide (10 mL) was added and the product was extracted with ethyl acetate (3×15 mL). The combined organic layers were washed with brine (2×10 mL), dried and concentrated to give the crude product which was diluted with MeOH (5 mL) and sodium borohydride (10 mg, 0.264 mmol) was added at 0° C. The ice-bath was removed and the mixture was stirred 2 hours. A solution of saturated sodium bicarbonate was added and the product was extracted with dichloromethane (3×15 mL). The combined organic layers were washed with brine (2×10 mL), dried and concentrated to give the crude product which was diluted with acetone (10 mL) and 10% HCl was added (2 mL) with stirring. The mixture was kept at room temperature for 1 hour with stirring. A solution of saturated sodium bicarbonate was added and the product was extracted with dichloromethane (3×15 mL). The combined organic layers were washed with brine (2×10 mL), dried with and concentrated to give the crude product which was purified by column chromatography over silica gel to provide the pure EM-6511 (11 mg, 52% for the three steps). $^1$H NMR(400 MHz, acetone-d$_6$) δ: 7.19 (t, 1H, J=7.8 Hz), 7.01 (s, 1H), 6.90-6.95 (m, 1H), 6.80-6.82 (m, 1H), 4.55-4.60 (m, 1H), 4.12 (m, 1H), 3.71-3.82 (m, 3H), 1.09 (s, 3H).

EM-6339 (compound 59, R$_1$=C$_2$H$_5$, R$_2$=diethylmethyl)

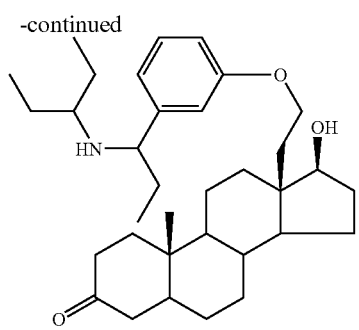

EM-6339 to a solution of aminophenol (32 mg, 0.141 mmol) in dry DMF (2 mL), under argon, was added cesium carbonate (92 mg, 0.282 mmol). The reaction mixture was stirred for 10 min at room temp and then, bromide 122 (40 mg, 0.094 mmol) was added and the reaction brought to 80 0° C. and stirred for 2 h. The reaction mixture was cooled down, diluted with ethyl acetate (15 mL) and washed successively with 10% sodium hydroxide (3×8 mL) and brine (8 mL). The organic phase is dried, filtered and concentrated. Flash chromatography on silica gel using a gradient of 30 to 50% acetone in hexanes gave the ketone (35 mg, 66%). $^1$H NMR (400 MHz, methanol-d$_4$) δ: 0.76-0.88 (m, 12H), 2.52 (d, 1H, J=18 Hz), 3.60-3.64 (m, 1H), 3.92-3.95 (m, 6H), 3.99-4.03 (m, 1H), 6.77 (d, 1H, J=7 Hz), 6.83 (s, 1H), 6.86 (d, 1H, 8 Hz), 7.24 (t, 1H, 8 Hz). To a solution of ketone (35 mg, 0.0679 mmol) in methanol (2 mL) at 0 0° C., was added sodium borohydride (2 mg, 0.0679 mmol). The reaction was allowed to warm up to room temp and stirred for 30 min. The solvent was evaporated and the residue in acetone (1 mL) and a 10% aqueous solution of hydrochloric acid (0.5 mL) was stirred for 90 min at room temp and then quenched with a 5% aqueous solution of potassium carbonate and extracted with dichloromethane (3×10 mL). The organic layer was dried, filtered and concentrated. Flash chromatography on silica gel using a gradient of 30 to 50% acetone in hexanes gave EM-6339 (24 mg, 67%). $^1$H NMR (400 MHz, methanol-d$_4$) δ: 0.76-0.86 (m, 9H), 1.08 (2s, 3H), 2.39 (t, 1H, J=17 Hz) 2.46 (td, 1H, J=17 & 7 Hz), 3.56-3.60 (m, 1H), 3.73 (t, 1H, J=6 Hz), 4.10-4.14 (m, 1H), 4.36-4.40 (m, 1H), 6.85 (d, 2H, 7.5 Hz), 6.92 (s, 1H), 7.24 (t, 1H, 7.8 Hz).

EM-6415 (compound 59, R$_1$=C$_2$H$_5$, R$_2$=cyclohexyl)

SCHEME 33

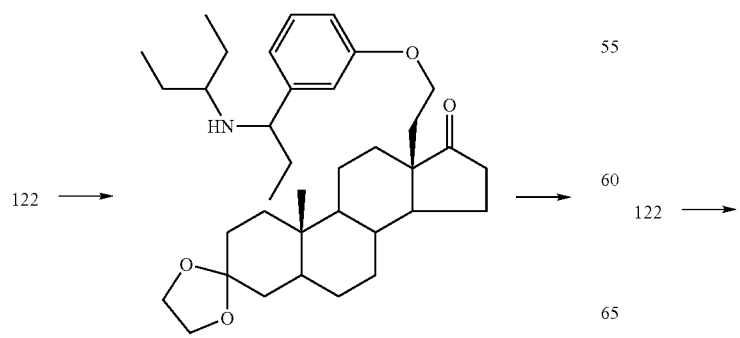

SCHEME 34

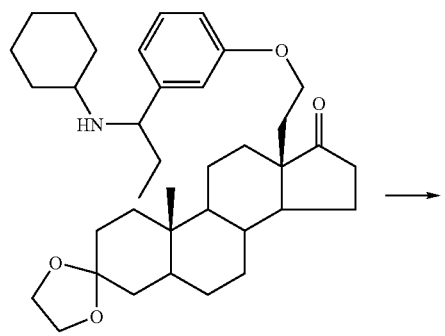

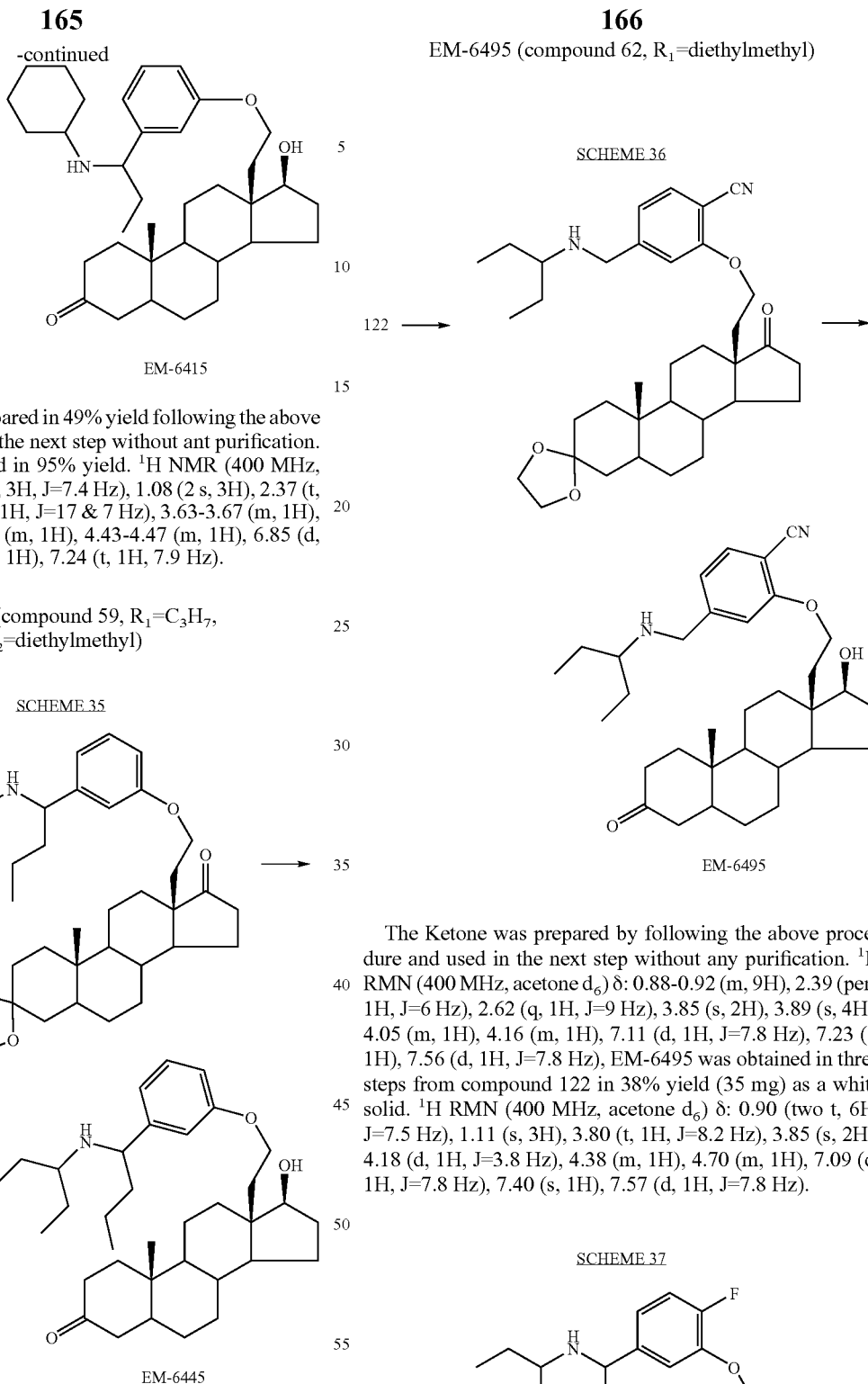

-continued

EM-6415

The Ketone was prepared in 49% yield following the above procedure and used in the next step without ant purification. EM-6415 was obtained in 95% yield. $^1$H NMR (400 MHz, methanol-$d_4$) δ: 0.75 (t, 3H, J=7.4 Hz), 1.08 (2 s, 3H), 2.37 (t, 1H & 17 Hz), 2.52 (td, 1H, J=17 & 7 Hz), 3.63-3.67 (m, 1H), 3.72 (t, 1H), 4.15-4.17 (m, 1H), 4.43-4.47 (m, 1H), 6.85 (d, 1H, J=7.8 Hz), 6.92 (s, 1H), 7.24 (t, 1H, 7.9 Hz).

EM-6445 (compound 59, $R_1$=$C_3H_7$, $R_2$=diethylmethyl)

SCHEME 35

122 →

EM-6445

The Ketone was prepared in 55% yield. $^1$H NMR (300 MHz, methanol-$d_4$) δ: 0.79-0.90 (m, 12H), 2.21-2.29 (m, 1H), 2.53 (2d, 1H, J=8.8 Hz), 3.72-3.76 (m, 1H), 3.85-3.90 (m, 5H), 3.97-4.01 (m, 1H), 6.77 (d, 1H, J=8.2 Hz), 6.82 (s, 1H), 6.85 (d, 1H, J=7.8 Hz), 7.23 (t, 1H, 7.8 Hz). EM-6445 was obtained in 99% yield. $^1$H NMR (400 MHz, methanol-$d_4$) δ: 0.82-0.93 (m, 9H), 1.07 (s, 3H), 2.39 (t, 1H, J=17 Hz), 2.52 (td, 1H, J=17 & 7 Hz), 3.68-3.79 (m, 2H), 4.08-4.19 (m, 1H), 4.42-4.55 (m, 1H), 6.80-6.85 (m, 2H), 6.88-6.92 (m, 1H), 7.24 (t, 1H, J=8 Hz).

EM-6495 (compound 62, $R_1$=diethylmethyl)

SCHEME 36

122 →

EM-6495

The Ketone was prepared by following the above procedure and used in the next step without any purification. $^1$H RMN (400 MHz, acetone $d_6$) δ: 0.88-0.92 (m, 9H), 2.39 (pent 1H, J=6 Hz), 2.62 (q, 1H, J=9 Hz), 3.85 (s, 2H), 3.89 (s, 4H), 4.05 (m, 1H), 4.16 (m, 1H), 7.11 (d, 1H, J=7.8 Hz), 7.23 (s, 1H), 7.56 (d, 1H, J=7.8 Hz), EM-6495 was obtained in three steps from compound 122 in 38% yield (35 mg) as a white solid. $^1$H RMN (400 MHz, acetone $d_6$) δ: 0.90 (two t, 6H, J=7.5 Hz), 1.11 (s, 3H), 3.80 (t, 1H, J=8.2 Hz), 3.85 (s, 2H), 4.18 (d, 1H, J=3.8 Hz), 4.38 (m, 1H), 4.70 (m, 1H), 7.09 (d, 1H, J=7.8 Hz), 7.40 (s, 1H), 7.57 (d, 1H, J=7.8 Hz).

SCHEME 37

122 →

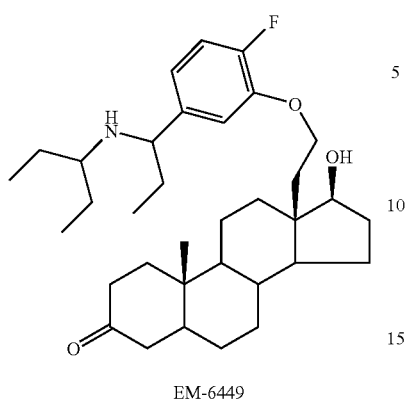

EM-6449

The ketone was prepared in 37% yield. ¹H RMN (300 MHz, acetone d₆) δ: 0.81 (t, 6H, J=7.4 Hz), 0.83 (t, 3H, J=7.2 Hz), 0.87 (s, 3H), 2.54 (q, 1H, J=9 Hz), 3.59 (t, 1H, J=6.7 Hz), 3.87 (s, 4H), 3.93 (m, 1H), 4.08 (m, 1H), 6.86 (m, 1H), 7.02 (dd, 1H, J=8 and 11 Hz), 7.11 (d, 1H, J=8.5 Hz). EM-6449 was prepared in 56% yield. ¹H RMN (300 MHz, acetone d₆) δ: 0,81 (t, 3H, J=7.2 Hz), 0.82 (t, 6H, J=7.5 Hz), 1.07 (s, 3H), 3.59 (td, 1H, J=2,5 and 6.7 Hz), 3.76 (t, 1H, J=8.3 Hz), 4.18 (m, 2H), 4.64 (m, 1H), 6.84 (m, 1H), 7.03 (dd, 1H, J=8 and 11.5 Hz), 7.26 (td, 1H, J=2 and 8.8 Hz).

EM-6534 (compound 59, R₁=dimethyl, R₂=isobuthyl)

SCHEME 38

122 ⟶

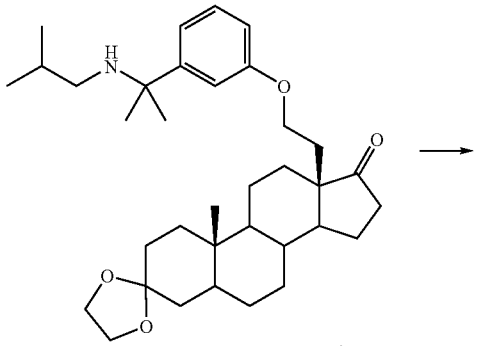

EM-6543

The ketone was prepared in 51% yield and used in the next step without any purufication. EM-6534 was prepared in 95% yield from the ketone. ¹H NMR (400 MHz, methanol-d₄) δ: 0.89 (d, 6H, J=6.6 Hz), 1.07 (s, 3H), 1.49 (s, 6H), 2.37 (t, 1H, J=16 Hz) 2.52 (td, 1H, J=16, 7 Hz), 3.55 (t, 1H, J=6 Hz), 4.10-4.16 (m, 1H), 4.42-4.48 (m, 1H), 6.82 (d, 1H, J=8 Hz), 6.99 (d, 1H, J=8.1 Hz), 7.03 (s, 1H), 7.24 (t, 1H, J=8 Hz).

Example XIII

Synthesis of 18-(dialkylamino-benzyl-3-oxymethylene)-5α-androstan-17β-hydroxy-3-ketone This synthesis is described in Scheme 39

SCHEME 39

122 ⟶

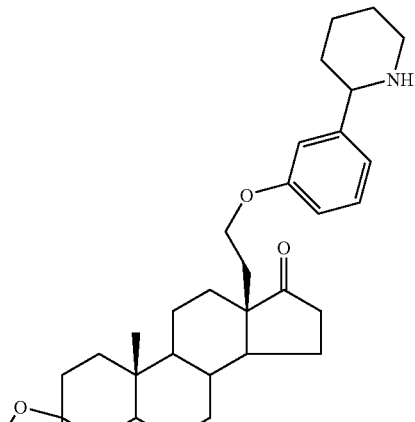

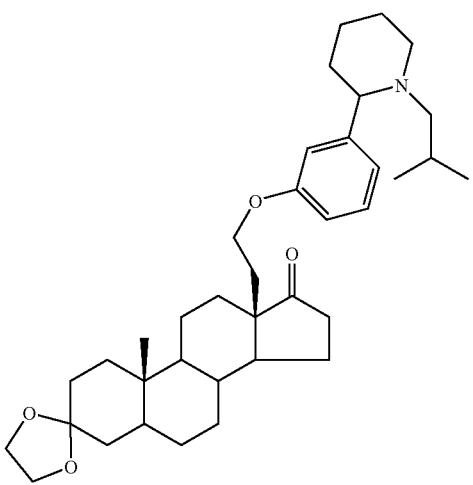

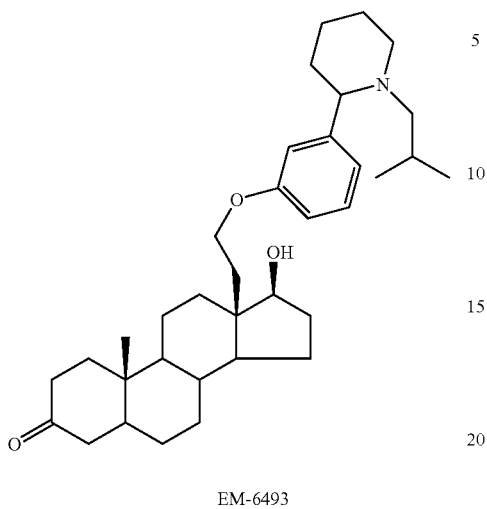

EM-6493

The ketone was prepared in 40% yield. $^1$H NMR (acetone d$^6$): 0.89 (s, 1H, 19-CH$_3$), 2.53-2.60 (2m, 2H), 2.75 (dt, 1H, J=11.5 & 2.8 Hz), 3.13 (dd, 1H, J=9.8 & 2.3 Hz), 3.52 (dd, 1H, J=10.5 & 2.3 Hz), 3.81-3.87 and 4.01-4.07 (m, 2H, CHH$_2$OPh), 3.88 (s, 4H, dioxolane), 6.72 (dd, 1H, J=7.6 & 2.2 Hz), 6.94 (m, 2H), 7.18 (t, 1H, J=8.0 Hz).

N-Isobutylpiperidine

To a stirred mixture of above amine (66 mg, 0.1265 mmol) in acetonitrile (5 mL) were added subsequently i-butyraldehyde (70 μl, 0.9 mmol), sodium triacetoxy borohydride (56 mg, 0.26 mmol) and glacial acetic acid (few drops to adjust the pH 5). The reaction mixture was stirred for 3 hr at room temp, then quenched with saturated sodium bicarbonate (2 mL) and extracted with dichloromethane. The combined organic phase was concentrated to give 78 mg of crude product which was used in the next step. $^1$H NMR (acetone-d$_6$).δ: 0.69 and 0.86 (2d, 6H, J=6.6 Hz, (CH$_3$)$_2$CH—), 0.89 (s, 1H, 19-CH$_3$), 2.53-2.60 (2m, 2H), 2.85-2.95 (m, 1H, masked under solvent peak), 3.20 (d, 1H, J=9.8 Hz), 3.80-2.87 and 3.96-4.10 (m, 2H, CH$_2$OPh), 3.88 (s, 4H, dioxolane), 6.72 (dd, 1H, J=7.6 & 2.2 Hz), 6.89 (m, 2H), 7.18 (t, 1H, J=8.0 Hz).

EM-6493 was prepared in 23% yield from ketone in 3 steps. $^1$H NMR (acetone-d$_6$).δ: 0.69 and 0.86 (2d, 6H, J=6.6 Hz, (CH$_3$)$_2$CH—), 1.09 (s, 1H, 19-CH$_3$), 2.34 (t, 1H, J=14.3 Hz), 2.44 (m, 1H), 2.91 (dd, 1H, J=10.9 & 2.6 Hz), 3.18 (d, 1H, J=9.8 Hz), 3.76 (m, 1H, 17□-H), 4.07 (m, 1H, 17β-OH), 4.11 and 4.55 (m, 2H, CH$_2$OPh), 6.79 (dd, 1H, J=7.6 & 2.7 Hz), 6.85 (d, 1H, J=7.6 Hz), 6.98 (d, 1H, J=6.6 Hz), 7.20 (t, 1H, J=7.8 Hz).

Example XIV

Synthesis of 18-(monoalkylamino-benzyl-3-oxymethylene)-5α-androstan-17β-methoxy-3-ketone This synthesis is described in Scheme 40

SCHEME 40

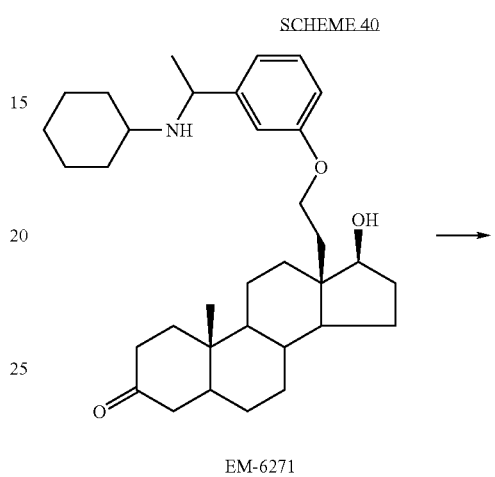

EM-6271

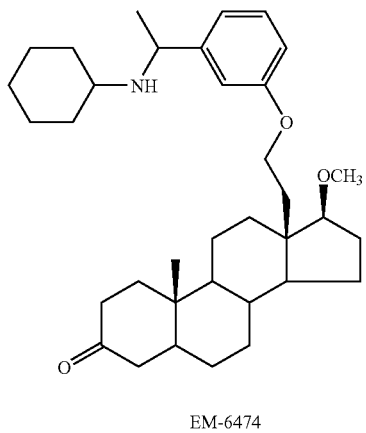

EM-6474

EM-6474

To a solution of EM-6271 (40 mg, 0.07 mmol) in CH$_2$Cl$_2$ (2 mL) were added of 2,6-di-tert-butyl-4-methyl-pyridine (63 mg, 0.3 mol), silver triflate (59 mg, 0.2 mmol) and methyl iodide (6 μL 0.09 mmol). The reaction was stirred at room temp for 12 hours. The mixture was diluted with CH$_2$Cl$_2$, washed with brine, dried and concentrated. Purification on silica gel (acetone:hex; 2:8) afforded the product (21 mg, 51%) as a mixture of diastereoisomers $^1$H NMR (400 MHz, acetone d$_6$) δ 1.08(2 s, 3H), 1.25(2 d, 3H, J=7 Hz), 2.45(td, 1H, J$_1$=7 & 15 Hz), 3.34(2 s, 3H), 3.36(m, 1H), 3.94(m, 1H), 4.13(m, 1H), 6.80(2 d, 1H, J=8 Hz), 6.90(t, 1H J=8 Hz), 7.01(2 d, 1H, J=8 Hz) 7.20(2 t, 1H, J=8 Hz).

Example XV

Synthesis of Amines

These syntheses are described in Schemes 41 and 42

A. 3-(exo-Norbornan-2yl-aminomethyl)-phenol

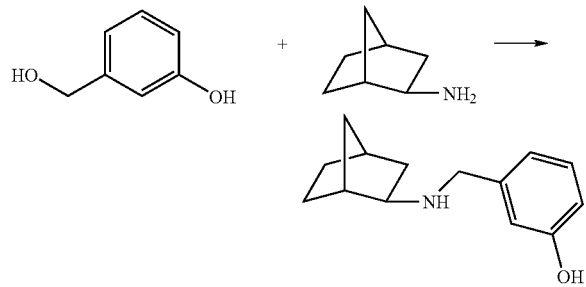

SCHEME 41

The following is a representative procedure: (Cyanomethyl)trimethylphosphonium iodide (782 mg, 3.22 mmol) and diisopropylethylamine (0.70 mL, 4.02 mmol) were added to a mixture of 3-hydroxybenzylalcohol (100 mg, 0.80 mmol) and (±)exo-2-aminonorbornane (0.47 mL, 4.02 mmol) in propionitrile (2.0 mL). The mixture was stirred at 90° C. for 2 hours. The mixture was allowed to cool to room temperature. A solution of saturated sodium bicarbonate was added and the product was extracted with dichloromethane (3×30 mL). The combined organic layers were washed with brine (2×20 mL), dried and concentrated to give the crude product which was purified by column chromatography over silica gel to provide the pure product (145 mg, 83%). $^1$H NMR(400 MHz, acetone-$d_6$): δ 7.10 (t, 1H, J=7.8 Hz), 6.85 (d, 1H, J=1.8), 6.79 (d, 1H, J=7.5 Hz, 1H), 6.68 (dd, 1H, J=2.4 & 6.0 Hz), 3.65 (d, 2H, J=3.3 Hz), 2.6 (m, 1H), 2.17 (m, 2H), 1.61 (m, 1H), 1.40-1.50 (m, 3H), 1.00-1.20 (m, 4H).

B. 3-[1-(1-Ethyl-propylamino)-propyl]-phenol

The following are representative procedures.

SCHEME 42

1-(3-Methoxy-phenyl)-propylamine

A flame-dried 250 mL R.B. flask equipped with a reflux condenser was charged, under argon, with 3-methoxybenzonitrile (2 g, 15 mmol) and dry THF (33.5 mL). Ethylmagnesium bromide (1 M) in THF (16.5 mL, 16.5 mmol) was then added followed by copper (I) bromide (43 mg, 0.3 mmol). The reaction mixture was refluxed for 30 min and then cool down to 0° C. before MeOH (0.61 mL, 15 mmol) was added. The reaction mixture was stirred for 10 min before LAH (1M) in THF (30 mL, 30 mmol) was added and stirred for 60 min at room temp. The reaction was quenched with an aqueous 2M solution of Rochelles' salts (200 mL), stirred for 60 min at room temperature, extracted with diethyl ether (4×30 mL), the organic extracts dried, filtered and concentrated to give the product (2.37 g, 96%) which was sufficiently pure for the next step. $^1$H NMR (400 MHz, methanol-$d_4$) δ: 0.85 (t, 3H, J=7.4 Hz), 1.68-1.77 (m, 2H), 3.70 (dd, 1H, J=6.6 Hz), 3.81 (s, 3H), 6.81 (d, 1H, J=8.2 Hz), 6.90 (d, 1H, J=8.0 Hz), 6.91 (s, 1H), 7.24 (t, 1H, J=7.8 Hz).

(1-Ethylpropyl)-[1-(3-methoxy-phenyl)-propyl]-amine

To a solution of amine (150 mg, 0.908 mmol) in dry acetonitrile (2 mL) was added 3-pentanone (0.1 mL, 0.999 mmol). The mixture was stirred for 10 min at room temp. After sodium cyanoborohydride (69 mg, 1.09 mmol) was added followed by acetic acid (0.06 mL, 1.09 mmol). The milky reaction mixture was stirred at room temp overnight, quenched with concentrated hydrochloric acid, acetonitrile was evaporated and the residue was diluted with water (15 mL) and washed with diethyl ether (2×8 mL). The aqueous phase was basified with potassium hydroxide and extracted with diethyl ether (4×8 mL). The combined organic layer was dried, filtered and concentrated to give amine (100 mg, 47%) which was used in the next step. $^1$H NMR (400 MHz, methanol-$d_4$) δ: 0.77 (t, 3H, J=7.4 Hz), 0.83 (m, 6H), 1.25-1.85 (m, 6H), 2.18 (m, 1H), 3.55 (dd, 1H), 3.81 (s, 3H), 6.83 (d, 1H, J=8.2 Hz), 6.86 (d, 1H, J=8.0 Hz), 6.88 (s, 1H), 7.24 (t, 1H, J=7.8 Hz).

3-[1-(1-Ethyl-propylamino)-propyl]-phenol

To a solution of secondary amine (98 mg, 0.416 mmol) in dry dichloromethane (1 mL), under argon at −10 0° C. was added slowly boron tribromide, 1M solution in dichloromethane (1.25 mL, 1.25 mmol). After the reaction mixture was allowed to reach room temp and stirred for 90 minutes at room temp. The reaction was quenched with saturated aqueous sodium bicarbonate, extracted with dicholromethane (3×10 mL) and the organic extracts dried, filtered and concentrated to give phenol (64 mg, 70%). $^1$H NMR (400 MHz, methanol-$d_4$) δ: 0.76 (t, 3H, J=7.4 Hz), 0.79-0.86 (m, 6H), 1.29-1.91 (m, 6H), 2.23 (m, 1H), 3.55 (dd, 1H, 4.9 Hz), 6.69 (d, 1H, J=7.7 Hz), 6.73 (s, 1H), 6.76 (d, 1H, J=7.6 Hz), 7.16 (t, 1H, J=7.8 Hz).

C. 4-[(1-Ethylpropylamino)-methyl]-2-hydroxybenzonitrile

SCHEME 43

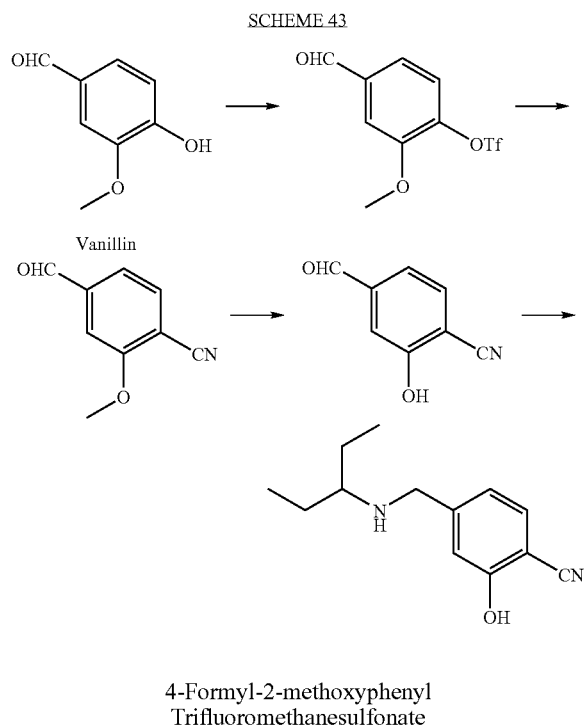

4-Formyl-2-methoxyphenyl Trifluoromethanesulfonate

To a solution of vanillin (500 mg, 3.286 mmol) in DMF (10 mL) at room temp, was added potassium carbonate (908 mg, 6,572 mmol) and 4-nitrophenyl trifluoromethanesulfonate (1,34 g, 4,929 mmol) and the reaction mixture was stirred for 3 h. Et$_2$O was added to the reaction mixture and the organic layer was washed 3 times with water, dried, filtered and concentrated. The crude compound was then purified by flash chromatography (ethyl acetate-hexanes/1:9 to 3:7) to provide sulfonate (880 mg, 94%). $^1$H RMN (400 MHz, CDCl$_3$) δ: 4.03 (s, 3H), 7.44 (d, J=8.2 Hz, 1H), 7.54 (dd,1H, J=1.7 and 8.2 Hz), 7.59 (d, 1H, J=1.7 Hz), 10.02 (s, 1H).

4-Formyl-2-methoxybenzonitrile

In an oven-dried flask purged with argon, a mixture of sulfonate (880 mg, 3,096 mmol), zinc cyanide (1,454 g, 12,385 mmol) and tetrakis triphenylphosphine palladium (0) (537 mg, 0,464 mmol) in DMF (30 ml) were stirred at 110° C. for 4 h. Et$_2$O was added to the reaction mixture and the organic layer was washed 3 times with water, dried, filtered and concentrated. The crude compound was then purified by flash chromatography (ethyl acetate-hexanes/3:7) to provide nitrile (280 mg, 56%). $^1$H RMN (400 MHz, acetone $d_6$) δ: 4.11 (s, 3H), 7.68 (dd, 1H, J=1.2 and 7.7 Hz), 7.72 (d,1H, J=1.2 Hz), 7.95 (d, 1H, J=7.7 Hz), 10.14 (s, 1H),

4-Formyl-2-hydroxybenzonitrile

A mixture of nitrile (280 mg, 1,737 mmol) and pyridine hydrochloride (excess) was stirred and refluxed for 30 min. Water was added to the reaction mixture and extracted 3 times with ethyl acetate. The organic layer was washed 3 times with 10% HCl, dried, filtered and concentratrated to provide crude hydroxynitrile (230 mg, 90%). $^1$H RMN (400 MHz, acetone $d_6$) δ: 7.58 (d, 1H, J=6.2 Hz), 7.59 (d, 1H, J=2.1 Hz), 7.88 (dd, 1H, J=2.1 and 6.2 Hz), 10.07 (s, 1H), 10.4 (s, 1H).

4-[(1-Ethylpropylamino)-methyl]-2-hydroxybenzonitrile

1-Ethylpropylamine (729 μL, 6.253 mmol) and NaBH$_3$CN (196 mg, 3.126 mmol) were added to a solution of hydroxynitrile (230 mg, 1.563 mmol) in CH$_3$CN (12 mL) at room temp. The pH of the solution was adjusted to 5-6 with AcOH and the reaction mixture was stirred overnight. The reaction mixture was poured in saturated NaHCO$_3$, extracted 3 times with CH$_2$Cl$_2$, dried and concentrated. The crude compound was purified by flash chromatography (acetone-hexanes/4:6) to provide aminocompound (107 mg, 31%). $^1$H RMN (400 MHz, CD$_3$OD) δ: 0.97 (t, 6H, J=7.5 Hz), 1.65 (dt, 4H, J=6 and 7.5 Hz), 2.73 (tt, 1H, J=6 Hz), 3.89 (s, 2H), 6.72 (dd, 1H, J=1.3 and 8.0 Hz), 6.83 (d, 1H, J=1.3 Hz), 7.41 (d, 1H, J=8.0 Hz),

SCHEME 44

D. 3-(1-Isobutylamino-1-methylethyl)-phenol

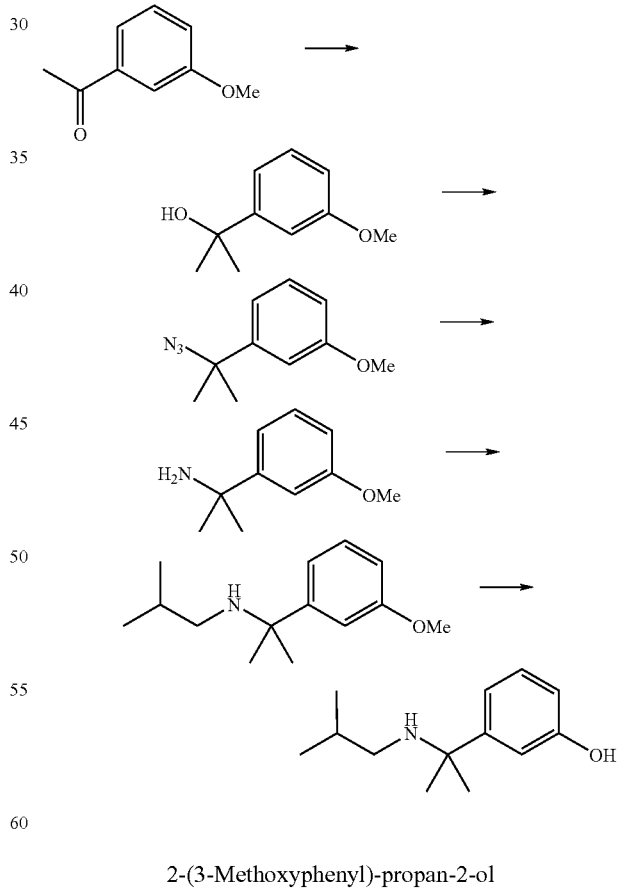

2-(3-Methoxyphenyl)-propan-2-ol

A flame-dried 25 mL R.B. flask equipped with a reflux condenser was charged, under argon, with 3-methoxyacetophenone (1 g, 6.66 mmol) at 0° C. Methylmagnesium iodide in diethylether (4.4 mL, 13.3 mmol, 3M) was then added. The reaction mixture was brought to reflux for 60 min and then cool down to 0° C. and quenched with successive addition of water (5 mL) and saturated ammonium chloride (25 mL). The mixture was extracted with diethyl ether (3×20 mL), the organic extracts were washed successively with 20% sodium bisulfite and saturated sodium bicarbonate, dried, filtered and concentrated. Purification by flash chromatography, using 15% acetone in hexanes, yields propan-2-ol (0.832 g, 75%). $^1$H NMR (400 MHz, acetone-d$_6$) δ: 1.51 (s, 6H), 3.79 (s, 3H), 6.77 (d, 1H, J=8.1 Hz), 7.07 (d, 1H, J=7.7 Hz), 7.13 (s, 1H), 7.22 (t, 1H, J=7.9 Hz).

1-(1-Azido-1-methylethyl)-3-methoxybenzene

To a mixture of propan-2-ol (1.16 g, 6.97 mmol) and sodium azide (904 mg, 13.9 mmol) in dry chloroform (7 mL) under argon at −5° C. was added dropwise a solution of trifluoroacetic acid (2.8 mL, 36.3 mmol) in chloroform (7 mL). The mixture was mechanicaly stirred at room temp overnight, then diluted with dichloromethane (15 mL), quenched with aqueous ammonia (30 mL), the organic phase was separated and the aqueous phase extracted with another portion of dichloromethane (15 mL). The combined organic phases were washed with water, dried, filtered and concentrated. Purification by flash chromatography, using 10% acetone in hexanes, yields azide (1.3 g, 97%); IR (film): 2101 (N$_3$) cm$^{-1}$; 1$^1$H NMR (400 MHz, methanol-d$_4$) δ: 1.62 (s, 6H), 3.82 (s, 3H), 6.87 (d, 1H, J=8.0 Hz), 7.02 (s, 1H), 7.13 (d, 1H, J=7.7 Hz), 7.29 (t, 1H, J=7.9 Hz).

1-(3-Methoxyphenyl)-1-methylethyamine

Azide (1.3 g, 6.8 mmol) was placed in 2-propanol and heated to 70° C. Raney Nickel (approx. 1.2 g) was slowly added and once the evolution of gas has stopped, the mixture was diluted with methanol and filtered on celite. The filtrate was acidified with 10% aqueous hydrochloric acid, the solvents were evaporated under reduced pressure and the aqueous residue washed with diethylether (2×15 mL), basified with potassium hydroxide and extracted with diethylether (4×15 ml). The organic phases are dried, filtered and concentrated to give amine (638 mg, 57%) which was sufficiently pure for the next step. $^1$H NMR (400 MHz, methanol-d$_4$) δ: 1.49 (s, 6H), 3.81 (s, 3H), 6.79 (d, 1H, J=8.0 Hz), 7.05-7.07 (m, 2H), 7.25 (t, 1H, J=8.3 Hz).

Isobutyl-[1-(3-methoxyphenyl)-1-methylethyl]-amine

To a solution of amine (50 mg, 0.303 mmol) in dry acetonitrile (1 mL) was added isobutyraldehyde (0.03 mL, 0.333 mmol). The mixture was stirred for 10 min at room temp. After sodium cyanoborohydride (23 mg, 0.363 mmol) was added followed by acetic acid (3-4 drops). The milky reaction mixture was stirred at room temp overnight, quenched with concentrated hydrochloric acid, acetonitrile is evaporated under reduced pressure and the residue is diluted with water (10 mL) and washed with diethyl ether (2×5 mL). The aqueous phase was basified with potassium hydroxide and extracted with diethyl ether (4×5 mL). The combined organic extracts were dried, filtered and concentrated to give isobutylamine (67 mg, 100%) which was used in the next step. $^1$H NMR (400 MHz, methanol-d$_4$) δ: 0.88 (d, 6H, J=6.6 Hz), 1.49 (s, 6H), 1.63-1.69 (m, 1H), 2.11 (d, 2H, J=6.8 Hz), 3.81 (s, 3H), 6.78 (d, 1H, J=7.9 Hz), 7.01-7.04 (m, 2H), 7.23 (t, 1H, J=8.1 Hz).

3-(1-Isobutylamino-1-methylethyl)-phenol

Boron tribromide, 1M solution in dichloromethane (0.95 mL, 0.95 mmol), was slowly added to a solution of isobutylamine 4 (70 mg, 0.316 mmol) in dry dichloromethane (1 mL), under argon, at −10° C. and the reaction mixture allowed to reach room temperature and stirred for 90 min at this temp. The reaction is quenched with saturate sodium bicarbonate, extracted with dicholromethane (3×10 mL) and the organic extracts dried, filtered and concentrated to give phenol (49 mg, 75%) which was used in the next step. $^1$H NMR (400 MHz, methanol-d$_4$) δ: 0.89 (d, 6H, J=6.7 Hz), 1.49 (s, 6H), 1.62-1.70 (m, 1H), 2.14 (d, 2H, J=6.8 Hz), 6.71 (d, 1H, J=8.0 Hz), 6.88 (s, 1H), 6.92 (d, 1H, J=8.1 Hz), 7.17 (t, 1H, J=7.9 Hz).

SCHEME 45

E. 3-Piperidin-2-yl-phenol acetic acid salt

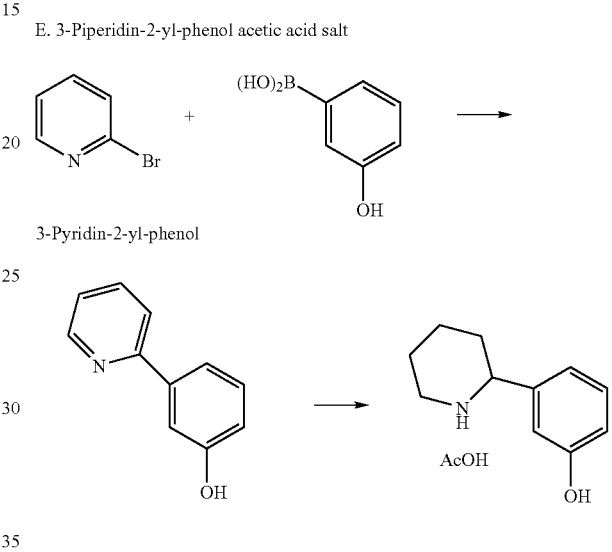

3-Pyridin-2-yl-phenol

In a vial, a mixture of potassium phosphate (1.28 g, 6 mmol), 2-bromo-pyridine (0.2 mL, 2 mmol), 3-hydroxy-phenylboronic acid (338 mg, 2.4 mmol) in DMF (4 mL) was purged with argon while stirring for 15 min. After Pd(PPh3)$_4$ (235 mg, 0.1 mmol) was added and the vial was sealed. The mixture was heated for 12 h at 80° C. and at room temp, the mixture was quenched with water (1 mL). The mixture was extracted with dichloromethane once the pH was adjusted to 7-8 with 10% HCl. The combined organic phase was concentrated. The residue in ethyl acetate (35 mL) was washed with brine (5×20 mL) and water (25 mL) then concentrated. Flash column chromatography provided the product (300 mg, 88%). $^1$H NMR (acetone-d$_6$).δ: 6.92 (ddd, 1H, J=8.0, 2.5 & 0.9 Hz), 7.32 (m, 2H), 7.59 (ddd, 1H, J=7.8, 2.5 & 1.0 Hz), 7.67 (dd, 1H, J=2.3 & 1.9 Hz), 7.88 (m, 2H), 8.49 (s, 1H, OH), 8.66 (ddd, 1H, J=4.8, 1.7 &1.0 Hz).

3-Piperidin-2-yl-phenol acetic acid salt

Pyridine (300 mg, 1.75 mmol) in acetic acid (10 mL) and platinum oxide (60 mg, 20% w/w) were stirred at room temperature under hydrogen atmosphere. After 5 hr, the mixture filtered over Celite. The filtrate was then concentrated to provide 396 mg of crude salt. Flash chromatography with dichloromethane:methanol (90:10) provided the acetic salt (300 mg, 72%). $^1$H NMR (acetone-d$_6$): δ 2.75 (dt, 1H, J=11.5 & 2.4 Hz), 3.13 (dd, 1H, J=9.8 & 2.4 Hz), 3.52 (dd, 1H, J=10.5 & 2.3 Hz), 6.68 (dd, 1H, J=8.0 & 2.4 Hz), 6.84 (d, 1H, J=7.8 Hz), 6.91 (s, 1H), 7.10 (t, 1H, J=7.8 Hz).

Example XVI
Synthesis of 4-aza-dihydrotestosterone Derivatives
This synthesis is described in Scheme 46
SCHEME 46
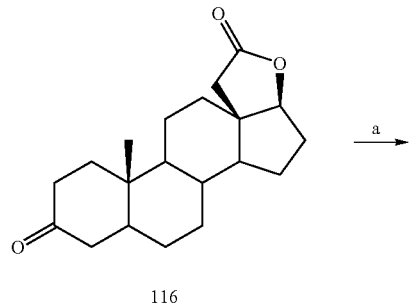
116
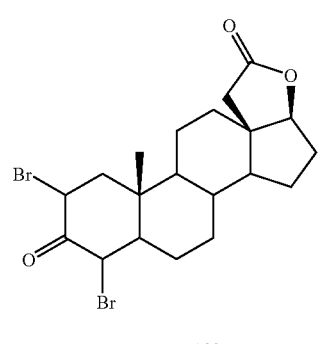
129
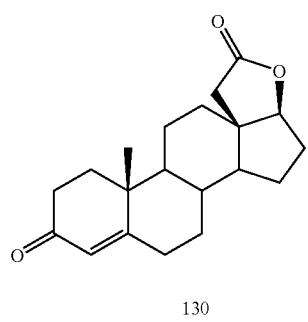
130
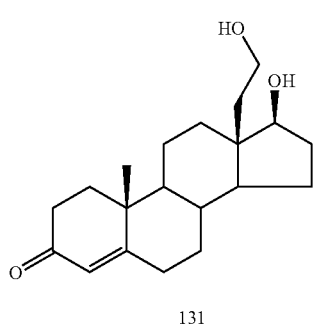
131
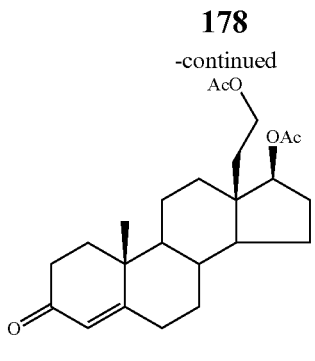
132
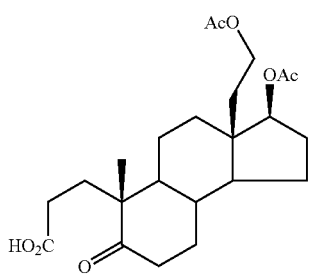
133
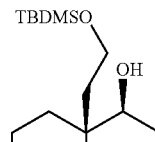
134
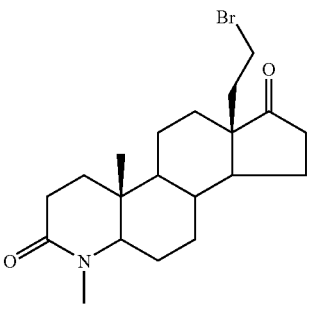
135

-continued

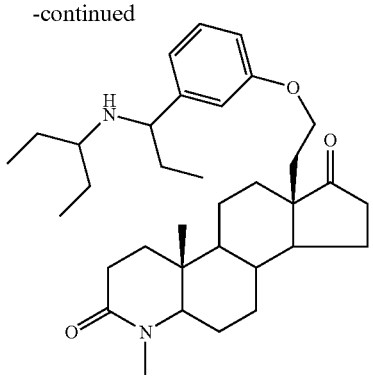

EM-6549 conditions: a) Br$_2$, AcOH; b) NaI, acetone, reflux; c) 1) LAH, THF, 2) MnO$_2$, CH$_2$Cl$_2$; d) AcCl, pyridine, CH$_2$Cl$_2$; e) NaIO$_4$, Na$_2$CO$_3$, t-BuOH/H$_2$O, 70° C.; f) $_1$)CH$_3$NH$_2$, (CH$_2$OH)$_2$, 175° C., 2) PtO$_2$, AcOH, 50 psi, H$_2$, 60° C., 3) TBDMSCl, Et$_3$N, DMAP, CH$_2$Cl$_2$; g) 1) TPAP, MNO, CH$_2$Cl$_2$, 2) TBAF, THF, $_3$) PPh$_3$, CBr$_4$, CH$_2$Cl$_2$; h) 1) sub-phenol, Cs$_2$CO$_3$, DMF, 80° C., 2) NaBH$_4$, MeOH, 0° C.

Dibromoketone 65

To a solution of lactone 116 (529 mg, 1.67 mmol) in glacial acetic acid (30 mL) were added a few drops of 30% hydrogen bromide in acetic acid, followed by slow addition of bromine (0.18 mL, 3.49 mmol) in acetic acid (5 mL) at room temperature. After 1 h, a few drops of 30% hydrogen bromide was added again and the mixture was stirred for 24 h. The mixture was poured into ice water. The solid was recovered by filtration and dried under vacuum. The crude compound was used without further purification (793 mg). $^1$H NMR (400 MHz, actone-d$_6$) δ: 1.29 (s, 3H), 2.27 (d, 1H, J=18 Hz), 2.55 (d, 1H, J$_{AB}$=18 Hz), 2.65-2.75 (m, 1H), 4.06 (d, 1H, J=7 Hz), 5.12 (d, 1H, J=13 Hz), 5.20-5.30 (m, 1H).

Enone 66

A mixture of the crude compound 129 (793 mg, 1.67 mmol) and sodium iodide (1.0 g, 6.67 mmol) in acetone (30 mL) was refluxed for 2 h. The sodium bromide was filtered and the filtrate was heated at the boiling point for 24 h. Acetone was evaporated under reduced pressure and the residue was diluted with diethyl ether. The organic layer was washed with 5% NaHSO$_3$, brine and dried. The solvent was removed and the residue was purified by flash chromatography on silica gel (hex; Acetone: 8:2) to afford 282 mg (54% for 2 steps) of compound 130. $^1$H NMR (400 MHz, actone-d$_6$) δ: 1.24 (s, 3H), 2.31 (d, 1H, J$_{AB}$=18 Hz), 2.56 (d, 1H, J$_{AB}$=18 Hz), 4.54 (dd, 1H, J=8.4 & 1.6 Hz), 5.65 (s, 1H).

Diol 131

To a cooled solution (0° C.) of the enone 130 (146 mg, 0.46 mmol) in CH$_2$Cl$_2$ (5 mL) was added LAH (60 mg, 1.58 mmol) and the mixture was allowed to warm to room temp. After overnight, the reaction was quenched with a solution of Rochelle salt (0.5M) at 0° C. The mixture was extracted with diethyl ether and organic layer was washed with brine, dried and concentrated. The crude material was used in the next step without further purification (148 mg). To a stirred solution of triol (148 mg, 0.46 mmol) in dichloromethane (10 mL) was added MnO$_2$ (400 mg, 4.6 mmol) at room temperature. After 30 min., an excess of MnO$_2$ (400 mg, 4.6 mmol) was added and the solution was stirred overnight. Filtration on a celite pad and concentration gave the residue which was purified by flash chromatography on silica gel (hex:acetone; 7:3) to give 50 mg (34% for 2 steps) of diol 131. $^1$H NMR (400 MHz, actone-d$_6$) δ: 1.24 (s, 3H), 3.60-3.68 (m, 2H), 3.70-3.85 (m, 1H), 4.40-4.45 (m, 1H), 4.88 (d, 1H, J=5.1 Hz), 5.63 (s, 1H).

Diacetoxy-enone 132

To a stirred solution of diol 131 (195 mg, 0.61 mmol) in CH$_2$Cl$_2$ (12 mL) were successively treated with pyridine (0.3 mL, 3.71 mmol) and acetyl chloride (0.18 mL, 2.52 mmol). After 1 h, the mixture was poured in a saturated NH$_4$Cl solution and extracted with diethyl ether. The organic layers were washed with brine, dried and evaporated. The crude compound was purified by flash chromatography on silica gel (hex:acetone; 8:2) to afford 154 mg (63%) of product 132. $^1$H NMR (400 MHz, actone-d$_6$) δ: 1.26 (s, 3H), 2.02 (s, 3H), 2.04 (s, 3H), 4.18-4.29 (m, 1H), 4.30-4.45 (m, 1H), 4.64 (t, 1H, J=8.3 Hz), 4.88 (d, 1H, J=5.1 Hz), 5.64 (s, 1H).

Seco-acid 133

To a solution of compound 132 (154 mg, 0.38 mmol) in 2-methyl-2-propanol (4 mL) were added Na$_2$CO$_3$ (60 mg, 0.56 mmol) and a few drops of water. The mixture, at 70° C., was treated with a mixture (previously heated at 70° C.) of KMnO$_4$ (5 mg, 0.03 mmol) and NaIO$_4$ (410 mg, 1.91 mmol) in H$_2$O (4 mL). The mixture was stirred for 10 min. at this temperature. The reaction mixture was diluted with water and acidified (pH=4) with 10% HCl. The aqueous layer was extracted with diethyl ether, washed with brine, dried and evaporated. The crude compound 133 was used without further purification (156 mg). $^1$H NMR (400 MHz, actone-d$_6$) δ: 1.20 (s, 3H), 2.02 (s, 3H), 2.04 (s, 3H), 2.62-2.73 (m, 1H), 4.20-4.28 (m, 1H), 4.33-4.42 (m, 1H), 4.66 (t, 1H, J=8.3 Hz).

Azasteroid 134

To a stirred solution of the product 133 (156 mg, 0.37 mmol) in ethylene glycol (4 mL) was bubbled methylamine for 15 min. The mixture was heated gradually to 175° C. and was held at this temperature 15 min. He mixture was allowed to cool to room temp and water was added. The solution was extracted with diethyl ether, washed with brine, dried and concentrated in vaccuo. The residue was filtered through silica gel (hex; acetone: 6:4) to afford 51 mg of deprotected azasteroid as solid. The azasteroid was hydrogenated at 60° C. in 3 mL of glacial acetic acid in the presence of 10% PtO$_2$ at 50 psi of H$_2$. After 4 h, the solution was filtered on a celite pad and evaporated to dryness. The crude product was dissolved in CH$_2$Cl$_2$ (3 mL) and Et$_3$N (0.05 mL, 0.35 mmol). Catalytic amount of DMAP and tertbutyldimethylsilyl chloride (40 mg, 0.26 mmol) were added to above mixture at room temperature. After 1 h later, the mixture was poured in a saturated ammonium chloride solution and was extracted with ethyl acetate, washed with brine, dried and evaporated. The residue was purified by flash chromatography on silica gel (hex; acetone: 5:5) to give 8.5 mg (3% for 5 steps) of product 134. $^1$H NMR (400 MHz, CD$_3$OD) δ: 0.12 (s, 3H), 0.13 (s, 3H), 0.92 (s, 3H), 0.94 (s, 9H), 2.40-2.45 (m, 1H), 2.94 (s, 3H), 3.18 (dd, 1H, J=12.6 & 3.4 Hz), 3.62 (t, 1H, J=8.5 Hz), 3.77-3.82 (m, 1H), 4.00-4.04 (m, 1H).

Bromoazasteroid 135

To a stirred solution of azasteroid 134 (8.5 mg, 0.02 mmol) in CH$_2$Cl$_2$ (1 mL) were added of 4-methylmorpholine-N-oxide (4 mg, 0.03 mmol) and a catalytic amount of tetrapropylammonium perruthenate at room temp. After 1 h, the mixture was filtered on silica gel column (hex:acetone; 6:4) to give 17-ketoproduct. The 17-ketoazasteroid was dissolved in THF (2 mL) and treated with n-tetrabutylammonium fluoride solution (0.08 mL, 0.08 mmol). After 15 min, the mixture was diluted with water and extracted with ethyl acetate, washed with brine, dried and concentrated. The crude compound was dissolved in CH$_2$Cl$_2$ (2 mL) at 0° C. and were added successively triphenylphosphine (15 mg, 0.05 mmol) and carbon tetrabromide (20 mg, 0.06 mmol). The reaction was complete in 30 min and the compound was purified by flash chromatography on silica gel (hex:acetone; 7:3) to 8 mg (79% for 3 steps) of bromocompund 135. $^1$H NMR (400 MHz, actone-$d_6$) δ: 0.96 (s, 3H), 2.88 (s, 3H), 3.10-3.25 (m, 2H), 3.40-3.50 (m, 1H).

EM-6549

A mixture of bromocompound 135 (8 mg, 0.02 mmol), 1-(3'-hydroxyphenyl)-N-(3-pentyl)-propylamine (13 mg, 0.05 mmol) and $Cs_2CO_3$ (15 mg) in DMF (1 mL) was heated at 80° C. for 2 h. The solution was diluted with ethyl acetate and washed with water and brine, dried, concentrated. The residue was dissolved in MeOH (1 mL) at 0° C. and was added 1.5 equi of $NaBH_4$. The mixture was allowed to warm to room temperature. After 30 min, the reaction was quenched with saturated ammonium chloride and extracted with ethyl acetate, washed with brine, dried and evaporated. EM-6549 was purified by two successive flash chromatography on silica gel (hex:acetone; 4:6) and ($CH_2Cl_2$:MeOH; 9.5:0.5) to give 5 mg (46% for 2 steps) of pure compound 9 as a diastereoisomer mixture. $^1$H NMR (400 MHz, $CD_3OD$).δ: 0.90 (s, 3H), 0.91 (s, 3H), 2.94 (s, 3H), 3.19 (dd, 1H, J=12.6 & 3.2 Hz), 3.58-3.63 (m, 1H), 3.74 (t, 1H, J=8.5 Hz), 4.10-4.15 (m, 1H), 4.43-4.47 (m, 1H), 6.86 (d, 2H, J=7.6 Hz), 6.92 (s, 1H), 7.25 (t, 1H, J=7.8 Hz).

Example XVII

Synthesis of Testosterone Derivatives

This synthesis is described in Scheme 47

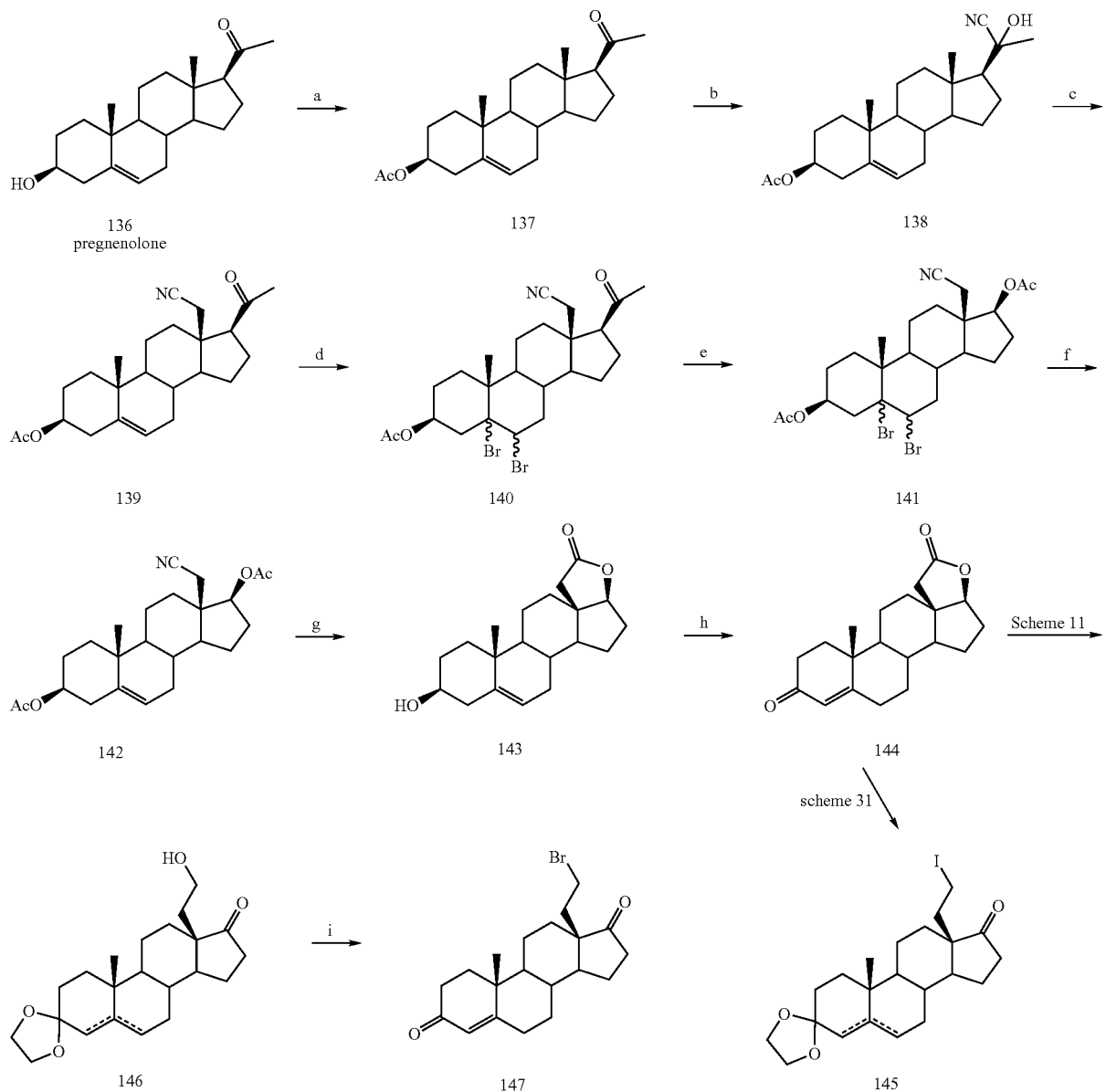

Conditions: a) Ac$_2$O, pyridine, 99%; b) 1) TMSCN, ZnI$_2$, CH$_2$Cl$_2$, 2) HCl 10%, dioxane, 97%; c) Pb(OAc)$_4$, CaCO$_3$, I$_2$, hv, cyclohexane/benzene, 51%; d) Br$_2$, AcOH/Et$_2$O, 99%; e) H$_2$O$_2$ (anhydrous), (CF$_3$CO)$_2$O, CH$_2$Cl$_2$/Et$_2$O, 64%; f) Zn, AcOH/Et$_2$O, 99%; g) 1) NaOMe, MeOH, 2) HCl 10%, 97%; h) Oppenauer oxidation, 99%; i) 1) CBr$_4$, PPh$_3$, 2) Acetone/MeOH (1:1), 10% HCl, 40° C., 34%.

Compound 137

Pregnenolone 136 (25 g, 0.079 Mol) was treated according to the procedure in scheme 31 to give acetylated compound 137 (27.7 g, 98%); $^1$H NMR (400 MHz, CDCl$_3$)δ: 5.36(br. d, 1H, J=5 Hz), 4.57-4.62(m, 1H), 2.53(t, 1H, J=9 Hz), 2.12(s, 3H), 2.03(s, 3H), 1.01(s, 3H), 0.62(s, 3H).

Compound 138 was prepared according to the procedure in scheme 31 in a 99% yield. 1,4-Dioxane was used for the hydrolysis instead of acetone; $^1$H NMR (400 MHz, CDCl$_3$)δ: 5.36(d, 1H, J=5 Hz), 4.56-4.63(m, 1H), 2.04(s, 3H), 1.63(s, 3H), 1.03(s, 3H), 1.02(s, 3H).

Compound 139 was prepared according to the procedure in scheme 31 in a 51% yield; $^1$H NMR (400 MHz, CDCl$_3$) δ 5.36(d, 1H, J=5 Hz), 4.58(m, 1H), 2.72(t, 1H, J=J=9 Hz), 2.54(dt, 1H, J$_1$=13 Hz, J$_2$=3 Hz), 2.30(s, 3H), 2.04(s, 3H), 1.02(s, 3H).

Compound 140

Bromine (1.07 mL, 0.021 Mol) in acetic acid (75 mL) was added dropwise to an ice-cold solution of 139 (5 g, 0.013 Mol) and potassium acetate (14 g, 0.143 Mol) in a mixture of Et$_2$O (250 mL) and acetic acid (75 mL). After 2 hr of stirring at 0° C., $^1$H NMR of an aliquot showed the completion of the reaction. The suspension was diluted with ethyl acetate and most of the solid KOAc was removed by filtration. The solid was well rinsed with ethyl acetate and the filtrate was concentrated under vacuuo. The resulting syrup was dissolved in ethyl acetate, washed with 5% Na$_2$S$_2$O$_3$, brine, dried (MgSO$_4$) and concentrated to give 7.1 g of dibromo-compound 140 which was used in the next step without any purification; $^1$H NMR (400 MHz, CDCl$_3$)δ: 5.43-5.51(m, 1H), 4.80(dd, 1H, J$_1$=4 Hz, J$_2$=2 Hz), 2.30(s, 3H), 2.06(s, 3H), 1.47(s, 3H).

Compound 141

Hydrogen peroxide 50% solution (43.8 mL, 0.644 Mol) was extracted with ethyl ether (4×25 mL), dried over MgSO$_4$ and added dropwise to a cold solution of trifluoroacetic anhydride (91 mL, 0.644 Mol) in 200 mL dichloromethane in a rate to keep temperature below 10-12° C. After aging for 1 hr, compound 140 (7 g, 0.013 Mol) was added directly into the mixture and the cooling bath was removed and the temperature went to 27-28° C. After 1 hr, the reaction was followed by TLC and was complete in 2 hr. The mixture was diluted with 500 mL of dichloromethane, cooled and neutralised by a slow addition of a saturated solution of NaHCO$_3$ with vigorous stirring. Layers were separated and the organic phase was washed with a 5% solution of Na$_2$S$_2$O$_3$, brine, dried over MgSO$_4$. The organic layer was tested for the presence of peroxide (Quantofix peroxide test sticks, Aldrich) before concentration under reduced pressure. The residue was purified on silica gel (hex/EtOAc 7:3) to give 4.65 g (64%) of pure 141; $^1$H NMR (400 MHz, CDCl$_3$)δ:5.43-5.49(m, 1H), 4.89 (dd, 1H, J$_1$=9 Hz, J$_2$=7 Hz), 4.81(dd, 1H, J$_1$=4 Hz, J$_2$=2 Hz), 2.13(s, 3H), 2.05(s, 3H), 1.47(s, 3H).

Compound 142

To a stirred solution of 141 (587 mg, 1.05×10$^{-3}$ Mol) in a mixture of acetic acid (15 mL) and ethyl ether (15 mL) at 0° C., was added zinc dust (137 mg, 2.1×10$^{-3}$ Mol) and the cooling bath was removed. After 2 hr, $^1$H NMR of an aliquot showed the completion of the reaction. Filtration through celite, neutralisation with saturated solution of NaHCO$_3$, drying over MgSO$_4$ and concentration gave crude 142 (416 mg, 99%) which was used in the next step without purification; $^1$H NMR (400 MHz, CDCl$_3$) δ 5.34(br. s, 1H), 4.85(dd, 1H, J$_1$=10 Hz, J$_2$=7 Hz), 4.54-4.62(m, 1H), 2.11(s, 3H), 2.02(s, 3H), 1.00(s, 3H).

Compound 143 was prepared according to the procedure in scheme 11 in a quantitative yield; $^1$H NMR (400 MHz, CDCl$_3$) δ 5.35(t, 1H, J=2 Hz), 4.55(dd, 1H, J$_1$=8 Hz, J$_2$=2 Hz), 3.49-3.57(m, 1H), 0.97(s, 3H).

Compound 144

Compound 143 (1.3 g, 3.16×10$^{-3}$ Mol) and cyclohexanone (3.2 mL, 0.032 Mol) were dissolved in 150 mL of toluene and the mixture was refluxed to removed approx. 15 mL of toluene using a Dean-Stark trap. The solution was cooled just below the boiling point for the addition of aluminium isopropoxide (775 mg, 3.79×10$^{-3}$ Mol) and after the addition, the reflux was continued for 3 hr. After cooling to room temperature, 60 mL of a 10% HCl solution was added and the mixture was extracted with dichloromethane, washed with brine, dried over MgSO$_4$ and concentrated. The oily residue was diluted with hexanes with vigorous stirring to give a pale yellow solid which was removed by filtration, rinsed with hexanes and dried to give 1.27 g (99%) of pure 144; $^1$H NMR (400 MHz, CDCl$_3$)δ: 5.75(s, 1H), 4.55(dd, 1H, J$_1$=8 Hz, J$_2$=2 Hz), 1.16(s, 3H).

Compound 145 was prepared from compound 144 by using the method reported in the scheme 31; $^1$H NMR (400 MHz, CDCl$_3$))δ: 5.30-5.32 (m, 1H), 5.2 (s, 1H), 3.8-3.9 (m, 4H), 3.2-3.3 (m, 1H), 2.95-3.05 (m, 1H), 1.09-1.10 (m, 1H).

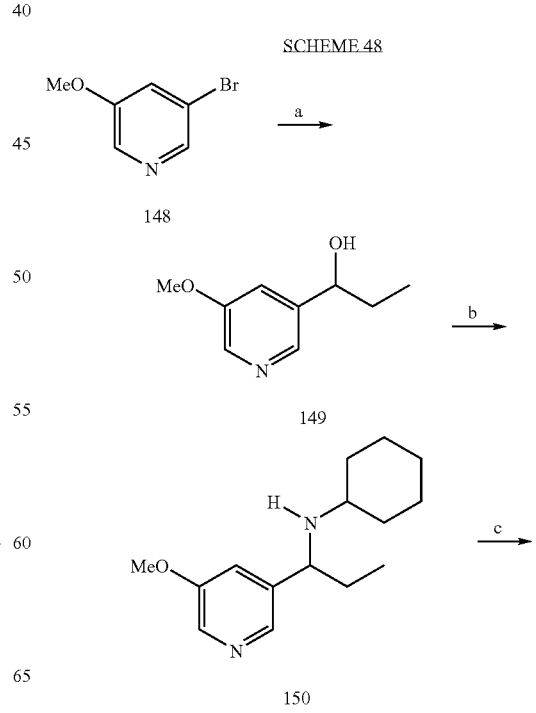

SCHEME 48

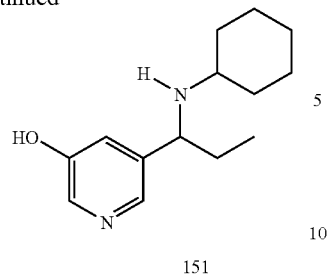

151

Conditions: a) i-PrMgCl, CH₃CH₂CHO, THF, RT, 57%; b) 1) CH₃SO₂Cl, Et₃N, 0° C. to RT, CH₂Cl₂, 2) Cyclohexylamine or morpholine, K₂CO₃, DMA, RT, 30% (2 steps); c) TMAH Al₂Cl₇, CH₂Cl₂, RT to reflux, 85%;

Compound 149

A solution of (940 mg, 5.0 mmol) of 3-bromo-5-methoxypyridine 148 in 25 mL of THF at rt, was treated with 5 mL of isopropylmagnesium chloride (2M). After 2 h, 0.72 mL of propionaldehyde (10.0 mmol) was added at room temperature. After 10 min., the reaction mixture was quenched with water, extracted with Et₂O, washed with brine solution, dried over Na₂SO₄ and evaporated. The compound 149 was purified by flash chromatography on silica gel (hexanes/acetone (8:2)) to give 476 mg (57%) of the alcohol 149; ¹H NMR (400 MHz, CD₃COCD₃)δ: 8.16-8.14 (m, 2H), 7.34-7.32 (m, 1H), 4.66 (q, 1H, J=5.6 Hz), 4.42-4.40 (m, 1H), 3.88 (s, 3H), 1.79-1.70 (m, 2H), 0.92 (t, 3H, J=7.4 Hz).

Compound 150:

To a stirred solution of 476 mg (2.9 mmol) of compound 149 in 25 mL of methylene chloride at 0° C., was added successively 0.6 mL (4.3 mmol) of triethylamine and 0.3 mL (3.9 mmol) of methanesulfonyl chloride. After 10 min., the reaction mixture was allowed to warm to room temperature. The reaction was monitored by TLC. The solution was poured into water, extracted with methylene chloride, washed with brine solution and then dried over Na₂SO₄. The solvent was removed under reduced pressure. The crude mesylate was used without further purification (704 mg). A mixture of 704 mg (2.9 mmol) of the crude mesylate, 0.66 mL (5.8 mmol) of cyclohexylamine and 795 mg (5.8 mmol) of K₂CO₃ in 10 mL of DMA was stirred at room temperature for 72 h. The reaction mixture was diluted with Et₂O, washed with H₂O and brine solution, dried over Na₂SO₄, concentrated. The residue was purified by flash chromatography on silica gel (hexanes/acetone (5:5)) to give 210 mg (30%) of compound 150; ¹H NMR (400 MHz, CD₃COCD₃) δ: 8.15-8.12 (m, 2H), 7.36-7.35 (m, 1H), 3.88 (s, 3H), 3.76 (t, 1H, J=6.8 Hz), 2.26-2.19 (m, 1H), 1.99-1.96 (m, 1H), 1.80-1.45 (m, 6H), 1.15-0.95 (m, 5H), 0.83 (t, 3H, J=7.4 Hz).

Compound 151

A solution of 210 mg (0.85 mmol) of the compound 150 in 8 mL of methylene chloride was added at room temperature 0.75 mL (2.55 mmol) of the ionic liquid (TMAH Al₂Cl₇). The heterogeneous solution was refluxed for overnight. The reaction was transferred into a saturated NaHCO₃ solution and extracted with diethyl ether. The extract was washed with saturated aqueous NaCl, dried over Na₂SO₄, concentrated. The crude phenol 151 was used without further purification 169 mg (85%); ¹H NMR (400 MHz, CD₃OD)δ: 7.99 (d, 1H, J=2.6 Hz), 7.91 (d,1H, J=1.3 Hz) 7.20 (dd, 1H, J=2.1 Hz J=2.1 Hz), 3.80-3.75 (dd, 1H, J=9.6 Hz J=4.8 Hz), 2.30-2.28 (m, 1H), 2.10-2.00 (m, 1H), 1.99-1.80 (m, 1H), 1.80-1.50 (m, 5H), 1.25-1.00 (m, 5H), 0.79 (t, 3H, J=7.4 Hz).

SCHEME 49

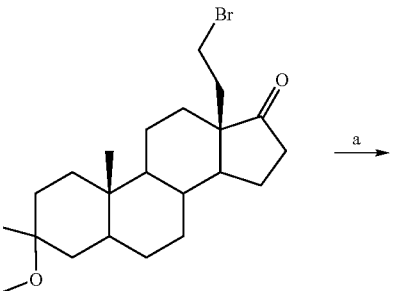

122

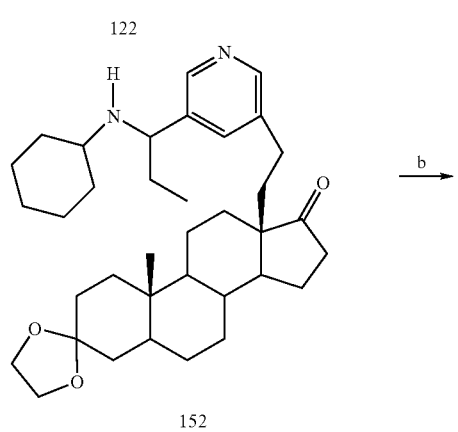

152

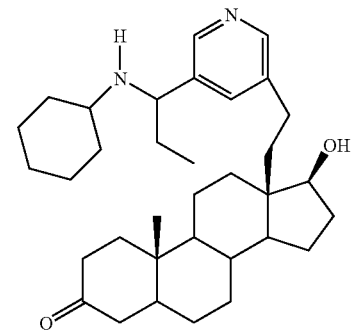

EM-7093

Conditions: a) 151, Cs₂CO₃, DMF, 80° C., 51%; b) 1) NaBH₄, MeOH, 0° C. to RT, 2) Acetone/MeOH (1:1), HCl 10%, 40° C., 79% (2 steps);

Compound 152

A solution of 65 mg (0.15 mmol) of the bromo compound 122 in 1.5 mL of DMF containing 54 mg (0.23 mmol) of phenol 151 and 99 mg (0.30 mmol) of cesium carbonate was heated at 80° C. for overnight. The reaction mixture was diluted with diethyl ether, washed with 5% NaOH, H₂O and brine solution. The organic phase was dried over Na₂SO₄ and concentrated under vacuum. The residue was purified by flash chromatography on silica gel (hexanes/acetone (7:3)) to give 45 mg (51%) of compound 152; ¹H NMR (400 MHz, CD₃COCD₃)δ: 8.12-8.08 (m, 2H), 7.31-7.30 (m, 1H), 4.05-4.18 (m, 1H), 4.00-3.80 (m, 5H), 3.80-3.70 (m, 1H), 2.60-2.40 (m, 1H), 2.30-0.70 (m, 42H).

EM-7093

A solution of 45 mg (0.078 mmol) of 152 in 1.5 mL of methanol at 0° C. was treated with 1 equivalent of sodium borohydride. After stirring 30 min. at room temperature, 1 mL of acetone and 1 mL of 10% HCl were added. After stirring 30 min. at 40° C., the reaction mixture was poured into saturated aqueous sodium bicarbonate and extracted with diethyl ether, the combined organic layers was washed with brine solution, dried over Na$_2$SO$_4$ and evaporated. The crude compound was purified by flash chromatography (CH$_2$Cl$_2$/MeOH (95:5)) to give EM-7093 as a white solid: yield 33 mg (79%); $^1$H NMR (400 MHz, CD$_3$OD)δ: 8.17-8.15 (m, 1H), 8.06-8.04 (m,1H), 7.52-7.50 (m, 1H), 4.60-4.45 (m, 1H), 4.35-4.18 (m, 1H), 3.85-3.65 (m, 2H), 2.60-2.40 (m, 1H), 2.39-2.30 (m, 1H), 2.30-0.70 (m, 41H).

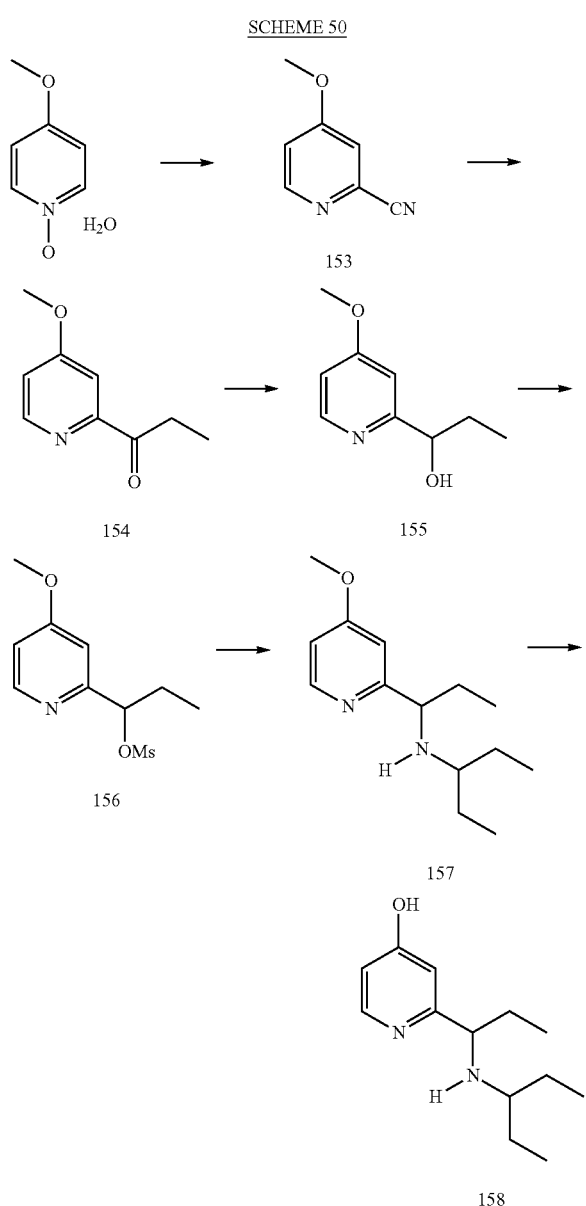

SCHEME 50

Conditions: a) Mol sieves 4 A, TMSCN, (CH$_3$)$_2$NCOCl, DCM, 0° C.-rt, 16 h; b) EtMgBr, benzene:ether (1:1), 0° C.-rt, 2 h; c) NaBH$_4$, MeOH, 0° C.-rt, 2 h; d) Et$_3$N, CH$_3$SO$_2$Cl, DCM, 0° C.-rt, 2 h; e) alkylamine, CH3CN, 60-80° C., 16-24 h; f) Me$_3$NHAl$_2$Cl$_7$, DCM, 45° C., 16 h.

2-Cyano-4-methoxypyridine 153

To a solution of 4-methoxypyridine-N-oxide hydrate (1.25 g, 10 mmol) in DCM (mL) were added molecular sieves (4 A, 3 g, 300 mg/mmol) and the mixture was stirred overnight. The resulting suspension was then cooled at 0° C. and trimethylsilyl cyanide (1.6 mL, 12 mmol) and N,N-dimethyl carbamoyl chloride (1 mL, 10.5 mmol) were added successively. The reaction mixture was stirred at room temperature overnight. Finally, the mixture was filtered over celite and the filtrate was diluted with dichloromethane (80 mL) and an aqueous solution of potassium carbonate (1 M, 70 mL). The mixture was extracted at pH 10-12 with dichloromethane (3×80 mL). The combined organic phase was dried by filtration over anhydrous magnesium sulfate, and the filtrate was concentrated to afford 1.2 g of crude product. Separation by column chromatography using hexanes: acetone (95:05 to 70:30, 5% gradient) gave 1.023 g (76% yield) of cyanopyridine 18 as a white solid; $^1$H NMR (acetone d$^6$)δ: 4.01 (s, 3H, OCH$_3$), 7.27 (dd, 1H, J=5.8 & 2.6 Hz), 7.55 (d, 1H, J=2.6 Hz), 8.54 (d, 1H, J=5.8 Hz).

2-Propanoyl-4-methoxypyridine 154

To a solution of 2-cyano-4-methoxypyridine 153 (503 mg, 3.75 mmol) in benzene: ether (20 mL, 1:1, v/v) cooled at 0° C. was added dropwise 1 M solution of EtMgBr (5 mL, 5 mmol) in THF and the mixture was allowed to warm to room temperature with stirring. After 4 hr, the reaction flask was cooled again at 0° C. and 2.3 mL of hydrochloric acid (10%) was added dropwise, with additional five minutes stirring. Then, the mixture was poured in dichloromethane (80 mL) and water (60 mL) and the pH of the aqueous layer was adjusted to 10 with a 10% aqueous solution of sodium hydroxide. The resulted mixture was extracted with dichloromethane (3×80 mL). The combined organic layer was dried by filtration over anhydrous MgSO$_4$ and the filtrate was concentrated to provide 694 mg of the crude ketone 154. The product was used without purification for the step; $^1$H NMR (acetone d$^6$)δ: 1.14 (t, 3H, J=7.3 Hz), 3.20 (q, 2H, J=7.3 Hz), 3.97 (s, 3H), 7.16 (dd, 1H, J=5.6 & 2.6 Hz), 7.50 (d, 1H, J=2.6 Hz), 8.52 (d, 1H, =5.6 Hz).

2-propyl-(1'-ol)-4-methoxypyridine 155

To a stirred solution of ketone 154 (694 mg) in methanol at 0° C. was added NaBH$_4$ (430 mg, 11.25 mmol). The reaction mixture was allowed to return to room temperature and after 2 hr, quenched with 5 mL of acetone and 3 mL of 10% HCl. The mixture was extracted with ethyl acetate (100 mL) at pH=10 (with addition of 10% NaOH) and washed with water (3×50 mL). The organic phase was dried over MgSO$_4$ and concentrated to give 694 mg of alcohol, as crude product. Purification by column chromatography using hexanes: acetone (95:05 to 70:30, 5% gradient) gave 572 mg (91% yield, 2 steps) of 155; $^1$H NMR (acetone d$^6$)δ: 0.92 (t, 3H, J=7.4 Hz), 1.61-1.90(2m, 2H), 3.89 (s, 3H), 4.51 (d, 1H, J=5.2 Hz), 4.50-4.59 (m, 1H), 6.81 (dd, 1H, J=5.7 & 2.6 Hz), 7.04 (d, 1H, J=2.6 Hz), 8.52 (d, 1H, J=5.7 Hz).

2-Propyl-(1'-methylsulfonyl)+methoxypyridine 156

To a solution of secondary alcohol 155 (195 mg, 1.17 mmol) and triethylamine (250 μL, 1.80 mmol) in dichloromethane (5 mL) at 0° C., was added methanesulfonyl chloride (120 μL, 1.52 mmol) and After the addition, the mixture was allowed to warm to room temperature. After 1 hr, the reaction mixture was quenched with saturated NaHCO$_3$ by adjusting the pH at 10. The mixture was extracted with EtOAc (20 mL) and washed with water (3×15 mL). The organic phase was dried by filtration over MgSO$_4$, then concentrated to provide the mesylate 156 in quantitative yield (313.4 mg); $^1$H NMR (acetone d$^6$)δ: 0.96 (t, 3H, J=7.4 Hz), 2.01-2.10 (m, 2H), 3.02 (s, 3H), 3.93 (s, 3H), 5.48 (t, 1H, J=7.0 Hz), 6.93 (dd, 1H, J=5.7 & 2.6 Hz), 7.10 (d, 1H, J=2.6 Hz), 8.40 (d, 1H, J=5.7 Hz).

Amine 157

To an acetonitrile (3 mL) solution of mesylate 156 (53 mg, 0.215 mmol) in a reaction vial was added 1-ethyl propylamine (165 μL, 1.37 mmol). The reaction vial was sealed and stirred overnight at 70° C. The vial was cooled to room temperature, the reaction mixture poured into dichloromethane (80 mL) and water and pH was adjusted to 10 with a saturated solution of NaHCO$_3$. The organic extracts (3×80 mL dichloromethane) were combined and dried by filtration over MgSO$_4$. The filtrate was concentrated to provide 32.3 mg of desired amine. The product was used in the next step without purification; $^1$H NMR (acetone d$^6$)δ: 0.79 and 0.86 (3t, 9H, J=7.4 Hz), 1.21-1.40 (2m, 2H), 1.41-1.66 (2m, 4H), 2.06-2.08 (m, 1H), 3.65 (t, 1H, J=6.8 Hz), 3.88 (s, 1H), 6.78 (dd, 1H, J=5.7 & 2.6 Hz), 6.99 (d, 1H, J=2.6 Hz), 8.33 (d, 1H, J=5.7 Hz).

Phenol 158

To a dichloromethane (3 mL) solution of 157 (33 mg, 0.136 mmol) in a reaction vial was added freshly prepared ionic liquid (CH$_3$)$_3$NH$^+$Al$_2$Cl$_7^-$ (125 μL, 0.41 mmol). The reaction vial was sealed and stirred overnight at 45° C. overnight. The vial was cooled to room temperature and the reaction mixture poured into dichloromethane (80 mL) and water. The pH was adjusted to 8 with a saturated solution of NaHCO$_3$. The organic extracts (8×80 mL dichloromethane) were combined and dried by filtration over MgSO$_4$. The filtrate was concentrated to provide 25 mg of desired amine. The product was used in the next step without any purification; $^1$H NMR (acetone d$^6$)δ: 0.83, 0.85 and 0.90 (3t, 9H, J=7.4 Hz), 1.27-1.73 (4m, 6H), 2.25-2.28 (m, 1H), 3.61 (t, 1H, J=7.1 Hz), 6.28 (dd, 1H, J=6.9 & 1.9 Hz), 6.35 (d, 1H, J=1.9 Hz), 7.80 (d, 1H, J=6.9 Hz).

SCHEME 51

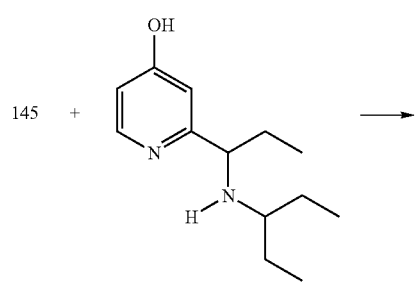

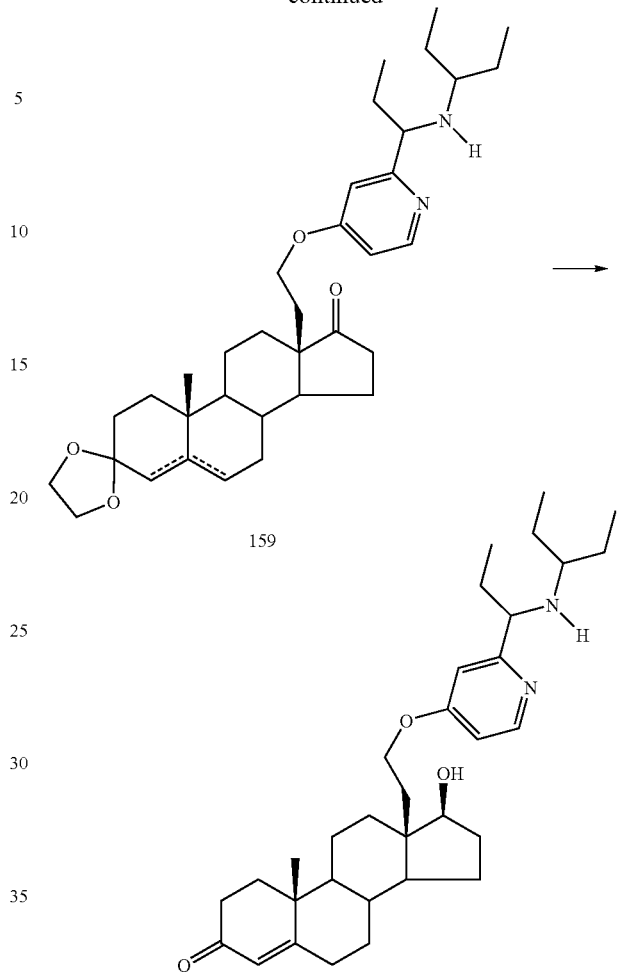

EM-7136

Conditions: a) Cs$_2$CO$_3$, acetone, 50-60° C., 16 h; b) 1) NaBH$_4$, 0° C.-rt, 2 h, 2) 10% HCl, acetone, rt, 1 h.

Compound 159

A 6 mL vial with magnetic stirrer was charged with C13-iodoethyl steroid 145 (85 mg, 0.18 mmol), 4-hydroxy-pyridine 158 (25 mg, 0.112 mmol), cesium carbonate (70 mg, 0.210 mmol) and 3.5 mL acetone. The vial was sealed with a Teflon cap and was heated while stirring for 12 hr at 50° C. on a graphite bath. The reaction mixture was transferred to an extraction funnel with water (20 mL) and extracted with dichloromethane (4×30 mL). The combined organic phase was filtered over a pad of cotton and magnesium sulfate and concentrated. Separation of products by flash column chromatography with hexanes:acetone (85:15 to 65:35, 5% gradient) gave 40 mg of phenol-ether 159 (64% yield); $^1$H NMR (acetone d$^6$)δ: 0.80, 0.84 and 0.86 (3t, 9H, J=7.4 Hz), 1.07 (s, 1H), 2.40-2.60 (m, 1H), 3.61 (t, 1H, J=7.1 Hz), 3.82-4.20 (m, 6H), 5.2-5.40 (m, 1H), 6.72 (dd, 1H, J=5.6 & 1.9 Hz), 6.94 (d, 1H, J=1.9 Hz), 7.80 (d, 1H, J=5.6 Hz).

EM-7136

To a stirred solution of ketone 159 (40 mg, 0.071 mmol) in methanol at 0° C. was added sodium borohydride (1-2 mg, excess). The reaction mixture was allowed to return to room temperature and after 2 hr, quenched with 2 mL of a saturated solution of ammonium chloride, then extracted with ethyl acetate. The organic phase was dried over magnesium sulfate, filtered and concentrated to give 40 mg of alcohol. This was solubilized in 5 mL acetone and 10% hydrochloric acid (0.2 mL) was added. After 1 hr of stirring, the reaction mixture was poured into in a mixture of ethyl acetate (30 mL) and 10% sodium hydroxide. After extraction and subsequent washing with water, the organic phase was dried over magnesium sulfate and concentrated. Purification by flash chromatography provided 20 mg (54% yield) of pure compound EM-7136. White foam. $^1$H NMR (acetone d$^6$)δ: 0.79, 0.84 and 0.86 (3t, 9H, J=7.4 Hz), 1.26 (s, 1H), 2.45 (m, 1H), 3.61 (t, 1H, J=7.1 Hz), 3.70-3.80 (m, 1H), 4.20-4.37 (m, 1H) 4.60-4.78 (m, 1H), 5.64 (s, 1H), 6.80 (d, 1H, J=5.6 Hz), 7.03 (dd, 1H, J=5.6 & 2.4 Hz), 8.31 (d, 1H, J=5.6 Hz).

SCHEME 52

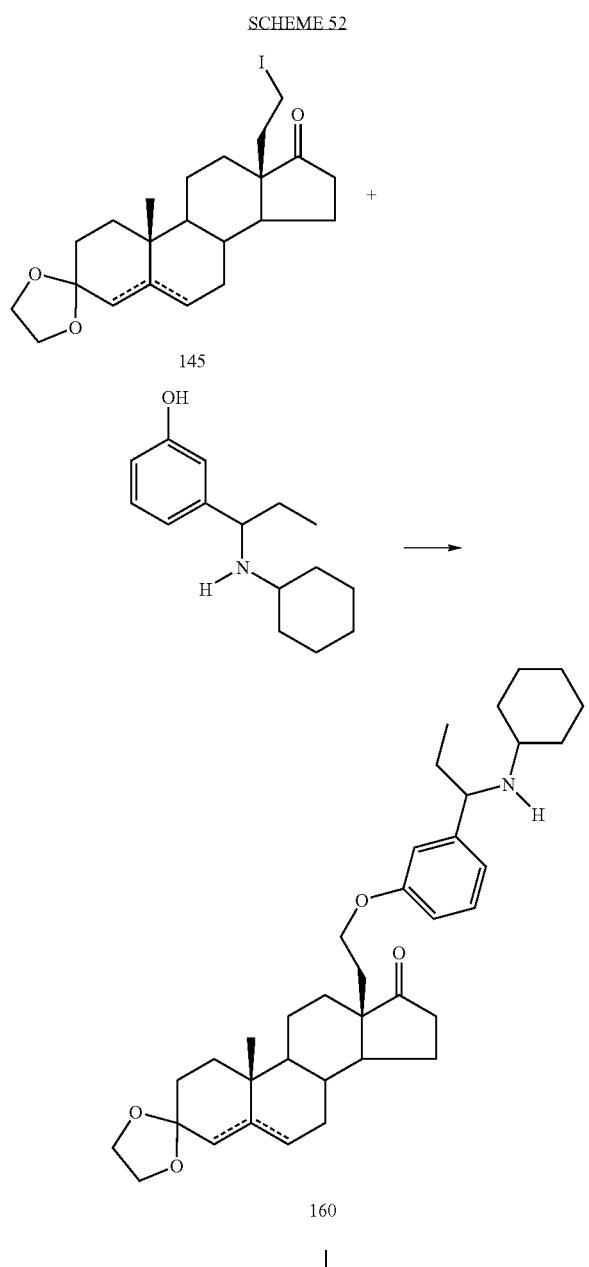

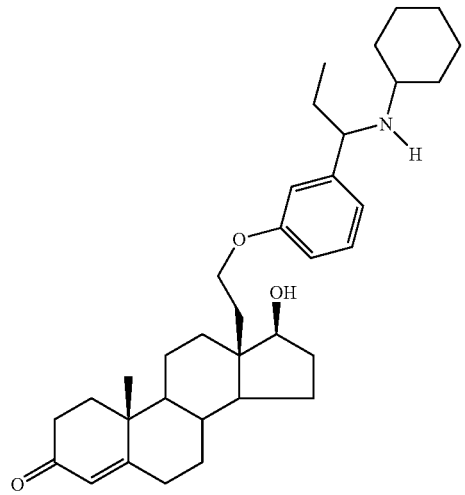

EM-6798

EM-6798

A 6 mL vial with magnetic stirrer was charged with the corresponding C13-iodoethyl steroid 145 (25 mg, 0.05 mmol), phenolic amine (19 mg, 0.08 mmol), cesium carbonate (33 mg, 0.11 mmol) and 3.5 mL acetone. The vial was sealed with a Teflon cap and the mixture was heated while stirring for 12 hr at 50° C. on graphite bath. After this time the bath was removed and the system was allowed to return to room temperature. The reaction mixture was transferred to an extraction funnel charged with water (20 mL), the pH adjusted to pH=12 with 10% NaOH and extracted with dichloromethane (4×15 mL). The combined organic phase was filtered over a pad of cotton and magnesium sulfate and concentrated to give 33 mg of ketone 160. To ketone (33 mg) in methanol at 0° C. was added sodium borohydride (1-2 mg, excess). The reaction mixture was allowed to return at room temperature and after 2 hr, quenched with 2 mL of aq ammonium chloride. The solution was then adjusted to pH=12 with 10% NaOH and extracted with dichloromethane (4×15 mL). The organic phase was dried over magnesium sulfate, filtered and concentrated to give 24 mg of alcohol. This was solubilized in 5 mL acetone and 10% hydrochloric acid (0.2 mL) was added with stirring. After 1 hr, the reaction mixture was poured into an extraction funnel containing ethyl acetate (30 mL) and 10% sodium hydroxide. After extraction and subsequent washing with water, the organic phase was dried over magnesium sulfate and concentrated. Purification by flash chromatography provided 10 mg (38% yield, in 3 steps) of pure EM-6798; $^1$H NMR (acetone d$^6$)δ: 0.82 (t, 3H, J=7.4 Hz), 1.26 (s, 1H), 3.68 (t, 1H, J=7.1 Hz), 3.76 (t, 1H, J=8.4 Hz), 4.13-4.20 (m, 1H), 4.55-4.60 (m, 1H), 5.65 (s, 1H), 6.82 (d,1H J=7.4 Hz), 6.86 (d, 1H, J=7.4 Hz), 7.03 (s, 1H), 7.21 (t, 1H, J=7.4 Hz).

Example XVIII

Synthesis of Diamino Dihydrotestosterone Derivatives

This synthesis is described in Scheme 53

SCHEME 53

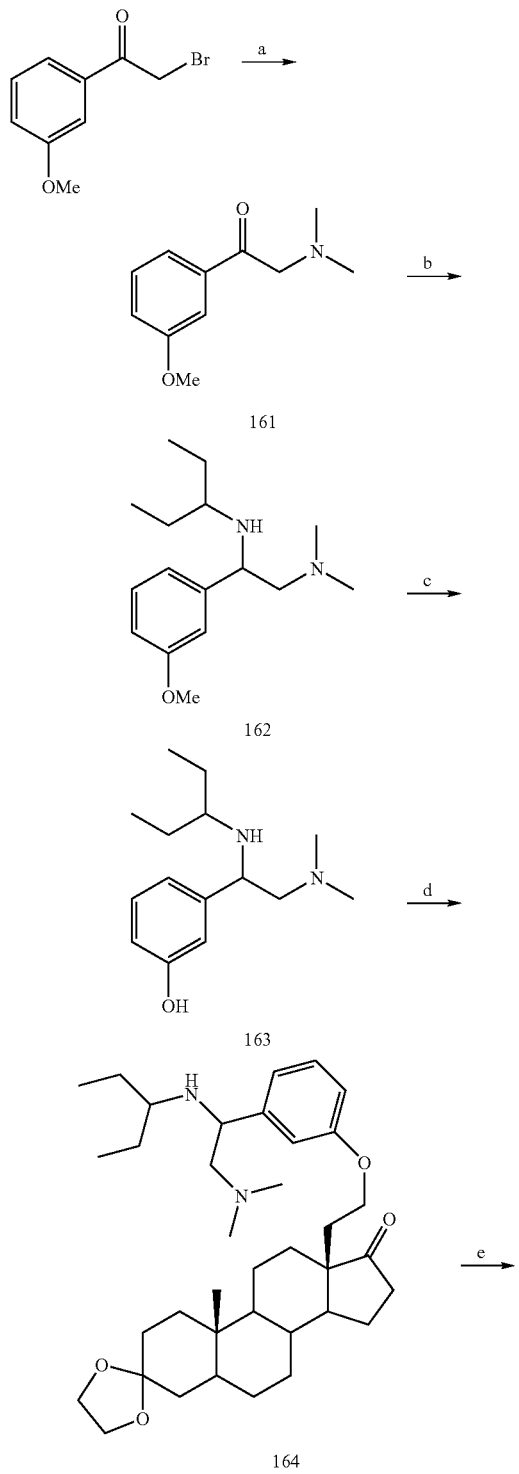

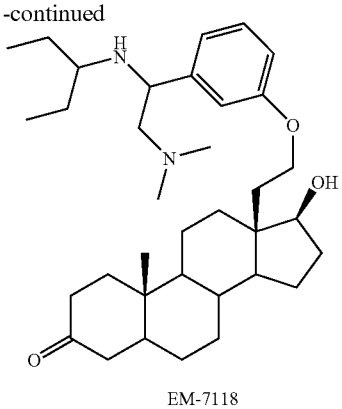

EM-7118

Conditions: a) 2M Me$_2$NH in THF, 90%; b) Ethylpropylamine, EtOH, AcOH, NaBH$_3$CN 40%; c) BBr$_3$, DCM, 29%; d) Phenol, 57, Cs$_2$CO$_3$, DMF, 60%; e) 1) NaBH$_4$, MeOH, 2) Acetone, 10% HCl, 72%.

Keto-amine 161

To a solution of 2-bromo-3'-methoxyacetophenone (2.00 g, 8.73 mmol) in tetrahydrofuran (40.0 mL) was added a 2M solution of dimethylamine in tetrahydrofuran (40.0 mL, 78.6 mmol). The mixture was stirred at room temperature 20 min. A saturated solution of sodium bicarbonate was added and the product was extracted with ethyl acetate (3×50 mL). Organic layers were combined, dried over magnesium sulfate and concentrated to give the crude product (1.52 g, 90%). $^1$H NMR (400 MHz, CDCl$_3$) δ: 7.56 (d, 1H, J=7 Hz), 7.51 (s, 1H), 7.36 (t, 1H, J=7 Hz), 7.13 (d, 1H, J=7 Hz), 3.85 (s, 3H), 3.81, (s, 2H), 2.43 (s, 6H).

Diamine 162

To a solution of ethylpropylamine (0.800 mL, 6.83 mmol) in ethanol (2.0 mL) was added acetic acid (0.456 mL, 7.08 mmol). The resulting solution was stirred at 65° C. for 15 min, then ketone 161 (440 mg, 2.28 mmol) in ethanol (1.0 mL) was added followed by Sodium cyanoborohydride (429 mg, 6.83 mmol). The reaction mixture was stirred under reflux overnight. An aqueous solution of 10% sodium hydroxyde was added and the product was extracted with ethyl acetate (3×15 mL). Organic layers were combined, dried over magnesium sulfate and concentrated to give the crude product. The crude product was purified by column chromatography over silica gel to give pure product 162 (240.0 mg, 40%). $^1$H NMR (400 MHz, acetone-d$_6$) δ: 7.20 (t, 1H, J=7 Hz), 7.08 (s, 1H), 6.97 (d, 1H, J=7 Hz), 6.77 (d, 1H, J=7 Hz), 3.89 (dd, 1H, J=6 Hz), 3.78 (s, 1H), 2.39 (t, 1H, J=11 Hz), 2.10, (s, 6H), 2.05-2.10 (m, 2H), 1.4-1.6 (m, 2H), 1.18-1.35, (m, 2H), 0.88 (m, 3H), 0.81 (m, 3H).

Phenolic Diamine 163

To a solution of diamine 162 (85.0 mg, 0.321 mmol) in dichloromethane (10.0 mL) was added 1M solution of boron tribromide (0.964 mL, 0.964 mmol) at 0° C. The resulting solution was stirred at 0° C. for 20 min. A saturated solution of sodium bicarbonate was added and the product was extracted with ethyl acetate (3×15 mL). Organic layers were combined, dried over magnesium sulfate and concentrated to give the crude product. The crude product was purified by column chromatography over silica gel using a gradient of 5% to 10% methanol in dichloromethane to give pure product 163 (23.0 mg, 29%). $^1$H NMR (400 MHz, MeOD) δ: 7.13 (t, 1H, J=8 Hz), 6.83 (d, 1H, J=8 Hz), 6.81 (s, 1H), 6.69 (d, 1H, J=8 Hz), 3.78-3.80 (m, 1H), 3.32 (t, 1H, J=11 Hz), 2.28 (s, 8H), 1.43-1.53 (m, 2H), 1.21-1.40 (m, 2H), 0.88 (t, 3H, J=7 Hz), 081 (t, 3H, J=7 Hz).

Compound 164

To a solution of phenol 163 (22.0 mg, 0.0879 mmol) in dimethylformamide (1.0 mL) was added cesium carbonate (86.0 mg, 0.264 mmol). The resulting mixture was stirred at 60° C. for 10 min. and bromosteroid (86.0 mg, 0.131 mmol) was added. The reaction was stirred at 60° C. for 3 hrs. An aqueous solution of 10% sodium hydroxyde was added and the product was extracted with ethyl acetate (3×15 mL). Organic layers were combined, dried over magnesium sulfate and concentrated to give the crude product. The crude product was purified by column chromatography over silica gel using a gradient of 1% to 5% methanol in dichloromethane to give pure product 164 (31.0 mg, 60%). $^1$H NMR (400 MHz, MeOD) δ: 7.21 (t, 1H, J=7 Hz), 6.93 (s, 1H), 6.92 (d, 1H, J=7 Hz), 6.71 (d, 1H, J=7 Hz), 3.97-4.10 (m, 1H), 3.92 (s, 4H), 3.90-3.95 (m, 1H), 2.28 (s, 6H), 0.88 (s, 3H), 0.87 (t, 3H, J=7 Hz), 0.82 (t, 3H, J=7 Hz).

EM-7118

To a solution of ketone 164 (45.0 mg, 0.00756 mmol) in methanol (2 mL) was added sodium borohydride (86.0 mg, 0.227 mmol) at 0° C. The reaction was allowed to warm up to room temperature and was stirred for 30 min. The solvent was evaporated and the residue was dissolved in acetone (2 mL) and 10% aqueous solution of hydrochloric acid (2 mL). The solution was stirred at room temperature 3 hrs. An aqueous solution of 10% sodium hydroxyde was added and the product was extracted with ethyl acetate (3×15 mL). Organic layers were combined, dried over magnesium sulfate and concentrated to give the crude product. The crude product was purified by column chromatography over silica gel using a gradient of 5% to 10% methanol in dichloromethane to give pure product EM-7118 (30.0 mg, 72%). $^1$H NMR (400 MHz, MeOD) δ: 7.21 (t, 1H, J=7 Hz), 7.00 (s, 1H), 6.91 (d, 1H, J=7 Hz), 6.80 (d, 1H, J=7 Hz), 4.39-4.50 (m, 1H), 4.07-4.20 (m,1H), 3.85-3.90 (m, 1H), 3.65 (t, 1H, J=7 Hz), 2.28 (s, 6H), 1.16 (s, 3H), 0.81-0.88 (m, 6H).

Example XIX

Synthesis of Amino Methoxy Dihydrotestosterone Derivatives

This synthesis is described in Scheme 54

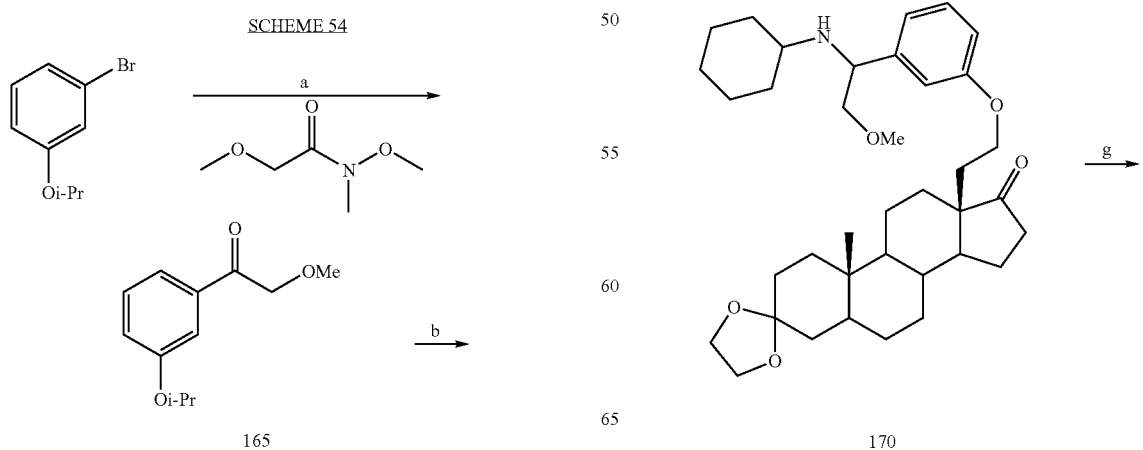

-continued

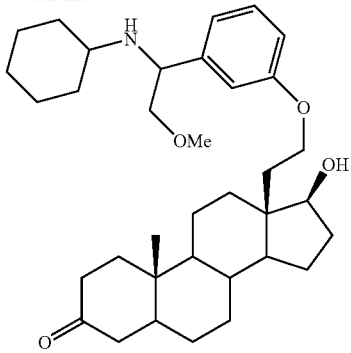

EM-6972

Conditions: a) n-BuLi, THF, −78° C., 60%; b) LAH, THF, 75%; c) MsCl, Et₃N, DCM, 99%; d) Cyclohexylamine, DMF, 42%; e) BCl₃, DCM, 0° C., 59%; f) 122, Cs₂CO₃, DMF, 60%; g) 1) NaBH₄, MeOH, 2) Acetone, 10% HCl, 86%.

Ketone 165

To a solution of 3-bromoisopropoxybenzene (1.33 g, 6.20 mmol) in tetrahydrofuran (12.0 mL) was added a 2.5M solution of n-butyllithium in hexane (2.72 mL, 6.82 mmol) at −78° C. The resulting mixture was stirred at −78° C. for 15 min. then Weinreb amide (908 mg, 6.82 mmol) in tetrahydrofuran (2.0 mL) was added. The reaction was allowed to warm up to room temperature and was stirred for 1 hr. A saturated solution of ammonium chloride was added and the product was extracted with ethyl acetate (3×20 mL). Organic layers were combined, dried over magnesium sulfate and concentrated to give the crude product. The crude product was purified by column chromatography over silica gel to give pure product 165 (761.0 mg, 60%). ¹H NMR (400 MHz, acetone) δ: 7.53 (d, 1H, J=8 Hz), 7.47 (s, 1H), 7.42 (t,1H, J=7 Hz), 7.20 (d, 1H, J=8 Hz), 4.74 (s, 2H), 4.72-4.77 (m, 1H), 3.43 (s, 3H), 1.32 (d, 6H, J=6 Hz).

Alcohol 166

To a solution of ketone 165 (761 mg, 3.65 mmol) in tetrahydrofuran (12.0 mL) was added a 1M solution of lithium alumunium hydride in tetrahydrofuran (5.50 mL, 15.5 mmol) at 0° C. The reaction was stirred at 0° C. for 30 min., then a solution of Rochelle salt was added. The product was extracted with ethyl acetate (3×20 mL). Organic layers were combined, dried over magnesium sulfate and concentrated to give the crude product. The crude product was purified by column chromatography over silica gel (50% ethyl acetate/hexane) to give pure product 166 (670 mg, 75%). ¹H NMR (400 MHz, acetone) δ: 7.21 (t, 1H, J=8 Hz), 6.98 (s, 1H), 6.81 (d, 1H, J=8 Hz), 6.78 (d, 1H, J=8 Hz), 4.78-4.82 (m, 1H), 4.59-4.67 (m, 1H), 4.26 (d, 1H, J=4 Hz), 3.36-3.50 (m, 2H), 3.33 (s, 3H), 1.30 (d, 6H, J=6 Hz).

Mesylate 167

To a solution of alcohol 166 (670 mg, 3.20 mmol) in dichloromethane (3.0 mL) was added triethylamine (0.9 mL, 6.40 mmol) and methanesulfonyl chloride (0.32 mL, 4.16 mmol) at 0° C. The reaction was stirred at 0° C. for 3 hrs. Water was added and the product was extracted with dichloromethane (3×20 mL). Organic layers were combined, dried over magnesium sulfate and concentrated to give the crude product 167 (957 mg, 99%). ¹H NMR (400 MHz, acetone) δ: 7.32 (t,1H, J=8 HZ), 6.98 (s, 1H), 6.97 (d,1H, J=8 Hz), 6.92 (d,1H, J=8 Hz), 5.60-5.65 (m, 1H), 4.60-4.69 (m, 1H), 3.58-3.83 (m, 2H), 3.41 (s, 3H), 3.00 (s, 3H), 1.31 (d, 6H, J=6 Hz).

Amine 168

To a solution of mesylate 167 (100 mg, 0.350 mmol) in dimethylformamide (2.0 mL) was added cyclohexylamine (0.120 mL, 1.05 mmol). The resulting mixture was stirred at 40° C. overnight. An aqueous solution of 10% sodium hydroxyde was added and the product was extracted with ethyl acetate (3×15 mL). Organic layers were combined, dried over magnesium sulfate and concentrated to give the crude product. The crude product was purified by column chromatography over silica gel to give pure 168 (40.0 mg, 42%). ¹H NMR (400 MHz, MeOD) δ: 7.20 (t, 1H, J=8 Hz), 7.00 (s, 1H), 6.95 (d, 1H, J=8 Hz), 6.78 (d, 1H, J=8 Hz), 4.58-4.63 (m, 1H), 4.06 (dd, 1H, J=5 Hz), 3.31 (s, 3H) 3.20-3.37 (m, 2H), 3.31 (s, 1H), 2.21-2.27 (m, 1H), 1.60-1.45 (m, 4H), 1.30 (d, 7H, J=6 Hz), 1.05 (m, 5H).

Phenol 169

To a solution of amine 168 (40.0 mg, 0.137 mmol) in dichloromethane (2.0 mL) was added a 1M solution of boron trichloride in dichloromethane (0.288 mL, 0.289 mmol) at 0° C. The reaction was stirred at 0° C. for 45 min. A saturated solution of sodium bicarbonate was added and the product was extracted with ethyl acetate (3×15 mL). Organic layers were combined, dried over magnesium sulfate and concentrated to give the crude product. The crude product was purified by column chromatography over silica gel (70% ethyl acetate/hexane) to give pure 169 (20.0 mg, 59%). ¹H NMR (400 MHz, MeOD) δ: 7.12 (t, 1H, J=8 Hz), 6.87 (s, 1H), 6.86 (d, 1H, J=8 Hz), 6.66 (d, 1H, J=8 Hz), 4.01 (dd, 1H, J=5 Hz), 3.40 (m, 2H), 3.29 (s, 3H), 2.20-2.26 (m, 1H) 1.60-1.45 (m, 4H), 1.20-0.95 (m, 5H).

Compound 170

To a solution of phenol 169 (20.0 mg, 0.0778 mmol) in dimethylformamide (1.0 mL) was added cesium carbonate (39.0 mg, 0.121 mmol). The resulting mixture was stirred at 60° C. for 10 min. and bromosteroid (22.0 mg, 0.0517 mmol) was added. The reaction was stirred at 60° C. for 3 hrs. An aqueous solution of 10% NaOH was added and the product was extracted with ethyl acetate (3×15 mL). Organic layers were combined, dried over magnesium sulfate and concentrated to give the crude product. The crude product was purified by column chromatography over silica gel (50% ethyl acetate/hexane) to give pure product 170 (19.0 mg, 60%).

EM-6972

To a solution of ketone 170 (24.0 mg, 0.04 mmol) in methanol (2 mL) was added sodium borohydride (4.5 mg, 0.120 mmol) at 0° C. The reaction was allowed to warm up to room temperature and was stirred for 30 min. The solvent was evaporated and the residue was dissolved in acetone (2 mL) and 10% aqueous solution of hydrochloric acid (2 mL). The solution was stirred at room temperature 3 hrs. An aqueous solution of 10% sodium hydroxide was added and the product was extracted with ethyl acetate (3×15 mL). Organic layers were combined, dried over magnesium sulfate and concentrated to give the crude product. The crude product was purified by column chromatography over silica (100% ethyl acetate) to give pure product EM-6972 (19.0 mg, 86%). ¹H NMR (400 MHz, acetone) δ: 7.21 (t,1H, J=8 Hz), 7.07 (s, 1H), 6.91 (d, 1H, J=8 Hz), 6.81 (d, 1H, J=8 Hz), 4.43-4.62 (m, 1H), 4.00-4.10 (m, 2H), 3.71 (t, 1H, J=7 Hz), 3.31 (s, 3H), 1.09 (s, 3H).

Example XX

Synthesis of Morpholino Dihydrotestosterone Derivatives

This synthesis is described in Scheme 5

SCHEME 55

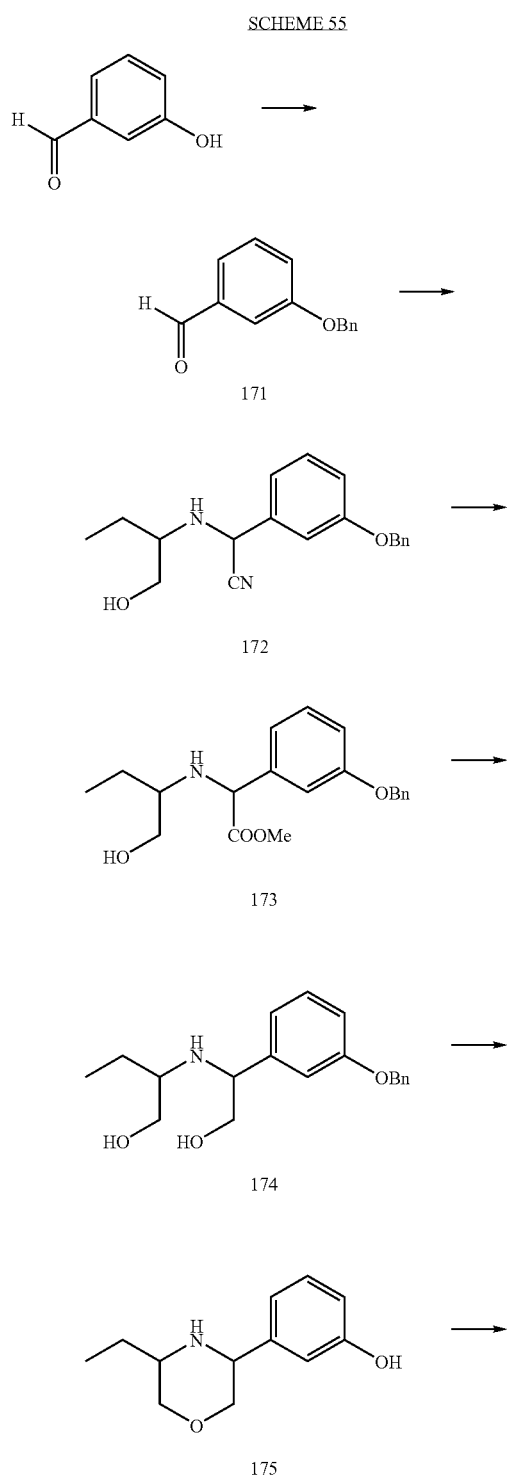

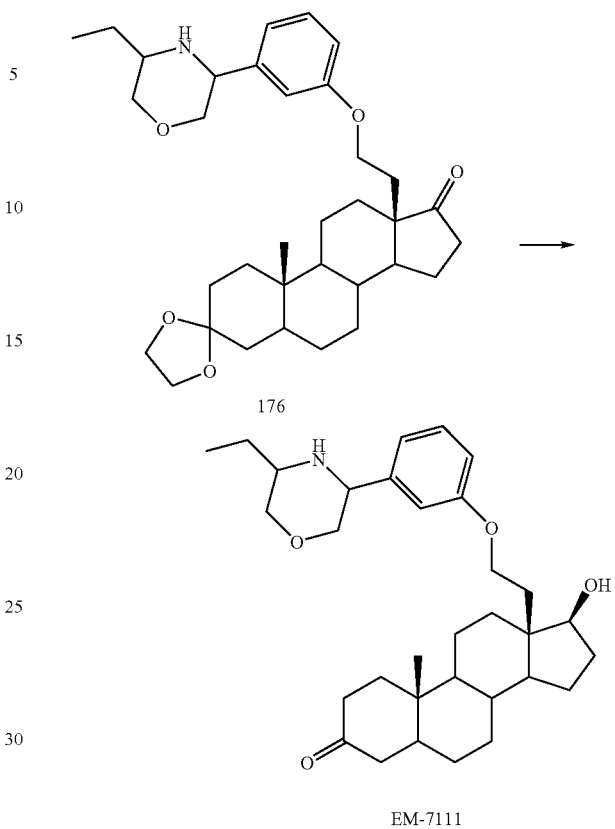

Benzaldehyde 171

In a 200 mL RB flask were added with 4 g (32.8 mmol) of 3-hydroxybenzaldehyde, 4.3 mL (36 mmol) of benzylbromide and 12.8 g (39.3 mmol) of cesium carbonate in 40 mL of acetonitrile. The reaction mixture was stirred for 4 h at room temperature before the solvent was removed under reduced pressure and the residue taken in 50 mL of ethyl acetate and washed successively with 20 mL saturated aqueous sodium bicarbonate, 20 mL 1N aqueous sodium hydroxide and 20 mL brine, dried over magnesium sulfate, filtered and concentrated to give 171 in a quantitative yield, which was sufficiently pure to be used in the next step. $^1$H NMR (400 MHz, CDCl$_3$) δ: 5.13 (s, 2H), 7.34-7.50 (m, 9H), 9.96 (s, 1H).

Benzylamine 172

Aldehyde 171 (3 g, 22.0 mmol) was diluted with CHCl$_3$ (60 mL) in a RB flask. 2-Aminobutan-1-ol (2.08 mL, 22 mmol) was added and the mixture is stirred 1 h at room temperature. Trimethylsilylcyanide (5.5 mL, 44.1 mmol) was then added slowly at 0° C. and the reaction mixture was stirred for an additional 2 h at room temperature. The reaction was then quenched with 40 mL of 10% aqueous HCl, and stirred for 1 h and neutralized with sodium bicarbonate. The aqueous phase is extracted with ethyl acetate (3×30 mL), the combined organic phase was washed with brine, dried over magnesium sulfate, filtered and concentrated. Flash chromatography of the residue using 20 to 40% acetone in hexane provided 3.65 g (53%) of 172. $^1$H NMR (400 MHz, CD$_3$OD) δ: 0.88-1.00 (2t, 3H), 1.50-1.72 (2m, 2H), 2.90-2.94 and 3.20-3.24 (2m, 1H), 3.34-3.71 (m, 2H), 5.03 and 5.10 (2s, 1H), 5.14 and 5.15 (2s, 2H), 7.04-7.53 (m, 9H).

Methyl Ester 173

Compound 172 (1.4 g) was placed in a saturated methanolic solution of HCl (30 mL) and stirred 3 h at room temperature. The solvent was removed under reduced pressure and the residue was neutralized with a saturated aqueous solution of sodium bicarbonate. The aqueous phase is extracted with dichloromethane (3×20 mL) and the combined organic phase was dried over magnesium sulfate, filtered and concentrated. Flash chromatography of the residue using 20 to 40% acetone in hexane as a gradient provided 860 mg (56%) of 173. $^1$H NMR (400 MHz, CD$_3$OD) δ: 0.87 and 0.89 (2t, 3H), 1.41-1.44 (m, 2H), 2.40-2.46 (m, 1H), 3.39-3.69 (m, 2H), 3.68 (s, 3H), 4.57 and 4.61 (2s, 1H), 5.11 (s, 1H), 6.95-7.46 (m, 9H).

Diol 174

Compound 173 (860 mg, 2.50 mmol) was diluted with 10 mL of THF and brought to 0° C. LAH (5 mL, 5 mmol, 1M in THF) was added and the reaction mixture was stirred at room temperature for 2 h. The reaction was quenched with 15 mL of a 20% aqueous solution of sodium potassium tartrate and stirred for 45 minutes at room temperature. The solvent was removed under reduced pressure and the residue was extracted with ethyl acetate (3×10 mL). The combined organic phase are washed with brine, dried over magnesium sulfate, filtered and concentrated. The crude diol 174 (844 mg) was used in the next step without further purification.

Morpholine 175

The diol 174 (400 mg) was placed in 4 mL of methanesulfonic acid and heated at 140° C. for 18 h. The reaction mixture was cooled down, diluted with 15 mL of water, neutralized with sodium bicarbonate and extracted with ethyl acetate (3×15 mL). The combined organic portion was washed with brine, dried over magnesium sulfate, filtered and concentrated. Flash chromatography of the residue using 30 to 50% acetone in hexane as a gradient provided 31 mg (12%) of 175. $^1$H NMR (400 MHz, CD$_3$OD) δ: 0.96 (t, 3H, J=7.5 Hz), 1.59-1.77 (m, 2H), 2.77-2.80 (m, 1H), 3.60-3.68 (m, 2H), 3.78-3.85 (m, 2H), 4.02 (dd, 1H, J=8 Hz), 6.71 (d, 1H, J=8 Hz), 6.90-6.92 (m, 2H), 7.17 (t, 1H, J=8 Hz).

Steroid 176

Morpholine 175 (1 mg, 0.141 mmol) was coupled with bromosteroid 57 (60 mg, 0.141 mmol) according to the known procedure, described earlier to give 48 mg (62%) of steroid 176.

EM-7111

Steroid 176 (22 mg) was reduced and deprotected according to the known procedure and purified by flash-chromatography using a gradient of 40 to 50% acetone in hexanes to give 15 mg (76%) of EM-7111. $^1$H NMR (400MHz, CD$_3$OD) δ: 0.97 (t, 3H, J=8 Hz), 1.08 (s, 3H), 2.39 (t, 1H, J=17 Hz), 2.48 (td, 1H, J=17 Hz), 2.78-2.82 (m, 1H), 3.62-3.88 (m, 4H), 4.07-4.18 (m, 2H), 4.42-4.49 (m, 1H), 6.88 (d, 1H, J=8 Hz), 7.00 (d, 1H, J=8 Hz), 7.09 (s, 1H), 7.26 (t, 1H, J=8 Hz).

Pharmaceutical Composition Examples

Set forth below, by way of example and not of limitation, are several pharmaceutical compositions utilizing a preferred active compound EM-6549 for systemic use and EM-6445 for topical application. Other compounds of the invention or combination thereof, may be used in place of (or in addition to) EM-6549 or EM-6445. The concentration of active ingredient may be varied over a wide range as discussed herein. The amounts and types of other ingredients that may be included are well known in the art.

Example A

Composition Suitable for Injection

| Ingredient | Weight % (by weight of total composition) |
| --- | --- |
| EM-6549 | 5.0 |
| Ethanol | 6.4 |
| NaCl | 0.8 |
| Water | 86.9 |
| Benzyl alcohol | 0.9 |

Example B

Composition Suitable for Use as Topical Lotion

| Ingredient | Weight % (by weight of total composition) |
| --- | --- |
| EM-6445 | 1.0 |
| Ethanol | 70.0 |
| Propylene glycol | 29.0 |

Example C

Composition Suitable for Use as Topical Gel

| Ingredient | Weight % (by weight of total composition) |
| --- | --- |
| EM-6445 | 1.0 |
| Kucel | 1.5 |
| Ethanol | 70.0 |
| Propylene glycol | 27.5 |

Example D

Tablet

| Ingredient | Weight % (by weight of total composition) |
| --- | --- |
| EM-6549 | 20.0 |
| Gelatin | 5.0 |
| Lactose | 47.5 |
| Starch | 27.5 |

Example E

Gelatin Capsule

| Ingredient | Weight % (by weight of total composition) |
|---|---|
| EM-6549 | 20.0 |
| Lactose hydrous | 62.0 |
| Starch | 4.8 |
| Cellulose microcrystalline | 12.8 |
| Magnesium stearate | 0.4 |

Other antiandrogens may be substituted for EM-6549 or EM-6445 in the above formulations. For combination therapies, 5alpha reductase inhibitors, 17beta-hydroxysteroid dehydrogenase type 5 inhibitors and Prostate Short-Chain Dehydrogenase Reductase inhibitors could be added at weight % (with prorata reduction of other components).

Example F

Composition Suitable for Injection

| Ingredient | Weight % (by weight of total composition) |
|---|---|
| EM-6549 | 5.0 |
| Finasteride | 0.4 |
| Ethanol | 6.0 |
| NaCl | 0.8 |
| Water | 86.9 |
| Benzyl alcohol | 0.9 |

Example G

Composition Suitable for Use as Topical Lotion

| Ingredient | Weight % (by weight of total composition) |
|---|---|
| EM-6445 | 1.0 |
| Finasteride | 1.0 |
| Ethanol | 69.0 |
| Propylene glycol | 29.0 |

Example H

Composition Suitable for Use as Topical Gel

| Ingredient | Weight % (by weight of total composition) |
|---|---|
| EM-6445 | 20.0 |
| Finasteride | 1.0 |
| Kucel | 1.5 |
| Ethanol | 69.0 |
| Propylene glycol | 27.5 |

Example I

Tablet

| Ingredient | Weight % (by weight of total composition) |
|---|---|
| EM-6549 | 20.0 |
| Finasteride | 1.0 |
| Gelatin | 5.0 |
| Lactose | 46.5 |
| Starch | 27.5 |

Example J

Gelatin Capsule

| Ingredient | Weight % (by weight of total composition) |
|---|---|
| EM-6549 | 20.0 |
| Finasteride | 1.0 |
| Lactose hydrous | 61.0 |
| Starch | 4.8 |
| Cellulose microcrystalline | 12.8 |
| Magnesium stearate | 0.4 |

Example K

Composition Suitable for Injection

| Ingredient | Weight % (by weight of total composition) |
|---|---|
| EM-6549 | 5.0 |
| EM-1404 | 5.0 |
| Ethanol | 6.0 |
| NaCl | 0.8 |
| Water | 82.3 |
| Benzyl alcohol | 0.9 |

Example L

Composition Suitable for Use as Topical Lotion

| Ingredient | Weight % (by weight of total composition) |
|---|---|
| EM-6445 | 1.0 |
| EM-1404 | 2.0 |
| Ethanol | 68.0 |
| Propylene glycol | 29.0 |

Example M

Composition Suitable for Use as Topical Gel

| Ingredient | Weight % (by weight of total composition) |
|---|---|
| EM-6445 | 1.0 |
| EM-1404 | 2.0 |
| Kucel | 1.5 |
| Ethanol | 68.0 |
| Propylene glycol | 27.5 |

Example N

Tablet

| Ingredient | Weight % (by weight of total composition) |
|---|---|
| EM-6549 | 20.0 |
| EM-1404 | 20.0 |
| Gelatin | 5.0 |
| Lactose | 27.5 |
| Starch | 27.5 |

Example O

Gelatin Capsule

| Ingredient | Weight % (by weight of total composition) |
|---|---|
| EM-6549 | 20.0 |
| EM-1404 | 20.0 |
| Lactose hydrous | 42.0 |
| Starch | 4.8 |
| Cellulose microcrystalline | 12.8 |
| Magnesium stearate | 0.4 |

Example P

Composition Suitable for Injection

| Ingredient | Weight % (by weight of total composition) |
|---|---|
| EM-6549 | 5.0 |
| EM-1791 | 0.4 |
| Ethanol | 6.0 |
| NaCl | 0.8 |
| Water | 86.9 |
| Benzyl alcohol | 0.9 |

Example Q

Composition Suitable for Use as Topical Lotion

| Ingredient | Weight % (by weight of total composition) |
|---|---|
| EM-6445 | 1.0 |
| EM-1791 | 2.0 |
| Ethanol | 68.0 |
| Propylene glycol | 29.0 |

Example R

Composition Suitable for Use as Topical Gel

| Ingredient | Weight % (by weight of total composition) |
|---|---|
| EM-6445 | 1.0 |
| EM-1791 | 2.0 |
| Ethanol | 68.0 |
| Propylene glycol | 27.5 |

Example S

Tablet

| Ingredient | Weight % (by weight of total composition) |
|---|---|
| EM-6549 | 20.0 |
| EM-1791 | 20.0 |
| Starch | 27.5 |
| Gelatin | 5.0 |
| Lactose | 27.5 |

Example T

Gelatin Capsule

| Ingredient | Weight % (by weight of total composition) |
|---|---|
| EM-6549 | 20.0 |
| EM-1791 | 20.0 |
| Lactose hydrous | 42.0 |
| Cellulose microcrystalline | 12.8 |
| Magnesium stearate | 0.4 |
| Starch | 4.8 |

The invention has been described in terms of preferred embodiments and examples, but is not limited thereby. Those of skill in the art will readily recognize the broader applicability and scope of the invention which is limited only by the patent claims that issue from this application or any patent application claiming priority (directly or indirectly) hereto.

What is claimed is:

1. A compound of the molecular formula (or a salt thereof):

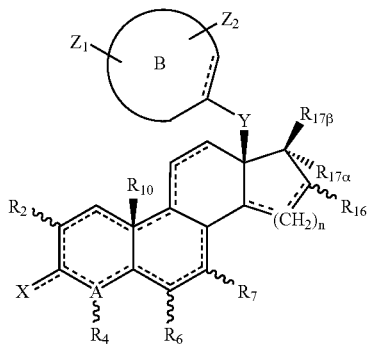

wherein n is 1;
Wherein dotted lines represent optional π-bonds;
Wherein A is selected from the group consisting of a carbon atom and a nitrogen atom;
Wherein B is an aromatic moiety;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing and a moiety that together with $R_{17\beta}$ is a keto group;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, or $C_2$-$C_{20}$ acyl) and a moiety which together with $R_{17\alpha}$ is a keto group;
Wherein X is selected from the group consisting of hydrogen, fluoride, chloride, bromide, iodide, cyanide, keto-oxygen, hydroxyl, NOH and a group transformed in vivo into hydroxyl or keto function;
Wherein Y is —$CH_2CH_2O$—;
Wherein $Z_1$ is a hydrocarbon moiety additionally having at least one nitrogen atom separated from B by one intervening atom, and said nitrogen atom being an amine, an amide, an N-oxide, or a quaternary ammonium salt, $Z_1$, optionally, having other oxygen, sulphur, or nitrogen atoms;
Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl.

2. The compound of claim 1 wherein B is selected from the group consisting of phenylene and mono-substituted pyridyl and wherein $Z_1$ is located in meta position with respect to the group Y and the nitrogen atom of $Z_1$ is separated from the phenylene or mono-substituted pyridyl ring by one intervening atoms.

3. The compound of claim 1 wherein $Z_1$ is selected from the list of following moieties:

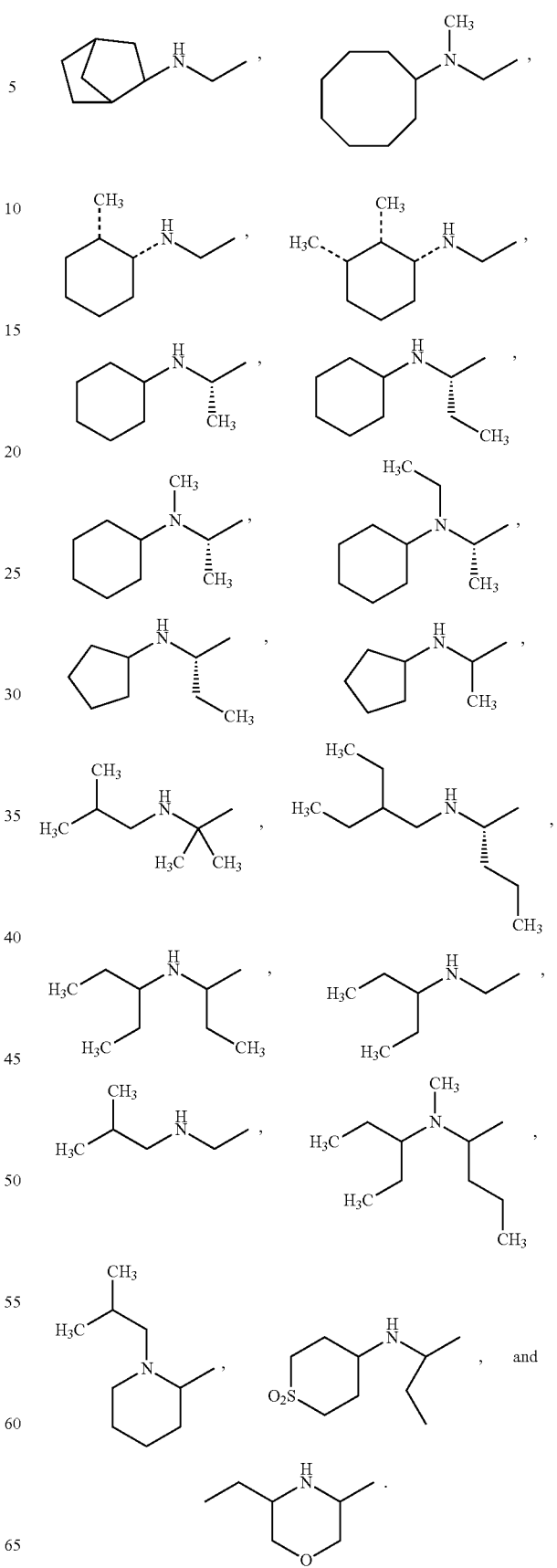

and

-continued

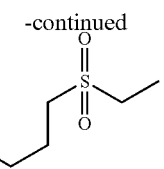

4. The compound of claim 1 wherein $R_7$ is selected from the group consisting of methyl, ethyl, and 2-propenyl.

5. The compound of claim 1 having the following molecular formula (or a salt thereof):

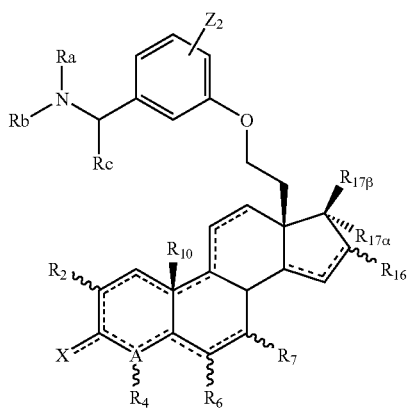

Wherein dotted lines represent optional π-bonds;
Wherein A is selected from the group consisting of carbon and nitrogen;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, $C_2$-$C_{20}$ acyl);
Wherein X is selected from the group consisting of hydrogen, fluoride, chloride, bromide, iodide, cyanide, keto-oxygen, hydroxyl, NOH and a group transformed in vivo into hydroxyl or keto function;
Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;
Wherein Ra, Rb, and Rc are independently selected from the group consisting of hydrogen, $C_1$-$C_{10}$ straight, or branched alkyl, $C_2$-$C_{10}$ straight or branched alkenyl, a $C_2$-$C_{10}$ straight or branched alkynyl, a $C_3$-$C_7$ saturated or unsaturated cyclic hydrocarbon moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionally substituted with fluoro, chloro, bromo, iodo, or cyano); or Rb an Rc together form a ring (optionally substituted with fluoro, chloro, bromo, iodo, or cyano); wherein Ra, Rb, and Rc may, optionally, have oxygen, sulphur, or nitrogen atoms.

6. The compound of claim 5 having the following molecular formula (or a salt thereof)

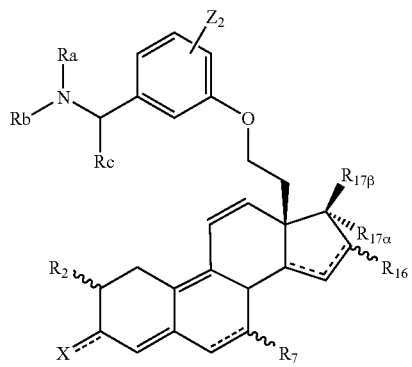

Wherein dotted lines represent optional π-bonds;
Wherein $R_2$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, $C_2$-$C_{20}$ acyl);
Wherein X is selected from the group consisting of hydrogen, fluoride, chloride, bromide, iodide, cyanide, keto-oxygen, hydroxyl, NOH and a group transformed in vivo into hydroxyl or keto function;
Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;
Wherein Ra, Rb, and Rc are independently selected from the group consisting of hydrogen, $C_1$-$C_{10}$ straight, or branched alkyl, $C_2$-$C_{10}$ straight or branched alkenyl, $C_2$-$C_{10}$ straight or branched alkynyl, a $C_3$-$C_7$ saturated or unsaturated cyclic hydrocarbon moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionally substituted with fluoro, chloro, bromo, iodo, or cyano); or Rb an Rc together form a ring (optionally substituted with fluoro, chloro, bromo, iodo, or cyano); wherein Ra, Rb, and Rc may, optionally, have oxygen, sulphur, or nitrogen atoms.

7. The compound having a molecular structure or a salt thereof selected from the group consisting of:

211

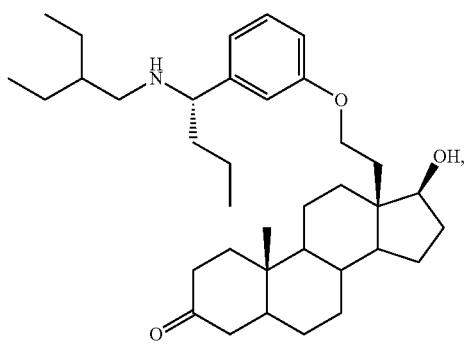

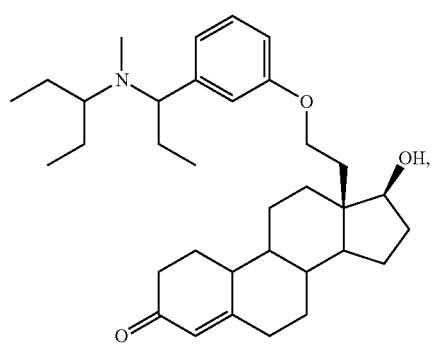

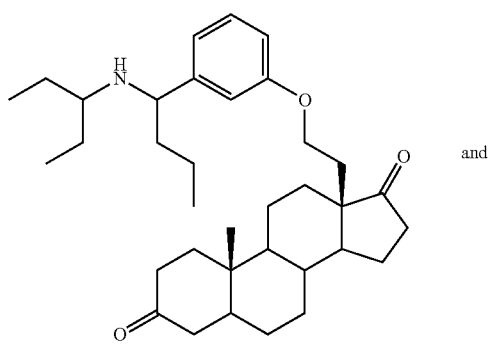

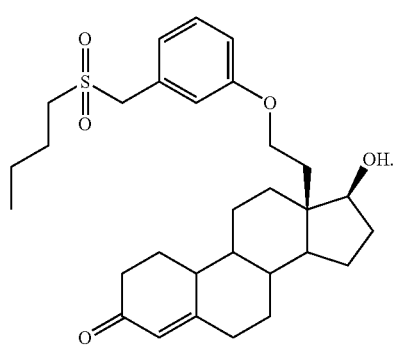

8. The compound having a molecular structure or a salt thereof selected from the group consisting of:

212

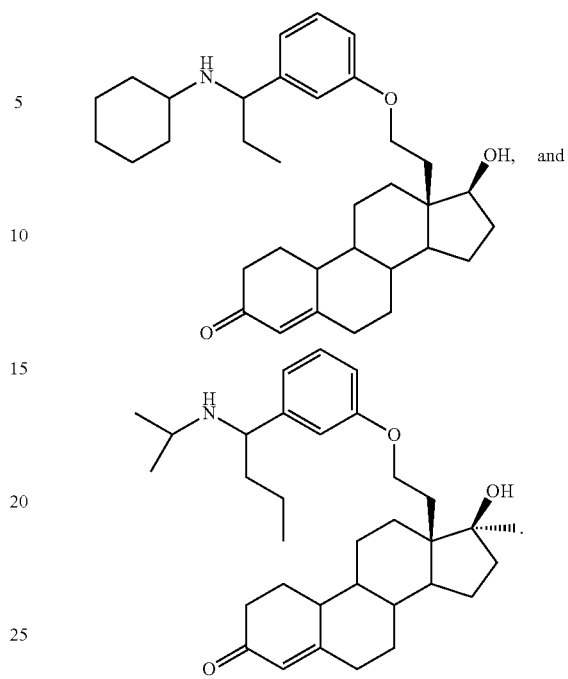

9. The compound of claim 1 possessing a tissue-specific antiandrogenic activity and a tissue-specific androgenic activity.

10. A pharmaceutical composition comprising a pharmaceutically acceptable diluent or carrier and a therapeutically effective amount of at least one compound of the molecular formula (or a salt thereof):

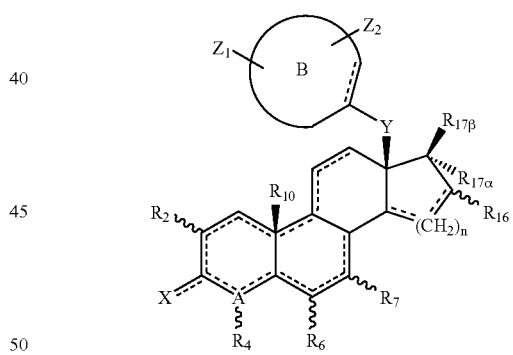

wherein n is 1;
Wherein dotted lines represent optional π-bonds;
Wherein A is selected from the group consisting of a carbon atom and a nitrogen atom;
Wherein B is selected from the group consisting of an aromatic moiety, a heterocyclic moiety, a cyclic moiety and a polycyclic moiety;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;

Wherein R$_{17\alpha}$ is selected from the group consisting of hydrogen, C$_1$-C$_5$ straight or branched alkyl, C$_2$-C$_5$ straight or branched alkenyl, C$_2$-C$_5$ straight or branched alkynyl, aryl, benzyl, picolyl, and fluoro, chloro, bromo, iodo, or cyano analogs of the foregoing and a moiety that together with R$_{17\beta}$ is a keto group;

Wherein R$_{17\beta}$ is selected from the group consisting of hydrogen, hydroxyl, OR' (wherein R' is C$_1$-C$_{20}$ straight or branched alkyl, C$_2$-C$_{20}$ straight or branched alkenyl, C$_2$-C$_{20}$ straight or branched alkynyl, or C$_2$-C$_{20}$ acyl) and a moiety which together with R$_{17\alpha}$ is a keto group);

Wherein X is selected from the group consisting of hydrogen, fluoride, chloride, bromide, iodide, cyanide, keto-oxygen, hydroxyl, NOH and a group transformed in vivo into hydroxyl or keto function;

Wherein Y is —CH$_2$CH$_2$O—;

Wherein Z$_1$ is a hydrocarbon moiety additionally having at least one nitrogen atom separated from B by one intervening atom, and said nitrogen atom being an amine, an amide, an N-oxide, or a quaternary ammonium salt, Z$_1$, optionally, having other oxygen, sulphur, or nitrogen atoms;

Wherein Z$_2$ is selected from the group consisting of hydrogen, fluorine, chlorine, bromine, iodine, cyano, nitro, trifluoromethyl, alkoxy, C$_1$-C$_5$ straight or branched alkyl, C$_2$-C$_5$ straight or branched alkenyl, and C$_2$-C$_5$ straight or branched alkynyl.

11. The pharmaceutical composition of claim 10 wherein B is selected from the group consisting of phenylene and mono-substituted pyridyl and wherein Z$_1$ is located in meta position with respect to the group Y and the nitrogen atom of Z$_1$ is separated from the phenylene or mono-substituted pyridyl ring by one intervening atoms.

12. The pharmaceutical composition of claim 10 wherein Z$_1$ is selected from the list of following moieties:

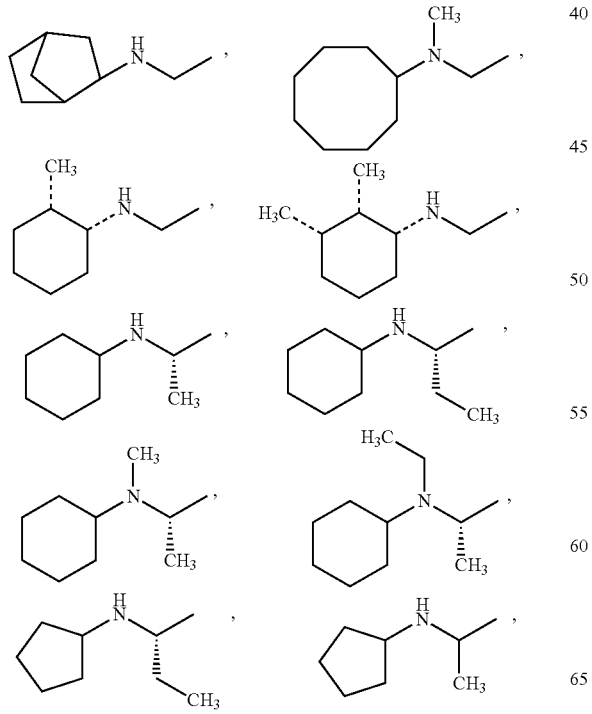

-continued

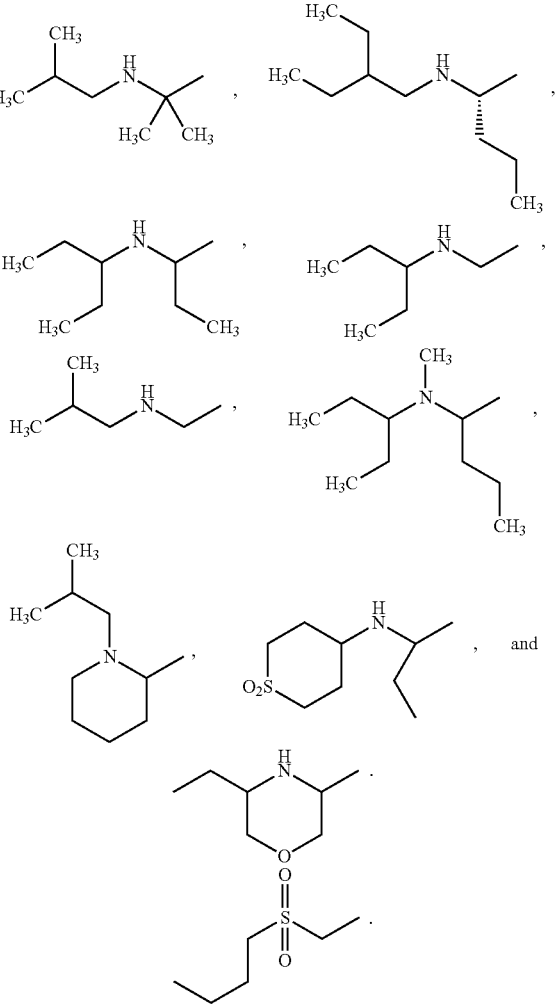

13. The pharmaceutical composition of claim 10 wherein R$_7$ is selected from the group consisting of methyl, ethyl, and 2-propenyl.

14. The pharmaceutical composition of claim 10 having the following molecular formula (or a salt thereof):

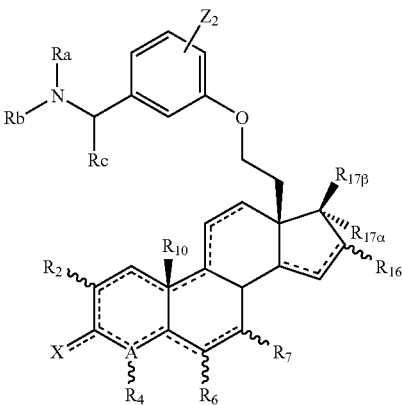

Wherein dotted lines represent optional π-bonds;
Wherein A is selected from the group consisting of carbon and nitrogen;

Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;

Wherein $R_{10}$ is absent or selected from the group consisting of hydrogen and methyl;

Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;

Wherein $R_{17\alpha}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, $C_2$-$C_{20}$ acyl);

Wherein X is selected from the group consisting of hydrogen, fluoride, chloride, bromide, iodide, cyanide, keto-oxygen, hydroxyl, NOH and a group transformed in vivo into hydroxyl or keto function;

Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;

Wherein Ra, Rb, and Rc are independently selected from the group consisting of hydrogen, $C_1$-$C_{10}$ straight, or branched alkyl, $C_2$-$C_{10}$ straight or branched alkenyl, $C_2$-$C_{10}$ straight or branched alkynyl, a $C_3$-$C_7$ saturated or unsaturated cyclic hydrocarbon moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionally substituted with fluoro, chloro, bromo, iodo, or cyano); or Rb an Rc together form a ring (optionally substituted with fluoro, chloro, bromo, iodo, or cyano); wherein Ra, Rb, and Rc may, optionally, have oxygen, sulphur, or nitrogen atoms.

15. The pharmaceutical composition of claim 14 having the following molecular formula (or a salt thereof):

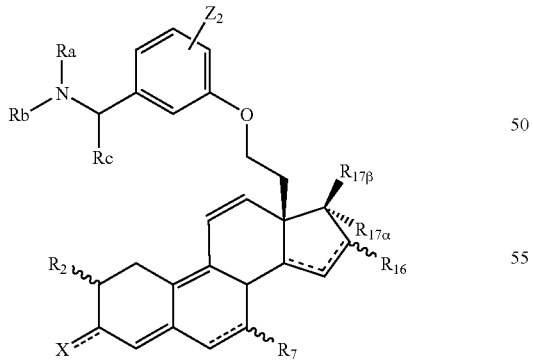

Wherein dotted lines represent optional π-bonds;

Wherein $R_2$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;

Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;

Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, acyl);

Wherein X is selected from the group consisting of hydrogen, fluoride, chloride, bromide, iodide, cyanide, keto-oxygen, hydroxyl, NOH and a group transformed in vivo into hydroxyl or keto function;

Wherein $Z_2$ is selected from the group consisting of hydrogen, fluorine, chlorine, bromine, iodine, cyano, nitro, trifluoromethyl, alkoxy, $C_1$-$C_5$ straight or branched alkyl, $C_2$-$C_5$ straight or branched alkenyl, and $C_2$-$C_5$ straight or branched alkynyl;

Wherein Ra, Rb, and Rc are independently selected from the group consisting of hydrogen, $C_1$-$C_{10}$ straight, or branched alkyl, $C_2$-$C_{10}$ straight or branched alkenyl, $C_2$-$C_{10}$ straight or branched alkynyl, a $C_3$-$C_7$ saturated or unsaturated cyclic hydrocarbon moiety, a $C_3$-$C_7$ moiety which forms with an other part of the molecule one ring, aryl, benzyl, and halogenated or cyano analogs of any of the foregoing; or Ra an Rb together with the nitrogen atom form a ring (optionally substituted with fluoro, chloro, bromo, iodo, or cyano); or Rb an Rc together form a ring (optionally substituted with fluoro, chloro, bromo, iodo, or cyano); wherein Ra, Rb, and Rc may, optionally, have oxygen, sulphur, or nitrogen atoms.

16. A pharmaceutical composition comprising a pharmaceutically acceptable diluent or carrier and a therapeutically effective amount of at least one compound having a molecular formula or a salt thereof selected from the group consisting of:

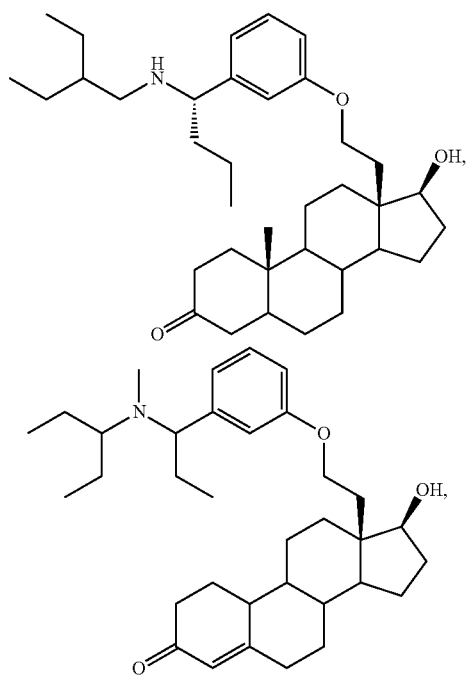

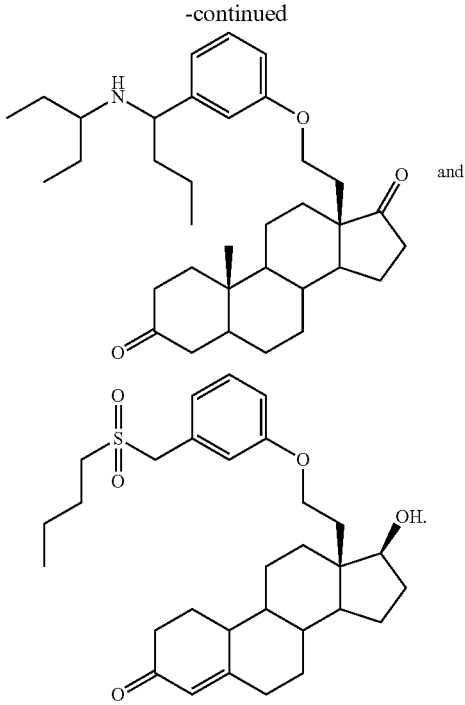

17. A pharmaceutical composition comprising a pharmaceutically acceptable diluent or carrier and a therapeutically effective amount of at least one compound having a molecular formula or a salt thereof selected from the group consisting of:

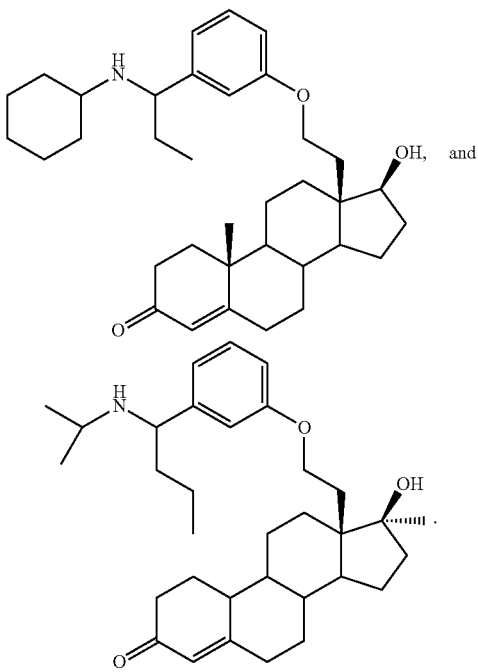

18. The pharmaceutical composition of claim 16 wherein said diluent or carrier is suitable for topical application.

19. The pharmaceutical composition of claim 17 wherein said diluent or carrier is suitable for oral administration.

20. The pharmaceutical composition of claim 10 wherein the active compound possesses a tissue-specific antiandrogenic activity and a tissue-specific androgenic activity.

21. A method of treating prostatic cancer, comprising administering to a patient in need of such treatment a therapeutically effective amount of the compound or pharmaceutical composition of any of claims 1, 2-6, 8-10, 11-15, 17 or 19.

22. A method of treating benign prostatic hyperplasia comprising administering to a patient in need of such treatment, a therapeutically effective amount of the compound or pharmaceutical composition of any of claims 1, 2-6, 8-10, 11-15, 17 or 19.

23. A method of treating polycystic ovarian syndrome comprising administering to a patient in need of such treatment a therapeutically effective amount of the compound or pharmaceutical composition of any of claims 1, 2-6, 8-10, 11-15, 17 or 19.

24. A method of treating acne, seborrhea, hirsutism or androgenic alopecia comprising administering to a patient in need of such treatment a therapeutically effective amount of the compound or pharmaceutical composition of any of claims 1, 2-7, 9-10, 11-16 or 18.

25. A compound of the molecular formula (or a salt thereof):

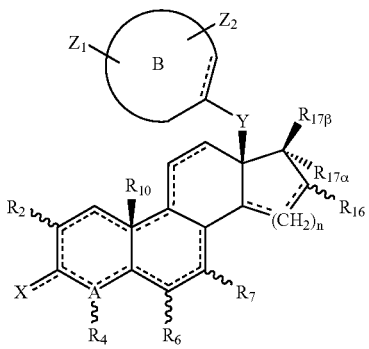

wherein n is 1;
Wherein dotted lines represent optional π-bonds;
Wherein A is selected from the group consisting of a carbon atom and a nitrogen atom;
Wherein B is an aromatic moiety;
Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;
Wherein $R_{10}$ is absent or selected from the group consisting of hydrogen and methyl;
Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;
Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$ $C_{20}$ straight or branched alkynyl, or acyl);
Wherein X is selected from the group consisting of an hydrogen, a fluoride, a chloride, a bromide, an iodide, a cyanide, an oxygen atom forming a keto function, an hydroxyl, NOH and a group transformed in vivo into hydroxyl or keto function;

Wherein Y is —$CH_2CH_2O$—;

Wherein $Z_1$ is a hydrocarbon moiety additionally having at least one nitrogen atom separated from the B by one intervening atom, and said nitrogen atom being an amine, an amide, an N-oxide, or a quaternary ammonium salt;

Wherein $Z_2$ is selected from the group consisting of hydrogen, fluorine, chlorine, bromine, iodine, cyano, nitro, $C_1$-$C_5$ straight or branched alkyl, $C_2$-$C_5$ straight or branched alkenyl, and $C_2$-$C_5$ straight or branched alkynyl.

26. A pharmaceutical composition comprising a pharmaceutically acceptable diluent or carrier and a therapeutically effective amount of at least one compound of the molecular formula (or a salt thereof):

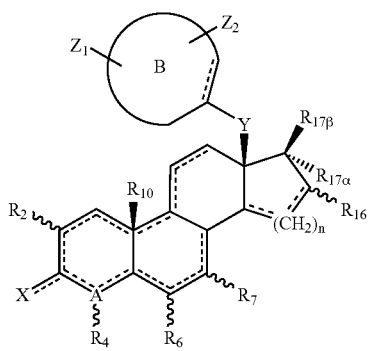

wherein n is 1;

Wherein dotted lines represent optional π-bonds;

Wherein A is selected from the group consisting of a carbon atom and a nitrogen atom;

Wherein B is selected from the group consisting of an aromatic moiety, a cyclic moiety and a polycyclic moiety;

Wherein $R_2$, $R_4$, $R_6$, $R_7$, and $R_{16}$ are independently selected from the group consisting of hydrogen, fluoride, chloride, bromide, iodide, cyanide, $C_1$-$C_5$ straight or branched alkyl, $C_2$-$C_5$ straight or branched alkenyl, $C_2$-$C_5$ straight or branched alkynyl, and fluoro, chloro, bromo, iodo, or cyano analogs of the foregoing;

Wherein $R_{10}$ is absent or selected from the group consisting of hydrogen and methyl;

Wherein $R_{17\alpha}$ is selected from the group consisting of hydrogen, $C_1$-$C_5$ straight or branched alkyl, $C_2$-$C_5$ straight or branched alkenyl, $C_2$-$C_5$ straight or branched alkynyl, aryl, benzyl, picolyl, and fluoro, chloro, bromo, iodo, or cyano analogs of the foregoing;

Wherein $R_{17\beta}$ is selected from the group consisting of hydrogen, hydroxyl, OR' (wherein R' is $C_1$-$C_{20}$ straight or branched alkyl, $C_2$-$C_{20}$ straight or branched alkenyl, $C_2$-$C_{20}$ straight or branched alkynyl, or acyl);

Wherein X is selected from the group consisting of an hydrogen, a fluoride, a chloride, a bromide, an iodide, a cyanide, an oxygen atom forming a keto function, an hydroxyl, NOH and a group transformed in vivo into hydroxyl or keto function;

Wherein Y is —$CH_2CH_2O$—;

Wherein $Z_1$ is a hydrocarbon moiety additionally having at least one nitrogen atom separated from the B by one intervening atom, and said nitrogen atom being an amine, an amide, an N-oxide, or a quaternary ammonium salt;

Wherein $Z_2$ is selected from the group consisting of hydrogen, fluorine, chlorine, bromine, iodine, cyano, nitro, $C_1$-$C_5$ straight or branched alkyl, $C_2$-$C_5$ straight or branched alkenyl, and $C_2$-$C_5$ straight or branched alkynyl.

27. A compound of the following molecular structure:

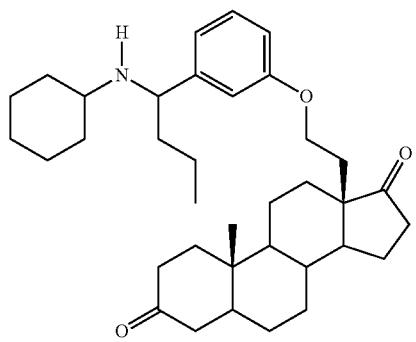

28. A pharmaceutical composition comprising the compound of claim 27 and a pharmaceutically acceptable excipient, diluent or carrier.

29. A compound of the following molecular structure:

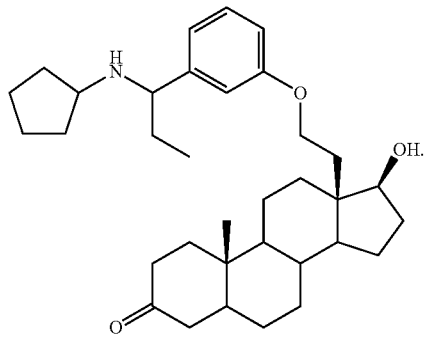 [SMILES: CCC(NC1CCCC1)c1cccc(OCC[C@]23CCC4C(CCC5CC(=O)CC[C@@]54C)C2CC[C@@H]3O)c1]

30. A pharmaceutical composition comprising the compound of claim 29 and a pharmaceutically acceptable excipient diluent or carrier.

31. A compound of the following molecular structure:

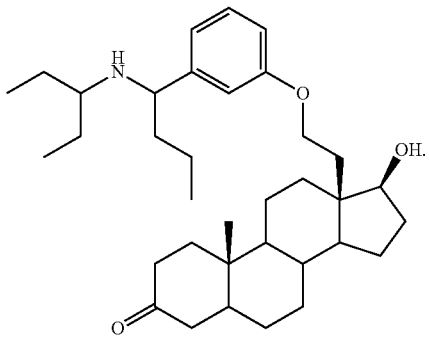 [SMILES: CCCC(NC(CC)CC)c1cccc(OCC[C@]23CCC4C(CCC5CC(=O)CC[C@@]54C)C2CC[C@@H]3O)c1]

32. A pharmaceutical composition comprising the compound of claim 31 and a pharmaceutically acceptable excipient diluent or carrier.

33. A method of treating acne, seborrhea, hirsutism or androgenic alopecia comprising administering to a patient in need of such treatment a therapeutically effective amount of the compound or pharmaceutical composition of any of claims 27-32.

\* \* \* \* \*